(12) United States Patent
Miwatashi et al.

(10) Patent No.: US 9,382,188 B2
(45) Date of Patent: *Jul. 5, 2016

(54) AROMATIC RING COMPOUND

(71) Applicant: TAKEDA PHARMACEUTICAL COMPANY LIMITED, Osaka (JP)

(72) Inventors: Seiji Miwatashi, Tokyo (JP); Hideo Suzuki, Kanagawa (JP); Tomohiro Okawa, Kanagawa (JP); Yasufumi Miyamoto, Kanagawa (JP); Takeshi Yamasaki, Kanagawa (JP); Yuko Hitomi, Kanagawa (JP); Yasuhiro Hirata, Kanagawa (JP); Akito Shibuya, Kanagawa (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,953

(22) PCT Filed: Feb. 12, 2013

(86) PCT No.: PCT/JP2013/053196
§ 371 (c)(1),
(2) Date: Aug. 11, 2014

(87) PCT Pub. No.: WO2013/122028
PCT Pub. Date: Aug. 22, 2013

(65) Prior Publication Data
US 2015/0018422 A1    Jan. 15, 2015

(30) Foreign Application Priority Data
Feb. 13, 2012   (JP) .................................. 2012-028942

(51) Int. Cl.
| | |
|---|---|
| *C07C 59/135* | (2006.01) |
| *C07D 405/14* | (2006.01) |
| *C07C 255/46* | (2006.01) |
| *C07D 309/06* | (2006.01) |
| *C07D 231/12* | (2006.01) |
| *C07D 333/38* | (2006.01) |

(Continued)

(52) U.S. Cl.
CPC .............. *C07C 59/135* (2013.01); *C07C 59/68* (2013.01); *C07C 59/70* (2013.01); *C07C 59/72* (2013.01); *C07C 229/34* (2013.01); *C07C 233/47* (2013.01); *C07C 235/34* (2013.01); *C07C 255/37* (2013.01); *C07C 255/41* (2013.01); *C07C 255/46* (2013.01); *C07C 309/65* (2013.01); *C07C 309/66* (2013.01); *C07C 311/21* (2013.01); *C07C 317/44* (2013.01); *C07C 323/56* (2013.01); *C07D 213/12* (2013.01); *C07D 213/30* (2013.01); *C07D 213/55* (2013.01); *C07D 213/64* (2013.01); *C07D 213/65* (2013.01); *C07D 213/68* (2013.01); *C07D 213/69* (2013.01); *C07D 231/12* (2013.01); *C07D 239/26* (2013.01); *C07D 239/34* (2013.01); *C07D 271/10* (2013.01); *C07D 277/24* (2013.01); *C07D 285/12* (2013.01); *C07D 309/06* (2013.01); *C07D 333/38* (2013.01); *C07D 401/12* (2013.01); *C07D 405/14* (2013.01); *C07C 2101/02* (2013.01); *C07C 2101/04* (2013.01); *C07C 2101/08* (2013.01)

(58) Field of Classification Search
CPC .. C07D 401/12; C07D 239/34; C07D 213/12; C07D 405/14; C07D 271/10; C07D 333/38; C07D 239/26; C07D 213/64
USPC .................... 546/268.1; 514/571; 562/469
See application file for complete search history.

(56) References Cited

U.S. PATENT DOCUMENTS

| 5,011,851 A | 4/1991 | Meanwell |
| 5,187,188 A | 2/1993 | Meanwell |

(Continued)

FOREIGN PATENT DOCUMENTS

| EP | 0434034 | 6/1991 |
| EP | 0442448 | 8/1991 |

(Continued)

OTHER PUBLICATIONS

Dorwald; "Side Reactions in Organic Synthesis: A Guide to Successful Synthesis Design" 2005 Wiley-VCH Verlag GmbH & Co. KGaA, Wienheim, chapter 1.*

(Continued)

*Primary Examiner* — Andrew D Kosar
*Assistant Examiner* — Daniel Carcanague
(74) *Attorney, Agent, or Firm* — Wenderoth, Lind & Ponack, L.L.P.

(57) ABSTRACT

Provided is an aromatic ring compound having a GPR40 agonist activity. A compound represented by the formula (I):

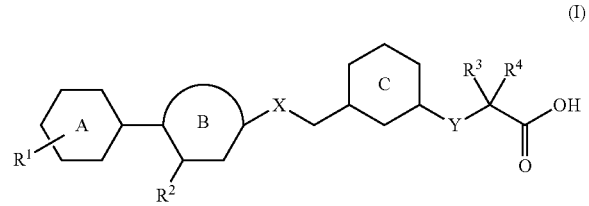

wherein each symbol is as described in the DESCRIPTION, or a salt thereof has a GPR40 agonist activity, and is useful as an agent for the prophylaxis or treatment of diabetes and the like.

10 Claims, No Drawings

(51) Int. Cl.

| | | |
|---|---|---|
| *C07D 401/12* | (2006.01) | |
| *C07D 239/26* | (2006.01) | |
| *C07D 239/34* | (2006.01) | |
| *C07C 317/44* | (2006.01) | |
| *C07C 229/34* | (2006.01) | |
| *C07C 233/47* | (2006.01) | |
| *C07D 271/10* | (2006.01) | |
| *C07D 277/24* | (2006.01) | |
| *C07C 255/37* | (2006.01) | |
| *C07D 285/12* | (2006.01) | |
| *C07D 213/30* | (2006.01) | |
| *C07D 213/55* | (2006.01) | |
| *C07D 213/64* | (2006.01) | |
| *C07D 213/65* | (2006.01) | |
| *C07D 213/68* | (2006.01) | |
| *C07D 213/69* | (2006.01) | |
| *C07C 59/68* | (2006.01) | |
| *C07C 59/70* | (2006.01) | |
| *C07C 59/72* | (2006.01) | |
| *C07D 213/12* | (2006.01) | |
| *C07C 309/65* | (2006.01) | |
| *C07C 309/66* | (2006.01) | |
| *C07C 311/21* | (2006.01) | |
| *C07C 323/56* | (2006.01) | |
| *C07C 235/34* | (2006.01) | |
| *C07C 255/41* | (2006.01) | |

(56) References Cited

U.S. PATENT DOCUMENTS

| | | | | |
|---|---|---|---|---|
| 7,205,302 | B2 | 4/2007 | Asaki et al. | |
| 7,553,867 | B2* | 6/2009 | Hamamura et al. | 514/438 |
| 7,572,934 | B2* | 8/2009 | Brown et al. | 562/492 |
| 7,960,369 | B2 | 6/2011 | Fukatsu et al. | |
| 9,181,186 | B2* | 11/2015 | Miwatashi | C07D 213/64 544/296 |
| 2007/0149608 | A1 | 6/2007 | Yasuma et al. | |
| 2008/0182854 | A1* | 7/2008 | Kato et al. | 514/252.18 |
| 2009/0012093 | A1 | 1/2009 | Fukatsu et al. | |
| 2011/0130438 | A1* | 6/2011 | Bolin et al. | 514/423 |
| 2015/0045378 | A1* | 2/2015 | Miwatashi et al. | 514/274 |

FOREIGN PATENT DOCUMENTS

| | | | |
|---|---|---|---|
| JP | 08-333287 | | 12/1996 |
| JP | 08333287 | * | 12/1996 |
| JP | 2003-238538 | | 8/2003 |
| JP | 2007246474 | * | 9/2007 |
| WO | 2005/000781 | | 1/2005 |
| WO | 2006/059245 | | 6/2006 |
| WO | 2009/048527 | | 4/2009 |
| WO | 2011/067174 | | 6/2011 |
| WO | WO 2012/149528 | * | 11/2012 |

OTHER PUBLICATIONS

Houze; Bioorganic and Medicinal Chemistry Letters, 2012, 22, 1267-1270.*
Silverman; The Organic Chemistry of Drug Design and Drug Action, 2nd Ed, 2004, Elsevier, pp. 29-34.*
Hashizume; JP08333287, Dec. 17, 1996; English machine translation.*
International Search Report issued Apr. 9, 2013 in International (PCT) Application No. PCT/JP2013/053196.
Asaki et al., "Structure-activity studies on diphenylpyrazine derivatives: A novel class of prostacyclin receptor agonists", Bioorganic & Medicinal Chemistry, vol. 15(21), Aug. 2007, pp. 6692-6704.
Meanwell et al., "Nonprostanoid Prostacyclin Mimetics. 2. 4,5-Diphenyloxazole Derivatives", J. Med. Chem., vol. 35(19), 1992, pp. 3483-3497.
Stoll et al., "Pharmacophore Definition and Three-Dimensional Quantitative Structure-Activity Relationship Study on Structurally Diverse Prostacyclin Receptor Agonists", Molecular Pharmacology, vol. 62(5), 2002, pp. 1103-1111.
Meanwell et al., "Nonprostanoid Prostacyclin Mimetics. 3. Structural Variations of the Diphenyl Heterocycle Moiety", J. Med. Chem., vol. 35(19), 1992, pp. 3498-3512.
Meanwell et al., "Nonprostanoid Prostacyclin Mimetics. 4. Derivatives of 2-[3-[2-(4,5-Diphenyl-2-oxazolyl)ethyl]phenoxy]acetic Acid Substituted α to the Oxazole Ring", J. Med. Chem., vol. 36(24), 1993, pp. 3871-3883.
CAS Registry No. 1302489-36-6, May 29, 2011.
CAS Registry No. 1299978-57-6, May 24, 2011.
CAS Registry No. 1297860-03-7, May 20, 2011.
Supplementary European Search Report issued Jul. 31, 2015, in corresponding European Application No. 13 74 9442.
Wermuth et al.; Chapter 15, "Molecular Variations Based on Isosteric Replacements", The Practice of Medicinal Chemistry (Third Edition), pp. 290-342, Jan. 1, 2008.

* cited by examiner

AROMATIC RING COMPOUND

TECHNICAL FIELD

The present invention relates to a novel aromatic ring compound having a GPR40 agonist activity.

BACKGROUND OF THE INVENTION

Patent document 1 describes the following compound.

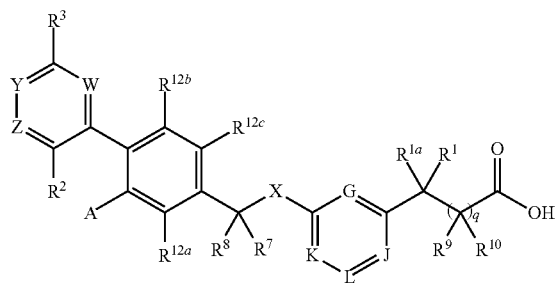

wherein each symbol is as described in patent document 1.

Non-patent document 1 describes the following compound.

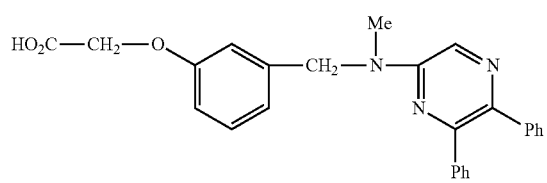 [SMILES: CN(Cc1cccc(OCC(=O)O)c1)c1cnc(-c2ccccc2)c(-c2ccccc2)n1]

Patent document 2 describes the following compound.

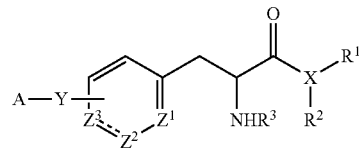

wherein each symbol is as described in patent document 2.

Patent document 3 describes the following compound.

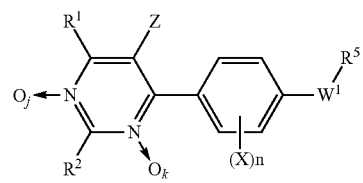

wherein each symbol is as described in patent document 3.

Patent document 4 describes the following compound.

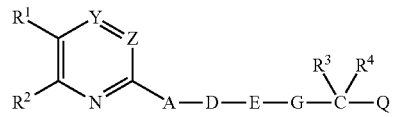

wherein each symbol is as described in patent document 4.

Patent document 5 describes the following compound.

wherein each symbol is as described in patent document 5.

Non-patent document 2 describes the following compounds.

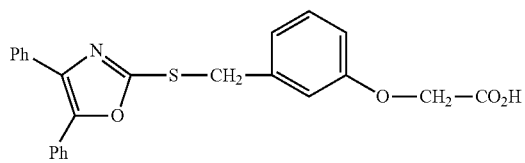

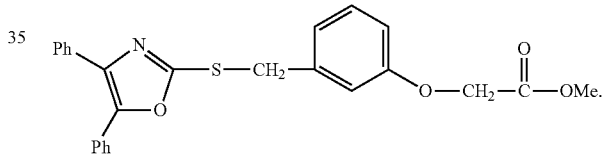

Patent documents 6 and 7 describe the following compound.

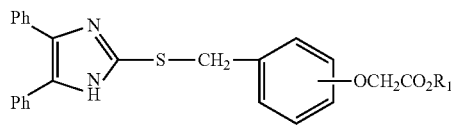

wherein each symbol is as described in patent documents 6 and 7.

Patent document 8 describes the following compound.

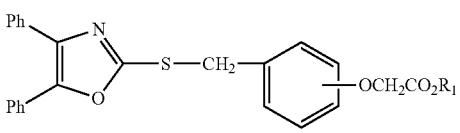

wherein each symbol is as described in patent document 8.

Non-patent document 3 describes the following compounds.

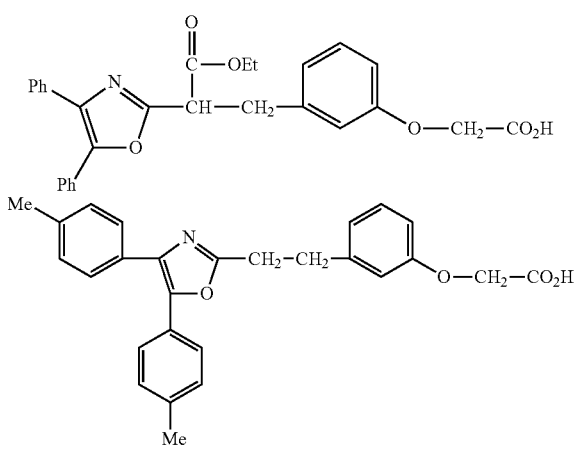

Non-patent document 4 describes the following compounds.

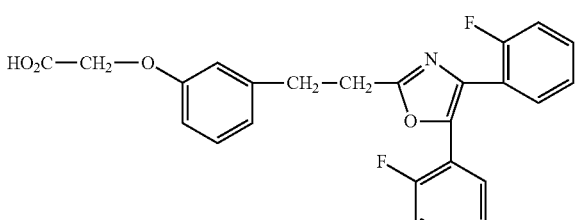

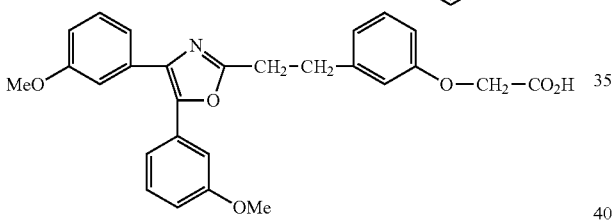

Non-patent document 5 describes the following compound.

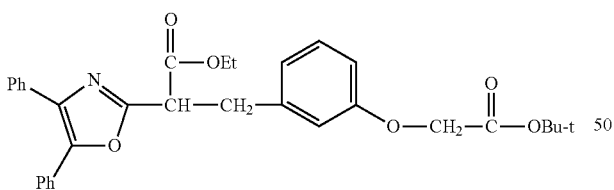

Patent document 9 describes the following compound.

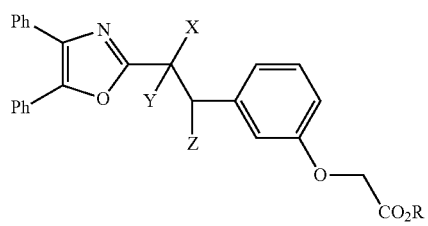

wherein each symbol is as described in patent document 9.

Patent document 10 describes the following compound.

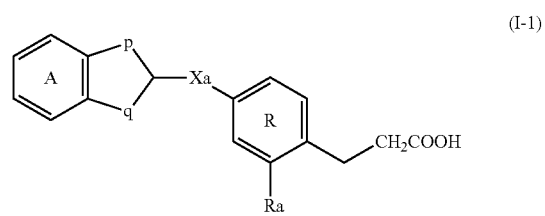

(I-1)

wherein each symbol is as described in patent document 10.

Patent document 11 describes the following compound.

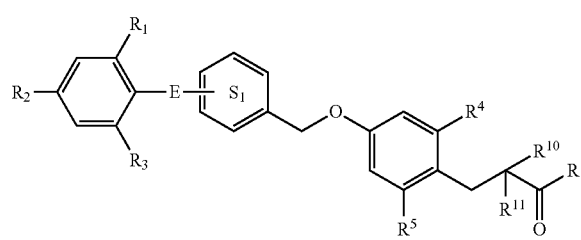

wherein each symbol is as described in patent document 11.

In addition, non-patent document 6 describes the following compound.

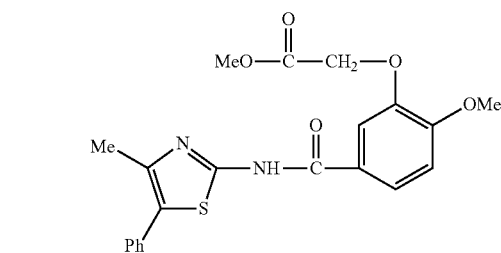 [SMILES: COC(=O)COc1cc(C(=O)Nc2nc(C)c(-c3ccccc3)s2)ccc1OC]

In addition, non-patent document 7 describes the following compound.

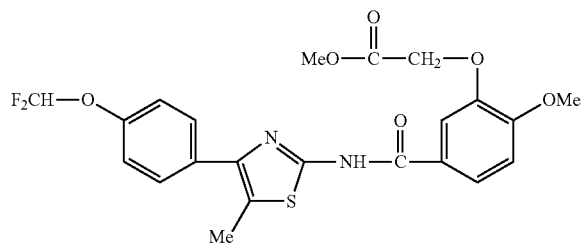

In addition, non-patent document 8 describes the following compound.

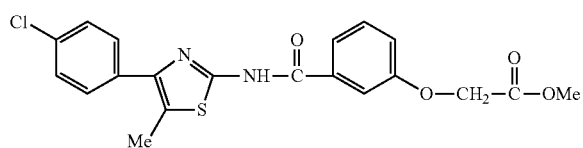 [SMILES: COC(=O)COc1cccc(C(=O)Nc2nc(-c3ccc(Cl)cc3)c(C)s2)c1]

However, no documents specifically disclose the compound of the present application.

DOCUMENT LIST

Patent Documents patent document 1: WO2009/048527
patent document 2: WO2006/059245
patent document 3: JP2003-238538
patent document 4: WO2002/088084
patent document 5: JP08-333287
patent document 6: EP442448
patent document 7: U.S. Pat. No. 5,011,851
patent document 8: EP434034
patent document 9: U.S. Pat. No. 5,187,188
patent document 10: WO2004/041266
patent document 11: WO2005/063729

Non-Patent Documents non-patent document 1: Bioorganic & Medicinal Chemistry 2007, 15(21), p. 6692-6704
non-patent document 2: Journal of Medicinal Chemistry 1992, 35(19), p. 3483-3497
non-patent document 3: Molecular Pharmacology 2002, 62(5), p. 1103-1111
non-patent document 4: Journal of Medicinal Chemistry, 1992, 35(19), p. 3498-3512
non-patent document 5: Journal of Medicinal Chemistry, 1993, 36(24), p. 3871-3883
non-patent document 6: CAS registry No. 1302489-36-6
non-patent document 7: CAS registry No. 1299978-57-6
non-patent document 8: CAS registry No. 1297860-03-7

SUMMARY OF THE INVENTION

Problems to be Solved by the Invention

The present invention aims to provide a novel aromatic ring compound having a GPR40 agonist activity, and useful as an agent for the prophylaxis or treatment of diabetes and the like.

Means of Solving the Problems

The present inventors have conducted various intensive studies and found that the compound represented by the following formula (I) unexpectedly has a superior GPR40 agonist activity, is superior in the property as a pharmaceutical product such as stability and the like, and particularly shows high solubility, low toxicity, good pharmacokinetics such as sustainability in blood and the like, and therefore, provides a safe and useful medicament to be an agent for the prophylaxis or treatment of mammalian GPR40 receptor-related pathology or disease. Based on these findings, they have completed the present invention.

Accordingly, the present invention relates to
[1] a compound represented by the formula (I):

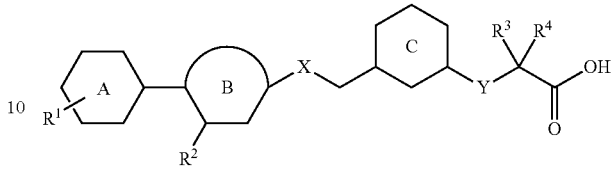

wherein ring A is an optionally further substituted 6-membered aromatic ring;
ring B is an optionally further substituted 5- or 6-membered aromatic ring;
ring C is an optionally further substituted 6-membered aromatic ring;
X is —$NR^{5A}$—, —$CR^{5B}R^{5C}$—, —O—, —CO—, or —$S(O)_m$—;
Y is —$NR^{6A}$—, —$CR^{6B}R^{6C}$—, —O—, or —$S(O)_n$—;
$R^1$ and $R^2$ are each independently a substituent;
$R^3$ and $R^4$ are each independently a hydrogen atom or a substituent;
$R^{5A}$ is a hydrogen atom, a $C_{1-6}$ alkyl group optionally substituted by a halogen atom, a $C_{1-6}$ alkyl-carbonyl group optionally substituted by a halogen atom, or a $C_{3-7}$ cycloalkyl group optionally substituted by a halogen atom;
$R^{5B}$ is a hydrogen atom or a substituent;
$R^{5C}$ is a substituent;
$R^{6A}$, $R^{6B}$ and $R^{6C}$ are each independently a hydrogen atom, an optionally substituted $C_{1-6}$ alkyl group, an optionally substituted $C_{2-6}$ alkenyl group, an optionally substituted $C_{2-6}$ alkynyl group, or an optionally substituted $C_{3-7}$ cycloalkyl group; and
m and n are each independently 0, 1 or 2,
or a salt thereof (hereinafter sometimes to be abbreviated as compound (I));
[2] the compound of [1], wherein ring A is a benzene ring or a pyridine ring, each of which is optionally further substituted by 1 to 3 halogen atoms or 1 to 3 $C_{1-6}$ alkoxy groups, or a salt thereof;
[3] the compound of [1] or [2], wherein ring B is a benzene ring or a pyridine ring, or a salt thereof;
[4] the compound of [1], [2] or [3], wherein ring C is a benzene ring, a pyridine ring or a pyrimidine ring, or a salt thereof;
[5] the compound of [1], [2], [3] or [4], wherein X is —NH—, —N(methyl)-, —N(trifluoroethyl)-, —N(acetyl)-, —CHF—, —O—, —S—, —S(O)— or —$S(O)_2$—, or a salt thereof;
[6] the compound of [1], [2], [3], [4] or [5], wherein Y is —$CR^{6B}R^{6C}$— or —O— [$R^{6B}$ and $R^{6C}$ are each independently (1) a $C_{3-7}$ cycloalkyl group optionally substituted by 1 to 3 substituents selected from a halogen atom and cyano, (2) a hydrogen atom, (3) a $C_{1-6}$ alkyl group optionally substituted by 1 to 3 substituents selected from a halogen atom, a $C_{3-7}$ cycloalkyl group, cyano, carboxyl, a $C_{1-6}$ alkoxy-carbonyl group and a carbamoyl group, (4) a $C_{2-6}$ alkenyl group optionally substituted by a halogen atom, or (5) a $C_{2-6}$ alkynyl group optionally substituted by 1 to 3 substituents selected from a halogen atom and a $C_{3-7}$ cycloalkyl group], or a salt thereof;
[7] the compound of [1], [2], [3], [4], [5] or [6], wherein $R^1$ is (1) a $C_{1-6}$ alkoxy group optionally substituted by a halogen atom, (2) a $C_{1-8}$ alkyl group, (3) hydroxy, (4) carboxyl, (5) a $C_{1-6}$ alkyl-sulfonyl-amino group, (6) a 5- to 10-membered non-aromatic heterocyclyl-oxy group, (7) a 5- to 10-membered non-aromatic heterocyclyl-sulfonyl group, or (8) cyano, or a salt thereof;

[8] the compound of [1], [2], [3], [4], [6] or [7], wherein $R^2$ is (1) a $C_{1-13}$ alkyl group optionally substituted by 1 to 3 substituents selected from (i) a halogen atom, (ii) hydroxy, (iii) cyano, (iv) a $C_{1-6}$ alkoxy group optionally substituted by a $C_{1-6}$ alkoxy group, and (v) a $C_{3-7}$ cycloalkyl group, (2) hydroxy, (3) a $C_{1-6}$ alkoxy group, (4) a $C_{6-14}$ aryl group optionally substituted by a $C_{1-6}$ alkyl group optionally substituted by 1 to 3 halogen atoms, or (5) a heterocyclic group optionally substituted by 1 to 3 substituents selected from cyano and a $C_{1-6}$ alkyl group, or a salt thereof;

[9] the compound of [1], [2], [3], [4], [5], [6], [7] or [8], wherein $R^3$ and $R^4$ are both hydrogen atoms, or a salt thereof;

[10] 3-cyclopropyl-3-(3-(((2-(2,2-dimethylpropyl)-2'-fluoro-5'-methoxybiphenyl-4-yl)oxy)methyl)phenyl)propanoic acid or a salt thereof;

[11] 3-cyclopropyl-3-(3-(((6-(2,2-dimethylpropyl)-5-(2-fluoro-5-methoxyphenyl)pyridin-2-yl)oxy)methyl)phenyl)propanoic acid or a salt thereof;

[12] 3-cyclopentyl-3-(3-(((2-(2,2-dimethylpropyl)-2'-fluoro-5'-methoxybiphenyl-4-yl)oxy)methyl)phenyl)propanoic acid or a salt thereof;

[13] a medicament comprising the compound of [1] or a salt thereof;

[14] the medicament of [13], which is a GPR40 receptor function modulator;

[15] the medicament of [13], which is a prophylactic or therapeutic agent for diabetes;

[16] a method for the prophylaxis or treatment of diabetes in a mammal, comprising administering an effective amount of the compound of [1] or a salt thereof to the mammal;

[17] a method of modulating a GPR40 receptor function in a mammal, comprising administering an effective amount of the compound of [1] or a salt thereof to the mammal;

[18] use of the compound of [1] or a salt thereof in the production of an agent for the prophylaxis or treatment of diabetes;

[19] the compound of [1] or a salt thereof for use in the prophylaxis or treatment of diabetes; and the like.

Effect of the Invention

Since compound (I) has a superior GPR40 agonist activity, is superior in the property as a pharmaceutical product such as stability and the like, and particularly shows high solubility, low toxicity, good kinetics such as sustainability in blood and the like, it can provide a safe and useful agent for the prophylaxis or treatment of mammalian GPR40 receptor-related pathology or disease.

DETAILED DESCRIPTION OF THE INVENTION

The present invention is explained in detail in the following.

Unless otherwise specified, examples of the "halogen atom" in the present specification include a fluorine atom, a chlorine atom, a bromine atom, and an iodine atom.

Unless otherwise specified, examples of the "optionally substituted hydrocarbon group" in the present specification include "optionally substituted $C_{1-13}$ (preferably $C_{1-8}$, more preferably $C_{1-6}$)alkyl group", "optionally substituted $C_{2-6}$ alkenyl group", "optionally substituted $C_{2-6}$ alkynyl group", "optionally substituted $C_{3-7}$ cycloalkyl group", "optionally substituted $C_{6-14}$ aryl group", "optionally substituted $C_{7-16}$ aralkyl group" and the like.

Unless otherwise specified, examples of the "$C_{1-13}$ alkyl group" in the present specification include methyl, ethyl, propyl, isopropyl, butyl, isobutyl, sec-butyl, tert-butyl, pentyl, isopentyl, neopentyl, hexyl, neohexyl, heptyl, 4,4-dimethylpentyl, octyl and the like. Unless otherwise specified, examples of the "$C_{1-8}$ alkyl group" and "$C_{1-6}$ alkyl group" in the present specification include $C_{1-8}$ and a $C_{1-6}$ alkyl groups, respectively, from among the above-mentioned "$C_{1-13}$ alkyl group".

Unless otherwise specified, examples of the "$C_{2-6}$ alkenyl group" in the present specification include vinyl, propenyl, isopropenyl, 2-buten-1-yl, 3-buten-1-yl, 4-penten-1-yl, 5-hexen-1-yl and the like.

Unless otherwise specified, examples of the "$C_{2-6}$ alkynyl group" in the present specification include 2-butyn-1-yl, 4-pentyn-1-yl, 5-hexyn-1-yl and the like.

Unless otherwise specified, examples of the "$C_{3-7}$ cycloalkyl group" in the present specification include cyclopropyl, cyclobutyl, cyclopentyl, cyclohexyl, cycloheptyl and the like.

Unless otherwise specified, examples of the "$C_{6-14}$ aryl group" in the present specification include phenyl, 1-naphthyl, 2-naphthyl, 2-biphenylyl, 3-biphenylyl, 4-biphenylyl, 2-anthryl and the like. The $C_{6-14}$ aryl group may be partially saturated, and examples of the partially saturated $C_{6-14}$ aryl group include tetrahydronaphthyl and the like.

Unless otherwise specified, examples of the "$C_{7-16}$ aralkyl group" in the present specification include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, 4-biphenylylmethyl and the like.

Unless otherwise specified, examples of the "optionally substituted hydroxy" in the present specification include "hydroxy", "optionally substituted $C_{1-6}$ alkoxy group", "optionally substituted heterocyclyl-oxy group", "optionally substituted $C_{6-14}$ aryloxy group", "optionally substituted $C_{7-16}$ aralkyloxy group" and the like.

Unless otherwise specified, examples of the "$C_{1-6}$ alkoxy group" in the present specification include methoxy, ethoxy, propoxy, isopropoxy, butoxy, isobutoxy, tert-butoxy, pentyloxy, neopentyloxy, hexyloxy and the like.

Unless otherwise specified, examples of the "$C_{1-6}$ alkoxy-$C_{1-6}$ alkoxy group" in the present specification include methoxymethoxy, methoxyethoxy, ethoxymethoxy, ethoxyethoxy and the like.

Unless otherwise specified, examples of the "heterocyclyl-oxy group" in the present specification include hydroxy substituted by a "heterocyclic group" to be mentioned below. Preferable examples of the heterocyclyl-oxy group include tetrahydropyranyloxy, thiazolyloxy, pyridyloxy, pyrazolyloxy, oxazolyloxy, thienyloxy, furyloxy and the like.

Unless otherwise specified, examples of the "$C_{6-14}$ aryloxy group" in the present specification include phenoxy, 1-naphthyloxy, 2-naphthyloxy and the like.

Unless otherwise specified, examples of the "$C_{7-16}$ aralkyloxy group" in the present specification include benzyloxy, phenethyloxy and the like.

Unless otherwise specified, examples of the "optionally substituted mercapto" in the present specification include "mercapto", "optionally substituted $C_{1-6}$ alkylthio group", "optionally substituted heterocyclyl-thio group", "optionally substituted $C_{6-14}$ arylthio group", "optionally substituted $C_{7-16}$ aralkylthio group" and the like.

Unless otherwise specified, examples of the "C$_{1-6}$ alkylthio group" in the present specification include methylthio, ethylthio, propylthio, isopropylthio, butylthio, sec-butylthio, tert-butylthio and the like.

Unless otherwise specified, examples of the "heterocyclylthio group" in the present specification include mercapto substituted by a "heterocyclic group" to be mentioned below. Preferable examples of the heterocylyl-thio group include tetrahydropyranylthio, thiazolylthio, pyridylthio, pyrazolylthio, oxazolylthio, thienylthio, furylthio and the like.

Unless otherwise specified, examples of the "C$_{6-14}$ arylthio group" in the present specification include phenylthio, 1-naphthylthio, 2-naphthylthio and the like.

Unless otherwise specified, examples of the "C$_{7-16}$ aralkylthio group" in the present specification include benzylthio, phenethylthio and the like.

Unless otherwise specified, examples of the "heterocyclic group" in the present specification include a 5- to 14-membered (monocyclic, bicyclic or tricyclic) heterocyclic group containing, as a ring-constituting atom besides carbon atom, one or two kinds of 1 to 4 hetero atoms selected from a nitrogen atom, a sulfur atom and an oxygen atom, preferably (i) a 5- to 14-membered (preferably 5- to 10-membered) aromatic heterocyclic group, (ii) a 5- to 10-membered non-aromatic heterocyclic group and the like. Among these, a 5- or 6-membered aromatic heterocyclic group is preferable. Specific examples thereof include aromatic heterocyclic groups such as thienyl (e.g., 2-thienyl, 3-thienyl), furyl (e.g., 2-furyl, 3-furyl), pyridyl (e.g., 2-pyridyl, 3-pyridyl, 4-pyridyl), thiazolyl (e.g., 2-thiazolyl, 4-thiazolyl, 5-thiazolyl), oxazolyl (e.g., 2-oxazolyl, 4-oxazolyl, 5-oxazolyl), pyrazinyl, pyrimidinyl (e.g., 2-pyrimidinyl, 4-pyrimidinyl), pyrrolyl (e.g., 1-pyrrolyl, 2-pyrrolyl, 3-pyrrolyl), imidazolyl (e.g., 1-imidazolyl, 2-imidazolyl, 4-imidazolyl), pyrazolyl (e.g., 1-pyrazolyl, 3-pyrazolyl, 4-pyrazolyl), triazolyl (e.g., 1-triazolyl, 2-triazolyl), tetrazolyl, pyridazinyl (e.g., 3-pyridazinyl, 4-pyridazinyl), isothiazolyl (e.g., 3-isothiazolyl, 4-isothiazolyl, 5-isothiazolyl), isoxazolyl (e.g., 3-isoxazolyl, 4-isoxazolyl, 5-isoxazolyl), oxadiazolyl (e.g., 1,3,4-oxadiazol-2-yl), thiadiazolyl (e.g., 1,3,4-thiadiazol-2-yl), indolyl (e.g., 1-indolyl, 2-indolyl, 3-indolyl), 2-benzothiazolyl, 2-benzoxazolyl, benzimidazolyl (e.g., 1-benzimidazolyl, 2-benzimidazolyl), benzo[b]thienyl (e.g., 2-benzo[b]thienyl, 3-benzo[b]thienyl), benzo[b]furanyl (e.g., 2-benzo[b]furanyl, 3-benzo[b]furanyl), quinolyl (e.g., 2-quinolyl, 3-quinolyl, 4-quinolyl, 5-quinolyl, 8-quinolyl), isoquinolyl (e.g., 1-isoquinolyl, 3-isoquinolyl, 4-isoquinolyl, 5-isoquinolyl) and the like;

non-aromatic heterocyclic groups such as pyrrolidinyl (e.g., 1-pyrrolidinyl, 2-pyrrolidinyl, 3-pyrrolidinyl), oxazolidinyl (e.g., 2-oxazolidinyl), imidazolinyl (e.g., 1-imidazolinyl, 2-imidazolinyl, 4-imidazolinyl), piperidinyl (e.g., piperidino, 2-piperidinyl, 3-piperidinyl, 4-piperidinyl), piperazinyl (e.g., 1-piperazinyl, 2-piperazinyl), morpholinyl (e.g., 2-morpholinyl, 3-morpholinyl, morpholino), thiomorpholinyl (e.g., 2-thiomorpholinyl, 3-thiomorpholinyl, thiomorpholino), tetrahydrofuryl, tetrahydropyranyl, and the like, and the like.

Unless otherwise specified, examples of the "5- or 6-membered aromatic ring" in the present specification include a benzene ring and a 5- or 6-membered aromatic heterocycle constituting a 5- or 6-membered aromatic heterocyclic group in the above-mentioned "5- to 14-membered (preferably 5- to 10-membered) aromatic heterocyclic group" and the like. Specific examples thereof include a benzene ring, a pyrrole ring, a pyrazole ring, an imidazole ring, a triazole ring (a 1,2,3-triazole ring, a 1,2,4-triazole ring, a 1,3,4-triazole ring), a tetrazole ring, an oxazole ring, an isoxazole ring, a thiazole ring, an isothiazole ring, an oxadiazole ring, a thiadiazole ring, a furan ring, a thiophene ring, a pyridine ring, a pyridazine ring, a pyrimidine ring, a pyrazine ring, a triazine ring and the like.

Unless otherwise specified, examples of the "6-membered aromatic ring" in the present specification include a benzene ring and a 6-membered aromatic heterocycle constituting a 6-membered aromatic heterocyclic group in the above-mentioned "5- to 14-membered (preferably 5- to 10-membered) aromatic heterocyclic group" and the like. Specific examples thereof include a benzene ring, a pyridine ring, a pyridazine ring, a pyrimidine ring, a pyrazine ring, a triazine ring and the like.

Unless otherwise specified, examples of the "C$_{1-6}$ alkyl-carbonyl group" in the present specification include acetyl, isobutanoyl, isopentanoyl and the like.

Unless otherwise specified, examples of the "C$_{1-6}$ alkoxy-carbonyl group" in the present specification include methoxycarbonyl, ethoxycarbonyl, propoxycarbonyl, tert-butoxycarbonyl and the like.

Unless otherwise specified, examples of the "C$_{3-7}$ cycloalkyl-carbonyl group" in the present specification include cyclopentylcarbonyl, cyclohexylcarbonyl and the like.

Unless otherwise specified, examples of the "C$_{6-14}$ aryl-carbonyl group" in the present specification include benzoyl, 1-naphthoyl, 2-naphthoyl and the like.

Unless otherwise specified, examples of the "C$_{7-16}$ aralkyl-carbonyl group" in the present specification include phenylacetyl, 2-phenylpropanoyl and the like.

Unless otherwise specified, examples of the "C$_{6-14}$ aryloxy-carbonyl group" in the present specification include phenoxycarbonyl, naphthyloxycarbonyl and the like.

Unless otherwise specified, examples of the "C$_{7-16}$ aralkyloxy-carbonyl group" in the present specification include benzyloxycarbonyl, phenethyloxycarbonyl and the like.

Unless otherwise specified, examples of the "nitrogen-containing heterocyclyl-carbonyl group" in the present specification include pyrrolidinylcarbonyl, piperidinocarbonyl and the like.

Unless otherwise specified, examples of the "C$_{1-6}$ alkylsulfonyl group" in the present specification include methylsulfonyl, ethylsulfonyl and the like.

Unless otherwise specified, examples of the "C$_{6-14}$ arylsulfonyl group" in the present specification include phenylsulfonyl, 1-naphthylsulfonyl, 2-naphthylsulfonyl and the like.

Unless otherwise specified, examples of the "C$_{1-6}$ alkylsulfinyl group" in the present specification include methylsulfinyl, ethylsulfinyl and the like.

Unless otherwise specified, examples of the "C$_{6-14}$ arylsulfinyl group" in the present specification include phenylsulfinyl, 1-naphthylsulfinyl, 2-naphthylsulfinyl and the like.

Unless otherwise specified, examples of the "optionally esterified carboxyl" in the present specification include carboxyl, C$_{1-6}$ alkoxy-carbonyl group, C$_{6-14}$ aryloxy-carbonyl group, C$_{7-16}$ aralkyloxy-carbonyl group and the like.

Unless otherwise specified, examples of the "C$_{1-6}$ alkyl group optionally substituted by a halogen atom" in the present specification include the above-mentioned "C$_{1-6}$ alkyl group" optionally substituted by the above-mentioned 1 to 5 "halogen atoms". When substituted by plural halogen atoms, respective halogen atoms may be the same or different. For example, methyl, ethyl, propyl, isopropyl, butyl, tert-butyl, isobutyl, trifluoromethyl, trifluoroethyl and the like can be mentioned.

Unless otherwise specified, examples of the "C$_{3-7}$ cycloalkyl group optionally substituted by a halogen atom" in the present specification include the above-mentioned "$C_{3-7}$ cycloalkyl group" optionally substituted by 1 to 5 "halogen atoms" mentioned above. When substituted by plural halogen atoms, respective halogen atoms may be the same or different. For example, cyclopropyl, cyclobutyl, cyclopentyl, cyclohexyl, fluorocyclopropyl, difluorocyclopropyl, fluorocyclobutyl, difluorocyclobutyl and the like can be mentioned.

Unless otherwise specified, examples of the "$C_{1-6}$ alkoxy group optionally substituted by a halogen atom" in the present specification include the above-mentioned "$C_{1-6}$ alkoxy group" optionally substituted by 1 to 5 "halogen atoms" mentioned above. When substituted by plural halogen atoms, respective halogen atoms may be the same or different. For example, methoxy, ethoxy, isopropoxy, tert-butoxy, trifluoromethoxy and the like can be mentioned.

Unless otherwise specified, examples of the "$C_{1-6}$ alkyl-carbonyl group optionally substituted by a halogen atom" in the present specification include the above-mentioned "$C_{1-6}$ alkyl-carbonyl group" optionally substituted by 1 to 5 "halogen atoms" mentioned above. When substituted by plural halogen atoms, respective halogen atoms may be the same or different. For example, acetyl, isobutanoyl, isopentanoyl, fluoroacetyl and the like can be mentioned.

Unless otherwise specified, examples of the "mono- or di-$C_{1-6}$ alkyl-amino group" in the present specification include amino mono- or di-substituted by the above-mentioned "$C_{1-6}$ alkyl group". For example, methylamino, ethylamino, propylamino, dimethylamino, diethylamino and the like can be mentioned.

Unless otherwise specified, examples of the "mono- or di-$C_{6-14}$ aryl-amino group" in the present specification include amino mono- or di-substituted by the above-mentioned "$C_{6-14}$ aryl group". For example, phenylamino, diphenylamino, 1-naphthylamino, 2-naphthylamino and the like can be mentioned.

Unless otherwise specified, examples of the "mono- or di-$C_{7-16}$ aralkyl-amino group" in the present specification include amino mono- or di-substituted by the above-mentioned "$C_{7-16}$ aralkyl group". For example, benzylamino, phenethylamino and the like can be mentioned.

Unless otherwise specified, examples of the "N—$C_{1-6}$ alkyl-N—$C_{6-14}$ aryl-amino group" in the present specification include amino substituted the above-mentioned "$C_{1-6}$ alkyl group" and the above-mentioned "$C_{6-14}$ aryl group". For example, N-methyl-N-phenylamino, N-ethyl-N-phenylamino and the like can be mentioned.

Unless otherwise specified, examples of the "N—$C_{1-6}$ alkyl-N—$C_{7-16}$ aralkyl-amino group" in the present specification include amino substituted by the above-mentioned "$C_{1-6}$ alkyl group" and the above-mentioned "$C_{7-16}$ aralkyl group". For example, N-methyl-N-benzylamino, N-ethyl-N-benzylamino and the like can be mentioned.

Unless otherwise specified, examples of the "mono- or di-$C_{1-6}$ alkyl-carbamoyl group" in the present specification include carbamoyl mono- or di-substituted by the above-mentioned "$C_{1-6}$ alkyl group". For example, methylcarbamoyl, ethylcarbamoyl, dimethylcarbamoyl, diethylcarbamoyl, ethylmethylcarbamoyl and the like can be mentioned.

Unless otherwise specified, examples of the "mono- or di-$C_{6-14}$ aryl-carbamoyl group" in the present specification include carbamoyl mono- or di-substituted by the above-mentioned "$C_{6-14}$ aryl group". For example, phenylcarbamoyl, 1-naphthylcarbamoyl, 2-naphthylcarbamoyl and the like can be mentioned.

Unless otherwise specified, examples of the "mono- or di-$C_{3-7}$ cycloalkyl-carbamoyl group" in the present specification include carbamoyl mono- or di-substituted by the above-mentioned "$C_{3-7}$ cycloalkyl group". For example, cyclopropylcarbamoyl and the like can be mentioned.

Unless otherwise specified, examples of the "mono- or di-$C_{7-16}$ aralkyl-carbamoyl group" in the present specification include carbamoyl mono- or di-substituted by the above-mentioned "$C_{7-16}$ aralkyl group". For example, benzylcarbamoyl and the like can be mentioned.

Unless otherwise specified, examples of the "mono- or di-5- to 7-membered heterocyclyl-carbamoyl group" in the present specification include carbamoyl mono- or di-substituted by a 5- to 7-membered heterocyclic group. Here, as the 5- to 7-membered heterocyclic group, a heterocyclic group containing, as a ring-constituting atom besides carbon atom, one or two kinds of 1 to 4 hetero atoms selected from a nitrogen atom, a sulfur atom and an oxygen atom can be mentioned. Preferable examples of the "mono- or di-5- to 7-membered heterocyclyl-carbamoyl group" include 2-pyridylcarbamoyl, 3-pyridylcarbamoyl, 4-pyridylcarbamoyl, 2-thienylcarbamoyl, 3-thienylcarbamoyl and the like.

Unless otherwise specified, as the "mono- or di-$C_{1-6}$ alkyl-sulfamoyl group" in the present specification, sulfamoyl mono- or di-substituted by the above-mentioned "$C_{1-6}$ alkyl group" is used and, for example, methylsulfamoyl, ethylsulfamoyl, dimethylsulfamoyl, diethylsulfamoyl and the like can be mentioned.

Unless otherwise specified, as the "mono- or di-$C_{6-14}$ aryl-sulfamoyl group" in the present specification, sulfamoyl mono- or di-substituted by the above-mentioned "$C_{6-14}$ aryl group" is used and, for example, phenylsulfamoyl, diphenylsulfamoyl, 1-naphthylsulfamoyl, 2-naphthylsulfamoyl and the like can be mentioned.

Unless otherwise specified, examples of the "mono- or di-$C_{7-16}$ aralkyl-sulfamoyl group" in the present specification include sulfamoyl mono- or di-substituted by the above-mentioned "$C_{7-16}$ aralkyl group". For example, benzylsulfamoyl and the like can be mentioned.

Unless otherwise specified, examples of the "optionally substituted $C_{1-13}$ (preferably $C_{1-8}$, more preferably $C_{1-6}$) alkyl group", "optionally substituted $C_{2-6}$ alkenyl group", "optionally substituted $C_{2-6}$ alkynyl group", "optionally substituted $C_{1-6}$ alkoxy group" and "optionally substituted $C_{1-6}$ alkylthio group" in the present specification include "$C_{1-13}$ (preferably $C_{1-8}$, more preferably $C_{1-6}$) alkyl group", "$C_{2-6}$ alkenyl group", "$C_{2-6}$ alkynyl group", "$C_{1-6}$ alkoxy group" and "$C_{1-6}$ alkylthio group" optionally having, at each substitutable position, 1 to 5 substituents selected from (1) a halogen atom;
(2) hydroxy;
(3) amino;
(4) nitro;
(5) cyano;
(6) a heterocyclic group (preferably furyl, pyridyl, thienyl, pyrazolyl, thiazolyl, oxazolyl) optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(7) mono- or di-$C_{1-6}$ alkyl-amino;
(8) mono- or di-$C_{6-14}$ aryl-amino;
(9) mono- or di-$C_{7-16}$ aralkyl-amino;
(10) N—$C_{1-6}$ alkyl-N—$C_{6-14}$ aryl-amino;

(11) N—$C_{1-6}$ alkyl-N—$C_{7-16}$ aralkyl-amino;
(12) $C_{3-7}$ cycloalkyl;
(13) $C_{1-6}$ alkoxy optionally substituted by a halogen atom;
(14) $C_{1-6}$ alkylthio;
(15) $C_{1-6}$ alkylsulfinyl;
(16) $C_{1-6}$ alkylsulfonyl;
(17) optionally esterified carboxyl;
(18) $C_{1-6}$ alkyl-carbonyl;
(19) $C_{3-7}$ cycloalkyl-carbonyl;
(20) $C_{6-14}$ aryl-carbonyl;
(21) carbamoyl;
(22) thiocarbamoyl;
(23) mono- or di-$C_{1-6}$ alkyl-carbamoyl;
(24) mono- or di-$C_{6-14}$ aryl-carbamoyl;
(25) mono- or di-5- to 7-membered heterocyclyl-carbamoyl;
(26) $C_{1-6}$ alkyl-carbonylamino (e.g., acetylamino, propionylamino) optionally substituted by carboxyl;
(27) $C_{6-14}$ aryloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or alkyl-sulfamoyl and mono- or di-$C_{6-14}$ aryl-sulfamoyl;
(28) $C_{6-14}$ aryl optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(29) heterocyclyl-oxy;
(30) sulfamoyl;
(31) mono- or di-$C_{1-6}$ alkyl-sulfamoyl;
(32) mono- or di-$C_{6-14}$ aryl-sulfamoyl;
(33) $C_{7-16}$ aralkyloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
and the like. When plural substituents are present, the respective substituents may be the same or different.

In the present specification, examples of the "optionally substituted $C_{3-7}$ cycloalkyl group", "optionally substituted $C_{6-14}$ aryl group", "optionally substituted $C_{7-16}$ aralkyl group", "optionally substituted heterocyclic group", "optionally substituted heterocyclyl-oxy group", "optionally substituted $C_{6-14}$ aryloxy group", "optionally substituted $C_{7-16}$ aralkyloxy group", "optionally substituted heterocyclyl-thio group", "optionally substituted $C_{6-14}$ arylthio group" and "optionally substituted $C_{7-16}$ aralkylthio group" include "$C_{3-7}$ cycloalkyl group", "$C_{6-14}$ aryl group", "$C_{7-16}$ aralkyl group", "heterocyclic group", "heterocyclyl-oxy group", "$C_{6-14}$ aryloxy group", "$C_{7-16}$ aralkyloxy group", "heterocyclyl-thio group", "$C_{6-14}$ arylthio group" and "$C_{7-16}$ aralkylthio group" optionally having, at each substitutable position, 1 to 5 substituents selected from
(1) a halogen atom;
(2) hydroxy;
(3) amino;
(4) nitro;
(5) cyano;
(6) optionally substituted $C_{1-8}$ alkyl (preferably, methyl, isobutyl, neopentyl, neohexyl, 4,4-dimethylpentyl);
(7) optionally substituted $C_{2-6}$ alkenyl;
(8) optionally substituted $C_{2-6}$ alkynyl;
(9) $C_{6-14}$ aryl (preferably, phenyl) optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(10) $C_{6-14}$ aryloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or alkyl-sulfamoyl and mono- or di-$C_{6-14}$ aryl-sulfamoyl;
(11) $C_{7-16}$ aralkyloxy optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or di-$C_{1-6}$ alkyl-sulfamoyl and mono- or di-$C_{6-14}$ aryl-sulfamoyl;
(12) a heterocyclic group (preferably, tetrahydropyranyl, furyl, pyridyl, thienyl, pyrazolyl, thiazolyl, oxazolyl, oxadiazolyl, thiadiazolyl) optionally substituted by 1 to 3 substituents selected from a halogen atom, hydroxy, amino, nitro, cyano, $C_{1-6}$ alkyl optionally substituted by a halogen atom, mono- or di-$C_{1-6}$ alkyl-amino, $C_{6-14}$ aryl, mono- or di-$C_{6-14}$ aryl-amino, $C_{3-7}$ cycloalkyl, $C_{1-6}$ alkoxy, $C_{1-6}$ alkoxy-$C_{1-6}$ alkoxy, $C_{1-6}$ alkylthio, $C_{1-6}$ alkylsulfinyl, $C_{1-6}$ alkylsulfonyl, optionally esterified carboxyl, carbamoyl, thiocarbamoyl, mono- or di-$C_{1-6}$ alkyl-carbamoyl, mono- or di-$C_{6-14}$ aryl-carbamoyl, sulfamoyl, mono- or alkyl-sulfamoyl and mono- or di-$C_{6-14}$ aryl-sulfamoyl;
(13) mono- or di-$C_{1-6}$ alkyl-amino;
(14) mono- or di-$C_{6-14}$ aryl-amino;
(15) mono- or di-$C_{7-16}$ aralkyl-amino;
(16) N—$C_{1-6}$ alkyl-N—$C_{6-14}$ aryl-amino;
(17) N—$C_{1-6}$ alkyl-N—$C_{7-16}$ aralkyl-amino;
(18) $C_{3-7}$ cycloalkyl;
(19) optionally substituted $C_{1-6}$ alkoxy (preferably, neopentyloxy);
(20) optionally substituted $C_{1-6}$ alkylthio;
(21) $C_{1-6}$ alkylsulfinyl;
(22) $C_{1-6}$ alkylsulfonyl;
(23) optionally esterified carboxyl;

(24) $C_{1-6}$ alkyl-carbonyl;
(25) $C_{3-7}$ cycloalkyl-carbonyl;
(26) $C_{6-14}$ aryl-carbonyl;
(27) carbamoyl;
(28) thiocarbamoyl;
(29) mono- or di-$C_{1-6}$ alkyl-carbamoyl;
(30) mono- or di-$C_{6-14}$ aryl-carbamoyl;
(31) mono- or di-5- to 7-membered heterocyclyl-carbamoyl;
(32) sulfamoyl;
(33) mono- or di-$C_{1-6}$ alkyl-sulfamoyl;
(34) mono- or di-$C_{6-14}$ aryl-sulfamoyl;
(35) $C_{1-6}$ alkyl-carbonylamino (e.g., acetylamino, propionylamino) optionally substituted by carboxy;
(36) heterocyclyl-oxy;
and the like. When plural substituents are present, the respective substituents may be the same or different.

Unless otherwise specified, examples of the "optionally substituted amino" in the present specification include amino optionally substituted by 1 or 2 substituents selected from
(1) optionally substituted $C_{1-6}$ alkyl;
(2) optionally substituted $C_{2-6}$ alkenyl;
(3) optionally substituted $C_{2-6}$ alkynyl;
(4) optionally substituted $C_{3-7}$ cycloalkyl;
(5) optionally substituted $C_{6-14}$ aryl;
(6) optionally substituted $C_{1-6}$ alkoxy;
(7) optionally substituted acyl;
(8) an optionally substituted heterocyclic group (preferably furyl, pyridyl, thienyl, pyrazolyl, thiazolyl, oxazolyl);
(9) sulfamoyl;
(10) mono- or di-$C_{1-6}$ alkyl-sulfamoyl;
(11) mono- or di-$C_{6-14}$ aryl-sulfamoyl;
and the like. When the "optionally substituted amino" is amino substituted by two substituents, these substituents may be the same or different, or these substituents may form, together with the adjacent nitrogen atom, a nitrogen-containing heterocycle. Examples of the "nitrogen-containing heterocycle" include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

Unless otherwise specified, examples of the "optionally substituted acyl" in the present specification include groups represented by the formulas: —$COR^7$, —CO—$OR^7$, —$SO_2R^7$, —$SOR^7$, —$PO(OR^7)(OR^8)$, —CO—$NR^{7a}R^{8a}$ and —CS—$NR^{7a}R^{8a}$ wherein $R^7$ and $R^8$ are the same or different and each is a hydrogen atom, an optionally substituted hydrocarbon group or an optionally substituted heterocyclic group, $R^{7a}$ and $R^{8a}$ are the same or different and each is a hydrogen atom, an optionally substituted hydrocarbon group or an optionally substituted heterocyclic group, or $R^{7a}$ and $R^{8a}$ may form, together with the adjacent nitrogen atom, an optionally substituted nitrogen-containing heterocycle] and the like.

Examples of the "nitrogen-containing heterocycle" of the "optionally substituted nitrogen-containing heterocycle" formed by $R^{7a}$ and $R^{8a}$ together with the adjacent nitrogen atom include a 5- to 7-membered nitrogen-containing heterocycle containing, as a ring-constituting atom besides carbon atoms, at least one nitrogen atom and optionally further containing one or two hetero atoms selected from an oxygen atom, a sulfur atom and a nitrogen atom. Preferable examples of the nitrogen-containing heterocycle include pyrrolidine, imidazolidine, pyrazolidine, piperidine, piperazine, morpholine, thiomorpholine, thiazolidine, oxazolidine and the like.

The nitrogen-containing heterocycle optionally has 1 or 2 substituents at substitutable position(s). Examples of such substituent include hydroxy, $C_{1-6}$ alkyl optionally substituted by a halogen atom, $C_{6-14}$ aryl, $C_{7-16}$ aralkyl and the like. When the number of the substituents is 2, the respective substituents may be the same or different.

Preferable examples of the "optionally substituted acyl" include
formyl;
carboxyl;
carbamoyl;
$C_{1-6}$ alkyl-carbonyl;
$C_{1-6}$ alkoxy-carbonyl;
$C_{3-7}$ cycloalkyl-carbonyl;
$C_{6-14}$ aryl-carbonyl;
$C_{7-16}$ aralkyl-carbonyl;
$C_{6-14}$ aryloxy-carbonyl;
$C_{7-16}$ aralkyloxy-carbonyl;
mono- or di-$C_{1-6}$ alkyl-carbamoyl;
mono- or di-$C_{6-14}$ aryl-carbamoyl;
mono- or di-$C_{3-7}$ cycloalkyl-carbamoyl;
mono- or di-$C_{7-16}$ aralkyl-carbamoyl;
$C_{1-6}$ alkylsulfonyl;
$C_{6-14}$ arylsulfonyl optionally substituted by nitro;
nitrogen-containing heterocyclyl-carbonyl;
$C_{1-6}$ alkylsulfinyl;
$C_{6-14}$ arylsulfinyl;
thiocarbamoyl;
sulfamoyl;
mono- or di-$C_{1-6}$ alkyl-sulfamoyl;
mono- or di-$C_{6-14}$ aryl-sulfamoyl;
mono- or di-$C_{7-16}$ aralkyl-sulfamoyl;
and the like.

The definition of each symbol in the formula (I) is described in detail in the following.

Ring A is an optionally further substituted 6-membered aromatic ring.

As the "6-membered aromatic ring" of the "optionally further substituted 6-membered aromatic ring" for ring A, a benzene ring, a pyridine ring, a pyridazine ring, a pyrimidine ring, a pyrazine ring, a triazine ring and the like can be mentioned. Preferred is a benzene ring, a pyridine ring or a pyrimidine ring, and more preferred is a benzene ring or a pyridine ring.

The "6-membered aromatic ring" of the "optionally further substituted 6-membered aromatic ring" for ring A is more preferably a benzene ring.

The "6-membered aromatic ring" is optionally further substituted by 1-4 (preferably 1-3, more preferably 1 or 2) substituents other than $R^1$ and ring B(—$R^2$)—X—$CH_2$—, at substitutable position(s).

Examples of such substituent include
(1) a $C_{3-10}$ cycloalkyl group (e.g., cyclopropyl, cyclohexyl);
(2) a $C_{6-14}$ aryl group (e.g., phenyl, naphthyl) optionally substituted by 1 to 3 substituents selected from
  (a) a $C_{1-6}$ alkyl group optionally further substituted by 1 to 3 halogen atoms,
  (b) a hydroxy group,
  (c) a $C_{1-6}$ alkoxy group optionally substituted by 1 to 3 halogen atoms, and
  (d) a halogen atom;
(3) an aromatic heterocyclic group (e.g., thienyl, furyl, pyridyl, pyrazolyl, imidazolyl, tetrazolyl, oxazolyl, thiazolyl, oxadiazolyl, thiadiazolyl) optionally substituted by 1 to 3 substituents selected from (a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms, and
(d) a halogen atom;
(4) a non-aromatic heterocyclic group (e.g., tetrahydrofuryl, tetrahydropyranyl, morpholinyl, thiomorpholinyl, piperidinyl, pyrrolidinyl, piperazinyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group optionally substituted by 1 to 3 halogen atoms,
(d) a halogen atom, and
(e) an oxo group;
(5) an amino group optionally mono- or di-substituted by substituent(s) selected from
(a) a $C_{1-6}$ alkyl group optionally substituted by 1 to 3 halogen atoms,
(b) a $C_{1-6}$ alkyl-carbonyl group optionally substituted by 1 to 3 halogen atoms,
(c) a $C_{1-6}$ alkoxy-carbonyl group optionally substituted by 1 to 3 halogen atoms,
(d) a $C_{1-6}$ alkylsulfonyl group (e.g., methylsulfonyl) optionally substituted by 1 to 3 halogen atoms,
(e) a carbamoyl group optionally mono- or di-substituted by a $C_{1-6}$ alkyl group optionally substituted by 1 to 3 halogen atoms, and
(f) an aromatic heterocyclic group (e.g., thienyl, furyl, pyridyl, pyrazolyl, imidazolyl, tetrazolyl, oxazolyl, thiazolyl, oxadiazolyl, thiadiazolyl);
(6) a $C_{1-6}$ alkyl-carbonyl group optionally substituted by 1 to 3 halogen atoms;
(7) a $C_{1-6}$ alkoxy-carbonyl group optionally substituted by 1 to 3 substituents selected from
(a) a halogen atom,
(b) a $C_{1-6}$ alkoxy group,
(c) a $C_{6-14}$ aryl group (e.g., phenyl), and
(d) a heterocyclic group (e.g., tetrahydrofuryl);
(8) a $C_{1-6}$ alkylsulfonyl group (e.g., methylsulfonyl, ethylsulfonyl, isopropylsulfonyl) optionally substituted by 1 to 3 halogen atoms;
(9) a carbamoyl group optionally mono- or di-substituted by a $C_{1-6}$ alkyl group optionally substituted by 1 to 3 halogen atoms;
(10) a thiocarbamoyl group optionally mono- or di-substituted by a $C_{1-6}$ alkyl group optionally substituted by 1 to 3 halogen atoms;
(11) a sulfamoyl group optionally mono- or di-substituted by a $C_{1-6}$ alkyl group optionally substituted by 1 to 3 halogen atoms;
(12) a carboxy group;
(13) a hydroxy group;
(14) a $C_{1-6}$ alkoxy group (e.g., methoxy, neopentyloxy) optionally substituted by 1 to 3 substituents selected from
(a) a halogen atom,
(b) a carboxy group,
(c) a $C_{1-6}$ alkoxy group,
(d) a $C_{1-6}$ alkoxy-carbonyl group optionally substituted by 1 to 3 $C_{6-14}$ aryl groups (e.g., phenyl),
(e) an amino group optionally mono- or di-substituted by substituent(s) selected from a $C_{1-6}$ alkyl group and a $C_{1-6}$ alkoxy-carbonyl group,
(f) a heterocyclic group (e.g., tetrahydrofuryl), and
(g) a $C_{3-10}$ cycloalkyl group;
(15) a $C_{2-6}$ alkenyloxy group (e.g., ethenyloxy) optionally substituted by 1 to 3 halogen atoms;
(16) a $C_{7-13}$ aralkyloxy group (e.g., benzyloxy);
(17) a $C_{6-14}$ aryloxy group (e.g., phenyloxy, naphthyloxy);
(18) a $C_{1-6}$ alkyl-carbonyloxy group (e.g., acetyloxy, tert-butylcarbonyloxy);
(19) a $C_{6-14}$ aryl-carbonyl group (e.g., benzoyl) optionally substituted by 1 to 3 substituents selected from
(a) a halogen atom, and
(b) a $C_{1-6}$ alkyl group optionally substituted by 1 to 3 halogen atoms;
(20) a non-aromatic heterocyclylcarbonyl group (e.g., pyrrolidinylcarbonyl, morpholinylcarbonyl) optionally substituted by 1 to 3 substituents selected from a $C_{1-6}$ alkyl group optionally substituted by 1 to 3 halogen atoms;
(21) a mercapto group;
(22) a $C_{1-6}$ alkylthio group (e.g., methylthio, ethylthio) optionally substituted by 1 to 3 substituents selected from
(a) a halogen atom, and
(b) a $C_{1-6}$ alkoxy-carbonyl group;
(23) a $C_{7-13}$ aralkylthio group (e.g., benzylthio);
(24) a $C_{6-14}$ arylthio group (e.g., phenylthio, naphthylthio);
(25) a cyano group;
(26) a nitro group;
(27) a halogen atom (e.g., fluorine atom);
(28) a $C_{1-3}$ alkylenedioxy group;
(29) a $C_{1-3}$ alkyleneoxy group (e.g., methyleneoxy, ethyleneoxy);
(30) aromatic heterocyclylcarbonyl group (e.g., pyrazolylcarbonyl, pyrazinylcarbonyl, isoxazolylcarbonyl, pyridylcarbonyl, thiazolylcarbonyl) optionally substituted by 1 to 3 substituents selected from a $C_{1-6}$ alkyl group optionally substituted by 1 to 3 halogen atoms;
(31) a $C_{3-10}$ cycloalkoxy group (e.g., cyclopropoxy, cyclopentyloxy) optionally substituted by 1 to 3 substituents selected from
(a) a halogen atom (e.g., fluorine atom), and
(b) a $C_{1-6}$ alkoxy group (e.g., methoxy);
(32) a $C_{1-8}$ alkyl group (e.g., methyl, ethyl, propyl, butyl, isobutyl, neopentyl, neohexyl, 4,4-dimethylpentyl) optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by a $C_{1-6}$ alkyl group;
(33) a $C_{2-6}$ alkenyl group (e.g., ethenyl, 1-propenyl) optionally substituted by 1 to 3 substituents selected from
(a) a halogen atom,
(b) a carboxy group,
(c) a hydroxy group,
(d) a $C_{1-6}$ alkoxy-carbonyl group,
(e) a $C_{1-6}$ alkoxy group, and
(f) an amino group optionally mono- or di-substituted by a $C_{1-6}$ alkyl group;
(34) a $C_{7-13}$ aralkyl group (e.g., benzyl) optionally substituted by 1 to 3 substituents selected from
(a) a $C_{1-6}$ alkyl group optionally substituted by 1 to 3 halogen atoms,
(b) a hydroxy group,
(c) a $C_{1-6}$ alkoxy group, and
(d) a halogen atom;
and the like. When the number of the substituents is two or more, the respective substituents may be the same or different.

The substituent is preferably a halogen atom (e.g., fluorine atom), a $C_{1-6}$ alkyl group and the like, more preferably a halogen atom (e.g., fluorine atom).

In another embodiment of the present invention, the substituent is preferably a halogen atom (e.g., fluorine atom) or a $C_{1-6}$ alkoxy group (e.g., methoxy).

Ring A is preferably a benzene ring, a pyridine ring or a pyrimidine ring, each of which is optionally further substituted, more preferably, a benzene ring or a pyridine ring, each of which is optionally further substituted by 1 to 3 halogen atoms (e.g., fluorine atom) or 1 to 3 $C_{1-6}$ alkoxy groups (e.g., methoxy).

Ring A is more preferably a benzene ring optionally further substituted by 1 to 3 halogen atoms (e.g., fluorine atom), or an (unsubstituted) pyridine ring.

Ring A is particularly preferably a benzene ring optionally further substituted by 1 to 3 halogen atoms (e.g., fluorine atom).

Ring B is an optionally further substituted 5-membered or 6-membered aromatic ring.

As the "5-membered or 6-membered aromatic ring" of the "optionally further substituted 5-membered or 6-membered aromatic ring" for ring B, a benzene ring, a pyridine ring, a pyridazine ring, a pyrimidine ring, a pyrazine ring, a triazine ring and the like can be mentioned. Preferred is a benzene ring or a pyridine ring.

The "5-membered or 6-membered aromatic ring" is optionally further substituted by 1-3 (preferably 1 or 2, more preferably 1) substituents other than $R^2$, $R^1$-ring A, X—$CH_2$-ring C—, at substitutable position(s).

Examples of such substituent include those similar to the substituents that the "6-membered aromatic ring" of the "optionally further substituted 6-membered aromatic ring" for ring A optionally has. When the number of the substituents is two or more, the respective substituents may be the same or different. The substituent is preferably a halogen atom (e.g., fluorine atom).

Ring B is preferably a benzene ring or a pyridine ring, each of which is optionally further substituted, more preferably, a benzene ring or a pyridine ring, each of which is optionally further substituted by 1 to 3 halogen atoms (e.g., fluorine atom).

Ring B is more preferably a benzene ring or a pyridine ring.

In another embodiment of the present invention, ring B is preferably a pyridine ring.

Ring C is an optionally further substituted 6-membered aromatic ring.

As the "6-membered aromatic ring" of the "optionally further substituted 6-membered aromatic ring" for ring C, a benzene ring, a pyridine ring, a pyrimidine ring, a pyridazine ring, a pyrazine ring, a triazine ring and the like can be mentioned. Preferred is a benzene ring, a pyridine ring or a pyrimidine ring.

The "6-membered aromatic ring" of the "optionally further substituted 6-membered aromatic ring" for ring C is more preferably a benzene ring.

The "6-membered aromatic ring" is optionally further substituted by 1-4 (preferably 1-3, more preferably 1 or 2) substituents other than -ring B—X—$CH_2$ and Y—$CR^3R^4$—CO—OH, at substitutable position(s).

Examples of such substituent include those similar to the substituents that the "6-membered aromatic ring" of the "optionally further substituted 6-membered aromatic ring" for ring A optionally has. When the number of the substituents is two or more, the respective substituents may be the same or different. The substituent is preferably a halogen atom (e.g., fluorine atom), a $C_{1-6}$ alkyl group (e.g., methyl) optionally substituted by a halogen atom, or a $C_{1-6}$ alkoxy group (e.g., methoxy) optionally substituted by a halogen atom, more preferably, a halogen atom (e.g., fluorine atom), methyl or methoxy.

Ring C is preferably a benzene ring, a pyridine ring or a pyrimidine ring, each of which is optionally further substituted, more preferably, a benzene ring, a pyridine ring or a pyrimidine ring each of which is optionally further substituted by a halogen atom (e.g., fluorine atom), a $C_{1-6}$ alkyl group (e.g., methyl) optionally substituted by a halogen atom or a $C_{1-6}$ alkoxy group (e.g., methoxy) optionally substituted by a halogen atom, further preferably, a benzene ring, a pyridine ring or a pyrimidine ring.

Ring C is particularly preferably a benzene ring.

X is —$NR^{5A}$—, —$CR^{5B}R^{5C}$—, —O—, —CO—, or —$S(O)_m$— wherein $R^{5A}$ is a hydrogen atom, a $C_{1-6}$ alkyl group optionally substituted by a halogen atom, a $C_{1-6}$ alkyl-carbonyl group optionally substituted by a halogen atom, or a $C_{3-7}$ cycloalkyl group optionally substituted by a halogen atom; $R^{5B}$ is a hydrogen atom or a substituent; $R^{5C}$ is a substituent; and m is 0, 1 or 2.

The "$C_{1-6}$ alkyl group" of the "$C_{1-6}$ alkyl group optionally substituted by a halogen atom" for $R^{5A}$ is preferably methyl, ethyl, propyl, isopropyl, butyl, isobutyl, sec-butyl, tert-butyl and the like, more preferably methyl or ethyl.

The "$C_{1-6}$ alkyl-carbonyl group" of the "$C_{1-6}$ alkyl-carbonyl group optionally substituted by a halogen atom" for $R^{5A}$ is preferably acetyl, propanoyl, butanoyl and the like, more preferably acetyl.

The "$C_{3-7}$ cycloalkyl group" of the "$C_{3-7}$ cycloalkyl group optionally substituted by a halogen atom" for $R^{5A}$ is preferably cyclopropyl, cyclobutyl, cyclopentyl, cyclohexyl or the like.

$R^{5A}$ is preferably a hydrogen atom, a $C_{1-6}$ alkyl group (e.g., methyl, ethyl) optionally substituted by 1 to 3 halogen atoms (e.g., fluorine atom), or a $C_{1-6}$ alkyl-carbonyl group (e.g., acetyl), more preferably, a hydrogen atom, methyl, trifluoroethyl or acetyl.

Examples of the "substituent" for $R^{5B}$ or $R^{5C}$ include "halogen atom", "optionally substituted hydrocarbon group", "optionally substituted heterocyclic group", "optionally substituted hydroxy", "optionally substituted amino", "optionally substituted mercapto", "optionally substituted acyl" and the like, preferably, a halogen atom (e.g., fluorine atom).

$R^{5B}$ is preferably a hydrogen atom.

$R^{5C}$ is preferably a halogen atom (e.g., fluorine atom), more preferably, a fluorine atom.

X is specifically —NH—, —N(methyl)-, —N(trifluoroethyl)-, —N (acetyl)-, —CHF—, —O—, —S—, —S(O)— or —$S(O)_2$—.

X is preferably —O—.

Y is —$NR^{6A}$—, —$CR^{6B}R^{6C}$—, —O— or —$S(O)_n$— wherein $R^{6A}$, $R^{6B}$ and $R^{6C}$ are each independently a hydrogen atom, an optionally substituted $C_{1-6}$ alkyl group, an optionally substituted $C_{2-6}$ alkenyl group, an optionally substituted $C_{2-6}$ alkynyl group, or an optionally substituted $C_{3-7}$ cycloalkyl group; and n is 0, 1 or 2.

The "$C_{1-6}$ alkyl group" of the "optionally substituted $C_{1-6}$ alkyl group" for $R^{6A}$, $R^{6B}$ or $R^{6C}$" is preferably methyl, ethyl, n-propyl or isopropyl.

The "$C_{2-6}$ alkenyl group" of the "optionally substituted $C_{2-6}$ alkenyl group" for $R^{6A}$, $R^{6B}$ or $R^{6C}$" is preferably 3-buten-1-yl.

The "$C_{2-6}$ alkynyl group" of the "optionally substituted $C_{2-6}$ alkynyl group" for $R^{6A}$, $R^{6B}$ or $R^{6C}$" is preferably ethynyl or 1-propynyl.

The "$C_{3-7}$ cycloalkyl group" of the "optionally substituted $C_{3-7}$ cycloalkyl group" for $R^{6A}$, $R^{6B}$ or $R^{6C}$" is preferably cyclopropyl, cyclobutyl, cyclopentyl or cyclohexyl.

$R^{6A}$ is preferably a methyl group.

$R^{6B}$ is (1) a hydrogen atom, (2) a $C_{1-6}$ alkyl group (e.g., methyl, ethyl, n-propyl, isopropyl) optionally substituted by 1 to 3 substituents selected from a halogen atom (e.g., fluorine atom), a $C_{3-7}$ cycloalkyl group, cyano, carboxyl, a $C_{1-6}$ alkoxy-carbonyl group (e.g., ethoxycarbonyl) and a carbamoyl group, (3) a $C_{2-6}$ alkenyl group (e.g., ethenyl, 3-buten-1-yl) optionally substituted by a halogen atom, (4) a $C_{2-6}$ alkynyl group (e.g., ethynyl, 1-propynyl) optionally substituted by 1 to 3 substituents selected from a halogen atom and a $C_{3-7}$ cycloalkyl group (e.g., cyclopropyl), or (5) a $C_{3-7}$ cycloalkyl group (e.g., cyclopropyl, cyclobutyl, cyclopentyl, cyclohexyl) optionally substituted by 1 to 3 substituents selected from a halogen atom and cyano, preferably, a hydrogen atom.

$R^{6C}$ is (1) a hydrogen atom, (2) a $C_{1-6}$ alkyl group (e.g., methyl, ethyl, n-propyl, isopropyl) optionally substituted by 1 to 3 substituents selected from a halogen atom (e.g., fluorine atom), a $C_{3-7}$ cycloalkyl group, cyano, carboxyl, a $C_{1-6}$ alkoxy-carbonyl group (e.g., ethoxycarbonyl) and a carbamoyl group, (3) a $C_{2-6}$ alkenyl group (e.g., ethenyl, 3-buten-1-yl) optionally substituted by a halogen atom, (4) a $C_{2-6}$ alkynyl group (e.g., ethynyl, 1-propynyl) optionally substituted by 1 to 3 substituents selected from a halogen atom and a $C_{3-7}$ cycloalkyl group (e.g., cyclopropyl), or (5) a $C_{3-7}$ cycloalkyl group (e.g., cyclopropyl, cyclobutyl, cyclopentyl, cyclohexyl) optionally substituted by 1 to 3 substituents selected from a halogen atom and cyano, preferably, a hydrogen atom, a $C_{2-6}$ alkenyl group (e.g., 3-buten-1-yl) optionally substituted by a halogen atom, or a $C_{3-7}$ cycloalkyl group (e.g., cyclopropyl, cyclobutyl, cyclopentyl, cyclohexyl) optionally substituted by 1 to 3 substituents selected from a halogen atom and cyano, more preferably, a hydrogen atom, 3-buten-1-yl, cyclopropyl, cyclobutyl, cyclopentyl or cyclohexyl.

$R^{6C}$ is more preferably cyclopropyl or cyclopentyl.

Y is specifically —CH$_2$—, —CH(3-buten-1-yl)-, —CH(cyclopropyl)-, —CH(cyclobutyl)-, —CH(cyclopentyl)-, —CH(cyclohexyl)- or —O—.

In another embodiment of the present invention, Y is preferably —CR$^{6B}$R$^{6C}$— or —O— wherein R$^{6B}$ and R$^{6C}$ are each independently (1) a $C_{3-7}$ cycloalkyl group (e.g., cyclopropyl, cyclobutyl, cyclopentyl, cyclohexyl) optionally substituted by 1 to 3 substituents selected from a halogen atom and cyano, (2) a hydrogen atom, (3) a $C_{1-6}$ alkyl group (e.g., methyl, ethyl, n-propyl, isopropyl) optionally substituted by 1 to 3 substituents selected from a halogen atom (e.g., fluorine atom), a $C_{3-7}$ cycloalkyl group, cyano, carboxyl, a $C_{1-6}$ alkoxy-carbonyl group (e.g., ethoxycarbonyl) and a carbamoyl group, (4) a $C_{2-6}$ alkenyl group (e.g., ethenyl, 3-buten-1-yl) optionally substituted by a halogen atom, or (5) a $C_{2-6}$ alkynyl group (e.g., ethynyl, 1-propynyl) optionally substituted by 1 to 3 substituents selected from a halogen atom and a $C_{3-7}$ cycloalkyl group (e.g., cyclopropyl), more preferably, —CR$^{6B}$R$^{6C}$— wherein one of R$^{6B}$ and R$^{6C}$ is a hydrogen atom and the other is (1) a hydrogen atom, (2) a $C_{1-6}$ alkyl group (e.g., methyl, ethyl, n-propyl, isopropyl) optionally substituted by 1 to 3 substituents selected from a halogen atom (e.g., fluorine atom), a $C_{3-7}$ cycloalkyl group, cyano, carboxyl, a $C_{1-6}$ alkoxy-carbonyl group (e.g., ethoxycarbonyl) and a carbamoyl group, (3) a $C_{2-6}$ alkenyl group (e.g., ethenyl, 3-buten-1-yl) optionally substituted by a halogen atom, (4) a $C_{2-6}$ alkynyl group (e.g., ethynyl, 1-propynyl) optionally substituted by 1 to 3 substituents selected from a halogen atom and a $C_{3-7}$ cycloalkyl group (e.g., cyclopropyl), or (5) a $C_{3-7}$ cycloalkyl group (e.g., cyclopropyl, cyclobutyl, cyclopentyl, cyclohexyl) optionally substituted by 1 to 3 substituents selected from a halogen atom and cyano] or —O—.

Y is more preferably —CR$^{6B}$R$^{6C}$— wherein one of R$^{6B}$ and R$^{6C}$ is a hydrogen atom and the other is a $C_{3-7}$ cycloalkyl group (e.g., cyclopropyl, cyclobutyl, cyclopentyl, cyclohexyl) optionally substituted by 1 to 3 substituents selected from a halogen atom and cyano.

$R^1$ is a substituent.

Examples of the substituent for $R^1$ include "halogen atom", "optionally substituted hydrocarbon group", "optionally substituted heterocyclic group", "optionally substituted hydroxy", "optionally substituted amino", "optionally substituted mercapto", "optionally substituted acyl", "cyano" and the like, preferably, (1) a $C_{1-8}$ alkyl group (e.g., methyl, 4,4-dimethylpentyl) optionally substituted by a halogen atom (e.g., fluorine atom), (2) hydroxy, (3) a $C_{1-6}$ alkoxy group (e.g., methoxy, ethoxy, isopropoxy, pentyloxy) optionally substituted by a halogen atom (e.g., fluorine atom), (4) a 5- to 10-membered non-aromatic heterocyclyl-oxy group (e.g., tetrahydropyranyloxy), (5) a $C_{1-6}$ alkyl-sulfonyl-amino group (e.g., methylsulfonylamino), (6) carboxyl, (7) a 5- to 10-membered non-aromatic heterocyclyl-sulfonyl group (e.g., morpholinylsulfonyl), or (8) cyano.

$R^1$ is more preferably (1) a $C_{1-6}$ alkoxy group (e.g., methoxy, ethoxy, isopropoxy, pentyloxy) optionally substituted by a halogen atom (e.g., fluorine atom), (2) a $C_{1-8}$ alkyl group (e.g., methyl, 4,4-dimethylpentyl), (3) hydroxy, (4) carboxyl, (5) a $C_{1-6}$ alkyl-sulfonyl-amino group (e.g., methylsulfonylamino), (6) a 5- to 10-membered non-aromatic heterocyclyl-oxy group (e.g., tetrahydropyranyloxy), (7) a 5- to 10-membered non-aromatic heterocyclyl-sulfonyl group (e.g., morpholinylsulfonyl), or (8) cyano.

$R^1$ is more preferably an optionally substituted $C_{1-6}$ alkoxy group (e.g., methoxy, ethoxy, isopropoxy, pentoxy).

$R^1$ is particularly preferably a $C_{1-6}$ alkoxy group (e.g., methoxy).

$R^2$ is a substituent.

Examples of the substituent for $R^2$ include "halogen atom", "optionally substituted hydrocarbon group", "optionally substituted heterocyclic group", "optionally substituted hydroxy", "optionally substituted amino", "optionally substituted mercapto", "optionally substituted acyl" and the like, preferably, hydroxy, an optionally substituted $C_{1-13}$ alkyl group, an optionally substituted $C_{1-6}$ alkoxy group, an optionally substituted $C_{6-14}$ aryl group, and an optionally substituted heterocyclic group.

$R^2$ is more preferably (1) hydroxy, (2) a $C_{1-13}$ alkyl group (e.g., methyl, isobutyl, isopentyl, neopentyl, neohexyl, 2,2-dimethylbutyl, 2,2-dimethylpentyl, 4,4-dimethylpentyl, 2-methyl-2-ethylbutyl, 2,2-diethylbutyl) optionally substituted by 1 to 3 substituents selected from (i) a halogen atom (e.g., fluorine atom), (ii) hydroxy, (iii) cyano, (iv) a $C_{1-6}$ alkoxy group (e.g., methoxy, ethoxy, neopentyloxy) optionally substituted by a $C_{1-6}$ alkoxy group (e.g., methoxy) and (v) a $C_{3-7}$ cycloalkyl group (e.g., cyclopropyl, cyclobutyl, cyclopentyl, cyclohexyl) optionally substituted by cyano or a $C_{1-13}$ alkyl group, (3) a $C_{1-6}$ alkoxy group (e.g., isobutoxy, tert-butoxy, neopentyloxy), (4) a $C_{6-14}$ aryl group (e.g., phenyl) optionally substituted by a $C_{1-6}$ alkyl group (e.g., methyl) optionally substituted by 1 to 3 halogen atoms (e.g., fluorine atom), or (5) a heterocyclic group (e.g., tetrahydropyranyl, thienyl, pyrazolyl, thiazolyl, oxadiazolyl, thiadiazolyl) optionally substituted by 1 to 3 substituents selected from cyano and a $C_{1-6}$ alkyl group (e.g., methyl, tert-butyl).

$R^2$ is further preferably (1) a $C_{1-13}$ alkyl group (e.g., methyl, isobutyl, isopentyl, neopentyl, neohexyl, 2,2-dimethylbutyl, 2,2-dimethylpentyl, 4,4-dimethylpentyl, 2-methyl- 2-ethylbutyl, 2,2-diethylbutyl) optionally substituted by 1 to 3 substituents selected from (i) a halogen atom (e.g., fluorine atom), (ii) hydroxy, (iii) cyano, (iv) a $C_{1-6}$ alkoxy group (e.g., methoxy, ethoxy, neopentyloxy) optionally substituted by a $C_{1-6}$ alkoxy group (e.g., methoxy) and (v) a $C_{3-7}$ cycloalkyl group (e.g., cyclopropyl, cyclobutyl, cyclopentyl, cyclohexyl), (2) hydroxy, (3) a $C_{1-6}$ alkoxy group (e.g., isobutoxy, tert-butoxy, neopentyloxy), (4) a $C_{6-14}$ aryl group (e.g., phenyl) optionally substituted by a $C_{1-6}$ alkyl group (e.g., methyl) optionally substituted by 1 to 3 halogen atoms (e.g., fluorine atom), or (5) a heterocyclic group (e.g., tetrahydropyranyl, thienyl, pyrazolyl, thiazolyl, oxadiazolyl, thiadiazolyl) optionally substituted by 1 to 3 substituents selected from cyano and a $C_{1-6}$ alkyl group (e.g., methyl, tert-butyl).

$R^2$ is further more preferably (1) hydroxy, (2) a $C_{1-8}$ alkyl group (e.g., methyl, isobutyl, neopentyl, neohexyl, 4,4-dimethylpentyl) optionally substituted by 1 to 3 substituents selected from cyano, a $C_{1-6}$ alkoxy group (e.g., methoxy) and a $C_{3-7}$ cycloalkyl group (e.g., cyclopentyl), (3) a $C_{1-6}$ alkoxy group (e.g., isobutoxy, neopentyloxy), (4) a $C_{6-14}$ aryl group (e.g., phenyl) optionally substituted by 1 to 3 $C_{1-6}$ alkyl groups (e.g., methyl) optionally substituted by 1 to 3 halogen atoms (e.g., fluorine atom), or (5) a heterocyclic group (e.g., tetrahydropyranyl, thienyl, pyrazolyl, thiazolyl, oxadiazolyl, thiadiazolyl) optionally substituted by 1 to 3 substituents selected from cyano and a $C_{1-6}$ alkyl group (e.g., methyl, tert-butyl).

$R^2$ is particularly preferably (1) hydroxy, (2) methyl, isobutyl, neopentyl, neohexyl, or 4,4-dimethylpentyl, each of which is optionally substituted by 1 to 3 substituents selected from cyano, methoxy and cyclopentyl, (3) neopentyloxy, (4) phenyl optionally substituted by 1 to 3 methyl optionally substituted by 1 to 3 fluorine atoms, or (5) tetrahydropyranyl, thienyl, pyrazolyl, thiazolyl, oxadiazolyl, or thiadiazolyl, each of which is optionally substituted by 1 to 3 substituents selected from cyano, methyl and tert-butyl.

In another embodiment of the present invention, $R^2$ is preferably a $C_{1-6}$ alkyl group (e.g., neopentyl).

$R^3$ and $R^4$ are each independently a hydrogen atom or a substituent.

Examples of the substituent for $R^3$ or $R^4$ include "halogen atom", "optionally substituted hydrocarbon group", "optionally substituted heterocyclic group", "optionally substituted hydroxy", "optionally substituted amino", "optionally substituted mercapto", "optionally substituted acyl" and the like.

Both $R^3$ and $R^4$ are preferably hydrogen atoms.

Preferable examples of compound (I) include the following compounds.

[Compound I-1]
Compound (I) wherein
ring A is a benzene ring or a pyridine ring, each of which is optionally further substituted;
ring B is a benzene ring or a pyridine ring, each of which is optionally further substituted;
ring C is a benzene ring, a pyridine ring or a pyrimidine ring, each of which is optionally further substituted;
X is —$NR^{5A}$—, —$CR^{5B}R^{5C}$—, —O— or —$S(O)_m$— wherein $R^{5A}$ is a hydrogen atom, a $C_{1-6}$ alkyl group (e.g., methyl, ethyl) optionally substituted by a halogen atom (e.g., fluorine atom), a $C_{1-6}$ alkyl-carbonyl group (e.g., acetyl) optionally substituted by a halogen atom or a $C_{3-7}$ cycloalkyl group (e.g., cyclopropyl) optionally substituted by a halogen atom; $R^{5B}$ is a hydrogen atom or a halogen atom (e.g., fluorine atom); $R^{5C}$ is a hydrogen atom or a halogen atom (e.g., fluorine atom); and m is 0, 1 or 2;
Y is —$CR^{6B}R^{6C}$— or —O— wherein $R^{6B}$ and $R^{6C}$ are each independently a hydrogen atom, an optionally substituted $C_{1-6}$ alkyl group (e.g., methyl, ethyl, propyl), an optionally substituted $C_{2-6}$ alkenyl group (e.g., 3-buten-1-yl), an optionally substituted $C_{2-6}$ alkynyl group (e.g., 1-propynyl, ethynyl) or an optionally substituted $C_{3-7}$ cycloalkyl group (e.g., cyclopropyl, cyclobutyl, cyclopentyl, cyclohexyl));
$R^1$ is an optionally substituted $C_{1-6}$ alkyl group (e.g., methoxy);
$R^2$ is hydroxy, an optionally substituted $C_{1-13}$ alkyl group, an optionally substituted $C_{1-6}$ alkoxy group, an optionally substituted $C_{6-14}$ aryl group or an optionally substituted heterocyclic group; and
$R^3$ and $R^4$ are each independently a hydrogen atom.

[Compound I-2]
Compound (I) wherein
ring A is a benzene ring or a pyridine ring, each of which is optionally substituted 1 to 3 halogen atoms (e.g., fluorine atom);
ring B is a benzene ring or a pyridine ring optionally further substituted by a halogen atom (e.g., fluorine atom);
ring C is a benzene ring, a pyridine ring or a pyrimidine ring optionally further substituted by a halogen atom (e.g., fluorine atom), a $C_{1-6}$ alkyl group (e.g., methyl) optionally substituted by a halogen atom or a $C_{1-6}$ alkoxy group (e.g., methoxy) optionally substituted by a halogen atom;
X is —$NR^{5A}$—, —$CR^{5B}R^{5C}$—, —O— or —$S(O)_m$— wherein $R^{5A}$ is a hydrogen atom, a $C_{1-6}$ alkyl group (e.g., methyl, ethyl) optionally substituted by 1 to 3 halogen atoms (e.g., fluorine atom) or a $C_{1-6}$ alkyl-carbonyl group (e.g., acetyl) optionally substituted by 1 to 3 halogen atoms; $R^{5B}$ is a hydrogen atom or a halogen atom (e.g., fluorine atom); $R^{5C}$ is a hydrogen atom or a halogen atom (e.g., fluorine atom); and m is 0, 1 or 2;
Y is —$CR^{6B}R^{6C}$— or —O— wherein $R^{6B}$ and $R^{6C}$ are each independently a hydrogen atom, a $C_{2-6}$ alkenyl group (e.g., 3-buten-1-yl), a $C_{2-6}$ alkynyl group (e.g., 1-propynyl, ethynyl) or a $C_{3-7}$ cycloalkyl group (e.g., cyclopropyl, cyclobutyl, cyclopentyl, cyclohexyl) optionally substituted by 1 to 3 substituents selected from a halogen atom, cyano and methylsulfonyl);
$R^1$ is a $C_{1-6}$ alkoxy group (e.g., methoxy);
$R^2$ is (1) hydroxy, (2) a $C_{1-13}$ alkyl group (e.g., methyl, isobutyl, neopentyl, neohexyl, 4,4-dimethylpentyl) optionally substituted by 1 to 3 substituents selected from cyano, a $C_{1-6}$ alkoxy group (e.g., methoxy) and a $C_{3-7}$ cycloalkyl group (e.g., cyclopentyl), (3) a $C_{1-6}$ alkoxy group (e.g., neopentyloxy), (4) a $C_{6-14}$ aryl group (e.g., phenyl) optionally substituted by 1 to 3 $C_{1-6}$ alkyl groups (e.g., methyl) optionally substituted by 1 to 3 halogen atoms (e.g., fluorine atom), or (5) a 5- to 14-membered heterocyclic group (e.g., tetrahydropyranyl, thienyl, pyrazolyl, thiazolyl, oxadiazolyl, thiadiazolyl) optionally substituted by 1 to 3 substituents selected from cyano and a $C_{1-6}$ alkyl group (e.g., methyl, tert-butyl); and
both $R^3$ and $R^4$ are hydrogen atoms.

[Compound I-3]
Compound (I) wherein
ring A is a benzene ring substituted by 1 to 3 halogen atoms (e.g., fluorine atom) or a pyridine ring;
ring B is a benzene ring or a pyridine ring;
ring C is a benzene ring, a pyridine ring or a pyrimidine ring;
X is —$NR^{5A}$—, —$CR^{5B}R^{5C}$—, —O— or —$S(O)_m$— wherein $R^{5A}$ is a hydrogen atom, a $C_{1-6}$ alkyl group (e.g., methyl, ethyl) optionally substituted by 1 to 3 halogen atoms (e.g., fluorine atom) or a $C_{1-6}$ alkyl-carbonyl group (e.g., acetyl); $R^{5B}$ is a hydrogen atom; $R^{5C}$ is a halogen atom (e.g., fluorine atom); and m is 0, 1 or 2;

Y is —CR$^{6B}$R$^{6C}$— or —O— wherein R$^{6B}$ is a hydrogen atom; and R$^{6C}$ is a hydrogen atom, 3-buten-1-yl, cyclopropyl, cyclobutyl, cyclopentyl or cyclohexyl;

R$^1$ is a C$_{1-6}$ alkoxy group (e.g., methoxy);

R$^2$ is (1) hydroxy, (2) methyl, isobutyl, neopentyl, neohexyl or 4,4-dimethylpentyl, each of which is optionally substituted by 1 to 3 substituents selected from cyano, methoxy and cyclopentyl, (3) neopentyloxy, (4) phenyl optionally substituted by 1 to 3 methyl optionally substituted by 1 to 3 fluorine atoms, (5) tetrahydropyranyl, thienyl, pyrazolyl, thiazolyl, oxadiazolyl or thiadiazolyl optionally substituted by 1 to 3 substituents selected from cyano, methyl and tert-butyl; and both R$^3$ and R$^4$ are hydrogen atoms.

[Compound I-4]

Compound (I) wherein ring A is a benzene ring or a pyridine ring, each of which is optionally further substituted by 1 to 3 halogen atoms (e.g., fluorine atom) or a C$_{1-6}$ alkoxy group (e.g., methoxy);

ring B is a benzene ring or a pyridine ring;

ring C is a benzene ring, a pyridine ring or a pyrimidine ring;

X is —NH—, —N(methyl)-, —N(trifluoroethyl)-, —N(acetyl)-, —CHF—, —O—, —S—, —S(O)— or —S(O)$_2$—;

Y is —CR$^{6B}$R$^{6C}$— or —O— wherein R$^{6B}$ and R$^{6C}$ are each independently (1) a C$_{3-7}$ cycloalkyl group (e.g., cyclopropyl, cyclobutyl, cyclopentyl, cyclohexyl) optionally substituted by 1 to 3 substituents selected from a halogen atom and cyano, (2) a hydrogen atom, (3) a C$_{1-6}$ alkyl group (e.g., methyl, ethyl, n-propyl, isopropyl) optionally substituted by 1 to 3 substituents selected from a halogen atom (e.g., fluorine atom), a C$_{3-7}$ cycloalkyl group, cyano, carboxyl, a C$_{1-6}$ alkoxy-carbonyl group (e.g., ethoxycarbonyl) and a carbamoyl group, (4) a C$_{2-6}$ alkenyl group (e.g., ethenyl, 3-buten-1-yl) optionally substituted by a halogen atom, or (5) a C$_{2-6}$ alkynyl group (e.g., ethynyl, 1-propynyl) optionally substituted by 1 to 3 substituents selected from a halogen atom and a C$_{3-7}$ cycloalkyl group (e.g., cyclopropyl);

R$^1$ is (1) a C$_{1-6}$ alkoxy group (e.g., methoxy, ethoxy, isopropoxy, pentyloxy) optionally substituted by a halogen atom (e.g., fluorine atom), (2) a C$_{1-8}$ alkyl group (e.g., methyl, 4,4-dimethylpentyl), (3) hydroxy, (4) carboxyl, (5) a C$_{1-6}$ alkyl-sulfonyl-amino group (e.g., methylsulfonylamino), (6) a 5- to 10-membered non-aromatic heterocyclyl-oxy group (e.g., tetrahydropyranyloxy), (7) a 5- to 10-membered non-aromatic heterocyclyl-sulfonyl group (e.g., morpholinylsulfonyl), or (8) cyano;

R$^2$ is (1) a C$_{1-13}$ alkyl group (e.g., methyl, isobutyl, isopentyl, neopentyl, neohexyl, 2,2-dimethylbutyl, 2,2-dimethylpentyl, 4,4-dimethylpentyl, 2-methyl-2-ethylbutyl, 2,2-diethylbutyl) optionally substituted by 1 to 3 substituents selected from (i) a halogen atom (e.g., fluorine atom), (ii) hydroxy, (iii) cyano, (iv) a C$_{1-6}$ alkoxy group (e.g., methoxy, ethoxy, neopentyloxy) optionally substituted by a C$_{1-6}$ alkoxy group (e.g., methoxy) and (v) a C$_{3-7}$ cycloalkyl group (e.g., cyclopropyl, cyclobutyl, cyclopentyl, cyclohexyl), (2) hydroxy, (3) a C$_{1-6}$ alkoxy group (e.g., isobutoxy, tert-butoxy, neopentyloxy), (4) a C$_{6-14}$ aryl group (e.g., phenyl) optionally substituted by a C$_{1-6}$ alkyl group (e.g., methyl) optionally substituted by 1 to 3 halogen atoms (e.g., fluorine atom) or (5) a heterocyclic group (e.g., tetrahydropyranyl, thienyl, pyrazolyl, thiazolyl, oxadiazolyl, thiadiazolyl) optionally substituted by 1 to 3 substituents selected from cyano and a C$_{1-6}$ alkyl group (e.g., methyl, tert-butyl); and both R$^3$ and R$^4$ are hydrogen atoms.

Specific examples of compound (I) include the compounds of Examples 1-114, of which 3-cyclopropyl-3-(3-(((2-(2,2-dimethylpropyl)-2'-fluoro-5'-methoxybiphenyl-4-yl)oxy)methyl)phenyl)propanoic acid or a salt thereof (Example 5);

3-cyclopropyl-3-(3-(((6-(2,2-dimethylpropyl)-5-(2-fluoro-5-methoxyphenyl)pyridin-2-yl)oxy)methyl)phenyl) propanoic acid or a salt thereof (Example 6); or 3-cyclopentyl-3-(3-(((2-(2,2-dimethylpropyl)-2'-fluoro-5'-methoxybiphenyl-4-yl)oxy)methyl)phenyl)propanoic acid or a salt thereof (Example 39)

is preferable.

Examples of salts of compounds represented by the formula (I) include metal salt, ammonium salt, salt with organic base, salt with inorganic acid, salt with organic acid, salt with basic or acidic amino acid and the like.

Preferable examples of the metal salt include alkali metal salts such as sodium salt, potassium salt and the like; alkaline earth metal salts such as calcium salt, magnesium salt, barium salt and the like; aluminum salt and the like.

Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like.

Preferable examples of the salt with inorganic acid include salt with hydrochloric acid, hydrobromic acid, nitric acid, sulfuric acid, phosphoric acid and the like.

Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Among the above-mentioned salts, a pharmaceutically acceptable salt is preferable.

Compound (I) may be used as a prodrug.

A prodrug of the compound (I) means a compound which is converted to the compound (I) with a reaction due to an enzyme, an gastric acid, etc. under the physiological condition in the living body, that is, a compound which is converted to the compound (I) with enzymatic oxidation, reduction, hydrolysis and the like; a compound which is converted to the compound (I) by hydrolysis and the like due to gastric acid and the like.

A prodrug of the compound (I) may be a compound obtained by subjecting amino in the compound (I) to an acylation, alkylation or phosphorylation (e.g., a compound obtained by subjecting amino in the compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation); a compound obtained by subjecting hydroxy in the compound (I) to an acylation, alkylation, phosphorylation or boration (e.g., a compound obtained by subjecting hydroxy in the compound (I) to an acetylation, palmitoylation, propanoylation, pivaloylation, succinylation, fumarylation, alanylation or dimethylaminomethylcarbonylation); a compound obtained by subjecting carboxy in the compound (I) to an esterification or amidation (e.g., a compound obtained by subjecting carboxy in the compound (I) to C$_{1-6}$ alkyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation) and the like. Particularly, a compound (I) wherein carboxy is esterified by $C_{1-6}$ alkyl such as methyl, ethyl, tert-butyl and the like is preferably used. These compounds can be produced from the compound (I) according to a method known per se.

A prodrug of compound (I) may also be one which is converted to compound (I) under a physiological condition, such as those described in IYAKUHIN no KAIHATSU, Development of Pharmaceuticals, Vol. 7, Design of Molecules, p. 163-198, Published by HIROKAWA SHOTEN, 1990.

In the present specification, a prodrug may be in the form of a salt. Examples of the salt include those exemplified as the salt of the compound represented by the aforementioned formula (I).

The production method of compound (I) is explained below.

While a representative production method of compound (I) is described below as an exemplary production method, the production method is not limited thereto.

Compound (I) can be produced by a method known per se, for example, reaction schemes 1-8 shown below or a method analogous thereto. In each of the following reaction schemes, the starting material compound may be used in the form of a salt. As such salt, those exemplified as the salt of a compound represented by the formula (I) can be used.

When a specific production method is not described, the starting compound may be easily commercially available, or can also be produced according to a method known per se, or a method analogous thereto.

The resultant product obtained by each reaction can be used directly as the reaction mixture or as a crude product for the next reaction, or can be isolated from the reaction mixture according a conventional method, and can be purified according to separation means such as recrystallization, distillation, chromatography and HPLC and the like. When the resultant product is a mixture of stereoisomers, the mixture can be purified by separation means (e.g., diastereomer salt method, chromatography, HPLC or SFC (supercritical fluid chromatography) and the like), for example, the method described in Example or a method analogous thereto and the like.

When the reagents and reactants used in each reaction are commercially available, such commercially available products can also be used directly, or can also be produced by a method known per se or a method analogous thereto, or the method described in the Examples. For example, the reagents and reactants described in the Examples can be used.

Unless otherwise specified, the leaving group used in each reaction is, for example, a halogen atom, —OSO$_2$Me, —OSO$_2$(4-tolyl), —OSO$_2$CF$_3$ and the like.

Unless particularly indicated, the solvent in each reaction is not particularly limited as long as the reaction proceeds, and the reaction can be performed in a solvent inert to the reaction, or without solvent, and two or more kinds thereof may be mixed at an appropriately ratio and used. For example, the solvents described in the Examples can be used.

Unless particularly indicated, the equivalent amount of the reagents and reactants used in each reaction is 0.001 equivalent-100 equivalents relative to the substrate in each reaction. For example, equivalent amounts of the reagents and reactants described in the Examples can be used.

Unless particularly indicated, the reaction time of each reaction is generally 5 min-72 hr. For example, the reaction time described in the Examples can be employed.

Unless particularly indicated, the reaction temperature of each reaction is under ice-cooling to reflux under heating. For example, the reaction temperatures described in the Examples can be employed.

While the solvent used for the reaction in each of the following reaction schemes is not particularly limited as long as it does not inhibit the reaction and dissolves the starting material to a certain degree, for example, aromatic hydrocarbons such as benzene, toluene, xylene and the like; aliphatic hydrocarbons such as hexane, heptane, cyclohexane and the like; ethers such as diethyl ether, diisopropyl ether, tert-butyl methyl ether, tetrahydrofuran, dioxane, 1,2-dimethoxyethane, diphenyl ether and the like; ketones such as acetone, 2-butanone and the like; nitriles such as acetonitrile, propionitrile and the like; esters such as ethyl acetate, isopropyl acetate, tert-butyl acetate and the like; amides such as N,N-dimethylformamide, N,N-dimethylacetamide, 1-methyl-2-pyrrolidinone, hexamethylphosphoric triamide and the like; imides such as 1,3-dimethyl-2-imidazolidinone and the like; alcohols such as methanol, ethanol, isopropanol, tert-butanol and the like; halogenated hydrocarbons such as chloroform, dichloromethane, 1,2-dichloroethane, carbon tetrachloride and the like; sulfoxides such as dimethyl sulfoxide and the like; organic acids such as acetic acid, propionic acid, trifluoroacetic acid and the like; water and the like can be mentioned. These solvents may be mixed at an appropriately ratio and used. The reaction temperature is generally −100° C.-250° C. which is not higher than the boiling point of the aforementioned solvent. In some cases, a pressure-resistant reaction conditions and the like may be used, and the reaction may be performed at a temperature not lower than the boiling point of the solvent. The reaction time is generally 0.5 hr-100 hr. In the following reaction schemes, ring A, ring B, ring C, $R^1$, $R^2$, $R^3$, $R^4$, X and Y are as defined above.

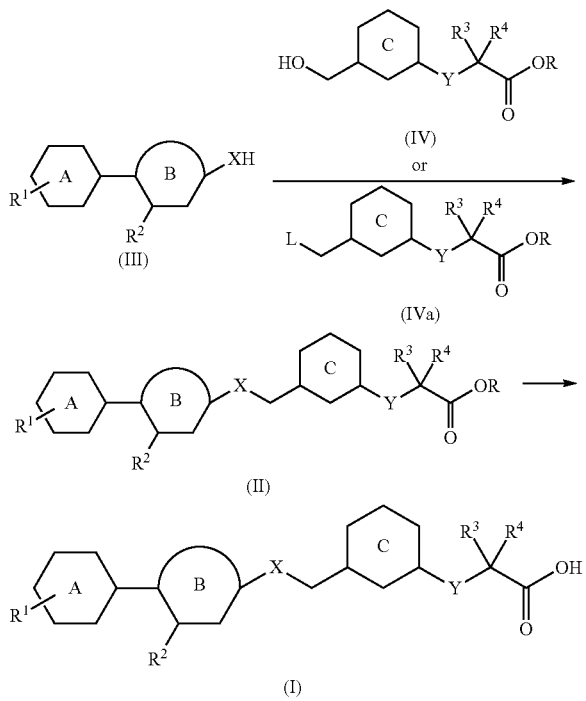

[reaction scheme 1]

Compound (I) can be produced, for example, according to the method shown in reaction scheme 1, or a method analogous thereto. Compound (I) can be produced from compound (II) by, for example, a method using hydrolysis in the presence of a base such as sodium hydroxide, lithium hydroxide and the like, or in the presence of an acid such as hydrochloric acid and the like, or a method analogous thereto. When X of compound (III) is oxygen, compound (II) can be produced, for example, by a method using the Mitsunobu reaction of compound (III) and compound (IV), or a method analogous thereto. The Mitsunobu reaction is performed, for example, by reacting compound (III) with compound (IV) in the presence of a hydroxy group activator (e.g., cyanomethylene tri-n-butylphosphorane, diisopropyl azodicarboxylate and triphenylphosphine, diethyl azodicarboxylate and triphenylphosphine, ADDP (1,1'-(azodicarbonyl)dipiperidine) and tributylphosphine and the like) in an inert solvent (e.g., toluene, THF and the like). In addition, compound (II) can also be produced, for example, by reacting compound (III) with compound (IVa) generally in the presence of a base (e.g., pyridine, 2,6-lutidine, 4-dimethylaminopyridine, triethylamine, diisopropylethylamine and the like). Here, R is a $C_{1-6}$ alkyl group, a $C_{7-16}$ aralkyl group and the like, and L is a leaving group (e.g., a halogen atom or —$OSO_2Me$, —$OSO_2$(4-tolyl), —$OSO_2CF_3$ and the like). Compound (III) can be produced by the method shown in the below-mentioned reaction scheme 5, or a method known per se, or a method analogous thereto.

[reaction scheme 2]

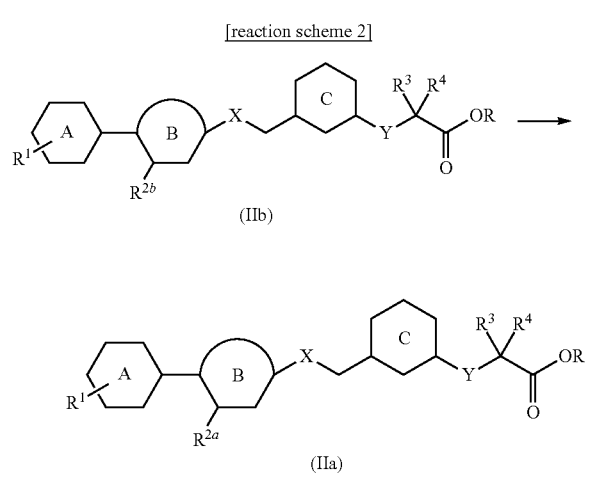

(IIb)

(IIa)

Compounds (IIa) wherein $R^{2a}$ is variously converted can be produced by, for example, the method shown in reaction scheme 2, which is a method including Suzuki reaction using compound (IIb) as a starting material, a method using other coupling reaction, or a method analogous thereto. The Suzuki reaction can be performed, for example, by a method known per se including reacting compound (IIb) with a boronic acid derivative generally in the presence of a base and in the presence of a catalyst (e.g., palladium catalyst, copper catalyst, nickel catalyst and the like) and an appropriate ligand. Here, $R^{2a}$ is a group similar to those exemplified for $R^2$ and $R^{2b}$ is a leaving group and the like.

[reaction scheme 3]

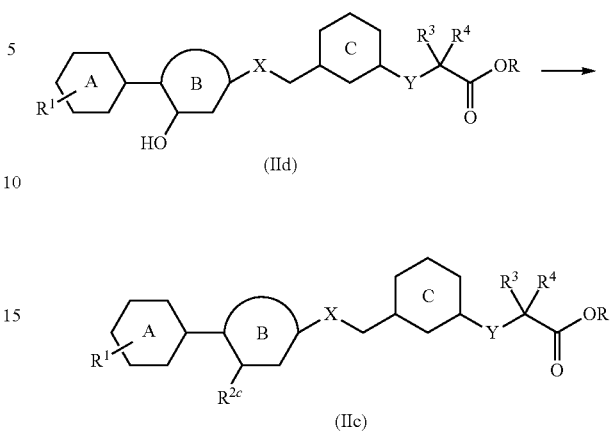

(IId)

(IIc)

Compounds (IIc) wherein $R^{2c}$ is variously converted can be produced by, for example, the method shown in reaction scheme 3, which is a method including an alkylation reaction in the presence of a base, using compound (IId) as a starting material, or a method analogous thereto. Here, $R^{2c}$ is a group similar to those exemplified for $R^2$.

[reaction scheme 4]

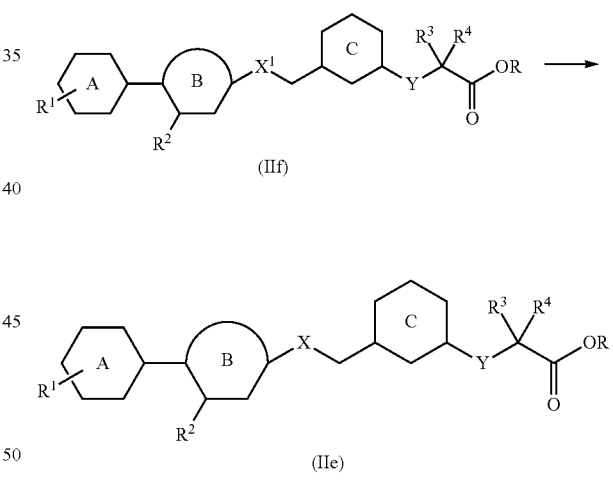

(IIf)

(IIe)

Compounds (IIe) wherein X is variously converted can be produced by, for example, the method shown in reaction scheme 4, which is a method including an oxidation reaction using compound (IIf, $X^1$=S) as a starting material, and using oxone or sodium periodate, meta-chloroperbenzoic acid, hydrogen peroxide and the like, or a method analogous thereto. In addition, compound (IIe) wherein X is variously converted can be produced by, for example, a method using a compound (IIf, $X^1$=NH) as a starting material and including an acylation reaction, a sulfonylation reaction, an alkylation reaction in the presence of a base, or a method analogous thereto.

[reaction scheme 5]

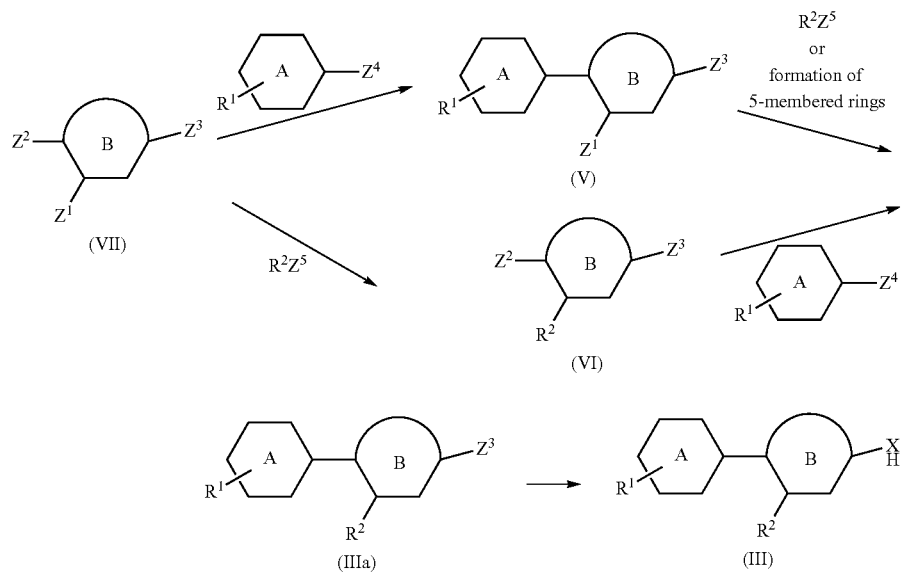

Compound (III) can be produced by, for example, the method shown in reaction scheme 5, or a method analogous thereto. Compound (III) can be produced by a method subjecting $Z^3$ of compound (IIIa) to deprotection or a coupling reaction, or a method analogous thereto. Here, $Z^3$ is an optionally protected hydroxyl group, amino group, mercapto group, or leaving group. Compound (IIIa) can be produced, for example, by a method known per se including reacting compound (V) or compound (VI) with halogenated aryl or aryl sulfonate, an organic metal reagent (e.g., lithium reagent or Grignard reagent, zinc reagent and the like), or a boronic acid reagent generally in the presence of a base, and in the presence of a catalyst and an appropriate ligand where necessary. In addition, compound (IIIa) can be produced by a method known per se including converting $Z^1$ of compound (V) to a 5-membered heterocycle. Here, $Z^1$ is carboxylic acid, an ester thereof, aldehyde, a substituent having an optionally protected hydroxyl group, a substituent having a leaving group, or a leaving group, $Z^2$ is a leaving group or a substituent of these precursors, $Z^4$ is a substituent of a dihydroboron or boron derivative, or a leaving group, and $Z^5$ is a metal (lithium, magnesium, zinc and the like), a substituent of a dihydroboron or boron derivative, or a leaving group. Compound (V) or compound (VI) can be produced, for example, by a method known per se including reacting compound (VII) with halogenated aryl or aryl sulfonate, an organic metal reagent, or a boronic acid reagent generally in the presence of a base, and in the presence of a catalyst and an appropriate ligand where necessary.

[reaction scheme 6]

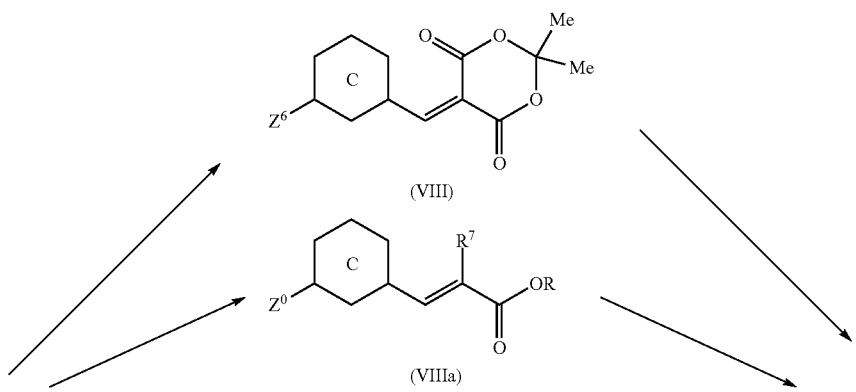

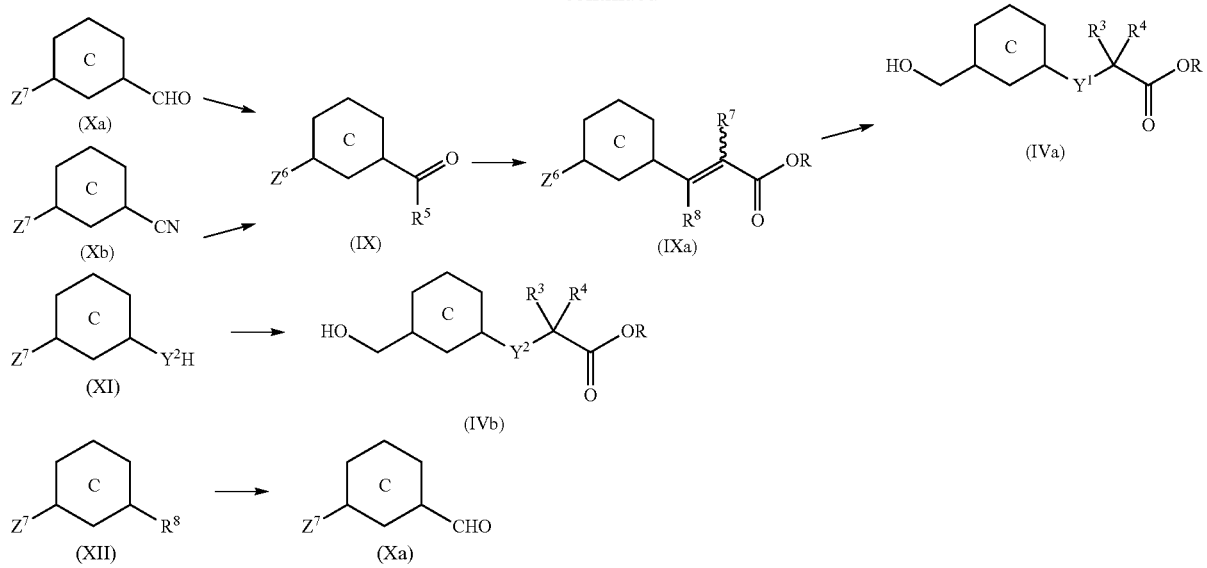

Compound (IV) wherein Y is an optionally substituted carbon (compound (IVa); $Y^1=-CR^{6B}R^{6C}-$) can be produced, for example, by the method shown in reaction scheme 6, or a method analogous thereto. Compound (IVa) can be produced, for example, by reacting compound (VIII) and an organic metal reagent by a method known per se or a method analogous thereto to convert the meldrum's acid moiety to an ester. Compound (IVa) can be produced, for example, by reacting compound (VIIIa) and an organic metal reagent by a method known per se or a method analogous thereto. Here, $R^7$ is a group similar to those exemplified for $R^3$ and $R^4$, and $Z^6$ is an ester or an optionally protected hydroxymethyl group. Compound (IVa) can be produced, for example, by reacting compound (IX) and a Wittig reagent or phosphonic acid ester according to the Horner-Emmons reaction or a method analogous thereto, and subjecting the resulting compound (IXa) to, for example, catalytic reduction (e.g., hydrogen-palladium/carbon, hydrogen-platinum oxide, hydrogen-palladium hydroxide/carbon, hydrogen-palladium/carbon ethylenediamine complex) or a reduction using cupper hydride and the like. Here, $R^8$ is a group similar to those exemplified for $R^{6B}$ and $R^{6C}$. Compound (VIII) can be produced, for example, by reacting compound (Xa) and meldrum's acid by a method known per se or a method analogous thereto. Compound (IX) can be produced, for example, by reacting compound (Xa) and an organic metal reagent, and oxidizing the resulting hydroxyl group. Moreover, compound (IX) can also be produced, for example, by reacting compound (Xb) and an organic metal reagent by a method known per se or a method analogous thereto. Compound (IV) wherein Y is oxygen, sulfur or optionally substituted nitrogen (compound (IVb); $Y^2=-O-$, $-S(O)_n-$, $-NR^{6A}-$) can be produced, for example, by alkylating compound (XI) using alkyl halide generally in the presence of a base. Compound (Xa) can be produced, for example, by converting $R^9$ of compound (XII) to a formyl group by oxidation or reduction by a method known per se or a method analogous thereto. Here, $Z^7$ is an ester or an optionally protected hydroxymethyl group and $R^9$ is carboxylic acid, amide, ester or a hydroxymethyl group.

[reaction scheme 7]

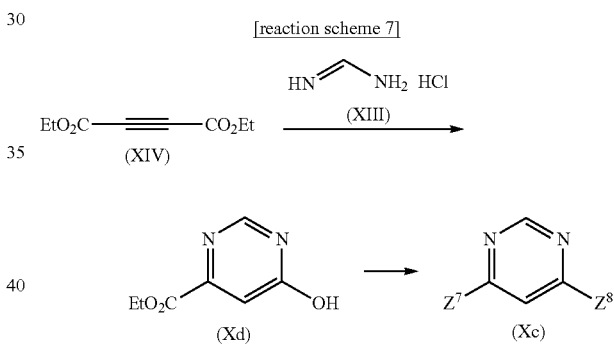

Compound (Xc) can be produced, for example, according to the method shown in reaction scheme 7, or a method analogous thereto. Compound (Xc) can be produced, for example, by converting the ester and the hydroxyl group of compound (Xd) to $Z^7$ and $Z^8$, respectively, by a method known per se. Compound (Xd) can be produced from compound (XIII) and compound (XIV) by a method known per. Here, $Z^8$ is a cyano group, an optionally protected hydroxyl group or a leaving group.

[reaction scheme 8]

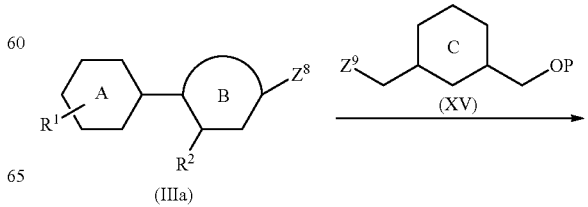

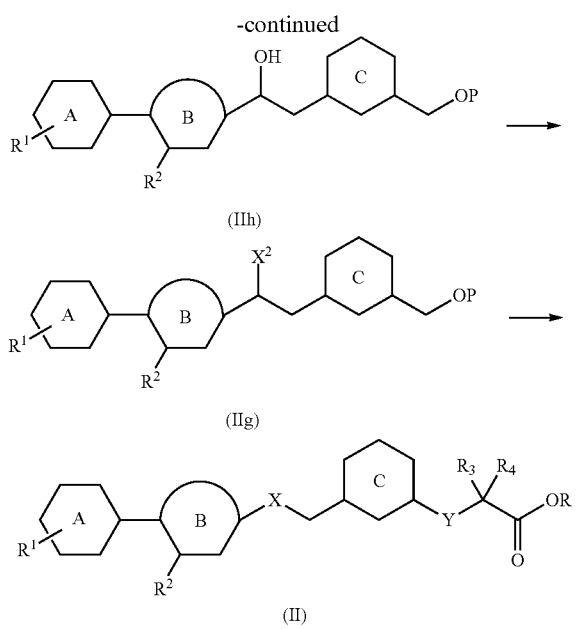

Compound (II) wherein X is optionally substituted carbon (—CR$^{5B}$R$^{5C}$—) can be produced, for example, by the method shown in reaction scheme 8, using compound (IIIa) as a starting material and compound (IIg) and compound (IIh) as intermediates, or a method analogous thereto. Here, X$^2$ is a group similar to those exemplified for R$^{5C}$ and P is a protecting group. Compound (II) can be produced, for example, by the method shown in reaction scheme 6 to produce compound (IVa) by using compound (IIg), or a method analogous thereto. Compound (IIg) can be produced, for example, from compound (IIh) by a method known per se, or a method analogous thereto. Compound (IIh) can be produced, for example, by reacting compound (IIIa) with compound (XV) by a method known per se or a method analogous thereto. Here, Z$^9$ is a leaving group or a metal (lithium, magnesium, zinc and the like).

In each of the aforementioned reactions, when the starting compound has an amino group, a carboxy group, a hydroxy group, a carbonyl group or a mercapto group as a substituent, a protecting group generally used in the peptide chemistry and the like may be introduced into these groups, and the object compound can be obtained by eliminating the protecting group as necessary after the reaction.

Examples of the amino-protecting group include a formyl group; a C$_{1-6}$ alkyl-carbonyl group, a C$_{1-6}$ alkoxy-carbonyl group, a benzoyl group, a $_{7-10}$ aralkyl-carbonyl group (e.g., benzylcarbonyl), a C$_{7-13}$ aralkyloxy-carbonyl group (e.g., benzyloxycarbonyl, 9-fluorenylmethoxycarbonyl), a trityl group, a phthaloyl group, an N,N-dimethylaminomethylene group, a substituted silyl group (e.g., trimethylsilyl, triethylsilyl, dimethylphenylsilyl, tert-butyldimethylsilyl, tert-butyldiethylsilyl), a C$_{2-6}$ alkenyl group (e.g., 1-allyl) and the like. These groups are optionally substituted by 1 to 3 substituents selected from a halogen atom, a C$_{1-6}$ alkoxy group and a nitro group.

Examples of the carboxyl-protecting group include a C$_{1-6}$ alkyl group, a C$_{7-11}$ aralkyl group (e.g., benzyl), a phenyl group, a trityl, a substituted silyl group (e.g., trimethylsilyl, triethylsilyl, dimethylphenylsilyl, tert-butyldimethylsilyl, tert-butyldiethylsilyl), a C$_{2-6}$ alkenyl group (e.g., 1-allyl) and the like. These groups are optionally substituted by 1 to 3 substituents selected from a halogen atom, a C$_{1-6}$ alkoxy group and a nitro group.

Examples of the hydroxy-protecting group include a C$_{1-6}$ alkyl group, a phenyl group, a trityl group, a C$_{7-10}$ aralkyl group (e.g., benzyl), a formyl group, a C$_{1-6}$ alkyl-carbonyl group, a benzoyl group, a C$_{7-10}$ aralkyl-carbonyl group (e.g., benzylcarbonyl), a 2-tetrahydropyranyl group, a 2-tetrahydrofuranyl group, a substituted silyl group (e.g., trimethylsilyl, triethylsilyl, dimethylphenylsilyl, tert-butyldimethylsilyl, tert-butyldiethylsilyl), a C$_{2-6}$ alkenyl group (e.g., 1-allyl), and the like. These groups are optionally substituted by 1 to 3 substituents selected from a halogen atom, a C$_{1-6}$ alkyl group, a C$_{1-6}$ alkoxy group and a nitro group.

Examples of the carbonyl-protecting group include a cyclic acetal (e.g., 1,3-dioxane), a non-cyclic acetal (e.g., a di-C$_{1-6}$ alkylacetal) and the like.

Examples of the mercapto-protecting group include a C$_{1-6}$ alkyl group, a phenyl group, a trityl group, a C$_{7-10}$ aralkyl group (e.g., benzyl), a C$_{1-6}$ alkyl-carbonyl group, a benzoyl group, a C$_{7-10}$ aralkyl-carbonyl group (e.g., benzylcarbonyl), a C$_{1-6}$ alkoxy-carbonyl group, a C$_{6-14}$ aryloxy-carbonyl group (e.g., phenyloxycarbonyl), a C$_{7-14}$ aralkyloxy-carbonyl group (e.g., benzyloxycarbonyl, 9-fluorenylmethoxycarbonyl), a 2-tetrahydropyranyl group, a C$_{1-6}$ alkylamino-carbonyl group (e.g., methylaminocarbonyl, ethylaminocarbonyl) and the like. These groups are optionally substituted by 1 to 3 substituents selected from a halogen atom, a C$_{1-6}$ alkyl group, a C$_{1-6}$ alkoxy group and a nitro group.

The above-mentioned protecting groups can be removed by a method known per se, for example, the method described in Protective Groups in Organic Synthesis, John Wiley and Sons (1980) and the like. Specifically, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

In compound (I) thus obtained, a functional group in a molecule can also be converted to a desired functional group by a combination of chemical reactions known per se. Examples of the chemical reaction include oxidation reaction, reduction reaction, alkylation reaction, acylation reaction, ureation reaction, hydrolysis reaction, amination reaction, esterification reaction, aryl coupling reaction, deprotection reaction and the like.

The compound of the formula (I) obtained by each of the above-mentioned production methods can be isolated and purified by a known means such as concentration, concentration under reduced pressure, solvent extraction, crystallization, recrystallization, phase transfer, chromatography and the like. In addition, the starting compounds used for each of the above-mentioned production methods can be isolated and purified by a known means similar to the aforementioned methods. These starting compounds may be used in the form of a reaction mixture without isolation, as a starting material for the next step.

When compound (I) contains an isomer such as an optical isomer, a stereoisomer, a regioisomer or a rotamer, any one of them and a mixture thereof are also encompassed in compound (I). For example, when compound (I) contains an optical isomer, an optical isomer resolved from racemate is also encompassed in compound (I). Each of these isomers can be obtained as a single product by a synthesis means, separation means (e.g., concentration, solvent extraction, column chromatography, recrystallization etc.), optical resolution means (e.g., fractional recrystallization, chiral column method, diastereomer method etc.) and the like, which are known per se.

Compound (I) may be a crystal, and the crystal form may be single or a mixture of crystal forms, both of which are encompassed in compound (I). The crystal can be produced by a crystallization method known per se.

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

In the present specification, the melting point means that measured using, for example, a micromelting point apparatus (Yanako, MP-500D or Buchi, B-545), a DSC (differential scanning calorimetry) device (SEIKO, EXSTAR6000) or the like.

In general, the melting points vary depending on the measurement apparatuses, the measurement conditions and the like. The crystal in the present specification may show different values from the melting point described in the present specification, as long as they are within each of a general error range.

The crystal of the present invention is superior in physicochemical properties (e.g., melting point, solubility, stability) and biological properties (e.g., pharmacokinetics (absorption, distribution, metabolism, excretion), efficacy expression), and thus it is extremely useful as a medicament.

Compound (I) may be a solvate (e.g., hydrate etc.), or a non-solvate (e.g., non-hydrate etc.), and both are encompassed in compound (I).

A compound labeled with an isotope (e.g., $^3$H, $^{13}$C, $^{14}$C, $^{18}$F, $^{35}$S, $^{125}$I etc.) and the like is also encompassed in compound (I).

Compound (I) also encompasses a deuterium conversion form wherein $^1$H is converted to $^2$H(D).

Compound (I) labeled or substituted with an isotope can be used as, for example, a tracer (PET tracer) used for Positron Emission Tomography (PET), and is useful in the fields of medical diagnosis and the like.

Compound (I) and a prodrug thereof (hereinafter, these are collectively abbreviated as the compound of the present invention) have a GPR40 receptor function modulating action, particularly, a GPR40 agonist activity. GPR40 agonist activates GPR40 expressed in pancreatic β cells to promote insulin secretion, and activates GPR40 expressed in the intestine to promote glucagon-like peptide-1 (glucagon-like peptide-1; GLP-1) secretion. That is, the compound of the present invention has a hypoglycemic action, an insulin secretagogue action, a GLP-1 secretagogue action and a pancreatic β cell protecting action. Moreover, the compound of the present invention may have a glucose-dependent insulinotropic polypeptide (GIP) secretagogue action, a food ingestion suppressive action and a glucagon secretion suppressive action.

The compound of the present invention shows low toxicity (e.g., acute toxicity, chronic toxicity, genetic toxicity, reproductive toxicity, cardiotoxicity, carcinogenicity and the like) and can be safely administered a mammal (e.g., mouse, rat, hamster, rabbit, cat, dog, bovine, sheep, monkey, human) directly or as a pharmaceutical composition by mixing same with a pharmacologically acceptable carrier and the like.

The compound of the present invention is useful as modulators of physiological function in which GPR40 receptor is involved or as agents for the prophylaxis or treatment of pathology or disease in which GPR40 receptor is involved.

To be specific, the compound of the present invention is useful as an agent for the prophylaxis or treatment of diabetes (e.g., type 1 diabetes, type 2 diabetes, gestational diabetes, obese diabetes), an insulin secretagogue, a pancreatic β cell protector, a GLP-1 secretion promoter, a GIP secretion promoter, an agent for the prophylaxis or treatment of impaired glucose tolerance (IGT) and an agent for preventing progression of impaired glucose tolerance to diabetes.

Particularly, the compound of the present invention is useful as blood glucose level-dependent insulin secretagogues based on the GPR40 agonist activity thereof. That is different from sulfonylureas, the compound of the present invention is useful as insulin secretagogues that do not cause hypoglycemia.

Furthermore, the compound of the present invention can be used as an agent for the prophylaxis or treatment of obesity, hyperlipidemia (e.g., hypertriglyceridemia, hypercholesterolemia, high LDL-cholesterolemia, hypoHDL-emia, postprandial hyperlipemia), hypertension, cardiac failure, diabetic complications [e.g., neuropathy, nephropathy, retinopathy, diabetic cardiomyopathy, cataract, macroangiopathy, osteopenia, hyperosmolar diabetic coma, infections (e.g., respiratory infection, urinary tract infection, gastrointestinal infection, dermal soft tissue infections, inferior limb infection), diabetic gangrene, xerostomia, hypacusis, cerebrovascular disorder, peripheral blood circulation disorder], metabolic syndrome (according to the diagnostic criteria for Japanese people as reported in 2005 by the Japan Society for the Study of Obesity and the like, the metabolic syndrome refers to males having an abdominal circumference of 85 cm or above and females having an abdominal circumference of 90 cm or above and satisfying two items out of three items of: systolic blood pressure of not less than 130 or diastolic blood pressure of not less than 85 mmHg, neutral triglyceride not less than 150 mg/dl or HDLc less than 40 mg/dl, and fasting blood sugar level (venous plasma glucose concentration) not less than 110 mg/dl) and the like.

For diagnostic criteria of diabetes, Japan Diabetes Society reported diagnostic criteria in 1999.

According to this report, diabetes is a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl. A condition not falling under the above-mentioned diabetes and different from "a condition showing a fasting blood glucose level (glucose concentration of intravenous plasma) of less than 110 mg/dl or a 75 g oral glucose tolerance test (75 g OGTT) 2 h level (glucose concentration of intravenous plasma) of less than 140 mg/dl" (normal type) is called a "borderline type".

In addition, ADA (American Diabetes Association) and WHO reported diagnostic criteria of diabetes.

According to these reports, diabetes is a condition showing a fasting blood glucose level (glucose concentration of intravenous plasma) of not less than 126 mg/dl, or a 75 g oral glucose tolerance test 2 h level (glucose concentration of intravenous plasma) of not less than 200 mg/dl.

According to the above-mentioned reports by ADA and WHO, impaired glucose tolerance is a condition showing a 75 g oral glucose tolerance test 2 h level (glucose concentration of intravenous plasma) of not less than 140 mg/dl and less than 200 mg/dl. According to the report of ADA, a condition showing a fasting blood glucose level (glucose concentration of intravenous plasma) of not less than 110 mg/dl and less than 126 mg/dl is called IFG (Impaired Fasting Glucose). According to the report of WHO, among the IFG (Impaired Fasting Glucose), a condition showing a fasting blood glucose level (glucose concentration of intravenous plasma) of not less than 110 mg/dl and less than 126 mg/dl is called IFG (Impaired Fasting Glycemia).

The compound of the present invention can also be used as an agent for the prophylaxis or treatment of diabetes, borderline type, impaired glucose tolerance, IFG (Impaired Fasting Glucose) and IFG (Impaired Fasting Glycemia), as determined according to the above-mentioned diagnostic criteria. Moreover, the compound of the present invention can prevent progress of borderline type, impaired glucose tolerance, IFG (Impaired Fasting Glucose) or IFG (Impaired Fasting Glycemia) into diabetes.

The compound of the present invention is also useful as a therapeutic agent for diabetes with sulfonylurea secondary failure and affords a superior insulin secretion effect and a hypoglycemic effect for diabetic patients for whom sulfonylurea compounds and fast-acting insulin secretagogues fail to provide an insulin secretion effect, and therefore, fail to provide a sufficient hypoglycemic effect.

As the sulfonylurea compound here, a compound having a sulfonylurea skeleton or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic B cell in the same manner as a sulfonylurea compound, though it does not have a sulfonylurea skeleton, such as glinide compounds (e.g., repaglinide, senaglinide, nateglinide, mitiglinide or a calcium salt hydrate thereof etc.), and the like, can be mentioned.

The compound of the present invention can also be used as an agent for the prophylaxis or treatment of, for example, cognitive impairment, osteoporosis, cachexia (e.g., cancerous cachexia, tuberculous cachexia, diabetic cachexia, hemopathic cachexia, endocrinopathic cachexia, infectious cachexia or cachexia induced by acquired immunodeficiency syndrome), fatty liver, polycystic ovary syndrome, renal disease (e.g., diabetic nephropathy, glomerulonephritis, glomerulosclerosis, nephrotic syndrome, hypertensive nephrosclerosis, end-stage renal disorder), muscular dystrophy, myocardial infarction, angina pectoris, cerebrovascular disorder (e.g., cerebral infarction, cerebral apoplexy), insulin resistance syndrome, syndrome X, hyperinsulinemia, perception disorder in hyperinsulinemia, tumor (e.g., leukemia, breast cancer, prostate cancer, skin cancer), irritable bowel syndrome, acute or chronic diarrhea, inflammatory disease (e.g., arteriosclerosis (e.g., atherosclerosis), rheumatoid arthritis, spondylitis deformans, osteoarthritis, lumbago, gout, postoperative or post-traumatic inflammation, swelling, neuralgia, pharyngolaryngitis, bladder inflammation, hepatitis (including nonalcoholic steatohepatitis), pneumonia, pancreatitis, inflammatory colitis, ulcerative colitis, chronic obstructive pulmonary diseases (COPD)), visceral fat syndrome, foot ulcer, sepsis, psoriasis and the like.

In addition, the compound of the present invention can also be used for the improvement of the symptoms of abdominal pain, nausea, vomiting, uncomfortable feeling in the upper abdomine and the like, which are associated with peptic ulcer, acute or chronic gastritis, biliary dyskinesia, cholecystitis and the like and the like.

Since the compound of the present invention has a pancreatic β cell protection action, it can be used for the prognosis improvement in pancreatic islet transplantation.

The compound of the present invention can also be used for decreasing the visceral fat, suppressing visceral fat accumulation, improving sugar metabolism, improving lipid metabolism, insulin sensitizing, suppressing oxidized LDL production, improving lipoprotein metabolism, improving coronary metabolism, preventing or treating cardiovascular complication, preventing or treating heart failure complication, decreasing blood remnant, preventing or treating anovulation, preventing or treating hirsutism, preventing or treating hyperandrogenism and the like.

The compound of the present invention can also be used for the secondary prevention and the suppression of progression of the above-mentioned various diseases (e.g., cardiovascular event such as myocardial infarction and the like).

A medicament containing the compound of the present invention can be safely administered solely to a mammal or by mixing with a pharmacologically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal tablet and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal and intratumor administrations, administration to the vicinity of tumor, and direct administration to the lesion).

A pharmaceutical composition can be produced by a method conventionally used in the technical field of pharmaceutical preparation, for example, the method described in the Japanese Pharmacopoeia and the like.

During production of an oral preparation, coating may be applied as necessary for the purpose of masking of taste, enteric property or durability.

Examples of the coating base to be used for coating include sugar coating base, aqueous film coating base, enteric film coating base and sustained-release film coating base.

As the sugar coating base, sucrose is used. Moreover, one or more kinds selected from talc, precipitated calcium carbonate, gelatin, gum arabic, pullulan, carnauba wax and the like may be used in combination.

Examples of the aqueous film coating base include cellulose polymers such as hydroxypropyl cellulose, hydroxypropylmethyl cellulose, hydroxyethyl cellulose, methylhydroxyethyl cellulose etc.; synthetic polymers such as polyvinylacetal diethylaminoacetate, aminoalkyl methacrylate copolymer E [Eudragit E (trade name)], polyvinylpyrrolidone etc.; and polysaccharides such as pullulan etc.

Examples of the enteric film coating base include cellulose polymers such as hydroxypropylmethyl cellulose phthalate, hydroxypropylmethyl cellulose acetate succinate, carboxymethylethyl cellulose, cellulose acetate phthalate etc.; acrylic polymers such as methacrylic acid copolymer L [Eudragit L (trade name)], methacrylic acid copolymer LD [Eudragit L-30D55 (trade name)], methacrylic acid copolymer S [Eudragit S (trade name)] etc.; and naturally occurring substances such as shellac etc.

Examples of the sustained-release film coating base include cellulose polymers such as ethyl cellulose etc.; and acrylic polymers such as aminoalkyl methacrylate copolymer RS [Eudragit RS (trade name)], ethyl acrylate-methyl methacrylate copolymer suspension [Eudragit NE (trade name)] etc.

The above-mentioned coating bases may be used after mixing with two or more kinds thereof at appropriate ratios. For coating, for example, a light shielding agent such as titanium oxide, red ferric oxide and the like can be used.

The content of the compound of the present invention in a pharmaceutical preparation is about 0.01 to about 100% by weight relative to the whole preparation. While the dose varies depending on the administration subject, administration route, diseases, condition and the like, for example, the compound of the present invention (as an active ingredient) can be orally administered to a patient with diabetes (body weight about 60 kg) in about 0.01 to about 30 mg/kg body weight per day, preferably about 0.1 to about 20 mg/kg body weight per day, more preferably about 1 to about 20 mg/kg body weight per day, which may be given at once or in several portions (e.g., 1-3 portions) a day.

As the above-mentioned pharmacologically acceptable carrier, various organic or inorganic carrier substances conventionally used as a preparation material. For example, excipient, lubricant, binder and disintegrant for solid preparations; solvent, solubilizing agents, suspending agent, isotonicity agent, buffer and soothing agent for liquid preparations and the like can be mentioned. Where necessary, conventional additives such as preservatives, antioxidants, colorants, sweetening agents, adsorbing agents, wetting agents and the like can be used.

As the excipient, for example, lactose, sucrose, D-mannitol, starch, corn starch, crystalline cellulose, light anhydrous silicic acid and the like can be mentioned.

As the lubricant, for example, magnesium stearate, calcium stearate, talc, colloidal silica and the like can be mentioned.

As the binder, for example, crystalline cellulose, sucrose, D-mannitol, dextrin, hydroxypropylcellulose, hydroxypropylmethylcellulose, polyvinylpyrrolidone, starch, saccharose, gelatin, methylcellulose, carboxymethylcellulose sodium and the like can be mentioned.

As the disintegrant, for example, starch, carboxymethylcellulose, carboxymethylcellulose calcium, carboxymethylstarch sodium, L-hydroxypropylcellulose and the like can be mentioned.

As the solvent, for example, water for injection, alcohol, propylene glycol, macrogol, sesame oil, corn oil, olive oil and the like can be mentioned.

As the solubilizing agents, for example, polyethylene glycol, propylene glycol, D-mannitol, benzyl benzoate, ethanol, trisaminomethane, cholesterol, triethanolamine, sodium carbonate, sodium citrate and the like can be mentioned.

As the suspending agent, for example, surfactants such as stearyltriethanolamine, sodium lauryl sulfate, lauryl aminopropionate, lecithin, benzalkonium chloride, benzethonium chloride, glycerol monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like, and the like can be mentioned.

As the isotonicity agent, for example, glucose, D-sorbitol, sodium chloride, glycerin, D-mannitol and the like can be mentioned.

As the buffer, for example, buffers such as phosphates, acetates, carbonates, citrates and the like, and the like can be mentioned.

As the soothing agent, for example, benzyl alcohol and the like can be mentioned.

As the preservative, for example, p-hydroxybenzoates, chlorobutanol, benzyl alcohol, phenethyl alcohol, dehydroacetic acid, sorbic acid and the like can be mentioned.

As the antioxidant, for example, sulfites, ascorbic acid, α-tocopherol and the like can be mentioned.

As the colorant, for example, water-soluble edible tar pigments (e.g., foodcolors such as Food Color Red Nos. 2 and 3, Food Color Yellow Nos. 4 and 5, Food Color Blue Nos. 1 and 2 and the like), water insoluble lake pigments (e.g., aluminum salt of the aforementioned water-soluble edible tar pigment and the like), natural pigments (e.g., β-carotene, chlorophil, ferric oxide red etc.) and the like can be mentioned.

As the sweetening agent, for example, saccharin sodium, dipotassium glycyrrhizinate, aspartame, stevia and the like can be mentioned.

Moreover, the compound of the present invention can be used in combination with drugs other than the compound of the present invention.

As the drugs that can be used in combination with the compound of the present invention (hereinafter sometimes to be abbreviated as a concomitant drug), for example, other therapeutic agents for diabetes, therapeutic agents for diabetic complications, therapeutic agents for hyperlipidemia, antihypertensive agents, antiobesity agents, diuretics, chemotherapeutic agents, immunotherapeutic agents, antiinflammatory agents, antithrombotic agents, therapeutic agents for osteoporosis, vitamins, antidementia agents, erectile dysfunction improving drugs, therapeutic agents for pollakiuria or urinary incontinence, therapeutic agents for dysuria and the like can be mentioned. Specifically, the following agents can be mentioned.

Examples of other therapeutic agents for diabetes include insulin preparations (e.g., animal insulin preparations extracted from pancreas of bovine or swine; human insulin preparations genetically synthesized using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), Metaglidasen, AMG-131, Balaglitazone, MBX-2044, Rivoglitazone, Aleglitazar, Chiglitazar, Lobeglitazone, PLX-204, PN-2034, GFT-505, THR-0921, compounds described in WO2007/013694, WO2007/018314, WO2008/093639 and WO2008/099794), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogues [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or calcium salt hydrate thereof], dipeptidyl-peptidase IV inhibitors (e.g., Alogliptin or a salt thereof (preferably benzoate), Vildagliptin, Sitagliptin, Saxagliptin, BI1356, GRC8200, MP-513, PF-00734200, PHX1149, SK-0403, ALS2-0426, TA-6666, TS-021, KRP-104, 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof), β3 agonists (e.g., N-5984), GPR40 agonists (e.g., compounds described in WO2004/041266, WO2004/106276, WO2005/063729, WO2005/063725, WO2005/087710, WO2005/095338, WO2007/013689 and WO2008/001931), GLP-1 receptor agonists (e.g., GLP-1, GLP-1MR agent, Liraglutide, Exenatide, AVE-0010, BIM-51077, Aib (8,35)hGLP-1(7,37)NH$_2$, CJC-1131, Albiglutide), amylin agonists (e.g., pramlintide), phosphotyrosine phosphatase inhibitors (e.g., sodium vanadate), gluconeogenesis inhibitors (e.g., glycogen phosphorylase inhibitors, glucose-6-phosphatase inhibitors, glucagon antagonists, FBPase inhibitors), SGLT2 (sodium-glucose cotransporter 2) inhibitors (e.g., Depagliflozin, AVE2268, TS-033, YM543, TA-7284, Remogliflozin, ASP1941), SGLT1 inhibitor, 11β-hydroxysteroid dehydrogenase inhibitors (e.g., BVT-3498, INCB-13739), adiponectin or agonist thereof, IKK inhibitors (e.g., AS-2868), leptin resistance improving drugs, somatostatin receptor agonists, glucokinase activators (e.g., Piragliatin, AZD1656, AZD6370, TTP-355, compounds described in WO2006/112549, WO2007/028135, WO2008/047821, WO2008/050821, WO2008/136428 and WO2008/156757), GIP (Glucose-dependent insulinotropic peptide), GPR119 agonists (e.g., PSN821, MBX-2982, APD597), FGF21, FGF analogue and the like.

Examples of the therapeutic agents for diabetic complications include aldose reductase inhibitors (e.g., Tolrestat, Epalrestat, Zopolrestat, Fidarestat, CT-112, ranirestat (AS-3201), Lidorestat), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy)propyl]oxazole), compound described in WO2004/039365), PKC inhibitors (e.g., ruboxistaurin mesylate), AGE inhibitors (e.g., ALT-946, N-phenacylthiazolium bromide (ALT-766), EXO-226, Pyridorin, Pyridoxamine), GABA receptor agonists (e.g., gabapentin, Pregabalin), serotonin.noradrenaline reuptake inhibitors (e.g., duloxetine), sodium channel inhibitors (e.g., Lacosamide), active oxygen scavengers (e.g., thioctic acid), cerebral vasodilators (e.g., tiapuride, mexiletine), somatostatin receptor agonists (BIM23190), apoptosis signal regulating kinase-1 (ASK-1) inhibitors and the like.

Examples of the therapeutic agent for hyperlipidemia include HMG-CoA reductase inhibitors (e.g., pravastatin, simvastatin, lovastatin, atorvastatin, fluvastatin, rosuvastatin, pitavastatin or a salt thereof (e.g., sodium salt, calcium salt)), squalene synthase inhibitors (e.g., compound described in WO97/10224, for example, N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid), fibrate compounds (e.g., bezafibrate, clofibrate, simfibrate, clinofibrate), anion exchange resins (e.g., colestyramine), probucol, nicotinic acid drugs (e.g., nicomol, niceritrol, niaspan), ethyl icosapentate, phytosterol (e.g., soysterol, gamma oryzanol), cholesterol absorption inhibitors (e.g., Zetia), CETP inhibitors (e.g., dalcetrapib, anacetrapib), ω-3 fatty acid preparations (e.g., ω-3-acid ethyl esters 90) and the like.

Examples of the antihypertensive agent include angiotensin converting enzyme inhibitors (e.g., captopril, enalapril, delapril and the like), angiotensin II antagonists (e.g., candesartan cilexetil, candesartan, losartan, losartan potassium, eprosartan, valsartan, telmisartan, irbesartan, tasosartan, olmesartan, olmesartan medoxomil, azilsartan, azilsartan medoxomil and the like), calcium antagonists (e.g., manidipine, nifedipine, amlodipine, efonidipine, nicardipine, amlodipine, cilnidipine and the like), β blockers (e.g., metoprolol, atenolol, propranolol, carvedilol, pindolol and the like), clonidine and the like.

Examples of the antiobesity agent include monoamine uptake inhibitors (e.g., phentermine, sibutramine, mazindol, fluoxetine, tesofensine), serotonin 2C receptor agonists (e.g., lorcaserin), serotonin 6 receptor antagonists, histamine H3 receptor GABA modulator (e.g., topiramate), neuropeptide Y antagonists (e.g., velneperit), cannabinoid receptor antagonists (e.g., rimonabant, taranabant), ghrelin antagonists, ghrelin receptor antagonists, ghrelin acylation enzyme inhibitors, opioid receptor antagonists (e.g., GSK-1521498), orexin receptor antagonists, melanocortin 4 receptor agonists, 11β-hydroxysteroid dehydrogenase inhibitors (e.g., AZD-4017), pancreatic lipase inhibitors (e.g., orlistat, cetilistat), β agonists (e.g., N-5984), diacylglycerol acyltransferase 1 (DGAT1) inhibitors, acetylCoA carboxylase (ACC) inhibitors, stearoyl-CoA desaturated enzyme inhibitors, microsomal triglyceride transfer protein inhibitors (e.g., R-256918), Na-glucose cotransporter inhibitors (e.g., JNJ-28431754, remogliflozin), NFκ inhibitors (e.g., HE-3286), PPAR agonists (e.g., GFT-505, DRF-11605), phosphotyrosine phosphatase inhibitors (e.g., sodium vanadate, Trodusquemin), GPR119 agonists (e.g., PSN-821, MBX-2982, APD597), glucokinase activators (e.g., AZD-1656), leptin, leptin derivatives (e.g., metreleptin), CNTF (ciliary neurotrophic factor), BDNF (brain-derived neurotrophic factor), cholecystokinin agonists, glucagon-like peptide-1 (GLP-1) preparations (e.g., animal GLP-1 preparations extracted from the pancreas of bovine or swine; human GLP-1 preparations genetically synthesized using *Escherichia coli* or yeast; fragments or derivatives of GLP-1 (e.g., exenatide, liraglutide)), amylin preparations (e.g., pramlintide, AC-2307), neuropeptide Y agonists (e.g., PYY3-36, derivatives of PYY3-36, obineptide, TM-30339, TM-30335), oxyntomodulin preparations: FGF21 preparations (e.g., animal FGF21 preparations extracted from the pancreas of bovine or swine; human FGF21 preparations genetically synthesized using *Escherichia coli* or yeast; fragments or derivatives of FGF21)), anorexigenic agents (e.g., P-57) and the like.

Examples of the diuretics include xanthine derivatives (e.g., sodium salicylate and theobromine, calcium salicylate and theobromine), thiazide preparations (e.g., ethiazide, cyclopenthiazide, trichloromethiazide, hydrochlorothiazide, hydroflumethiazide, benzylhydrochlorothiazide, penflutizide, poly 5 thiazide, methyclothiazide), antialdosterone preparations (e.g., spironolactone, triamterene), carbonate dehydratase inhibitors (e.g., acetazolamide), chlorobenzenesulfonamide preparations (e.g., chlortalidone, mefruside, indapamide), azosemide, isosorbide, etacrynic acid, piretanide, bumetanide, furosemide and the like.

Examples of the chemotherapeutic agents include alkylating agents (e.g., cyclophosphamide, ifosfamide), metabolic antagonists (e.g., methotrexate, 5-fluorouracil), antitumor antibiotics (e.g., mitomycin, adriamycin), plant-derived antitumor agents (e.g., vincristine, vindesine, Taxol), cisplatin, carboplatin, etoposide and the like. Of these, Furtulon or NeoFurtulon, which are 5-fluorouracil derivatives, and the like are preferable.

Examples of the immunotherapeutic agents include microorganism or bacterial components (e.g., muramyl dipeptide derivatives, Picibanil), polysaccharides having immunity potentiating activity (e.g., lentinan, schizophyllan, krestin), cytokines obtained by genetic engineering techniques (e.g., interferon, interleukin (IL)), colony stimulating factors (e.g., granulocyte colony stimulating factor, erythropoietin) and the like, with preference given to interleukins such as IL-1, IL-2, IL-12 and the like.

Examples of the antiinflammatory agents include non-steroidal antiinflammatory agents such as aspirin, acetaminophen, indomethacin and the like.

Examples of the antithrombotic agents include heparin (e.g., heparin sodium, heparin calcium, enoxaparin sodium, dalteparin sodium), warfarins (e.g., warfarin potassium), anti-thrombin drugs (e.g., aragatroban, dabigatran)), FXa inhibitors (e.g., rivaroxaban, apixaban, edoxaban, YM150, compounds described in WO02/06234, WO2004/048363, WO2005/030740, WO2005/058823 and WO2005/113504), thrombolytic agents (e.g., urokinase, tisokinase, alteplase, nateplase, monteplase, pamiteplase), platelet aggregation inhibitors (e.g., ticlopidine hydrochloride, clopidogrel, prasugrel, E5555, SHC530348, cilostazol, ethyl icosapentate, beraprost sodium, sarpogrelate hydrochloride) and the like.

Examples of the therapeutic agents for osteoporosis include alfacalcidol, calcitriol, elcatonin, calcitonin salmon, estriol, ipriflavone, pamidronate disodium, alendronate sodium hydrate, incadronate disodium, risedronate disodium and the like.

Examples of the vitamins include vitamin $B_1$, vitamin $B_{12}$ and the like.

Examples of the antidementia agents include tacrine, donepezil, rivastigmine, galanthamine and the like.

Examples of the erectile dysfunction improving drug include apomorphine, sildenafil citrate and the like.

Examples of the therapeutic agents for pollakiuria or urinary incontinence include flavoxate hydrochloride, oxybutynin hydrochloride, propiverine hydrochloride and the like.

Examples of the therapeutic agents for dysuria include acetylcholine esterase inhibitors (e.g., distigmine) and the like.

Furthermore, drugs having a cachexia-improving action established in animal models and clinical situations, such as cyclooxygenase inhibitors (e.g., indomethacin), progesterone derivatives (e.g., megestrol acetate), glucosteroids (e.g., dexamethasone), metoclopramide agents, tetrahydrocannabinol agents, fat metabolism improving agents (e.g., eicosapentanoic acid), growth hormones, IGF-1, or antibodies to a cachexia-inducing factor such as TNF-α, LIF, IL-6, oncostatin M and the like, can be used in combination with the compound of the present invention.

Furthermore, glycosylation inhibitors (e.g., ALT-711), nerve regeneration promoting drugs (e.g., Y-128, VX853, prosaptide), antidepressants (e.g., desipramine, amitriptyline, imipramine), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR agent), $α_2$ receptor agonists (e.g., clonidine), local analgesics (e.g., capsaicin), antianxiety drugs (e.g., benzothiazepines), phosphodiesterase inhibitors (e.g., sildenafil), dopamine receptor agonists (e.g., apomorphine), midazolam, Ketoconazole and the like can be also used in combination with the compound of the present invention.

The concomitant drug is preferably an insulin preparation, a PPAR function modulator (preferably pioglitazone or its hydrochloride), an α-glucosidase inhibitor (preferably voglibose), a biguanide (preferably metformin or hydrochloride thereof), a sulfonylurea (preferably glibenclamide, glimepiride), mitiglinide or calcium salt hydrate thereof, nateglinide, a dipeptidyl peptidase IV inhibitor (preferably alogliptin or benzoate thereof, 2-[[6-[(3R)-3-amino-1-piperidinyl]-3,4-dihydro-3-methyl-2,4-dioxo-1(2H)-pyrimidinyl]methyl]-4-fluorobenzonitrile or succinate thereof, 2-[2-(3-(R)-amino-piperidin-1-yl)-5-fluoro-6-oxo-6H-pyrimidin-1-ylmethyl]-benzonitrile or tartrate thereof), GLP-1 receptor agonist and the like. For enhancing the food ingestion suppressive action, a combined use with a dipeptidyl peptidase IV inhibitor (preferably, alogliptin or a salt thereof) is more preferable. Two or more kinds of the above-mentioned concomitant drugs may be used in combination at an appropriate ratio.

When the compound of the present invention is used in combination with a concomitant drug, the amounts thereof can be increased or decreased within the safe range in consideration of the side effects thereof. Particularly, the doses of insulin sensitizer, dipeptidyl peptidase IV inhibitor, α-glucosidase inhibitor, biguanide, insulin secretagogue and GLP-1 receptor agonist can be reduced from the general doses. Therefore, the side effects that will be caused by these agents can be prevented safely. In addition, the doses of therapeutic agents for diabetic complications, therapeutic agents for hyperlipidemia, and antihypertensive agents can be reduced and, as a result, the side effects that will be caused by these agents can be prevented effectively.

By combining the compound of the present invention with a concomitant drug, superior effects such as (1) decreased dose of the compound of the present invention or a concomitant drug as compared to single administration of the compound of the present invention or a concomitant drug, (2) possible setting of a long treatment period by selecting a concomitant drug having different action and mechanism from those of the compound of the present invention, (3) possible designing of a sustained treatment effect by selecting a concomitant drug having different action and mechanism from those of the compound of the present invention, (4) a synergistic effect afforded by a combined use of the compound of the present invention and a concomitant drug, and the like can be achieved.

When the compound of the present invention and a concomitant drug are used in combination, the administration time of the compound of the present invention and the concomitant drug is not restricted, and the compound of the present invention and the concomitant drug may be administered simultaneously, or may be administered at staggered times, to an administration subject. The dosage of the concomitant drug may be determined according to the dose clinically used, and can be appropriately selected depending on an administration subject, administration route, disease, combination and the like.

As the administration mode of the compound of the present invention and the concomitant drug, the following methods can be mentioned: (1) The compound of the present invention and the concomitant drug are simultaneously formulated to give a single preparation which is administered. (2) The compound of the present invention and the concomitant drug are separately formulated to give two kinds of preparations which are administered simultaneously by the same administration route. (3) The compound of the present invention and the concomitant drug are separately formulated to give two kinds of preparations which are administered by the same administration route at staggered times. (4) The compound of the present invention and the concomitant drug are separately formulated to give two kinds of preparations which are administered simultaneously by the different administration routes. (5) The compound of the present invention and the concomitant drug are separately formulated to give two kinds of preparations which are administered by the different administration routes at staggered times (e.g., the compound of the present invention and the concomitant drug are administered in this order, or in the reverse order), and the like.

EXAMPLES

The present invention is further explained in detail by referring to the following Examples and Experimental Example which are not to be construed as limitative and may be changed without departing from the scope of the present invention.

The term "room temperature" in the following Examples indicates the range of generally from about 10° C. to about 35° C. The ratios indicated for mixed solvents are volume mixing ratios, unless otherwise specified. % means wt %, unless otherwise specified.

In silica gel column chromatography, NH means use of aminopropylsilane-bound silica gel. In HPLC (high performance liquid chromatography), C18 means use of octadecyl-bound silica gel. The ratios of elution solvents are volume mixing ratios, unless otherwise specified.

In the following Examples, the following abbreviations are used.

mp: melting point
THF: tetrahydrofuran
DMF: dimethylformamide
WSC: 1-(3-dimethylaminopropyl)-3-ethylcarbodiimide hydrochloride
HOBt: 1-hydroxybenzotriazole monohydrate $^1$H NMR (proton nuclear magnetic resonance spectrum) was measured by Fourier-transform type NMR. For the analysis, ACD/SpecManager (trade name) and the like were used. Peaks with very mild protons such as hydroxyl group, amino group and the like are not described.

The other symbols used herein mean the following:

s: singlet
d: doublet
t: triplet
q: quartet
m: multiplet
br: broad
J: coupling constant
Hz: Hertz
CDCl$_3$: deuterated chloroform
DMSO-d$_6$: d$_6$-dimethyl sulfoxide
$^1$H-NMR: proton nuclear magnetic resonance
TFA: trifluoroacetic acid MS (mass spectrum) was measured by LC/MS (liquid chromatography mass spectrometer). As the ionization method, ESI (ElectroSpray Ionization) method, or APCI (Atmospheric Pressure Chemical Ionization) method was used. As the ionization mode, both or either one of the positive mode (ESI+) and negative mode (ESI-) were/was used and either data are described. The data indicates those found. Generally, a molecular ion peak is observed. In the case of a compound having a tert-butoxycarbonyl group (-Boc), a peak after elimination of a tert-butoxycarbonyl group or tert-butyl group may be observed as a fragment ion. Depending on the compound, a peak after addition of a sodium ion (+Na) is sometimes observed as a fragment ion. In the case of a compound having a hydroxyl group (—OH), a peak after elimination of H$_2$O may be observed as a fragment ion. In the case of a salt, a molecular ion peak or fragment ion peak of free form is generally observed.

The unit of reagent concentration (c) in optical rotation ([α]$_D$) is g/100 mL.

The elemental analysis value (Anal.) shows Calculated (Calcd) and Found.

Example 1

(3-(((6-(2,2-dimethylpropyl)-5-(2-fluoro-5-methoxyphenyl)pyridin-2-yl)oxy)methyl)phenoxy)acetic acid A) ethyl 2-(3-formylphenoxy)acetate To a solution of 3-hydroxybenzaldehyde (10.0 g) and ethyl bromoacetate (15.0 g) in DMF (150 mL) was added potassium carbonate (17.0 g), and the mixture was stirred at 60° C. for 15 hr. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (16.7 g) as a colorless oil.

$^1$H NMR (300 MHz, CDCl$_3$) δ 1.31 (3H, t, J=7.2 Hz), 4.27 (2H, q, J=7.2 Hz), 7.24 (2H, s), 7.35-7.40 (1H, m), 7.42-7.54 (2H, m), 9.97 (1H, s).

B) ethyl 2-(3-(hydroxymethyl)phenoxy)acetate

To a suspension of sodium tetrahydroborate (3.64 g) in methanol (150 mL) was added dropwise ethyl 2-(3-(hydroxymethyl)phenoxy)acetate (16.7 g) under ice-cooling, and the mixture was stirred for 1 hr. To the reaction mixture was added 1N hydrochloric acid (100 mL), and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (9.10 g) as a colorless oil.

$^1$H NMR (300 MHz, CDCl$_3$) δ 1.30 (3H, t, J=7.2 Hz), 4.27 (2H, q, J=7.2 Hz), 4.63 (2H, s), 4.67 (2H, s), 6.82-6.85 (1H, m), 6.94-7.00 (1 H, m), 7.26-7.60 (2H, m).

C) ethyl 2-(3-(((methylsulfonyl)oxy)methyl)phenoxy)acetate

To a solution of ethyl 2-(3-(hydroxymethyl)phenoxy)acetate (2.00 g) and triethylamine (1.44 g) in THF (10 mL) was added methanesulfonyl chloride (1.31 g) at 0° C., and the mixture was stirred for 1 hr. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (2.80 g) as a colorless oil.

$^1$H NMR (300 MHz, CDCl$_3$) δ 1.31 (3H, t, J=7.2 Hz), 2.91 (3H, s), 4.27 (2H, q, J=7.2 Hz), 4.64 (2H, s), 5.21 (2H, s), 6.93-6.97 (2H, m), 7.00-7.06 (1H, m), 7.26-7.36 (1H, m).

D) 2-chloro-3-(2-fluoro-5-methoxyphenyl)-6-methoxypyridine

Under an argon atmosphere, to a solution of 3-bromo-2-chloro-6-methoxypyridine (4.61 g) in toluene (60 mL) were added (2-fluoro-5-methoxyphenyl)boronic acid (3.52 g), [1,1-bis(diphenylphosphino)ferrocene]dichloropalladium (II)dichlorome thane adduct (1.69 g) and 2.0 M aqueous sodium carbonate solution (31.1 mL), and the mixture was stirred at 80° C. for 1 hr. Water was added at room temperature, and the reaction mixture was extracted with ethyl acetate. The extract was washed with water and saturated brine and dried over anhydrous magnesium sulfate. The solvent was evaporated under reduced pressure and the residue was purified by silica gel column chromatography (ethyl acetate/hexane) to give the title compound (4.06 g) as a white amorphous solid.

$^1$H NMR (300 MHz, DMSO-$d_6$) δ 3.77 (3H, s), 3.91 (3H, s), 6.90-6.94 (1H, m), 6.96 (1H, d, J=8.3 Hz), 6.98-7.06 (1H, m), 7.24 (1H, t, J=9.1 Hz), 7.80 (1H, d, J=8.3 Hz).

E) 3-(2-fluoro-5-methoxyphenyl)-6-methoxy-2-neopentylpyridine

Under an argon atmosphere, a solution of 1-bromo-2,2-dimethylpropane (9.82 mL) in diethyl ether (100 mL) was added dropwise to magnesium (1.72 g) at a slow refluxing rate, and the reaction mixture was heated under reflux further for 1 hr. Under an argon atmosphere, the obtained solution was added dropwise to a solution of 2-chloro-3-(2-fluoro-5-methoxyphenyl)-6-methoxypyridine (3.79 g) and a PEPPSI™-SIPr catalyst (trade name) (970 mg) in THF (70 mL) at room temperature, and the mixture was stirred at room temperature for 15 min. To the reaction mixture was added saturated aqueous ammonium chloride solution at room temperature, and the mixture was extracted with ethyl acetate. The extract was washed with water and saturated brine and dried over anhydrous magnesium sulfate. The solvent was evaporated under reduced pressure and the residue was purified by silica gel column chromatography (ethyl acetate/hexane) to give the title compound (3.97 g) as a colorless oil.

$^1$H NMR (300 MHz, DMSO-$d_6$) δ 0.80 (9H, s), 2.50-2.60 (2H, m), 3.75 (3H, s), 3.88 (3H, s), 6.73 (1H, d, J=8.7 Hz), 6.82 (1H, dd, J=6.2, 3.2 Hz), 6.97 (1H, dt, J=8.8, 3.7 Hz), 7.21 (1H, t, J=9.0 Hz), 7.50 (1H, d, J=8.3 Hz).

F) 5-(2-fluoro-5-methoxyphenyl)-6-neopentylpyridin-2-ol

Under a nitrogen atmosphere, to a solution of 3-(2-fluoro-5-methoxyphenyl)-6-methoxy-2-neopentylpyridine (3.97 g) in DMF (10 mL) was added pyridinium chloride (7.56 g) at room temperature, and the mixture was stirred at 130° C. for 30 min. To the reaction mixture was added 1N hydrochloric acid at 0° C., and the resulting white precipitate was collected by filtration. The crude crystals were washed with water and hexane to give the title compound (3.64 g) as a white amorphous solid.

$^1$H NMR (300 MHz, DMSO-$d_6$) δ 0.69 (9H, s), 2.39-2.52 (2H, m), 3.74 (3H, s), 6.26 (1H, d, J=9.4 Hz), 6.83-6.97 (2H, m), 7.18 (1H, t, J=9.2 Hz), 7.30 (1H, d, J=8.7 Hz), 11.43 (1H, brs).

G) ethyl 2-(3-(((5-(2-fluoro-5-methoxyphenyl)-6-neopentylpyridin-2-yl)oxy)methyl)phenoxy)acetate To a solution of, ethyl 2-(3-(((methylsulfonyl)oxy)methyl)phenoxy)acetate (100 mg) and 5-(2-fluoro-5-methoxyphenyl)-6-neopentylpyridin-2-ol (100 mg) in DMF (3.0 mL) was added potassium carbonate (72 mg), and the mixture was stirred at 80° C. for 3 hr. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (77 mg) as a colorless oil.

MS (ESI+): [M+H]$^+$ 482.2

H) (3-(((6-(2,2-dimethylpropyl)-5-(2-fluoro-5-methoxyphenyl)pyridin-2-yl)oxy)methyl)phenoxy)acetic acid To a solution of ethyl 2-(3-(((5-(2-fluoro-5-methoxyphenyl)-6-neopentylpyridin-2-yl)oxy)methyl)phenoxy)acetate (77 mg) in THF (3.0 mL) and methanol (3.0 mL) was added 1N aqueous sodium hydroxide solution (1.0 mL), and the mixture was stirred at 50° C. for 30 min. To the reaction mixture was added 1N hydrochloric acid (1.0 mL), and the mixture was extracted with ethyl acetate. The extract was washed with saturated brine and dried over anhydrous sodium sulfate. The solvent was evaporated under reduced pressure to give the title compound (63 mg) as a colorless oil.

$^1$H NMR (300 MHz, DMSO-$d_6$) δ 0.77 (9H, s), 2.50 (2H, s), 3.75 (3H, s), 4.65 (2H, s), 5.36 (2H, s), 6.73-6.90 (3H, m), 6.92-7.08 (3H, m), 7.21 (1H, t, J=9.1 Hz), 7.25-7.34 (1H, m), 7.53 (1H, d, J=8.3 Hz).

MS (ESI+): [M+H]$^+$ 454.1

Example 2

(3-(((2-(2,2-dimethylpropyl)-2'-fluoro-5'-methoxybiphenyl-4-yl)oxy)methyl)phenoxy)acetic acid

A) (((4-bromo-1,3-phenylene)bis(oxy))bis(methylene))dibenzene

To a solution of 4-bromoresorcinol (10.0 g) and potassium carbonate (21.9 g) in DMF (100 mL) was added benzyl bromide (13.2 mL), and the mixture was stirred at room temperature for 4 hr. Water was added to the reaction mixture, and the mixture was extracted with ethyl acetate. The extract was washed with saturated brine and dried over anhydrous magnesium sulfate. The solvent was evaporated under reduced pressure to give the title compound (21.8 g) as a crude oil. This compound was used for the next step without further purification.

$^1$H NMR (300 MHz, DMSO-$d_6$) δ 5.10 (2H, s), 5.20 (2H, s), 6.60 (1H, dd, J=8.7, 2.6 Hz), 6.89 (1H, d, J=2.6 Hz), 7.27-7.56 (11H, m).

B) 2,4-bis(benzyloxy)-2'-fluoro-5'-methoxy-1,1'-biphenyl

Under an argon atmosphere, to a solution of (((4-bromo-1,3-phenylene)bis(oxy))bis(methylene))dibenzene (21.8 g) in toluene (160 mL) were added 2-fluoro-5-methoxyphenylboronic acid (13.8 g), 2-dicyclohexylphosphino-2',6'-dimethoxybiphenyl (2.23 g), tris(dibenzylideneacetone)dipalladium(0) (1.24 g) and 2.0 M aqueous sodium carbonate solution (81.0 mL), and the mixture was stirred at 80° C. for 14 hr. The reaction mixture was diluted with water, and filtered through celite. The filtrate was extracted with ethyl acetate, and the extract was washed with saturated brine and dried over anhydrous magnesium sulfate. The solvent was evaporated under reduced pressure and the residue was purified by silica gel column chromatography (ethyl acetate/hexane) to give the title compound (22.1 g) as a pale-yellow oil.

$^1$H NMR (300 MHz, DMSO-$d_6$) δ 1.99 (1H, s), 3.72 (3H, s), 5.11 (2H, s), 5.14 (2H, s), 6.70 (1H, dd, J=8.5, 2.1 Hz), 6.81-6.93 (3H, m), 7.08-7.54 (12H, m).

C) 2'-fluoro-5'-methoxy-[1,1'-biphenyl]-2,4-diol

To a solution of 2,4-bis(benzyloxy)-2'-fluoro-5'-methoxy-1,1'-biphenyl (23.9 g) in THF (300 mL) was added 10% palladium-activated carbon (9.60 g) and, under a hydrogen atmosphere, the mixture was stirred at room temperature for 2 hr. The reaction mixture was filtered through celite, and the filtrate was concentrated under reduced pressure to give the title compound (21.8 g) as a colorless crude oil. This compound was used for the next step without further purification.

$^1$H NMR (300 MHz, DMSO-$d_6$) δ 3.73 (3H, s), 6.28 (1H, dd, J=8.1, 2.5 Hz), 6.39 (1H, d, J=2.3 Hz), 6.75-6.88 (2H, m), 6.94 (1H, d, J=8.3 Hz), 7.02-7.12 (1H, m), 9.35 (2H, s).

D) 2'-fluoro-5'-methoxy-4-((triisopropylsilyl)oxy)-[1,1'-biphenyl]-2-ol

Under a nitrogen atmosphere, to a solution of 2'-fluoro-5'-methoxy-[1,1'-biphenyl]-2,4-diol (14.6 g) and 2,6-dimethylpyridine (10.2 mL) in toluene (100 mL) was added triisopropylsilyl trifluoromethanesulfonate (21.1 mL) at −15° C., and the mixture was stirred at −15° C. for 20 min. To the reaction mixture was added 1N hydrochloric acid, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound as a white amorphous solid.

E) 2'-fluoro-5'-methoxy-4-((triisopropylsilyl)oxy)-[1,1'-biphenyl]-2-yl trifluoromethanesulfonate Under a nitrogen atmosphere, to a solution of 2'-fluoro-5'-methoxy-4-((triisopropylsilyl)oxy)-[1,1'-biphenyl]-2-ol (entire amount) obtained in Example 2, step D, in pyridine (87 mL) was added trifluoromethanesulfonic anhydride (14.8 mL) at 0° C., and the mixture was stirred at 0° C. for 20 min. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (22.7 g) as a colorless oil.

$^1$H NMR (300 MHz, DMSO-$d_6$) δ 1.04-1.14 (18H, m), 1.22-1.40 (3H, m), 3.77 (3H, s), 6.94 (1H, dd, J=5.8, 3.2 Hz), 6.98-7.07 (2H, m), 7.11 (1H, dd, J=8.3, 2.3 Hz), 7.25 (1H, t, J=9.2 Hz), 7.50 (1H, d, J=8.7 Hz).

F) ((2'-fluoro-5'-methoxy-2-neopentyl-[1,1'-biphenyl]-4-yl)oxy)triisopropylsilane Under an argon atmosphere, a solution of 1-bromo-2,2-dimethylpropane (23.2 mL) in diethyl ether (250 mL) was added dropwise to magnesium (4.92 g) at a slow refluxing rate, and the reaction mixture was heated under reflux further for 30 min. Under an argon atmosphere, to a solution of 2'-fluoro-5'-methoxy-4-((triisopropylsilyl)oxy)-[1,1'-biphenyl]-2-yl trifluoromethanesulfonate (19.2 g) and a PEPPSI™-SIPr catalyst (trade name) (1.26 g) in THF (200 mL) was added the solution prepared above, and the mixture was stirred at room temperature for 1 hr. To the reaction mixture was added saturated aqueous ammonium chloride solution, and the mixture was extracted with ethyl acetate. The extract was washed with saturated brine and dried over anhydrous magnesium sulfate. The solvent was evaporated under reduced pressure to give the title compound as a crude oil. This compound was used for the next step without further purification.

G) 2'-fluoro-5'-methoxy-2-neopentyl-[1,1'-biphenyl]-4-ol

A 1.0M solution of tetrabutylammonium fluoride in THF (73.6 mL) was added to a solution of ((2'-fluoro-5'-methoxy-2-neopentyl-[1,1'-biphenyl]-4-yl)oxy)triisopropylsilane (total amount) obtained in Example 2, step F, in THF (30 mL) at room temperature, and the mixture was stirred for 15 min. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (8.68 g) as a pale-yellow amorphous solid.

$^1$H NMR (300 MHz, DMSO-$d_6$) δ 0.65 (9H, s), 2.28-2.50 (2H, m), 3.73 (3H, s), 6.64-6.71 (2H, m), 6.74 (1H, dd, J=6.0, 3.0 Hz), 6.90 (1H, dt, J=9.0, 3.4 Hz), 6.96 (1H, d, J=8.7 Hz), 7.14 (1H, t, J=9.1 Hz), 9.40 (1H, s).

H) ethyl 2-(3-(((2'-fluoro-5'-methoxy-2-neopentyl-[1,1'-biphenyl]-4-yl)oxy)methyl)phenoxy)acetate To a solution of ethyl 2-(3-(((methylsulfonyl)oxy)methyl)phenoxy)acetate (94 mg) and 2'-fluoro-5'-methoxy-2-neopentyl-[1,1'-biphenyl]-4-ol (120 mg) in DMF (3.0 mL) was added potassium carbonate (67 mg), and the mixture was stirred at 80° C. for 3 hr. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (102 mg) as a colorless oil.

I) (3-(((2-(2,2-dimethylpropyl)-2'-fluoro-5'-methoxy-biphenyl-4-yl)oxy)methyl)phenoxy)acetic acid To a solution of ethyl 2-(3-(((5-(2-fluoro-5-methoxyphenyl)-6-neopentylpyridin-2-yl)oxy)methyl)phenoxy)acetate (102 mg) in THF (3.0 mL) and methanol (3.0 mL) was added 1N aqueous sodium hydroxide solution (0.97 mL), and the mixture was stirred at 80° C. for 30 min. To the reaction mixture was added 1N hydrochloric acid (1.0 mL), and the mixture was extracted with ethyl acetate. The extract was washed with saturated brine and dried over anhydrous sodium sulfate. The solvent was evaporated under reduced pressure to give the title compound (83 mg) as a colorless oil.

$^1$H NMR (300 MHz, DMSO-$d_6$) δ 0.63 (9H, s), 2.50 (2H, s), 3.74 (3H, s), 4.67 (2H, s), 5.11 (2H, s), 6.77 (1H, d, J=6.2, 3.2 Hz), 6.82-6.97 (4H, m), 6.99-7.12 (3H, m), 7.12-7.20 (1H, m), 7.25-7.37 (1H, m).

MS (ESI+): [M+H]$^+$ 453.2

Example 3

3-cyclopropyl-3-(3-(((2-(2,2-dimethylpropyl)-2'-fluoro-5'-methoxybiphenyl-4-yl)oxy)methyl)phenyl)propanoic acid

A) (3-(((tert-butyldiphenylsilyl)oxy)methyl)phenyl)methanol

Under a nitrogen atmosphere, to a suspension of 60% sodium hydride (1.40 g) in THF (70 mL) was slowly added 1,3-phenylenedimethanol (4.84 g) at 0° C., and the mixture was stirred at 0° C. for 1 hr. tert-Butylchlorodiphenylsilane (9.63 g) was added, and the mixture was stirred at room temperature for 3 hr. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (6.97 g) as a colorless oil.

$^1$H NMR (300 MHz, DMSO-d$_6$) δ 1.04 (9H, s), 4.49 (2H, d, J=5.7 Hz), 4.77 (2H, s), 5.15 (1H, t, J=5.9 Hz), 7.18-7.25 (2H, m), 7.27-7.34 (2H, m), 7.40-7.51 (6H, m), 7.62-7.69 (4H, m).

B) 3-(((tert-butyldiphenylsilyl)oxy)methyl)benzaldehyde

To a solution of (3-(((tert-butyldiphenylsilyl)oxy)methyl) phenyl)methanol (6.96 g) in THF (37 mL) was added manganese(IV) oxide (8.03 g), and the mixture was stirred at room temperature for 5.5 hr. The reaction mixture was filtered through celite, and the filtrate was concentrated under reduced pressure. The residue was purified by silica gel column chromatography (ethyl acetate/hexane) to give the title compound (6.61 g) as a pale-yellow oil.

$^1$H NMR (300 MHz, DMSO-d$_6$) δ 1.06 (9H, s), 4.88 (2H, s), 7.41-7.51 (6H, m), 7.57-7.70 (6H, m), 7.83 (1H, d, J=7.6 Hz), 7.90 (1H, s), 10.01 (1H, s).

C) 5-(3-(((tert-butyldiphenylsilyl)oxy)methyl)benzylidene)-2,2-dimethyl-1,3-dioxane-4,6-dione To a solution of titanium (IV) chloride (9.88 g) in THF (80 mL) were added dropwise a solution of meldrum's acid (3.75 g) and 3-(((tert-butyldiphenylsilyl)oxy)methyl)benzaldehyde (6.50 g) in THF (50 mL) at 0° C., and pyridine (11.0 g) was further added dropwise at 0° C. over 30 min. The reaction mixture was stirred at 0° C. for 50 min, and water (100 mL) was added dropwise at 0° C. over 5 min. Water was further added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (6.40 g) as a white amorphous solid.

$^1$H NMR (300 MHz, DMSO-d$_6$) δ 1.06 (9H, s), 4.88 (2H, s), 7.40-7.50 (6H, m), 7.57-7.71 (6H, m), 7.82 (1H, d, J=7.6 Hz), 7.90 (1H, s), 10.01 (1H, s).

D) 5-((3-(((tert-butyldiphenylsilyl)oxy)methyl)phenyl) (cyclopropyl)methyl)-2,2-dimethyl-1,3-dioxane-4,6-dione Under an argon atmosphere, to a solution of 5-(3-(((tert-butyldiphenylsilyl)oxy)methyl)benzylidene)-2,2-dimethyl-1,3-dioxane-4,6-dione (6.39 g) in THF (85 mL) was added dropwise a 0.70 M solution of cyclopropylmagnesium bromide in THF (54.7 mL) at 0° C. over 15 min, and the mixture was stirred at 0° C. for 5.5 hr. 0.50N Hydrochloric acid (300 mL) was added dropwise at 0° C., and water was further added. The reaction mixture was extracted with ethyl acetate, and the extract was washed with saturated aqueous sodium hydrogen carbonate solution and saturated brine. The organic layer was dried over anhydrous sodium sulfate and the solvent was evaporated under reduced pressure. The residue was purified by silica gel column chromatography (ethyl acetate/hexane) to give the title compound (6.05 g) as a colorless oil.

$^1$H NMR (300 MHz, DMSO-d$_6$) δ 0.11-0.20 (1H, m), 0.38-0.46 (1H, m), 0.52-0.65 (2H, m), 1.04 (9H, s), 1.44 (3H, s), 1.72-1.81 (1H, m), 1.76 (3H, s), 2.83 (1H, dd, J=10.6, 2.6 Hz), 4.66 (1H, d, J=3.0 Hz), 4.74 (2H, s), 7.14-7.28 (3H, m), 7.40-7.49 (7H, m), 7.65 (4H, dd, J=7.0, 0.9 Hz).

E) ethyl 3-(3-(((tert-butyldiphenylsilyl)oxy)methyl) phenyl)-3-cyclopropylpropanoate To a solution of 5-((3-(((tert-butyldiphenylsilyl)oxy)methyl)phenyl) (cyclopropyl)methyl)-2,2-dimethyl-1,3-dioxane-4,6-dione (5.07 g) in DMF (40 mL) was added ethanol (20 mL), and the mixture was stirred at 100° C. for 4 hr. The reaction mixture was concentrated under reduced pressure, and water was added to the residue. The mixture was extracted with ethyl acetate, and the extract was washed with saturated brine and dried over anhydrous sodium sulfate. The solvent was evaporated under reduced pressure and the residue was purified by silica gel column chromatography (ethyl acetate/hexane) to give the title compound (4.55 g) as a pale-yellow oil.

$^1$H NMR (300 MHz, DMSO-d$_6$) δ 0.05-0.14 (1H, m), 0.18-0.37 (2H, m), 0.46-0.56 (1H, m), 0.94-1.12 (13H, m), 2.23-2.34 (1H, m), 2.62-2.78 (2H, m), 3.87-4.02 (2H, m), 4.76 (2H, s), 7.12-7.21 (2H, m), 7.22-7.30 (2H, m), 7.37-7.53 (6H, m), 7.57-7.70 (4H, m).

F) ethyl 3-cyclopropyl-3-(3-(hydroxymethyl)phenyl) propanoate

To a solution of ethyl 3-(3-(((tert-butyldiphenylsilyl)oxy) methyl)phenyl)-3-cyclopropylpropanoate (4.54 g) in THF (20 mL) was added a 1.0 M solution of tetrabutylammonium fluoride in THF (18.7 mL), and the mixture was stirred at room temperature for 4 hr. To the reaction mixture was added brine, and the mixture was extracted with ethyl acetate. The extract was dried over anhydrous sodium sulfate and the solvent was evaporated under reduced pressure. The residue was purified by silica gel column chromatography (ethyl acetate/hexane) to give the title compound (1.94 g) as a colorless oil.

$^1$H NMR (300 MHz, DMSO-d$_6$) δ 0.10 (1H, dt, J=9.1, 4.5 Hz), 0.17-0.26 (1H, m), 0.27-0.36 (1H, m), 0.45-0.56 (1H, m), 0.97-1.11 (4H, m), 2.22-2.32 (1H, m), 2.62-2.77 (2H, m), 3.90-4.02 (2H, m), 4.47 (2H, d, J=5.7 Hz), 5.12 (1H, t, J=5.9 Hz), 7.10-7.26 (4H, m).

G) ethyl 3-cyclopropyl-3-(3-(((2'-fluoro-5'-methoxy-2-neopentyl-[1,1'-biphenyl]-4-yl)oxy)methyl)phenyl) propanoate To a solution of 2'-fluoro-5'-methoxy-2-neopentyl-[1,1'-biphenyl]-4-ol (388 mg), ethyl 3-cyclopropyl-3-(3-(hydroxymethyl)phenyl)propanoate (261 mg) and triphenylphosphine (413 mg) in THF (10 mL) was added a 40% solution of diethyl azodicarboxylate in toluene (620 μL) at 0° C., and the mixture was stirred at room temperature for 70 min. The reaction mixture was concentrated under reduced pressure, and the residue was purified by silica gel column chromatography (ethyl acetate/hexane) to give the title compound (310 mg) as a pale-yellow oil.

$^1$H NMR (300 MHz, CDCl$_3$) δ 0.15 (1H, tt, J=9.4, 4.5 Hz), 0.28 (1H, dq, J=9.3, 4.7 Hz), 0.37-0.47 (1H, m), 0.54-0.63 (1H, m), 0.70 (9H, s), 0.97-1.10 (1H, m), 1.16 (3H, t, J=7.2 Hz), 2.33-2.65 (3H, m), 2.67-2.82 (2H, m), 3.79 (3H, s), 4.05 (2H, qd, J=7.2, 2.6 Hz), 5.07 (2H, s), 6.74 (1H, dd, J=5.9, 3.2

Hz), 6.78-6.85 (1H, m), 6.86-6.93 (2H, m), 6.96-7.05 (1H, m), 7.12 (1H, d, J=8.7 Hz), 7.18-7.23 (1H, m), 7.29-7.36 (3H, m).

H) 3-cyclopropyl-3-(3-(((2-(2,2-dimethylpropyl)-2'-fluoro-5'-methoxybiphenyl-4-yl)oxy)methyl)phenyl)propanoic acid To a solution of ethyl 3-cyclopropyl-3-(3-(((2'-fluoro-5'-methoxy-2-neopentyl-[1,1'-biphenyl]-4-yl)oxy)methyl)phenyl)propanoate (305 mg) in THF (6.0 mL) and methanol (12 mL) was added 1N aqueous sodium hydroxide solution (5.9 mL), and the mixture was stirred at room temperature for 1 hr. The reaction mixture was concentrated under reduced pressure, and the residue was purified by silica gel column chromatography (ethyl acetate/hexane) to give the title compound (282 mg) as a pale-yellow oil.
$^1$H NMR (300 MHz, CDCl$_3$) δ 0.05-0.15 (1H, m), 0.20-0.36 (2H, m), 0.46-0.54 (1H, m), 0.63 (9H, s), 0.95-1.08 (1H, m), 2.27-2.36 (1H, m), 2.59-2.73 (2H, m), 3.74 (3H, s), 5.11 (2H, s), 6.77 (1H, dd, J=6.0, 3.0 Hz), 6.85-7.00 (3H, m), 7.08-7.37 (6H, m), 12.06 (1H, brs), the peak of 2H overlaps with that of the residual DMSO.

Example 4

3-cyclopropyl-3-(3-(((6-(2,2-dimethylpropyl)-5-(2-fluoro-5-methoxyphenyl)pyridin-2-yl)oxy)methyl)phenyl)propanoic acid A) ethyl 3-cyclopropyl-3-(3-(((5-(2-fluoro-5-methoxyphenyl)-6-neopentylpyridin-2-yl)oxy)methyl)phenyl)propanoate To a solution of 5-(2-fluoro-5-methoxyphenyl)-6-neopentylpyridin-2-ol (300 mg) in THF (20 mL) were added a solution of ethyl 3-cyclopropyl-3-(3-(hydroxymethyl)phenyl)propanoate (283 mg) in THF (5.0 mL), 1,1'-(azodicarbonyl)dipiperidine (523 mg) and tri-n-butylphosphine (420 mg) at 0° C., and the mixture was stirred at 0° C. for 5 min. The mixture was further stirred at room temperature for 16 hr, and concentrated under reduced pressure. The residue was purified by silica gel column chromatography (ethyl acetate/hexane) to give the title compound (384 mg) as a colorless oil.
$^1$H NMR (300 MHz, DMSO-d$_6$) δ 0.06-0.15 (1H, m), 0.18-0.36 (2H, m), 0.46-0.56 (1H, m), 0.77 (9H, s), 1.06 (4H, t, J=7.0 Hz), 2.25-2.34 (1H, m), 2.65-2.80 (2H, m), 3.75 (3H, s), 3.95 (2H, qd, J=7.2, 2.3 Hz), 5.37 (2H, s), 6.74-6.85 (2H, m), 6.97 (1H, dt, J=9.0, 3.6 Hz), 7.16-7.37 (5H, m), 7.53 (1H, d, J=8.3 Hz), the peak of 2H overlaps with that of the residual DMSO.

B) 3-cyclopropyl-3-(3-(((6-(2,2-dimethylpropyl)-5-(2-fluoro-5-methoxyphenyl)pyridin-2-yl)oxy)methyl)phenyl)propanoic acid To a solution of ethyl 3-cyclopropyl-3-(3-(((5-(2-fluoro-5-methoxyphenyl)-6-neopentylpyridin-2-yl)oxy)methyl)phenyl)propanoate (379 mg) in THF (7.0 mL) and methanol (14 mL) was added 1N aqueous sodium hydroxide solution (7.3 mL), and the mixture was stirred at room temperature for 7 hr. The reaction mixture was concentrated under reduced pressure, and water and 1N hydrochloric acid were added. The reaction mixture was extracted with ethyl acetate, and the extract was washed with saturated brine and dried over anhydrous sodium sulfate. The solvent was evaporated under reduced pressure and the residue was purified by silica gel column chromatography (ethyl acetate/hexane) to give the title compound (334 mg) as a colorless oil.
$^1$H NMR (300 MHz, DMSO-d$_6$) δ 0.05-0.15 (1H, m), 0.19-0.36 (2H, m), 0.45-0.57 (1H, m), 0.77 (9H, s), 0.95-1.07 (1H, m), 2.26-2.35 (1H, m), 2.53-2.75 (4H, m), 3.75 (3H, s), 5.37 (2H, s), 6.76-6.86 (2H, m), 6.97 (1H, dt, J=8.7, 3.6 Hz), 7.15-7.33 (4H, m), 7.35 (1H, s), 7.53 (1H, d, J=8.3 Hz), 11.98 (1H, brs).

Example 5 sodium 3-cyclopropyl-3-(3-(((2-(2,2-dimethylpropyl)-2'-fluoro-5'-methoxybiphenyl-4-yl)oxy)methyl)phenyl)propanoate A 28% solution of sodium methoxide (100 mg) in methanol was added to a solution of 3-cyclopropyl-3-(3-(((2-(2,2-dimethylpropyl)-2'-fluoro-5'-methoxybiphenyl-4-yl)oxy)methyl)phenyl)propanoic acid (255 mg) in methanol (2.5 mL), and the mixture was stirred at room temperature for 5 min. The reaction mixture was concentrated under reduced pressure to give the title compound (252 mg) as a white amorphous solid.
$^1$H NMR (300 MHz, DMSO-d$_6$) δ 0.01-0.07 (1H, m), 0.18-0.29 (2H, m), 0.34-0.44 (1H, m), 0.63 (9H, s), 0.85-1.01 (1H, m), 2.16-2.48 (5H, m), 3.74 (3H, s), 5.09 (2H, s), 6.77 (1H, dd, J=6.0, 3.0 Hz), 6.87-6.99 (3H, m), 7.08-7.27 (5H, m), 7.30 (1H, s).

Example 6 sodium 3-cyclopropyl-3-(3-(((6-(2,2-dimethylpropyl)-5-(2-fluoro-5-methoxyphenyl)pyridin-2-yl)oxy)methyl)phenyl)propanoate A 28% solution of sodium methoxide (117 mg) in methanol was added to a solution of 3-cyclopropyl-3-(3-(((6-(2,2-dimethylpropyl)-5-(2-fluoro-5-methoxyphenyl)pyridin-2-yl)oxy)methyl)phenyl)propanoic acid (299 mg) in methanol (4.0 mL), and the mixture was stirred at room temperature for 5 min. The reaction mixture was concentrated under reduced pressure to give the title compound (316 mg) as a white amorphous solid.
$^1$H NMR (300 MHz, DMSO-d$_6$) δ −0.02-0.08 (1H, m), 0.17-0.28 (2H, m), 0.34-0.45 (1H, m), 0.78 (9H, s), 0.91 (1H, dt, J=9.0, 6.7 Hz), 2.15-2.60 (5H, m), 3.75 (3H, s), 5.35 (2H, s), 6.79 (1H, d, J=8.3 Hz), 6.83 (1H, dd, J=6.0, 3.0 Hz), 6.97 (1H, dt, J=8.9, 3.5 Hz), 7.11-7.27 (4H, m), 7.29 (1H, s), 7.52 (1H, d, J=8.3 Hz).

Example 7

3-(3-(((2-(2,2-dimethylpropyl)-2'-fluoro-5'-methoxybiphenyl-4-yl)oxy)methyl)phenyl)propanoic acid A) (E)-3-(3-ethoxy-3-oxoprop-1-en-1-yl)benzoic acid Under an argon atmosphere, to a solution of 3-iodobenzoic acid (20.2 g) in DMF (130 mL) were added ethyl acrylate (9.00 g), triethylamine (24 mL) and palladium (II) acetate (92 mg), and the mixture was stirred at 140° C. for 3 hr. The reaction mixture was cooled to room temperature, and 1N hydrochloric acid was added. The reaction mixture was extracted with ethyl acetate. The extract was washed with water and saturated brine and dried over anhydrous magnesium sulfate. The solvent was evaporated under reduced pressure and the residue was purified by silica gel column chromatography (ethyl acetate/hexane) to give the title compound (18.7 g) as an orange amorphous solid.

$^1$H NMR (300 MHz, CDCl$_3$) δ 1.36 (3H, t, J=7.2 Hz), 4.29 (2H, q, J=7.2 Hz), 6.54 (1H, d, J=16.0 Hz), 7.52 (1H, t, J=7.7 Hz), 7.69-7.79 (1H, m), 7.71 (1H, d, J=16.0 Hz), 8.09-8.19 (1H, m), 8.23-8.35 (1H, m).

B) 3-(3-ethoxy-3-oxopropyl)benzoic acid

To a solution of (E)-3-(3-ethoxy-3-oxoprop-1-en-1-yl) benzoic acid (8.60 g) in ethanol (500 mL) was added 10% palladium-activated carbon (4.10 g) and, under a hydrogen atmosphere, the mixture was stirred at room temperature for 3 hr. The reaction mixture was filtered, and the filtrate was concentrated under reduced pressure to give the title compound (8.70 g) as a white amorphous solid.

$^1$H NMR (300 MHz, CDCl$_3$) δ 1.24 (3H, t, J=7.0 Hz), 2.66 (2H, t, J=8.0 Hz), 3.03 (2H, t, J=7.6 Hz), 4.14 (2H, q, J=7.0 Hz), 7.30-7.54 (2H, m), 7.84-8.02 (2H, m).

C) 3-(3-(hydroxymethyl)phenyl)propan-1-ol

Under a nitrogen atmosphere, to a solution of 3-(3-ethoxy-3-oxopropyl)benzoic acid (2.99 g) in THF (100 mL) was added a 1.0 M solution of tetrahydrofuran-borane in tetrahydrofuran (26.9 mL) at 0° C., and the mixture was stirred in an ice bath for 18 hr. A 1.0 M solution of tetrahydrofuran-borane in tetrahydrofuran (20.0 mL) was added at 0° C., and the mixture was further stirred for 20 hr in an ice bath. 1N Hydrochloric acid (100 mL) and water were added at 0° C., and the reaction mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (1.80 g) as a colorless oil.

$^1$H NMR (300 MHz, DMSO-d$_6$) δ 1.65-1.75 (2H, m), 2.55-2.62 (2H, m), 3.41 (2H, td, J=6.4, 5.3 Hz), 4.40-4.48 (3H, m), 5.10 (1H, t, J=5.7 Hz), 7.00-7.15 (3H, m), 7.18-7.25 (1H, m).

D) 3-(3-(((2'-fluoro-5'-methoxy-2-neopentyl-[1,1'-biphenyl]-4-yl)oxy)methyl)phenyl)propan-1-ol To a solution of 2'-fluoro-5'-methoxy-2-neopentyl-[1,1'-biphenyl]-4-ol (312 mg), 3-(3-(hydroxymethyl)phenyl)propan-1-ol (199 mg) and triphenylphosphine (522 mg) in THF (10 mL) was added a 40% solution of diethyl azodicarboxylate in toluene (790 µL) at 0° C., and the mixture was stirred at 0° C. for 5 min and at room temperature for 16 hr. The reaction mixture was concentrated under reduced pressure, and the residue was purified by silica gel column chromatography (ethyl acetate/hexane) to give the title compound (277 mg) as a colorless oil.

$^1$H NMR (300 MHz, DMSO-d$_6$) δ 0.62 (9H, s), 1.66-1.79 (2H, m), 2.59-2.66 (2H, m), 3.38-3.46 (2H, m), 3.74 (3H, s), 4.45 (1H, t, J=5.1 Hz), 5.11 (2H, s), 6.77 (1H, dd, J=6.0, 3.4 Hz), 6.86-6.98 (3H, m), 7.08-7.20 (3H, m), 7.24-7.33 (3H, m), the peak of 2H overlaps with that of the residual DMSO.

E) 3-(3-(((2'-fluoro-5'-methoxy-2-neopentyl-[1,1'-biphenyl]-4-yl)oxy)methyl)phenyl)propanal To a solution of 3-(3-(((2'-fluoro-5'-methoxy-2-neopentyl-[1,1'-biphenyl]-4-yl)oxy)methyl)phenyl)propan-1-ol (357 mg) and triethylamine (0.68 mL) in DMSO (5.0 mL) was added sulfur trioxide pyridine complex (390 mg), and the mixture was stirred at room temperature for 2 hr. To the reaction mixture was added 0.50N hydrochloric acid, and the reaction mixture was extracted with ethyl acetate. The extract was washed with saturated aqueous sodium hydrogen carbonate solution and saturated brine and dried over anhydrous sodium sulfate. The solvent was evaporated under reduced pressure and the residue was purified by silica gel column chromatography (ethyl acetate/hexane) to give the title compound (167 mg) as a colorless oil.

$^1$H NMR (300 MHz, DMSO-d$_6$) δ 0.62 (9H, s), 2.74-2.83 (2H, m), 2.84-2.94 (2H, m), 3.74 (3H, s), 5.10 (2H, s), 6.77 (1H, dd, J=6.2, 3.2 Hz), 6.85-6.97 (3H, m), 7.06-7.22 (3H, m), 7.26-7.37 (3H, m), 9.72 (1H, t, J=1.3 Hz), the peak of 2H overlaps with that of the residual DMSO.

F) 3-(3-(((2-(2,2-dimethylpropyl)-2'-fluoro-5'-methoxybiphenyl-4-yl)oxy)methyl)phenyl)propanoic acid To a solution of 3-(3-(((2'-fluoro-5'-methoxy-2-neopentyl-[1,1'-biphenyl]-4-yl)oxy)methyl)phenyl)propanal (152 mg) in tert-butanol (3.5 mL) were successively added water (0.50 mL), sodium dihydrogen phosphate (126 mg), sodium chlorite (95 mg) and 2-methyl-2-butene (0.19 mL), and the mixture was stirred at room temperature for 45 min. 1N Hydrochloric acid and water were added, and the reaction mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (132 mg) as a colorless oil.

$^1$H NMR (300 MHz, DMSO-d$_6$) δ 0.63 (9H, s), 2.44 (2H, brs), 2.53-2.57 (2H, m), 2.80-2.87 (2H, m), 3.74 (3H, s), 5.10 (2H, s), 6.77 (1H, dd, J=6.0, 3.4 Hz), 6.86-6.97 (3H, m), 7.07-7.21 (3H, m), 7.28-7.34 (3H, m), 12.17 (1H, brs).

Example 8

3-cyclopropyl-3-(3-(((2-(2,2-dimethylpropyl)-2'-fluoro-5'-methoxybiphenyl-4-yl)amino)methyl)phenyl)propanoic acid A) 2'-fluoro-5'-methoxy-2-neopentyl-[1,1'-biphenyl]-4-yl trifluoromethanesulfonate To a solution of 2'-fluoro-5'-methoxy-2-neopentyl-[1,1'-biphenyl]-4-ol (3.34 g), triethylamine (3.04 mL) and 4-dimethylaminopyridine (133 mg) in acetonitrile (50 mL) was added trifluoromethanesulfonic acid anhydride (14.8 mL) at 0° C., and the mixture was stirred for 1 hr. To the reaction mixture was added aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (4.23 g) as a colorless oil.

$^1$H NMR (400 MHz, DMSO-d$_6$) δ 0.66 (9H, s), 2.52-2.59 (1H, m), 2.62-2.74 (1H, m), 3.76 (3H, s), 6.89 (1H, dd, J=5.8, 3.1 Hz), 6.96-7.05 (1H, m), 7.23 (1H, t, J=9.2 Hz), 7.38-7.46 (3H, m).

B) N-(diphenylmethylene)-2'-fluoro-5'-methoxy-2-neopentyl-[1,1'-biphenyl]-4-amine To a solution of 2'-fluoro-5'-methoxy-2-neopentyl-[1,1'-biphenyl]-4-yl trifluoromethanesulfonate (1.77 g) in THF (28 mL) were added benzophenoneimine (1.06 mL), 4,5-bis (diphenylphosphino)-9,9-dimethylxanthene (244 mg), cesium carbonate (2.74 g) and tris(dibenzylideneacetone)dipalladium(0) (193 mg) at room temperature, and the mixture was stirred at 80° C. for 20 hr. The reaction mixture was poured into water at room temperature, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (1.90 g) as a crude yellow oil. This compound was used for the next step without further purification.

C) 2'-fluoro-5'-methoxy-2-neopentyl-[1,1'-biphenyl]-4-amine

To a solution of a mixture (1.90 g) of N-(diphenylmethylene)-2'-fluoro-5'-methoxy-2-neopentyl-[1,1'-biphenyl]-4-amine in THF (42 mL) was added 3N hydrochloric acid (14.0 mL) at 0° C., and the mixture was stirred at room temperature for 1 hr. To the reaction mixture was added 8N aqueous sodium hydroxide solution at 0° C., and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (970 mg) as a pale-yellow solid.

$^1$H NMR (300 MHz, CDCl$_3$) δ 0.65-0.77 (9H, m), 2.49 (2H, d, J=15.5 Hz), 3.66 (2H, brs), 3.76-3.83 (3H, m), 6.57-6.66 (2H, m), 6.68-6.86 (2H, m), 6.94-7.06 (2H, m).

D) N-(2'-fluoro-5'-methoxy-2-neopentyl-[1,1'-biphenyl]-4-yl)-2-nitrobenzenesulfonamide To a solution of 2'-fluoro-5'-methoxy-2-neopentyl-[1,1'-biphenyl]-4-amine (970 mg) in THF (34 mL) were added triethylamine (706 μL) and o-nitrobenzenesulfonyl chloride (823 mg) at 0° C., and the mixture was stirred at room temperature for 5 hr. Triethylamine (706 μL) and o-nitrobenzenesulfonyl chloride (374 mg) were further added at 0° C., and the mixture was stirred at room temperature for 20 hr. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (1.31 g) as a yellow gummy substance.

$^1$H NMR (300 MHz, CDCl$_3$) δ 0.53-0.61 (9H, m), 2.44 (1H, brs), 2.52 (1H, brs), 3.78 (3H, s), 6.67 (1H, dd, J=5.9, 3.2 Hz), 6.82 (1H, dt, J=8.9, 3.7 Hz), 7.00 (1H, t, J=9.1 Hz), 7.04-7.08 (1H, m), 7.09-7.17 (2H, m), 7.56-7.64 (1H, m), 7.69 (1H, td, J=7.8, 1.5 Hz), 7.88 (2H, td, J=8.0, 1.3 Hz).

E) ethyl 3-cyclopropyl-3-(3-((N-(2'-fluoro-5'-methoxy-2-neopentyl-[1,1'-biphenyl]-4-yl)-2-nitrophenylsulfonamido)methyl)phenyl)propanoate To a solution of N-(2'-fluoro-5'-methoxy-2-neopentyl-[1,1'-biphenyl]-4-yl)-2-nitrobenzenesulfonamide (892 mg), ethyl 3-cyclopropyl-3-(3-(hydroxymethyl)phenyl)propanoate (445 mg) and triphenylphosphine (990 mg) in THF (19 mL) was added a 40% solution of diethyl azodicarboxylate in toluene (1.49 mL) at 0° C., and the mixture was stirred at room temperature for 2 hr. The reaction mixture was concentrated under reduced pressure, and the residue was purified by silica gel column chromatography (NH, ethyl acetate/hexane) to give the title compound (1.22 g) as a colorless gummy substance.

$^1$H NMR (300 MHz, CDCl$_3$) δ 0.01-0.09 (1H, m), 0.17-0.28 (1H, m), 0.28-0.40 (1H, m), 0.45-0.59 (10H, m), 0.87-1.02 (1H, m), 1.10-1.19 (3H, m), 2.27-2.40 (2H, m), 2.43 (1H, d, J=2.7 Hz), 2.56-2.74 (2H, m), 3.77 (3H, s), 4.03 (2H, qd, J=7.1, 2.5 Hz), 4.97 (2H, d, J=3.0 Hz), 6.65 (1H, dd, J=6.1, 3.0 Hz), 6.78-6.86 (1H, m), 6.94-7.06 (4H, m), 7.09 (2H, dd, J=3.6, 1.7 Hz), 7.14-7.22 (2H, m), 7.45-7.53 (1H, m), 7.60-7.69 (3H, m).

F) ethyl 3-cyclopropyl-3-(3-(((2'-fluoro-5'-methoxy-2-neopentyl-[1,1'-biphenyl]-4-yl)amino)methyl)phenyl)propanoate To a solution of ethyl 3-cyclopropyl-3-(3-((N-(2'-fluoro-5'-methoxy-2-neopentyl-[1,1'-biphenyl]-4-yl)-2-nitrophenylsulfonamido)methyl)phenyl)propanoate (1.22 g) in DMF (35 mL) were added mercaptoacetic acid (617 μL) and lithium hydroxide monohydrate (728 mg) at room temperature, and the mixture was stirred at 60° C. for 1 hr. To the reaction mixture was added saturated aqueous sodium hydrogen carbonate solution at 0° C., and the mixture was extracted with ethyl acetate. The extract was washed with saturated brine and dried over anhydrous sodium sulfate. The solvent was evaporated under reduced pressure and the residue was purified by silica gel column chromatography (NH, ethyl acetate/hexane) to give the title compound (801 mg) as a colorless oil.

$^1$H NMR (300 MHz, DMSO-d$_6$) δ 0.07 (1H, dt, J=9.0, 4.4 Hz), 0.13-0.38 (2H, m), 0.43-0.64 (10H, m), 0.93-1.13 (4H, m), 2.20-2.44 (3H, m), 2.58-2.80 (2H, m), 3.71 (3H, s), 3.87-3.99 (2H, m), 4.26 (2H, d, J=6.1 Hz), 6.29 (1H, t, J=6.1 Hz), 6.44 (1H, d, J=2.7 Hz), 6.51 (1H, dd, J=8.3, 2.3 Hz), 6.68 (1H, dd, J=6.1, 3.0 Hz), 6.81-6.91 (2H, m), 7.04-7.16 (2H, m), 7.17-7.30 (3H, m).

G) 3-cyclopropyl-3-(3-(((2-(2,2-dimethylpropyl)-2'-fluoro-5'-methoxybiphenyl-4-yl)amino)methyl)phenyl)propanoic acid To a solution of ethyl 3-cyclopropyl-3-(3-(((2'-fluoro-5'-methoxy-2-neopentyl-[1,1'-biphenyl]-4-yl)amino)methyl) phenyl)propanoate (104 mg) in ethanol (2.0 mL) was added 2N aqueous sodium hydroxide solution (502 μL) at room temperature, and the mixture was stirred for 5 hr. The reaction mixture was further stirred at 50° C. for 1 hr, and the reaction mixture was cooled to 0° C. The mixture was neutralized with 1N hydrochloric acid, and extracted with ethyl acetate. The extract was dried over anhydrous sodium sulfate and the solvent was evaporated under reduced pressure to give the title compound (88 mg) as a pale-yellow gummy substance.

$^1$H NMR (300 MHz, DMSO-d$_6$) δ 0.02-0.11 (1H, m), 0.17-0.33 (2H, m), 0.41-0.53 (1H, m), 0.53-0.63 (9H, m), 0.91-1.05 (1H, m), 2.23-2.42 (3H, m), 2.55-2.70 (2H, m), 3.71 (3H, s), 4.26 (2H, d, J=6.1 Hz), 6.28 (1H, t, J=5.9 Hz), 6.46 (1H, d, J=2.3 Hz), 6.52 (1H, dd, J=8.3, 2.3 Hz), 6.69 (1H, dd, J=6.1, 3.0 Hz), 6.81-6.89 (2H, m), 7.05-7.16 (2H, m), 7.16-7.29 (3H, m), 12.03 (1H, brs).

Example 9

3-cyclopropyl-3-(3-(((2-(2,2-dimethylpropyl)-2'-fluoro-5'-methoxybiphenyl-4-yl)(methyl)amino)methyl)phenyl)propanoic acid A) ethyl 3-cyclopropyl-3-(3-(((2'-fluoro-5'-methoxy-2-neopentyl-[1,1'-biphenyl]-4-yl)(methyl)amino)methyl)phenyl)propanoate To a solution of ethyl 3-cyclopropyl-3-(3-(((2'-fluoro-5'-methoxy-2-neopentyl-[1,1'-biphenyl]-4-yl)amino)methyl)phenyl)propanoate (203 mg), formaldehyde solution (88 μL) and acetic acid (67 μL) in acetonitrile (3.9 mL) was added sodium triacetoxyborohydride (125 mg) at 0° C., and the mixture was stirred at room temperature for 2 hr. To the reaction mixture was added saturated sodium hydrogen carbonate solution at 0° C., and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (148 mg) as a colorless transparent oil.

$^1$H NMR (300 MHz, DMSO-$d_6$) δ 0.01-0.10 (1H, m), 0.13-0.35 (2H, m), 0.41-0.53 (1H, m), 0.57 (9H, s), 0.90-1.02 (1H, m), 1.05 (3H, t, J=7.2 Hz), 2.18-2.32 (1H, m), 2.42 (2H, brs), 2.58-2.78 (2H, m), 3.04 (3H, s), 3.69-3.77 (3H, m), 3.86-4.01 (2H, m), 4.56 (2H, s), 6.55 (1H, d, J=2.7 Hz), 6.62-6.76 (2H, m), 6.87 (1H, dt, J=8.9, 3.7 Hz), 6.95 (1H, d, J=8.7 Hz), 7.01-7.18 (4H, m), 7.18-7.29 (1H, m).

B) 3-cyclopropyl-3-(3-(((2-(2,2-dimethylpropyl)-2'-fluoro-5'-methoxybiphenyl-4-yl)(methyl)amino)methyl)phenyl)propanoic acid To a solution of ethyl 3-cyclopropyl-3-(3-(((2'-fluoro-5'-methoxy-2-neopentyl-[1,1'-biphenyl]-4-yl)amino)methyl)phenyl)propanoate (148 mg) in ethanol (2.8 mL) was added 2N aqueous sodium hydroxide solution (695 μL) at room temperature, and the mixture was stirred for 5 hr. The mixture was further stirred at 50° C. for 2 hr, and the reaction mixture was cooled to 0° C. The mixture was neutralized with 1N hydrochloric acid, and extracted with ethyl acetate. The extract was dried over anhydrous sodium sulfate and the solvent was evaporated under reduced pressure to give the title compound (128 mg) as a colorless gummy substance.

$^1$H NMR (300 MHz, DMSO-$d_6$) δ 0.04-0.11 (1H, m), 0.15-0.34 (2H, m), 0.41-0.52 (1H, m), 0.57 (9H, s), 0.82-1.04 (1H, m), 2.22-2.35 (1H, m), 2.36-2.46 (2H, m), 2.55-2.68 (2H, m), 3.04 (3H, s), 3.72 (3H, s), 4.56 (2H, s), 6.53-6.61 (1H, m), 6.64-6.77 (2H, m), 6.83-6.92 (1H, m), 6.96 (1H, d, J=8.3 Hz), 7.01-7.07 (1H, m), 7.07-7.17 (3H, m), 7.18-7.26 (1H, m), 12.06 (1H, s).

Example 10

3-(3-((acetyl(2-(2,2-dimethylpropyl)-2'-fluoro-5'-methoxybiphenyl-4-yl)amino)methyl)phenyl)-3-cyclopropylpropanoic acid A) ethyl 3-cyclopropyl-3-(3-((N-(2'-fluoro-5'-methoxy-2-neopentyl-[1,1'-biphenyl]-4-yl)acetamido)methyl)phenyl)propanoate To a solution of ethyl 3-cyclopropyl-3-(3-(((2'-fluoro-5'-methoxy-2-neopentyl-[1,1'-biphenyl]-4-yl)amino)methyl)phenyl)propanoate (104 mg) in THF (2.0 mL) were added N-ethyldiisopropylamine (52 μL) and acetyl chloride (17 μL) at 0° C., and the mixture was stirred at room temperature for 1.5 hr. Ice water was added at 0° C., and the mixture was extracted with ethyl acetate. The extract was washed with saturated brine and dried over anhydrous sodium sulfate. The is solvent was evaporated under reduced pressure and the residue was purified by silica gel column chromatography (ethyl acetate/hexane) to give the title compound (104 mg) as a colorless oil.

$^1$H NMR (300 MHz, DMSO-$d_6$) δ 0.02-0.10 (1H, m), 0.13-0.37 (2H, m), 0.40-0.64 (10H, m), 0.89-1.02 (1H, m), 1.05 (3H, t, J=7.2 Hz), 1.90 (3H, brs), 2.17-2.31 (1H, m), 2.31-2.48 (2H, m), 2.55-2.77 (2H, m), 3.73 (3H, s), 3.84-4.00 (2H, m), 4.88 (2H, s), 6.79 (1H, dd, J=6.1, 3.0 Hz), 6.95 (1H, dt, J=9.1, 3.6 Hz), 7.00-7.27 (8H, m).

B) 3-(3-((acetyl(2-(2,2-dimethylpropyl)-2'-fluoro-5'-methoxybiphenyl-4-yl)amino)methyl)phenyl)-3-cyclopropylpropanoic acid To a solution of ethyl 3-cyclopropyl-3-(3-((N-(2'-fluoro-5'-methoxy-2-neopentyl-[1,1'-biphenyl]-4-yl)acetamido)methyl)phenyl)propanoate (104 mg) in ethanol (1.9 mL) was added 2N aqueous sodium hydroxide solution (466 μL) at room temperature, and the mixture was stirred at 50° C. for 2 hr. The reaction mixture was neutralized with 1N hydrochloric acid at 0° C., and extracted with ethyl acetate. The extract was dried over anhydrous sodium sulfate and the solvent was evaporated under reduced pressure to give the title compound (99 mg) as a white amorphous solid.

$^1$H NMR (300 MHz, DMSO-$d_6$) δ 0.03-0.13 (1H, m), 0.15-0.33 (2H, m), 0.38-0.62 (10H, m), 0.83-1.04 (1H, m), 1.90 (3H, brs), 2.18-2.35 (1H, m), 2.36-2.47 (2H, m), 2.55-2.71 (2H, m), 3.73 (3H, s), 4.88 (2H, s), 6.79 (1H, dd, J=6.1, 3.0 Hz), 6.95 (1H, dt, J=9.0, 3.5 Hz), 7.00-7.29 (8H, m), 12.02 (1H, s).

Example 11

3-cyclopropyl-3-(3-(((2-(2,2-dimethylpropyl)-2'-fluoro-5'-methoxybiphenyl-4-yl)(2,2,2-trifluoroethyl)amino)methyl)phenyl)propanoic acid A) ethyl 3-cyclopropyl-3-(3-(((2'-fluoro-5'-methoxy-2-neopentyl-[1,1'-biphenyl]-4-yl)(2,2,2-trifluoroethyl)amino)methyl)phenyl)propanoate To a solution of ethyl 3-cyclopropyl-3-(3-(((2'-fluoro-5'-methoxy-2-neopentyl-[1,1'-biphenyl]-4-yl)amino)methyl)phenyl)propanoate (92 mg) in DMF (0.89 mL) were added 2,2,2-trifluoroethyl trifluoromethanesulfonate (77 μL) and potassium carbonate (74 mg) at 0° C., and the mixture was stirred at 80° C. for 15 hr. The reaction mixture was cooled to 0° C., potassium carbonate (246 mg) was added, and the mixture was stirred at 80° C. for 2 days. The reaction mixture was cooled to 0° C., 2,2,2-trifluoroethyl trifluoromethanesulfonate (256 μL) was added, and the mixture was further stirred at 80° C. for 3 days. The mixture was cooled to room temperature, poured into water, and the mixture was extracted with ethyl acetate. The extract was washed with saturated brine and dried over anhydrous sodium sulfate. The solvent was evaporated under reduced pressure and the residue was directly used for the next reaction.

B) 3-cyclopropyl-3-(3-(((2-(2,2-dimethylpropyl)-2'-fluoro-5'-methoxybiphenyl-4-yl)(2,2,2-trifluoroethyl)amino)methyl)phenyl)propanoic acid To a solution of the mixture in ethanol (0.89 mL) was added aqueous 2N sodium hydroxide (446 µL) solution at room temperature, and the mixture was stirred at 50° C. for 5 hr. The reaction mixture was cooled to 0° C. and neutralized with 1N hydrochloric acid. The mixture was extracted with ethyl acetate, and the extract was washed with saturated brine and dried over anhydrous sodium sulfate. The solvent was evaporated under reduced pressure and the residue was purified by silica gel column chromatography (ethyl acetate/hexane) to give the title compound (24 mg) as a colorless oil.

$^1$H NMR (300 MHz, CDCl$_3$) δ 0.03-0.17 (1H, m), 0.21-0.33 (1H, m), 0.33-0.45 (1H, m), 0.58 (10H, s), 0.90-1.06 (1H, m), 1.16-1.28 (1H, m), 2.28-2.55 (2H, m), 2.64-2.83 (2H, m), 3.74-3.79 (3H, m), 4.01 (2H, q, J=8.8 Hz), 4.70 (2H, s), 6.64 (1H, d, J=2.6 Hz), 6.68-6.83 (3H, m), 6.94-7.16 (5H, m), 7.22 (1H, brs).

Example 12

3-cyclopropyl-3-(3-(((2-(2,2-dimethylpropyl)-2'-fluoro-5'-methoxybiphenyl-4-yl)sulfanyl)methyl)phenyl)propanoic acid A) (2'-fluoro-5'-methoxy-2-neopentyl-[1,1'-biphenyl]-4-yl)(4-methoxybenzyl)sulfane To a solution of 2'-fluoro-5'-methoxy-2-neopentyl-[1,1'-biphenyl]-4-yl trifluoromethanesulfonate (1.88 g) in toluene (22 mL) were added 4-methoxy-α-toluenethiol (748 µL), 4,5-bis(diphenylphosphino)-9,9-dimethylxanthene (78 mg), N-ethyldiisopropylamine (1.56 mL) and tris(dibenzylideneacetone)dipalladium(0) (123 mg) at room temperature, and the mixture was stirred at 120° C. for 20 hr. The mixture was poured into ice water at room temperature, and extracted with ethyl acetate. The extract was washed with saturated brine, and dried over anhydrous sodium sulfate. The solvent was evaporated under reduced pressure and the residue was purified by silica gel column chromatography (NH, ethyl acetate/hexane) to give the title compound (1.68 g) as a colorless oil.

$^1$H NMR (300 MHz, DMSO-d$_6$) δ 0.61 (9H, s), 2.35-2.47 (2H, m), 3.74 (3H, s), 3.72 (3H, s), 4.22 (2H, s), 6.78 (1H, dd, J=6.1, 3.0 Hz), 6.86 (2H, d, J=8.7 Hz), 6.95 (1H, dt, J=9.1, 3.6 Hz), 7.07-7.35 (6H, m).

B) 2'-fluoro-5'-methoxy-2-neopentyl-[1,1'-biphenyl]-4-thiol

To a solution of (2'-fluoro-5'-methoxy-2-neopentyl-[1,1'-biphenyl]-4-yl)(4-methoxybenzyl)sulfane (1.68 g) in trifluoroacetic acid (6.6 mL) was added anisole (2.15 mL) at room temperature, and the mixture was stirred at 90° C. for 8 hr. The reaction mixture was cooled to 0° C., neutralized with 8N aqueous sodium hydroxide solution, and extracted with ethyl acetate. The extract was washed with saturated brine, and dried over anhydrous sodium sulfate. The solvent was evaporated under reduced pressure and the residue was purified by silica gel column chromatography (NH, ethyl acetate/hexane) to give the title compound (918 mg) as a pale-yellow oil.

$^1$H NMR (300 MHz, CDCl$_3$) δ 0.69-0.75 (9H, m), 2.47 (1H, brs), 2.55 (1H, brs), 3.46 (1H, s), 3.79 (3H, s), 6.72 (1H, dd, J=5.9, 3.2 Hz), 6.84 (1H, s), 6.97-7.02 (1H, m), 7.04-7.10 (1H, m), 7.15-7.20 (2H, m).

C) ethyl 3-cyclopropyl-3-(3-(((methylsulfonyl)oxy)methyl)phenyl)propanoate

To a solution of ethyl 3-cyclopropyl-3-(3-(hydroxymethyl)phenyl)propanoate (690 mg) in THF (14 mL) were added triethylamine (775 µL) and methanesulfonyl chloride (258 µL) at 0° C., and the mixture was stirred at room temperature for 2 hr. The reaction mixture was cooled to 0° C., water was added, and the mixture was extracted with ethyl acetate. The extract was washed with saturated brine, and dried over anhydrous sodium sulfate. The solvent was evaporated under reduced pressure and the residue was purified by silica gel column chromatography (ethyl acetate/hexane) to give the title compound (934 mg) as a colorless oil.

$^1$H NMR (300 MHz, CDCl$_3$) δ 0.08-0.21 (1H, m), 0.29 (1H, dq, J=9.5, 4.8 Hz), 0.36-0.51 (1H, m), 0.55-0.68 (1H, m), 0.97-1.09 (1H, m), 1.16 (3H, t, J=7.1 Hz), 2.32-2.46 (1H, m), 2.65-2.84 (2H, m), 2.88 (3H, s), 3.96-4.15 (2H, m), 5.23 (2H, s), 7.29 (3H, s), 7.31-7.40 (1H, m).

D) ethyl 3-cyclopropyl-3-(3-(((2'-fluoro-5'-methoxy-2-neopentyl-[1,1'-biphenyl]-4-yl)thio)methyl)phenyl)propanoate To a solution of 2'-fluoro-5'-methoxy-2-neopentyl-[1,1'-biphenyl]-4-thiol (161 mg) in DMF (2.6 mL) were added ethyl 3-cyclopropyl-3-(3-(((methylsulfonyl)oxy)methyl)phenyl)propanoate (207 mg) and potassium carbonate (146 mg) at room temperature, and the mixture was stirred at 60° C. for 2 hr. The reaction mixture was poured into water at room temperature, and the mixture was extracted with ethyl acetate. The extract was washed with saturated brine and dried over anhydrous sodium sulfate. The solvent was evaporated under reduced pressure and the residue was purified by silica gel column chromatography (NH, ethyl acetate/hexane) to give the title compound (267 mg) as a colorless oil.

$^1$H NMR (300 MHz, CDCl$_3$) δ 0.04-0.16 (1H, m), 0.16-0.33 (1H, m), 0.33-0.48 (1H, m), 0.48-0.61 (1H, m), 0.67 (9H, s), 0.91-1.08 (1H, m), 1.16 (3H, t, J=7.2 Hz), 2.29-2.61 (3H, m), 2.62-2.79 (2H, m), 3.73-3.84 (3H, m), 3.98-4.10 (2H, m), 4.10-4.17 (2H, m), 6.72 (1H, dd, J=5.8, 2.8 Hz), 6.83 (1H, dt, J=8.6, 3.6 Hz), 6.96-7.07 (1H, m), 7.07-7.15 (2H, m), 7.15-7.25 (5H, m).

E) 3-cyclopropyl-3-(3-(((2-(2,2-dimethylpropyl)-2'-fluoro-5'-methoxybiphenyl-4-yl)sulfanyl)methyl)phenyl)propanoic acid To a solution of ethyl 3-cyclopropyl-3-(3-(((2'-fluoro-5'-methoxy-2-neopentyl-[1,1'-biphenyl]-4-yl)thio)methyl)phenyl)propanoate (136 mg) in ethanol (2.5 mL) was added 2N aqueous sodium hydroxide solution (634 µL) at room temperature, and the mixture was stirred at 50° C. for 2 hr. The reaction mixture was cooled to 0° C., neutralized with 1N hydrochloric acid, and extracted with ethyl acetate. The extract was dried over anhydrous sodium sulfate and the solvent was evaporated under reduced pressure to give the title compound (56 mg) as a white amorphous solid.

$^1$H NMR (300 MHz, CDCl$_3$) δ 0.02-0.11 (1H, m), 0.15-0.40 (2H, m), 0.40-0.55 (1H, m), 0.65 (9H, s), 0.83-1.00 (1H, m), 2.26-2.37 (1H, m), 2.37-2.71 (4H, m), 3.76 (3H, s), 4.09 (2H, s), 6.71 (1H, dd, J=5.7, 3.0 Hz), 6.76-6.85 (1H, m), 6.93-7.23 (8H, m).

Example 13

3-cyclopropyl-3-(3-(((2-(2,2-dimethylpropyl)-2'-fluoro-5'-methoxybiphenyl-4-yl)sulfonyl)methyl)phenyl)propanoic acid

A) ethyl 3-cyclopropyl-3-(3-(((2'-fluoro-5'-methoxy-2-neopentyl-[1,1'-biphenyl]-4-yl)sulfonyl)methyl)phenyl)propanoate To a mixed solution of ethyl 3-cyclopropyl-3-(3-(((2'-fluoro-5'-methoxy-2-neopentyl-[1,1'-biphenyl]-4-yl)thio)methyl)phenyl)propanoate (212 mg) in methanol (5.1 mL), THF (1.7 mL) and water (1.7 mL) was added a solution of oxone (trade name) (512 mg) in water (429 µL) at 0° C., and the mixture was stirred at room temperature for 3 days. The reaction mixture was cooled to 0° C., and saturated aqueous sodium thiosulfate solution was added. The reaction mixture was extracted with ethyl acetate, and the extract was washed with saturated brine and dried over anhydrous sodium sulfate. The solvent was evaporated under reduced pressure and the residue was purified by silica gel column chromatography (ethyl acetate/hexane) to give the title compound (204 mg) as a colorless oil.

$^1$H NMR (300 MHz, CDCl$_3$) δ 0.02-0.11 (1H, m), 0.16-0.29 (1H, m), 0.29-0.42 (1H, m), 0.47-0.75 (10H, m), 0.81-1.01 (1H, m), 1.17 (3H, t, J=7.2 Hz), 2.23-2.38 (1H, m), 2.44-2.75 (4H, m), 3.72-3.82 (3H, m), 3.97-4.09 (2H, m), 4.34 (2H, s), 6.70 (1H, dd, J=5.7, 3.4 Hz), 6.88 (1H, dt, J=9.0, 3.6 Hz), 6.93-7.09 (3H, m), 7.13-7.24 (3H, m), 7.38-7.49 (1H, m), 7.61 (1H, d, J=1.9 Hz).

B) 3-cyclopropyl-3-(3-(((2-(2,2-dimethylpropyl)-2'-fluoro-5'-methoxybiphenyl-4-yl)sulfonyl)methyl)phenyl)propanoic acid To a solution of ethyl 3-cyclopropyl-3-(3-(((2'-fluoro-5'-methoxy-2-neopentyl-[1,1'-biphenyl]-4-yl)sulfonyl)methyl)phenyl)propanoate (204 mg) in ethanol (3.6 mL) was added 2N aqueous sodium hydroxide solution (898 µl) at room temperature, and the mixture was stirred at 50° C. for 2 hr. The reaction mixture was cooled to 0° C., neutralized with 1N hydrochloric acid, and extracted with ethyl acetate. The extract was washed with saturated brine and dried over anhydrous sodium sulfate. The solvent was evaporated under reduced pressure to give the title compound (133 mg) as a white amorphous solid.

$^1$H NMR (300 MHz, CDCl$_3$) δ 0.03-0.11 (1H, m), 0.16-0.29 (1H, m), 0.29-0.41 (1H, m), 0.46-0.58 (1H, m), 0.58-0.70 (9H, m), 0.84-1.01 (1H, m), 2.21-2.35 (1H, m), 2.46-2.77 (4H, m), 3.74-3.83 (3H, m), 4.24-4.33 (2H, m), 6.65-6.75 (1H, m), 6.77-6.93 (2H, m), 6.98-7.22 (5H, m), 7.46 (1H, dd, J=7.2, 1.1 Hz), 7.61 (1H, s).

Example 14

3-cyclopropyl-3-(3-(((3-(3,3-dimethylbutyl)-2'-fluoro-5'-methoxybiphenyl-4-yl)oxy)methyl)phenyl)propanoic acid

A) 2-(benzyloxy)-5-bromobenzaldehyde

To a solution of 5-bromo-2-hydroxybenzaldehyde (10.0 g) in DMF (50 mL) were added potassium carbonate (13.8 g) and benzyl bromide (10.2 g) at room temperature, and the mixture was stirred at 60° C. for 30 min. The reaction mixture was cooled to room temperature, water was added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (12.5 g) as white crystals.

$^1$H NMR (300 MHz, DMSO-d$_6$) δ 5.30 (2H, s), 7.27-7.46 (4H, m), 7.47-7.55 (2H, m), 7.74-7.84 (2H, m), 10.33 (1H, s).

B) 4-(benzyloxy)-2'-fluoro-5'-methoxy-[1,1'-biphenyl]-3-carbaldehyde

To a solution of 2-(benzyloxy)-5-bromobenzaldehyde (5.00 g) in toluene (70 mL) were added (2-fluoro-5-methoxyphenyl)boronic acid (4.40 g), 2-dicyclohexylphosphino-2',6'-dimethoxybiphenyl (710 mg), tris(dibenzylideneacetone)dipalladium(0) (790 mg) and 2.0M aqueous sodium carbonate solution (25.8 mL) at room temperature, and the mixture was stirred at 100° C. for 1 hr. The reaction mixture was cooled to room temperature, water was added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (4.00 g) as orange crystals.

$^1$H NMR (400 MHz, DMSO-d$_6$) δ 3.80 (3H, s), 5.37 (2H, s), 6.90-6.98 (1H, m), 7.01-7.08 (1H, m), 7.24 (1H, t, J=9.7 Hz), 7.32-7.48 (4H, m), 7.55 (2H, d, J=7.4 Hz), 7.82-7.90 (2H, m), 10.47 (1H, s).

C) 1-(4-(benzyloxy)-2'-fluoro-5'-methoxy-[1,1'-biphenyl]-3-yl)-3,3-dimethylbutan-1-ol A solution of neopentylmagnesium bromide (2.00 g) prepared in Example 2, step F, in diethyl ether (10 mL) was added dropwise to a mixed solution of 4-(benzyloxy)-2'-fluoro-5'-methoxy-[1,1'-biphenyl]-3-carbaldehyde (2.00 g) in THF (10 mL) and diethyl ether (10 mL) at room temperature, and the mixture was stirred at 40° C. for 1 hr. The reaction mixture was cooled to room temperature, 1N hydrochloric acid was added dropwise, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (1.90 g) as a colorless oil.

$^1$H NMR (400 MHz, DMSO-d$_6$) δ 0.91 (9H, s), 1.36-1.51 (2H, m), 3.79 (3H, s), 4.80 (1H, d, J=5.3 Hz), 5.08-5.14 (1H, m), 5.14-5.20 (2H, m), 6.90 (1H, dt, J=8.9, 3.5 Hz), 6.96 (1H, dd, J=6.5, 3.1 Hz), 7.11 (1H, d, J=8.5 Hz), 7.20 (1H, dd, J=10.2, 9.1 Hz), 7.31-7.44 (4H, m), 7.46-7.51 (2H, m), 7.65 (1H, s).

D) 4'-(benzyloxy)-3'-(1-chloro-3,3-dimethylbutyl)-2-fluoro-5-methoxy-1,1'-biphenyl To a solution of 1-(4-(benzyloxy)-2'-fluoro-5'-methoxy-[1,1'-biphenyl]-3-yl)-3,3-dimethylbutan-1-ol (1.00 g) in toluene (10 mL) was added thionyl chloride (437 mg), and the mixture was stirred at 70° C. for 1 hr. The solvent was evaporated under reduced pressure to give the title compound as a crude product. This compound was used for the next step without further purification.

E) 3-(3,3-dimethylbutyl)-2'-fluoro-5'-methoxy-[1,1'-biphenyl]-4-ol

To a solution of 4'-(benzyloxy)-3'-(1-chloro-3,3-dimethylbutyl)-2-fluoro-5-methoxy-1,1'-biphenyl (entire amount)

obtained in Example 14, step D, in THF (20 mL) and methanol (20 mL) was added 20% palladium hydroxide-activated carbon (200 mg) and, under a hydrogen atmosphere, the mixture was stirred at room temperature for 12 hr. The reaction mixture was filtered, and the filtrate was concentrated under reduced pressure. The residue was purified by silica gel column chromatography (ethyl acetate/hexane) to give the title compound (670 mg) as a colorless oil.

$^1$H NMR (400 MHz, DMSO-$d_6$) δ 0.95 (9H, s), 1.39-1.47 (2H, m), 2.48-2.56 (2H, m), 3.78 (3H, s), 6.82-6.88 (2H, m), 6.94 (1H, dd, J=6.5, 3.1 Hz), 7.11-7.21 (2H, m), 7.23 (1H, s), 9.46 (1H, s).

F) ethyl 3-cyclopropyl-3-(3-(((3-(3,3-dimethylbutyl)-2'-fluoro-5'-methoxy-[1,1'-biphenyl]-4-yl)oxy)methyl)phenyl)propanoate To a solution of 3-(3,3-dimethylbutyl)-2'-fluoro-5'-methoxy-[1,1'-biphenyl]-4-ol (200 mg) in THF (5.0 mL) were added triphenylphosphine (260 mg), ethyl 3-cyclopropyl-3-(3-(hydroxymethyl)phenyl)propanoate (246 mg) and a 40% solution of diethyl azodicarboxylate in toluene (400 µL), and the reaction mixture was stirred at room temperature for 2 hr. The reaction mixture was concentrated under reduced pressure and the residue was purified by silica gel column chromatography (ethyl acetate/hexane) to give the title compound (170 mg) as a colorless oil.

$^1$H NMR (400 MHz, DMSO-$d_6$) δ 0.09 (1H, dq, J=9.3, 4.8 Hz), 0.22 (1H, dq, J=9.3, 4.7 Hz), 0.28-0.36 (1H, m), 0.51 (1H, td, J=8.6, 3.8 Hz), 0.91 (9H, s), 1.01-1.08 (4H, m, J=7.1, 7.1 Hz), 1.41-1.48 (2H, m), 2.27-2.36 (1H, m), 2.58-2.65 (2H, m), 2.72 (2H, qd, J=14.6, 7.6 Hz), 3.78 (3H, s), 3.94 (2H, qd, J=7.1, 3.6 Hz), 5.14 (2H, s), 6.89 (1H, dt, J=8.9, 3.5 Hz), 6.98 (1H, dd, J=6.5, 3.2 Hz), 7.10-7.27 (3H, m), 7.29-7.40 (5H, m).

G) 3-cyclopropyl-3-(3-(((3-(3,3-dimethylbutyl)-2'-fluoro-5'-methoxybiphenyl-4-yl)oxy)methyl)phenyl)propanoic acid To a solution of ethyl 3-cyclopropyl-3-(3-(((3-(3,3-dimethylbutyl)-2'-fluoro-5'-methoxy-[1,1'-biphenyl]-4-yl)oxy)methyl)phenyl)propanoate in ethanol (3.0 mL) was added 1N aqueous sodium hydroxide solution (3.0 mL), and the mixture was stirred at 50° C. for 1 hr. To the reaction mixture was added 1N hydrochloric acid, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (90 mg) as a colorless oil.

$^1$H NMR (400 MHz, DMSO-$d_6$) δ 0.06-0.14 (1H, m), 0.21-0.35 (2H, m), 0.46-0.55 (1H, m), 0.91 (9H, s), 0.96-1.08 (1H, m), 1.41-1.49 (2H, m), 2.29-2.38 (1H, m), 2.58-2.73 (4H, m), 3.79 (3H, s), 5.14 (2H, s), 6.89 (1H, dt, J=8.9, 3.5 Hz), 6.98 (1H, dd, J=6.5, 3.2 Hz), 7.11-7.27 (3H, m), 7.29-7.40 (5H, m), 12.05 (1H, brs).

Example 15

3-cyclopropyl-3-(3-(((2'-fluoro-5'-methoxy-3-(1-methoxy-3,3-dimethylbutyl)biphenyl-4-yl)oxy)methyl)phenyl)propanoic acid A) 4'-(benzyloxy)-2-fluoro-5-methoxy-3'-(1-methoxy-3,3-dimethylbutyl)-1,1'-biphenyl To a solution of 1-(4-(benzyloxy)-2'-fluoro-5'-methoxy-[1,1'-biphenyl]-3-yl)-3,3-dimethylbutan-1-ol (425 mg) prepared in Example 14, step C, in DMF (3.0 mL) was added 60% sodium hydride (100 mg), and the mixture was stirred at room temperature for 30 min. Iodomethane (443 mg) was added dropwise and the mixture was stirred at room temperature for 30 min. Water was added to the reaction mixture, and the mixture was extracted with ethyl acetate. The extract was washed with saturated brine and dried over anhydrous sodium sulfate. The solvent was evaporated under reduced pressure to give the title compound as a crude product. This compound was used for the next step without further purification.

B) 2'-fluoro-5'-methoxy-3-(1-methoxy-3,3-dimethylbutyl)-[1,1'-biphenyl]-4-ol

To a solution of 4'-(benzyloxy)-2-fluoro-5-methoxy-3'-(1-methoxy-3,3-dimethylbutyl)-1,1'-biphenyl (entire amount) obtained in Example 15, step A, in methanol (10 mL) was added 20% palladium hydroxide-activated carbon (100 mg) and, under a hydrogen atmosphere, the mixture was stirred at room temperature for 1 hr. The reaction mixture was filtered and the filtrate was concentrated under reduced pressure. The residue was purified by silica gel column chromatography (ethyl acetate/hexane) to give the title compound (290 mg) as a colorless oil.

$^1$H NMR (400 MHz, DMSO-$d_6$) δ 0.96 (9H, s), 1.36-1.46 (1H, m), 1.50-1.61 (1H, m), 3.11 (3H, s), 3.78 (3H, s), 4.65 (1H, dd, =8.7, 2.6 Hz), 6.82-6.96 (3H, m), 7.17 (1H, dd, J=10.4, 9.1 Hz), 7.26 (1H, d, J=8.4 Hz), 7.37 (1H, s), 9.68 (1H, brs).

C) ethyl 3-cyclopropyl-3-(3-(((2'-fluoro-5'-methoxy-3-(1-methoxy-3,3-dimethylbutyl)-[1,1'-biphenyl]-4-yl)oxy)methyl)phenyl)propanoate To a solution of 2'-fluoro-5'-methoxy-3-(1-methoxy-3,3-dimethylbutyl)-[1,1'-biphenyl]-4-ol (290 mg) in THF (5.0 mL) were added triphenylphosphine (343 mg), ethyl 3-cyclopropyl-3-(3-(hydroxymethyl)phenyl)propanoate (325 mg) and a 40% solution of diethyl azodicarboxylate in toluene (600 µL), and the reaction mixture was stirred at room temperature for 2 hr. The reaction mixture was concentrated under reduced pressure and the residue was purified by silica gel column chromatography (ethyl acetate/hexane) to give the title compound (385 mg) as a colorless oil.

$^1$H NMR (400 MHz, DMSO-$d_6$) δ 0.04-0.13 (1H, m), 0.18-0.26 (1H, m), 0.31 (1H, d, J=2.4 Hz), 0.47-0.56 (1H, m), 0.90 (9H, s), 0.98-1.08 (4H, m, J=7.1, 7.1 Hz), 1.39-1.46 (1H, m), 1.50-1.58 (1H, m), 2.27-2.36 (1H, m), 2.72 (2H, qd, J=14.8, 7.5 Hz), 3.11 (3H, s), 3.79 (3H, s), 3.88-3.98 (2H, m), 4.71 (1H, dd, J=8.7, 1.8 Hz), 5.16 (2H, s), 6.91 (1H, dt, J=8.8, 3.5 Hz), 6.97 (1H, dd, J=6.5, 3.1 Hz), 7.16-7.28 (3H, m), 7.29-7.34 (2H, m), 7.37 (1H, brs), 7.40-7.48 (2H, m).

D) 3-cyclopropyl-3-(3-(((2'-fluoro-5'-methoxy-3-(1-methoxy-3,3-dimethylbutyl)biphenyl-4-yl)oxy)methyl)phenyl)propanoic acid To a solution of ethyl 3-cyclopropyl-3-(3-(((2'-fluoro-5'-methoxy-3-(1-methoxy-3,3-dimethylbutyl)-[1,1'-biphenyl]-4-yl)oxy)methyl)phenyl)propanoate (385 mg) in ethanol (3.0 mL) was added 1N aqueous sodium hydroxide solution (3.0 mL), and the reaction mixture was stirred at 50° C. for 1 hr. 1N Hydrochloric acid was added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (250 mg) as a colorless oil.

$^1$H NMR (400 MHz, DMSO-$d_6$) δ 0.09 (1H, dd, J=9.2, 4.4 Hz), 0.19-0.36 (2H, m), 0.45-0.55 (1H, m), 0.90 (9H, s), 0.96-1.07 (1H, m), 1.38-1.47 (1H, m), 1.49-1.58 (1H, m), 2.34 (1H, q, J=7.9 Hz), 2.57-2.76 (2H, m), 3.11 (3H, s), 3.79 (3H, s), 4.72 (1H, dd, J=8.7, 1.8 Hz), 5.16 (2H, s), 6.91 (1H, dt, J=8.8, 3.4 Hz), 6.98 (1H, dd, J=6.5, 3.1 Hz), 7.14-7.27 (3H, m), 7.28-7.49 (5H, m), 12.03 (1H, brs).

Example 16

3-cyclopropyl-3-(3-(((2-(2,2-dimethylpropyl)-2'-fluoro-5'-methoxybiphenyl-4-yl)sulfinyl)methyl)phenyl)propanoic acid A) ethyl 3-cyclopropyl-3-(3-(((2'-fluoro-5'-methoxy-2-neopentyl-[1,1'-biphenyl]-4-yl)sulfinyl)methyl)phenyl)propanoate To a solution of ethyl 3-cyclopropyl-3-(3-(((2'-fluoro-5'-methoxy-2-neopentyl-[1,1'-biphenyl]-4-yl)thio)methyl)phenyl)propanoate (158 mg) in methanol (0.95 mL) was added a solution of sodium periodate (66 mg) in water (50 µL), and the mixture was stirred at room temperature for 7 hr. To the reaction mixture was added saturated aqueous sodium thiosulfate solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (143 mg) as a colorless oil.

$^1$H NMR (300 MHz, DMSO-$d_6$) δ 0.01-0.09 (1H, m), 0.12-0.35 (2H, m), 0.41-0.56 (1H, m), 0.63 (9H, s), 0.82-1.01 (1H, m), 1.09 (3H, t, J=7.1 Hz), 2.16-2.31 (1H, m), 2.52-2.75 (4H, m), 3.76 (3H, s), 3.97 (2H, qd, J=7.1, 2.5 Hz), 4.11 (1H, d, J=12.4 Hz), 4.27 (1H, dd, J=12.6, 5.1 Hz), 6.78-6.85 (1H, m), 6.93 (1H, d, J=5.4 Hz), 6.96-7.05 (2H, m), 7.17-7.27 (3H, m), 7.29-7.42 (2H, m), 7.46 (1H, brs).

B) 3-cyclopropyl-3-(3-(((2-(2,2-dimethylpropyl)-2'-fluoro-5'-methoxybiphenyl-4-yl)sulfinyl)methyl)phenyl)propanoic acid To a solution of ethyl 3-cyclopropyl-3-(3-(((2'-fluoro-5'-methoxy-2-neopentyl-[1,1'-biphenyl]-4-yl)sulfinyl)methyl)phenyl)propanoate (143 mg) in ethanol (2.6 mL) was added 2N aqueous sodium hydroxide solution (649 µL) at room temperature, and the mixture was stirred at 50° C. for 2 hr. The reaction mixture was cooled to 0° C., neutralized with 1N hydrochloric acid, and extracted with ethyl acetate. The extract was washed with saturated brine and dried over anhydrous sodium sulfate. The solvent was evaporated under reduced pressure to give the title compound (129 mg) as a white amorphous solid.

$^1$H NMR (300 MHz, DMSO-$d_6$) δ 0.01-0.10 (1H, m), 0.16-0.34 (2H, m), 0.40-0.52 (1H, m), 0.63 (9H, s), 0.81-0.99 (1H, m), 2.18-2.31 (1H, m), 2.54-2.70 (2H, m), 3.76 (3H, s), 4.07-4.18 (1H, m), 4.20-4.32 (1H, m), 6.82 (1H, dt, J=5.9, 2.9 Hz), 6.92-7.05 (3H, m), 7.16-7.27 (3H, m), 7.32 (1H, d, J=7.9 Hz), 7.40 (1H, dd, J=8.0, 1.7 Hz), 7.46 (1H, s), 12.02 (1H, brs).

Example 17

3-cyclopropyl-3-(3-(((2-fluoro-5-methoxy-4''-(trifluoromethyl)-1,1':2',1''-terphenyl-4'-yl)oxy)methyl)phenyl)propanoic acid A) 2'-fluoro-5'-methoxybiphenyl-2,4-diol Under a nitrogen atmosphere, to a solution of 4-bromoresorcinol (10.1 g) in 1-butanol (200 mL) were added 2-fluoro-5-methoxyphenylboronic acid (10.8 g), tetrakis(triphenylphosphine)palladium(0) (3.00 g) and 2.0 M aqueous sodium carbonate solution (54 mL), and the mixture was stirred at 90° C. for 3 hr. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (10.6 g) as a pale-yellow oil.

$^1$H NMR (400 MHz, DMSO-$d_6$) δ 3.73 (3H, s), 6.28 (1H, dd, J=8.3, 2.1 Hz), 6.37-6.43 (1H, m), 6.78-6.87 (2H, m), 6.89-6.97 (1H, m), 7.03-7.12 (1H, m), 9.35 (2H, brs).

B) 2'-fluoro-5'-methoxy-4-((triisopropylsilyl)oxy)biphenyl-2-ol

Under a nitrogen atmosphere, to a solution of 2'-fluoro-5'-methoxybiphenyl-2,4-diol (10.6 g) in toluene (80 mL) were added triisopropylsilyl trifluoromethanesulfonate (18 mL) and 2,6-dimethylpyridine (8.0 mL) at −15° C., and the mixture was stirred for 3 hr. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (10.5 g) as a pale-yellow oil.

$^1$H NMR (400 MHz, DMSO-$d_6$) δ 1.07-1.11 (18H, m), 1.22-1.31 (3H, m), 3.74 (3H, s), 6.38 (1H, dd, J=8.3, 2.1 Hz), 6.52 (1H, d, J=2.3 Hz), 6.81-6.89 (2H, m), 7.03 (1H, d, J=8.3 Hz), 7.11 (1H, t, J=9.3 Hz), 9.52 (1H, brs).

C) 2'-fluoro-4-hydroxy-5'-methoxybiphenyl-2-yl trifluoromethanesulfonate

To a solution of 2'-fluoro-5'-methoxy-4-((triisopropylsilyl)oxy)biphenyl-2-ol (9.42 g) in acetonitrile (130 mL) were added triethylamine (5.0 mL), 4-dimethylaminopyridine (302 mg) and trifluoromethanesulfonic anhydride (5.0 mL) at 0° C., and the mixture was stirred for 1 hr. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure, and the residue was dissolved in THF (100 mL). A 1.0 M solution of tetrabutylammonium fluoride in THF (48 mL) was added, and the mixture was stirred at room temperature for 30 min. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (7.41 g) as a yellow oil.

¹H NMR (400 MHz, DMSO-d₆) δ 3.76 (3H, s), 6.87-6.92 (2H, m), 6.95-7.04 (2H, m), 7.22 (1H, t, J=9.3 Hz), 7.38 (1H, d, J=8.5 Hz), 10.58 (1H, brs).

D) ethyl 3-cyclopropyl-3-(3-(((2'-fluoro-5'-methoxy-2-(((trifluoromethyl)sulfonyl)oxy)biphenyl-4-yl)oxy)methyl)phenyl)propanoate To a solution of 2'-fluoro-4-hydroxy-5'-methoxybiphenyl-2-yl trifluoromethanesulfonate (1.30 g) in THF (30 mL) were added ethyl 3-cyclopropyl-3-(3-(hydroxymethyl)phenyl)propanoate (1.02 g), triphenylphosphine (1.87 g) and a 40% solution of diethyl azodicarboxylate in toluene (3.2 mL), and the mixture was stirred at room temperature for 1 hr. Water was added to the reaction mixture, and the mixture was extracted with ethyl acetate. The extract was washed with saturated brine and dried over anhydrous sodium sulfate. The solvent was evaporated under reduced pressure, and the residue was purified by silica gel column chromatography (ethyl acetate/hexane) to give the title compound (1.71 g) as a colorless oil.

¹H NMR (400 MHz, DMSO-d₆) δ 0.06-0.16 (1H, m), 0.19-0.27 (1H, m), 0.28-0.36 (1H, m), 0.47-0.57 (1H, m), 1.00-1.10 (4H, m), 2.26-2.38 (1H, m), 2.64-2.81 (2H, m), 3.77 (3H, s), 3.88-4.01 (2H, m), 5.20 (2H, s), 6.93 (1H, dd, J=5.9, 3.1 Hz), 7.00-7.06 (1H, m), 7.20 (1H, d, J=2.3 Hz), 7.22-7.30 (3H, m), 7.30-7.40 (3H, m), 7.53 (1H, d, J=8.5 Hz).

E) ethyl 3-cyclopropyl-3-(3-(((2-fluoro-5-methoxy-4''-(trifluoromethyl)-1,1':2',1''-terphenyl-4'-yl)oxy)methyl)phenyl)propanoate Under a nitrogen atmosphere, to a solution of ethyl 3-cyclopropyl-3-(3-(((2'-fluoro-5'-methoxy-2-(((trifluoromethyl)sulfonyl)oxy)biphenyl-4-yl)oxy)methyl)phenyl)propanoate (173 mg) in toluene (5.0 mL) were added 4-(trifluoromethyl)phenylboronic acid (157 mg), tris(dibenzylideneacetone)dipalladium(0) (20 mg), 2-dicyclohexylphosphino-2',6'-dimethoxybiphenyl (39 mg) and 2.0 M aqueous sodium carbonate solution (0.43 mL), and the mixture was stirred at 90° C. for 15 hr. The reaction mixture was filtered through celite, water was added to the filtrate, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (97 mg) as a colorless oil.

¹H NMR (400 MHz, DMSO-d₆) δ 0.05-0.14 (1H, m), 0.19-0.34 (2H, m), 0.46-0.55 (1H, m), 0.98-1.10 (4H, m), 2.31 (1H, q, J=7.9 Hz), 2.65-2.81 (2H, m), 3.65 (3H, s), 3.88-4.00 (2H, m), 5.20 (2H, s), 6.75 (1H, dd, J=5.8, 3.1 Hz), 6.78-6.85 (1H, m), 6.90-6.99 (1H, m), 7.12 (1H, d, J=2.5 Hz), 7.17 (1H, dd, J=8.5, 2.6 Hz), 7.22-7.28 (1H, m), 7.29-7.42 (6H, m), 7.61 (2H, d, J=8.2 Hz).

F) 3-cyclopropyl-3-(3-(((2-fluoro-5-methoxy-4''-(trifluoromethyl)-1,1':2',1''-terphenyl-4'-yl)oxy)methyl)phenyl)propanoic acid To a solution of ethyl 3-cyclopropyl-3-(3-(((2-fluoro-5-methoxy-4''-(trifluoromethyl)-1,1':2',1''-terphenyl-4'-yl)oxy)methyl)phenyl)propanoate (92 mg) in ethanol (3.0 mL) was added 2N aqueous sodium hydroxide solution (0.16 mL), and the mixture was stirred at 50° C. for 15 hr. To the reaction mixture was added 1N hydrochloric acid, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (85 mg) as a white solid.

¹H NMR (400 MHz, DMSO-d₆) δ 0.06-0.13 (1H, m), 0.19-0.33 (2H, m), 0.44-0.55 (1H, m), 0.95-1.06 (1H, m), 2.32 (1H, q, J=7.7 Hz), 2.59-2.73 (2H, m), 3.65 (3H, s), 5.19 (2H, s), 6.75 (1H, dd, J=5.5, 3.1 Hz), 6.79-6.85 (1H, m), 6.90-6.98 (1H, m), 7.13 (1H, s), 7.15-7.20 (1H, m), 7.21-7.27 (1H, m), 7.29-7.41 (6H, m), 7.61 (2H, d, J=8.0 Hz), 12.05 (1H, brs).

Example 18

3-(2-(((2-(2,2-dimethylpropyl)-2'-fluoro-5'-methoxybiphenyl-4-yl)oxy)methyl)pyridin-4-yl)propanoic acid

A) (E)-ethyl 3-(2-methylpyridin-4-yl)acrylate

Under an argon atmosphere, to a solution of 4-bromo-2-methylpyridine (1.78 mL) in DMF (35 mL) were added ethyl acrylate (8.13 mL), palladium (II) acetate (168 mg), tri-o-tolylphosphine (685 mg) and triethylamine (6.27 mL), and the mixture was stirred at 100° C. for 1 hr. Water was added to the reaction mixture, and the mixture was extracted with ethyl acetate. The extract was washed with water and saturated brine, and dried over anhydrous magnesium sulfate. The solvent was evaporated under reduced pressure to give a crude product of the title compound as a yellow oil. This compound was used for the next step without further purification.

¹H NMR (400 MHz, DMSO-d₆) δ 1.27 (3H, t, J=7.1 Hz), 2.49 (3H, s), 4.21 (2H, q, J=7.1 Hz), 6.85 (1H, d, J=16.2 Hz), 7.48 (1H, d, J=5.0 Hz), 7.53-7.62 (2H, m), 8.49 (1H, d, J=5.1 Hz).

B) ethyl 3-(2-methylpyridin-4-yl)propanoate

To a solution of (E)-ethyl 3-(2-methylpyridin-4-yl)acrylate (entire amount) obtained in Example 18, step A, in acetic acid (40 mL) was added zinc powder (9.81 g), and the mixture was stirred at room temperature for 5 min. The reaction mixture was filtered, and the filtrate was neutralized with saturated aqueous sodium hydrogen carbonate solution at room temperature. The mixture was extracted with ethyl acetate, and the extract was washed with water and saturated brine, and dried over anhydrous magnesium sulfate. The solvent was evaporated under reduced pressure to give a crude product of the title compound as a pale-yellow oil. This compound was used for the next step without further purification.

¹H NMR (400 MHz, DMSO-d₆) δ 1.15 (3H, t, J=7.1 Hz), 2.41 (3H, s), 2.59-2.70 (2H, m), 2.75-2.87 (2H, m), 4.04 (2H, q, J=7.0 Hz), 7.04 (1H, d, J=5.0 Hz), 7.11 (1H, s), 8.31 (1H, d, J=5.1 Hz).

C) 4-(3-ethoxy-3-oxopropyl)-2-methylpyridine 1-oxide

To a solution of ethyl 3-(2-methylpyridin-4-yl)propanoate (entire amount) obtained in Example 18, step B, in acetonitrile (85 mL) was added m-chloroperbenzoic acid (8.38 g), and the mixture was stirred at room temperature for 1 hr. The solvent was evaporated under reduced pressure and the residue was purified by silica gel column chromatography (NH, methanol/ethyl acetate) to give the title compound (2.51 g) as a white solid.

$^1$H NMR (400 MHz, DMSO-d$_6$) δ 1.15 (3H, t, J=7.1 Hz), 2.31 (3H, s), 2.64 (2H, t, J=7.2 Hz), 2.80 (2H, t, J=7.5 Hz), 4.04 (2H, q, J=7.2 Hz), 7.15 (1H, dd, J=6.7, 2.4 Hz), 7.35 (1H, d, J=2.1 Hz), 8.14 (1H, d, J=6.5 Hz).

D) ethyl 3-(2-(acetoxymethyl)pyridin-4-yl)propanoate

A mixture of 4-(3-ethoxy-3-oxopropyl)-2-methylpyridine 1-oxide (1.99 g) and acetic anhydride (10 mL) was stirred at 100° C. for 30 min. The solvent was evaporated under reduced pressure and the residue was purified by silica gel column chromatography (NH, ethyl acetate/hexane) to give a crude product of the title compound as a colorless oil. This compound was used for the next step without further purification.

E) ethyl 3-(2-(hydroxymethyl)pyridin-4-yl)propanoate

To a solution of ethyl 3-(2-(acetoxymethyl)pyridin-4-yl) propanoate (entire amount) obtained in Example 18, step D, in methanol (6.0 mL) was added potassium carbonate (1.35 g), and the mixture was stirred at room temperature for 1 hr. The solvent was evaporated under reduced pressure and filtered through celite. The filtrate was concentrated and the residue was purified by silica gel column chromatography (NH, ethyl acetate/hexane) to give the title compound (99 mg) as a colorless oil.

$^1$H NMR (400 MHz, DMSO-d$_6$) δ 1.15 (3H, t, J=7.2 Hz), 2.57-2.75 (2H, m), 2.79-3.00 (2H, m), 4.04 (2H, q, J=7.0 Hz), 4.52 (2H, d, J=5.8 Hz), 5.33 (1H, t, J=5.7 Hz), 7.10 (1H, d, J=4.9 Hz), 7.32 (1H, s), 8.34 (1H, d, J=5.1 Hz).

F) ethyl 3-(2-(((2'-fluoro-5'-methoxy-2-neopentyl-[1,1'-biphenyl]-4-yl)oxy)methyl)pyridin-4-yl)propanoate Under an argon atmosphere, to a solution of 2'-fluoro-5'-methoxy-2-neopentyl-[1,1'-biphenyl]-4-ol (164 mg), ethyl 3-(2-(hydroxymethyl)pyridin-4-yl)propanoate (99 mg) and triphenylphosphine (248 mg) in THF (1.5 mL) was added a 40% solution of diethyl azodicarboxylate in toluene (430 μL), and the mixture was stirred for 1 hr. The solvent was evaporated under reduced pressure and the residue was purified by silica gel column chromatography (ethyl acetate/hexane) to give the title compound (72 mg) as a pale-yellow oil.

$^1$H NMR (400 MHz, DMSO-d$_6$) δ 0.61 (9H, s), 1.14 (3H, t, J=7.2 Hz), 2.31-2.53 (2H, m), 2.66 (2H, t, J=7.3 Hz), 2.88 (2H, t, J=7.3 Hz), 3.74 (3H, s), 4.03 (2H, q, J=7.2 Hz), 5.17 (2H, s), 6.77 (1H, dd, J=6.0, 3.0 Hz), 6.88 (1H, d, J=2.4 Hz), 6.90-7.01 (2H, m), 7.11 (1H, d, J=8.4 Hz), 7.16 (1H, t, J=9.3 Hz), 7.22 (1H, d, J=5.0 Hz), 7.41 (1H, s), 8.46 (1H, d, J=5.1 Hz).

G) 3-(2-(((2-(2,2-dimethylpropyl)-2'-fluoro-5'-methoxybiphenyl-4-yl)oxy)methyl)pyridin-4-yl)propanoic acid To a solution of ethyl 3-(2-(((2'-fluoro-5'-methoxy-2-neopentyl-[1,1'-biphenyl]-4-yl)oxy)methyl)pyridin-4-yl)propanoate (72 mg) in THF (1.5 mL) and methanol (0.75 mL) was added 1N aqueous sodium hydroxide solution (1.5 mL), and the mixture was stirred at room temperature for 20 min. The reaction mixture was neutralized with 1N hydrochloric acid (1.5 mL), and extracted with ethyl acetate. The extract was washed with water and saturated brine, and dried over anhydrous magnesium sulfate. The solvent was evaporated under reduced pressure to give the title compound (50 mg) as a white solid.

$^1$H NMR (400 MHz, DMSO-d$_6$) δ 0.61 (9H, s), 2.29-2.52 (2H, m), 2.58 (2H, t, J=7.4 Hz), 2.85 (2H, t, J=7.4 Hz), 3.74 (3H, s), 5.17 (2H, s), 6.77 (1H, dd, J=5.9, 3.1 Hz), 6.86-6.95 (2H, m), 6.98 (1H, dd, J=8.5, 2.3 Hz), 7.11 (1H, d, J=8.4 Hz), 7.16 (1H, t, J=9.2 Hz), 7.22 (1H, d, J=5.0 Hz), 7.42 (1H, s), 8.46 (1H, d, J=5.0 Hz), 12.23 (1H, brs).

MS (ESI+): [M+H]$^+$ 452.2

Example 19

3-cyclopropyl-3-(3-(((2'-fluoro-5'-methoxy-2-(2-methyl-1,3-thiazol-5-yl)biphenyl-4-yl)oxy)methyl) phenyl)propanoic acid By a method similar to that in Example 17, steps E and F, the title compound (34 mg) was obtained as a colorless oil.

$^1$H NMR (400 MHz, DMSO-d$_6$) δ 0.05-0.15 (1H, m), 0.19-0.36 (2H, m), 0.44-0.57 (1H, m), 0.97-1.04 (1H, m), 2.27-2.39 (1H, m), 2.53 (3H, s), 2.61-2.72 (2H, m), 3.72 (3H, s), 5.18 (2H, s), 6.80 (1H, dd, J=6.0, 3.2 Hz), 6.90-6.98 (1H, m), 7.04-7.16 (2H, m), 7.21-7.36 (5H, m), 7.39 (1H, s), 7.49 (1H, s).

Example 20

3-cyclopropyl-3-(3-(((2'-fluoro-5'-methoxy-2-(1-methyl-1H-pyrazol-4-yl)biphenyl-4-yl)oxy)methyl) phenyl)propanoic acid By a method similar to that in Example 17, steps E and F, the title compound (69 mg) was obtained as a pale-yellow solid.

$^1$H NMR (400 MHz, DMSO-d$_6$) δ 0.07-0.15 (1H, m), 0.21-0.35 (2H, m), 0.43-0.56 (1H, m), 0.94-1.06 (1H, m), 2.27-2.40 (1H, m), 2.59-2.74 (1H, m), 3.68-3.77 (6H, m), 5.15 (2H, s), 6.78 (1H, dd, J=5.9, 3.3 Hz), 6.89-7.01 (3H, m), 7.08 (1H, t, J=9.0 Hz), 7.14-7.21 (2H, m), 7.22-7.27 (1H, m), 7.28-7.34 (2H, m), 7.39 (1H, s), 7.48 (1H, s).

Example 21

3-cyclopropyl-3-(3-(((3-(4,4-dimethylpentyl)-2'-fluoro-5'-methoxybiphenyl-4-yl)oxy)methyl)phenyl) propanoic acid A) 3,3-dimethylbutyl methanesulfonate To a solution of 3,3-dimethylbutan-1-ol (20.2 g) and triethylamine (41.3 mL) in THF (200 mL) was added methanesulfonyl chloride (24.9 g) under ice-cooling, and the mixture was stirred for 1 hr. Water was added to the reaction mixture, and the mixture was extracted with ethyl acetate. The extract was washed with saturated brine and dried over anhydrous magnesium sulfate. The solvent was evaporated under reduced pressure and the residue was purified by silica gel column chromatography (ethyl acetate/hexane) to give the title compound (36.5 g) as a red-orange oil.

$^1$H NMR (300 MHz, DMSO-d$_6$) δ 0.93 (9H, s), 1.61 (2H, t, J=7.5 Hz), 3.16 (3H, s), 4.24 (2H, t, J=7.5 Hz).

B) (3,3-dimethylbutyl)(triphenyl)phosphonium methanesulfonate 3,3-Dimethylbutyl methanesulfonate (36.5 g) and triphenylphosphine (53.1 g) were stirred at 120° C. for 15 hr to give the title compound (88.0 g) as a white gummy substance.

¹H NMR (300 MHz, DMSO-d₆) δ 0.91 (9H, s), 1.35-1.45 (2H, m), 2.33 (3H, s), 3.46-3.54 (2H, m), 7.75-7.92 (15H, m).

C) 4'-(benzyloxy)-3'-(4,4-dimethylpent-1-en-1-yl)-2-fluoro-5-methoxy-1,1'-biphenyl To a solution of 4-(benzyloxy)-2'-fluoro-5'-methoxy-[1,1'-biphenyl]-3-carbaldehyde (1.40 g) in THF (10 mL) was added 60% sodium hydride (240 mg) at room temperature, and the mixture was stirred for 30 min. To the reaction mixture was added dropwise a solution of (3,3-dimethylbutyl)(triphenyl)phosphonium methanesulfonate (1.70 g) in THF (10 mL), and the mixture was stirred at 50° C. for 1 hr. 1N Hydrochloric acid was added and the mixture was extracted with ethyl acetate. The extract was washed with saturated brine and dried over anhydrous sodium sulfate. The solvent was evaporated under reduced pressure to give a crude product. This compound was used for the net step without further purification.

D) 3-(4,4-dimethylpentyl)-2'-fluoro-5'-methoxy-[1,1'-biphenyl]-4-ol

To a solution of 4'-(benzyloxy)-3'-(4,4-dimethylpent-1-en-1-yl)-2-fluoro-5-methoxy-1,1'-biphenyl (entire amount) obtained in Example 21, step C, in methanol (20 mL) was added 20% palladium hydroxide-activated carbon (585 mg) and, under a hydrogen atmosphere, the mixture was stirred at room temperature for 12 hr. The reaction mixture was filtered and the filtrate was evaporated under reduced pressure. The residue was purified by silica gel column chromatography (ethyl acetate/hexane) to give the title compound (270 mg) as a colorless oil.
¹H NMR (400 MHz, DMSO-d₆) δ 0.85 (9H, s), 1.20-1.29 (2H, m), 1.46-1.58 (2H, m), 2.51-2.56 (2H, m), 3.77 (3H, s), 6.82-6.89 (2H, m), 6.94 (1H, dd, J=6.4, 3.1 Hz), 7.11-7.22 (2H, m), 7.25 (1H, s), 9.47 (1H, brs).

E) ethyl 3-cyclopropyl-3-(3-(((3-(4,4-dimethylpentyl)-2'-fluoro-5'-methoxy-[1,1'-biphenyl]-4-yl)oxy)methyl)phenyl)propanoate To a solution of 3-(4,4-dimethylpentyl)-2'-fluoro-5'-methoxy-[1,1'-biphenyl]-4-ol (280 mg) in THF (5.0 mL) were added triphenylphosphine (348 mg), ethyl 3-cyclopropyl-3-(3-(hydroxymethyl)phenyl)propanoate (330 mg) and a 40% solution of diethyl azodicarboxylate in toluene (600 μL), and the mixture was stirred at room temperature for 2 hr. The reaction mixture was concentrated under reduced pressure and the residue was purified by silica gel column chromatography (ethyl acetate/hexane) to give the title compound (380 mg) as a colorless oil.
¹H NMR (400 MHz, DMSO-d₆) δ 0.06-0.14 (1H, m), 0.23 (1H, dd), 0.28-0.37 (1H, m), 0.47-0.56 (1H, m), 0.84 (9H, s), 1.05 (4H, t, J=7.0 Hz), 1.21-1.27 (2H, m), 1.51-1.63 (2H, m), 2.32 (1H, q, J=8.2 Hz), 2.62 (2H, t, J=7.5 Hz), 2.66-2.81 (2H, m), 3.78 (3H, s), 3.89-3.98 (2H, m), 5.15 (2H, s), 6.86-6.92 (1H, m), 6.95-7.02 (1H, m), 7.08-7.14 (1H, m), 7.15-7.27 (2H, m), 7.28-7.39 (5H, m).

F) 3-cyclopropyl-3-(3-(((3-(4,4-dimethylpentyl)-2'-fluoro-5'-methoxybiphenyl-4-yl)oxy)methyl)phenyl)propanoic acid To a solution of ethyl 3-cyclopropyl-3-(3-(((3-(4,4-dimethylpentyl)-2'-fluoro-5'-methoxy-[1,1'-biphenyl]-4-yl)oxy)methyl)phenyl)propanoate (385 mg) in ethanol (3.0 mL) was added 1N aqueous sodium hydroxide solution (3.0 mL), and the reaction mixture was stirred at 50° C. for 1 hr. 1N Hydrochloric acid was added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (320 mg) as a colorless oil.
¹H NMR (400 MHz, DMSO-d₆) δ 0.11 (1H, dt, J=9.2, 4.5 Hz), 0.21-0.36 (2H, m), 0.46-0.55 (1H, m), 0.84 (9H, s), 0.95-1.07 (1H, m), 1.21-1.28 (2H, m), 1.52-1.63 (2H, m), 2.34 (1H, q, J=7.9 Hz), 2.59-2.71 (4H, m), 3.78 (3H, s), 5.15 (2H, s), 6.86-6.92 (1H, m), 6.95-7.01 (1H, m), 7.10-7.25 (3H, m), 7.27-7.41 (5H, m), 12.05 (1H, brs).

Example 22

3-cyclopropyl-3-(3-(((5-(2,2-dimethylpropyl)-6-(2-fluoro-5-methoxyphenyl)pyridin-3-yl)oxy)methyl)phenyl)propanoic acid A) 3-bromo-2-methoxypyridine Under an argon atmosphere, to a solution of 3-bromo-2-chloropyridine (4.76 g) in DMF (30 mL) was added 28% sodium methoxide methanol solution (5.73 g) at room temperature, and the mixture was stirred at 80° C. for 30 min. Water was added at room temperature, and the mixture was extracted with ethyl acetate. The extract was washed with water and saturated brine and dried over anhydrous magnesium sulfate. The solvent was evaporated under reduced pressure to give a crude product of the title compound (4.43 g) as a pale-yellow oil. This compound was used for the next step without further purification.
¹H NMR (400 MHz, DMSO-d₆) δ 3.92 (3H, s), 6.96 (1H, dd, J=7.5, 4.9 Hz), 8.03 (1H, d, J=7.7 Hz), 8.17 (1H, d, J=4.9 Hz).

B) 2-methoxy-3-neopentylpyridine

Under an argon atmosphere, a solution of 1-bromo-2,2-dimethylpropane (14.8 mL) in diethyl ether (120 mL) was added dropwise to magnesium (3.15 g) at a slow refluxing rate. The reaction mixture was heated under reflux for 30 min, and the obtained solution was added dropwise to a solution of 3-bromo-2-methoxypyridine (4.43 g) and PEPPSI™-SIPr (trade name) (805 mg) in THF (80 mL) at room temperature. The reaction mixture was stirred at room temperature for 30 min, and saturated aqueous ammonium chloride solution was added at room temperature. The reaction mixture was extracted with ethyl acetate, and the extract was washed with water and saturated brine, and dried over anhydrous magnesium sulfate. The solvent was evaporated under reduced pressure to give a crude product of the title compound (4.24 g) as a pale-yellow oil. This compound was used for the next step without further purification.
¹H NMR (400 MHz, DMSO-d₆) δ 0.86 (9H, s), 2.47 (2H, s), 3.83 (3H, s), 6.80-7.00 (1H, m), 7.44 (1H, d, J=7.2 Hz), 8.02 (1H, d, J=4.9 Hz).

C) 5-bromo-2-methoxy-3-neopentylpyridine

To a solution of 2-methoxy-3-neopentylpyridine (4.22 g) in THF (40 mL) was added N-bromosuccinimide (6.29 g) at room temperature, and the mixture was stirred at 100° C. for 20 min. Water was added to the reaction mixture at room temperature, and the reaction mixture was extracted with ethyl acetate. The extract was washed with water, saturated aqueous sodium hydrogen carbonate solution and saturated brine, and dried over anhydrous magnesium sulfate. The solvent was evaporated under reduced pressure and the residue was purified by silica gel column chromatography (NH, hexane) to give the title compound (4.38 g) as a pale-yellow oil.

$^1$H NMR (400 MHz, DMSO-$d_6$) δ 0.86 (9H, s), 2.47 (2H, s), 3.83 (3H, s), 7.66 (1H, s), 8.14 (1H, s).

D) 6-methoxy-5-neopentylpyridin-3-ol

Under an argon atmosphere, to a solution of 5-bromo-2-methoxy-3-neopentylpyridine (4.38 g) in THF (40 mL) was added a 1.6 M solution of n-butyllithium in hexane (12.7 mL) at −78° C., and the mixture was stirred for 5 min. Trimethoxyborane (2.31 mL) was added at −78° C., and the mixture was stirred at room temperature for 14 hr. 8N Aqueous sodium hydroxide solution (2.54 mL) and 38% aqueous hydrogen peroxide (5.20 mL) were added to the reaction mixture at 0° C., and the mixture was stirred at room temperature for 5 hr. To the reaction mixture was added saturated aqueous sodium thiosulfate solution at 0° C., and the mixture was neutralized with 2N hydrochloric acid (23.4 mL). The reaction mixture was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (2.56 g) as a white solid.

$^1$H NMR (400 MHz, DMSO-$d_6$) δ 0.86 (9H, s), 2.40 (2H, s), 3.74 (3H, s), 6.94 (1H, d, J=2.8 Hz), 7.54 (1H, d, J=2.8 Hz), 9.11 (1H, s).

E) 5-(benzyloxy)-2-methoxy-3-neopentylpyridine

To a mixture of 6-methoxy-5-neopentylpyridin-3-ol (2.00 g), potassium carbonate (4.25 g) and DMF (20 mL) was added benzyl bromide (2.40 mL) at room temperature, and the mixture was stirred at 50° C. for 30 min. Water was added to the reaction mixture at room temperature, and the mixture was extracted with ethyl acetate. The extract was washed with water and saturated brine, and dried over anhydrous magnesium sulfate. The solvent was evaporated under reduced pressure to give a crude product of the title compound as a colorless oil. This compound was used for the next step without further purification.

$^1$H NMR (400 MHz, DMSO-$d_6$) δ 0.84 (9H, s), 2.43 (2H, s), 3.77 (3H, s), 5.10 (2H, s), 7.19 (1H, d, J=2.6 Hz), 7.27-7.51 (5H, m), 7.78 (1H, d, J=2.6 Hz).

F) 5-(benzyloxy)-3-neopentylpyridin-2-ol

Under a nitrogen atmosphere, to a solution of 5-(benzyloxy)-2-methoxy-3-neopentylpyridine (entire amount) obtained in Example 22, step E, in DMF (15 mL) was added pyridinium chloride (11.8 g) at room temperature, and the mixture was stirred at 100° C. for 2 hr. To the reaction mixture was added 1N hydrochloric acid at room temperature, and the resulting precipitate was collected by filtration. The obtained crude crystals were washed with 1N hydrochloric acid, water and hexane, and dissolved again in THF and acetonitrile. The solvent was evaporated under reduced pressure to give a crude product of the title compound (2.56 g) as a pale-orange solid. This compound was used for the next step without further purification.

$^1$H NMR (400 MHz, DMSO-$d_6$) δ 0.85 (9H, s), 2.33 (2H, s), 4.90 (2H, s), 6.86-6.97 (1H, m), 7.11 (1H, d, J=2.6 Hz), 7.26-7.47 (5H, m), 11.03 (1H, brs).

G) 5-(benzyloxy)-3-neopentylpyridin-2-yl trifluoromethanesulfonate

Under a nitrogen atmosphere, to a solution of 5-(benzyloxy)-3-neopentylpyridin-2-ol (2.56 g) in pyridine (31.4 mL) was added trifluoromethanesulfonic acid anhydride (3.19 mL) at 0° C., and the mixture was stirred for 5 min. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (3.64 g) as a colorless oil.

$^1$H NMR (400 MHz, DMSO-$d_6$) δ 0.87 (9H, s), 2.54 (2H, s), 5.24 (2H, s), 7.31-7.52 (5H, m), 7.59 (1H, d, J=2.6 Hz), 8.08 (1H, d, J=2.6 Hz).

H) 5-(benzyloxy)-2-(2-fluoro-5-methoxyphenyl)-3-neopentylpyridine

Under an argon atmosphere, to a solution of 5-(benzyloxy)-3-neopentylpyridin-2-yl trifluoromethanesulfonate (3.35 g) in toluene (25 mL) were added (2-fluoro-5-methoxyphenyl)boronic acid (2.12 g), tetrakis(triphenylphosphine) palladium (0) (961 mg) and 2.0 M aqueous sodium carbonate solution (12.5 mL), and the mixture was stirred at 90° C. for 3 hr. Water was added at room temperature, and the mixture was filtered through celite. The filtrate was extracted with ethyl acetate, and the extract was washed with water and saturated brine, and dried over anhydrous magnesium sulfate. The solvent was evaporated under reduced pressure and the residue was purified by silica gel column chromatography (ethyl acetate/hexane) to give the title compound (2.95 g) as a pale-yellow oil.

$^1$H NMR (400 MHz, DMSO-$d_6$) δ 0.62 (9H, s), 2.46-2.69 (2H, m), 3.74 (3H, s), 5.25 (2H, s), 6.86 (1H, dd, J=5.3, 3.3 Hz), 6.94-7.01 (1H, m), 7.17 (1H, t, J=9.1 Hz), 7.31 (1H, d, J=352.1 Hz), 7.35 (1H, d, J=7.3 Hz), 7.41 (2H, t, J=7.4 Hz), 7.46-7.56 (2H, m), 8.31 (1H, d, J=2.1 Hz).

I) 6-(2-fluoro-5-methoxyphenyl)-5-neopentylpyridin-3-ol

To a solution of 5-(benzyloxy)-2-(2-fluoro-5-methoxyphenyl)-3-neopentylpyridine (2.95 g) in ethyl acetate (50 mL) was added 10% palladium-carbon (628 mg) and, under a hydrogen atmosphere, the mixture was stirred at room temperature for 20 min. The catalyst was filtered and the filtrate was concentrated to give the title compound (2.26 g) as a white solid.

$^1$H NMR (400 MHz, DMSO-$d_6$) δ 0.67 (9H, s), 2.46 (2H, s), 3.74 (3H, s), 6.83 (1H, dd, J=5.6, 3.2 Hz), 6.91-7.00 (1H, m), 7.07 (1H, d, J=2.3 Hz), 7.15 (1H, t, J=9.2 Hz), 8.07 (1H, d, J=2.3 Hz), 9.92 (1H, brs).

J) ethyl 3-cyclopropyl-3-(3-(((6-(2-fluoro-5-methoxyphenyl)-5-neopentylpyridin-3-yl)oxy)methyl)phenyl)propanoate Under a nitrogen atmosphere, to a solution of 6-(2-fluoro-5-methoxyphenyl)-5-neopentylpyridin-3-ol (300 mg), ethyl 3-cyclopropyl-3-(3-(hydroxymethyl)phenyl)propanoate (257 mg) and triphenylphosphine (554 mg) in THF (5.0 mL) was added a 40% solution of diethyl azodicarboxylate in toluene (943 μL) at room temperature, and the mixture was stirred for 14 hr. The solvent of the reaction mixture was evaporated under reduced pressure and the residue was purified by silica gel column chromatography (ethyl acetate/hexane) to give the title compound (253 mg) as a yellow oil.

$^1$H NMR (400 MHz, DMSO-$d_6$) δ 0.06-0.15 (1H, m), 0.18-0.36 (2H, m), 0.44-0.56 (1H, m), 0.63 (9H, s), 0.97-1.05 (1H, m), 1.06 (3H, t, J=7.1 Hz), 2.26-2.36 (1H, m), 2.39-2.55 (2H, m), 2.65-2.81 (2H, m), 3.74 (3H, s), 3.89-3.99 (2H, m), 5.22 (2H, s), 6.82-6.87 (1H, m), 6.94-7.02 (1H, m), 7.17 (1H, t, J=9.2 Hz), 7.22-7.34 (4H, m), 7.37 (1H, s), 8.31 (1H, d, J=2.4 Hz).

K) 3-cyclopropyl-3-(3-(((5-(2,2-dimethylpropyl)-6-(2-fluoro-5-methoxyphenyl)pyridin-3-yl)oxy)methyl)phenyl)propanoic acid To a solution of ethyl 3-cyclopropyl-3-(3-(((6-(2-fluoro-5-methoxyphenyl)-5-neopentylpyridin-3-yl)oxy)methyl)phenyl)propanoate (253 mg) in THF (4.0 mL) and methanol (2.0 mL) was added 1N aqueous sodium hydroxide solution (4.0 mL), and the mixture was stirred at 50° C. for 1 hr. The reaction mixture was neutralized with 1N hydrochloric acid (4.0 mL) at room temperature, and extracted with ethyl acetate. The extract was washed with water and saturated brine, and dried over anhydrous magnesium sulfate. After silica gel filtration, the solvent was evaporated under reduced pressure to give the title compound (220 mg) as a white amorphous solid.

$^1$H NMR (400 MHz, DMSO-$d_6$) δ 0.04-0.15 (1H, m), 0.20-0.35 (2H, m), 0.50 (1H, d, J=8.9 Hz), 0.63 (9H, s), 0.95-1.07 (1H, m), 2.32 (1H, q, J=7.9 Hz), 2.51-2.63 (2H, m), 2.58-2.74 (2H, m), 3.74 (3H, s), 5.21 (2H, s), 6.86 (1H, d, J=5.6 Hz), 6.94-7.01 (1H, m), 7.17 (1H, t, J=9.2 Hz), 7.22-7.35 (4H, m), 7.37 (1H, s), 8.32 (1H, d, J=2.3 Hz), 12.04 (1H, brs).

MS (ESI+): [M+H]$^+$ 492.2

Example 23

3-cyclopropyl-3-(2-(((5-(2,2-dimethylpropyl)-6-(2-fluoro-5-methoxyphenyl)pyridin-3-yl)oxy)methyl)pyridin-4-yl)propanoic acid A) 2-(hydroxymethyl)isonicotinonitrile To a solution of 4-cyanopyridine (10.4 g) in methanol (180 mL), a solution of conc. sulfuric acid (6.98 mL) in water (90 mL) and ammonium peroxodisulfate (45.6 g) were successively added at room temperature, and the mixture was heated under reflux for 14 hr. The solvent was evaporated under reduced pressure, and 28% aqueous ammonia (40 mL) was added. The reaction mixture was extracted with a mixed solvent of ethyl acetate and THF, and the extract was washed with saturated brine, and dried over anhydrous magnesium sulfate. The solvent was evaporated under reduced pressure and the residue was purified by silica gel column chromatography (ethyl acetate/hexane) to give the title compound (5.08 g) as a pale-yellow solid.

$^1$H NMR (400 MHz, DMSO-$d_6$) δ 4.62 (2H, d, J=5.8 Hz), 5.63 (1H, t, J=5.8 Hz), 7.73 (1H, d, J=4.9 Hz), 7.80 (1H, s), 8.75 (1H, d, J=5.0 Hz).

B) 2-((methoxymethoxy)methyl)isonicotinonitrile

Under a nitrogen atmosphere, to a solution of 2-(hydroxymethyl)isonicotinonitrile (5.08 g) and N-ethyldiisopropylamine (26.5 mL) in DMF (76 mL) was added chloromethyl methyl ether (8.63 mL) at room temperature, and the mixture was stirred at room temperature for 20 min. Water was added to the reaction mixture, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (1.87 g) as an orange oil.

$^1$H NMR (400 MHz, DMSO-$d_6$) δ 3.31 (3H, s), 4.68 (2H, s), 4.74 (2H, s), 7.79 (1H, d, J=5.0 Hz), 7.84 (1H, s), 8.79 (1H, d, J=4.9 Hz).

C) cyclopropyl(2-((methoxymethoxy)methyl)pyridin-4-yl)methanone

Under a nitrogen atmosphere, to a solution of 2-((methoxymethoxy)methyl)isonicotinonitrile (1.87 g) in THF (20 mL) was added 0.70 M cyclopropylmagnesium bromide (30 mL) at 0° C., and the mixture was stirred at 0° C. for 1 hr. To the reaction mixture was added 1N hydrochloric acid (50 mL) at 0° C., and the mixture was stirred at room temperature for 15 min. The reaction mixture was neutralized with aqueous sodium hydroxide solution, and extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (1.20 g) as an orange oil.

$^1$H NMR (400 MHz, DMSO-$d_6$) δ 1.05-1.21 (4H, m), 2.84-2.97 (1H, m), 3.32 (3H, s), 4.71 (2H, s), 4.75 (2H, s), 7.84 (1H, d, J=5.0 Hz), 7.90 (1H, s), 8.77 (1H, d, J=5.0 Hz).

D) ethyl 3-cyclopropyl-3-(2-((methoxymethoxy)methyl)pyridin-4-yl)acrylate

To a suspension of 60% sodium hydride (1.09 g) in THF (30 mL) was added ethyl diethylphosphonoacetate (6.46 mL) at 0° C., and then cyclopropyl(2-((methoxymethoxy)methyl)pyridin-4-yl)methanone (1.20 g) was added. The reaction mixture was heated under reflux for 2 hr. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (1.36 g) as a pale-yellow oil.

MS (ESI+): [M+H]$^+$ 292.1

E) ethyl 3-cyclopropyl-3-(2-(hydroxymethyl)pyridin-4-yl)propanoate

To a solution of ethyl 3-cyclopropyl-3-(2-((methoxymethoxy)methyl)pyridin-4-yl)acrylate (1.28 g) in acetic acid (20 mL) was added zinc powder (2.87 g) at 20° C., and the mixture was stirred at room temperature for 10 min. The reaction mixture was filtered, and the solvent of the filtrate was evaporated under reduced pressure. The residue was dissolved in THF (30 mL), and conc. sulfuric acid (3.51 mL) was added. The reaction mixture was stirred at 60° C. for 1 hr, and further heated under reflux for 5 min. The reaction mixture was basified with aqueous potassium carbonate solution at 0° C., and extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (626 mg) as a colorless oil.

¹H NMR (400 MHz, DMSO-d₆) δ 0.14 (1H, dq, J=9.2, 4.5 Hz), 0.22-0.40 (2H, m), 0.47-0.59 (1H, m), 0.96-1.04 (1H, m), 1.08 (3H, t, J=7.0 Hz), 2.24-2.35 (1H, m), 2.69-2.83 (2H, m), 3.90-4.00 (2H, m), 4.53 (2H, d, J=5.8 Hz), 5.34 (1H, t, J=5.7 Hz), 7.16 (1H, d, J=4.9 Hz), 7.35 (1H, s), 8.36 (1H, d, J=5.0 Hz).

F) ethyl 3-cyclopropyl-3-(2-(((6-(2-fluoro-5-methoxyphenyl)-5-neopentylpyridin-3-yl)oxy)methyl)pyridin-4-yl)propanoate Under an argon atmosphere, to a solution of 6-(2-fluoro-5-methoxyphenyl)-5-neopentylpyridin-3-ol (300 mg), ethyl 3-cyclopropyl-3-(2-(hydroxymethyl)pyridin-4-yl)propanoate (259 mg) and triphenylphosphine (544 mg) in THF (5.0 mL) was added a 40% solution of diethyl azodicarboxylate in toluene (943 μL) at room temperature, and the mixture was stirred for 14 hr. The solvent of the reaction mixture was evaporated under reduced pressure, and the residue was purified by silica gel column chromatography (NH, ethyl acetate/hexane) to give the title compound (182 mg) as a pale-orange oil.

¹H NMR (400 MHz, DMSO-d₆) δ 0.07-0.17 (1H, m), 0.21-0.38 (2H, m), 0.47-0.55 (1H, m), 0.61 (9H, s), 0.96-1.04 (1H, m), 1.06 (3H, t, J=7.1 Hz), 2.25-2.38 (1H, m), 2.46-2.61 (2H, m), 2.70-2.85 (2H, m), 3.74 (3H, s), 3.87-3.99 (2H, m), 5.29 (2H, s), 6.79-6.90 (1H, m), 6.94-7.03 (1H, m), 7.18 (1H, t, J=9.2 Hz), 7.27-7.37 (2H, m), 7.46 (1H, s), 8.34 (1H, s), 8.48 (1H, d, J=5.0 Hz).

G) 3-cyclopropyl-3-(2-(((5-(2,2-dimethylpropyl)-6-(2-fluoro-5-methoxyphenyl)pyridin-3-yl)oxy)methyl)pyridin-4-yl)propanoic acid To a solution of ethyl 3-cyclopropyl-3-(2-(((6-(2-fluoro-5-methoxyphenyl)-5-neopentylpyridin-3-yl)oxy)methyl)pyridin-4-yl)propanoate (182 mg) in THF (2.0 mL) and methanol (1.0 mL) was added 1N aqueous sodium hydroxide solution (2.0 mL), and the mixture was stirred at room temperature for 30 min. The solvent was evaporated under reduced pressure and the residue was purified by silica gel column chromatography (methanol/ethyl acetate) to give the title compound (164 mg) as a white amorphous solid.

¹H NMR (400 MHz, DMSO-d₆) δ 0.04-0.16 (1H, m), 0.22-0.35 (2H, m), 0.45-0.56 (1H, m), 0.61 (9H, s), 0.92-1.06 (1H, m), 2.26-2.37 (1H, m), 2.44-2.58 (2H, m), 2.63-2.75 (2H, m), 3.74 (3H, s), 5.28 (2H, s), 6.82-6.89 (1H, m), 6.93-7.02 (1H, m), 7.18 (1H, t, J=9.1 Hz), 7.28 (1H, d, J=5.3 Hz), 7.33 (1H, d, J=2.4 Hz), 7.47 (1H, s), 8.35 (1H, d, J=2.4 Hz), 8.48 (1H, d, J=5.0 Hz), 12.13 (1H, brs).

MS (ESI+): [M+H]⁺ 493.2

Example 24

3-cyclopropyl-3-(2-(((2-(2,2-dimethylpropyl)-2'-fluoro-5'-methoxybiphenyl-4-yl)oxy)methyl)pyridin-4-yl)propanoic acid A) ethyl 3-cyclopropyl-3-(2-(((2'-fluoro-5'-methoxy-2-neopentyl-[1,1'-biphenyl]-4-yl)oxy)methyl)pyridin-4-yl)propanoate Under a nitrogen atmosphere, to a solution of 2'-fluoro-5'-methoxy-2-neopentyl-[1,1'-biphenyl]-4-ol (100 mg), ethyl 3-cyclopropyl-3-(2-(hydroxymethyl)pyridin-4-yl)propanoate (94 mg) and triphenylphosphine (182 mg) in THF (3.0 mL) was added a 40% solution of diethyl azodicarboxylate in toluene (315 μL) at room temperature, and the mixture was stirred for 14 hr. Triphenylphosphine (182 mg) and a 40% solution of diethyl azodicarboxylate in toluene (315 μL) were added to the reaction mixture, and the mixture was further stirred at room temperature for 14 hr. The solvent of the reaction mixture was evaporated under reduced pressure and the residue was purified by silica gel column chromatography (NH, ethyl acetate/hexane) to give the title compound (71 mg) as a pink oil.

¹H NMR (400 MHz, DMSO-d₆) δ 0.11 (1H, dd, J=9.2, 4.3 Hz), 0.20-0.36 (2H, m), 0.46-0.56 (1H, m), 0.61 (9H, s), 0.97-1.04 (1H, m), 1.06 (3H, t, J=7.2 Hz), 2.25-2.35 (1H, m), 2.37-2.56 (2H, m), 2.77 (2H, dd, J=7.3, 2.8 Hz), 3.74 (3H, s), 3.87-3.99 (2H, m), 5.19 (2H, s), 6.75 (1H, dd, J=5.7, 3.2 Hz), 6.89 (1H, s), 6.90-7.02 (2H, m), 7.10 (1H, d, J=8.4 Hz), 7.16 (1H, t, J=9.2 Hz), 7.29 (1H, d, J=4.9 Hz), 7.43 (1H, s), 8.47 (1H, d, J=5.1 Hz).

B) 3-cyclopropyl-3-(2-(((2-(2,2-dimethylpropyl)-2'-fluoro-5'-methoxybiphenyl-4-yl)oxy)methyl)pyridin-4-yl)propanoic acid To a solution of ethyl 3-cyclopropyl-3-(2-(((2'-fluoro-5'-methoxy-2-neopentyl-[1,1'-biphenyl]-4-yl)oxy)methyl)pyridin-4-yl)propanoate (71 mg) in THF (1.0 mL) and methanol (0.50 mL) was added 1N aqueous sodium hydroxide solution (1.0 mL), and the mixture was stirred at room temperature for 1 hr. To the reaction mixture was added 1N hydrochloric acid (1.0 mL) at room temperature, and the mixture was extracted with ethyl acetate. The extract was washed with water and saturated brine, and dried over anhydrous magnesium sulfate. After silica gel filtration, the solvent was evaporated under reduced pressure to give the title compound (62 mg) as a white amorphous solid.

¹H NMR (400 MHz, DMSO-d₆) δ 0.10 (1H, d, J=4.8 Hz), 0.21-0.36 (2H, m), 0.44-0.55 (1H, m), 0.61 (9H, s), 0.93-1.05 (1H, m), 2.25-2.35 (1H, m), 2.38-2.60 (2H, m), 2.70 (2H, d, J=7.3 Hz), 3.74 (3H, s), 5.18 (2H, s), 6.76 (1H, dd, J=5.8, 3.0 Hz), 6.86-6.95 (2H, m), 6.98 (1H, d, J=8.7 Hz), 7.11 (1H, d, J=8.4 Hz), 7.16 (1H, t, J=9.2 Hz), 7.27 (1H, d, J=4.8 Hz), 7.43 (1H, s), 8.47 (1H, d, J=5.1 Hz), 12.11 (1H, brs).

MS (ESI+): [M+H]⁺ 492.2

Example 25

3-cyclopropyl-3-(2-(((6-(2,2-dimethylpropyl)-5-(2-fluoro-5-methoxyphenyl)pyridin-2-yl)oxy)methyl)pyridin-4-yl)propanoic acid A) ethyl 3-cyclopropyl-3-(2-(((5-(2-fluoro-5-methoxyphenyl)-6-neopentylpyridin-2-yl)oxy)methyl)pyridin-4-yl)propanoate Under a nitrogen atmosphere, to a solution of 5-(2-fluoro-5-methoxyphenyl)-6-neopentylpyridin-2-ol (100 mg) and ethyl 3-cyclopropyl-3-(2-(hydroxymethyl)pyridin-4-yl)propanoate (94 mg) in THF (3.0 mL) were added 1,1'-(azodicarbonyl)dipiperidine (140 mg) and tributylphosphine (136 μL), and the mixture was stirred at room temperature for 14 hr. The solvent was evaporated under reduced pressure and the residue was purified by silica gel column chromatography (NH, ethyl acetate/hexane) to give the title compound (140 mg) as a colorless oil.

¹H NMR (400 MHz, DMSO-d₆) δ 0.10 (1H, dd, J=9.5, 4.3 Hz), 0.20-0.37 (2H, m), 0.45-0.57 (1H, m), 0.69 (9H, s), 0.95-1.04 (1H, m), 1.06 (3H, t, J=7.0 Hz), 2.20-2.37 (2H, m), 2.39-2.58 (1H, m), 2.64-2.85 (2H, m), 3.75 (3H, s), 3.87-3.99 (2H, m), 5.44 (2H, s), 6.81 (1H, dd, J=5.8, 2.9 Hz), 6.87 (1H, d, J=8.4 Hz), 6.94-7.01 (1H, m), 7.21 (1H, t, J=9.2 Hz), 7.25 (1H, d, J=5.0 Hz), 7.36 (1H, s), 7.56 (1H, d, J=8.7 Hz), 8.44 (1H, d, J=5.1 Hz).

B) 3-cyclopropyl-3-(2-(((6-(2,2-dimethylpropyl)-5-(2-fluoro-5-methoxyphenyl)pyridin-2-yl)oxy)methyl)pyridin-4-yl)propanoic acid To a solution of ethyl 3-cyclopropyl-3-(2-(((5-(2-fluoro-5-methoxyphenyl)-6-neopentylpyridin-2-yl)oxy)methyl)pyridin-4-yl)propanoate (140 mg) in THF (2.0 mL) and methanol (1.0 mL) was added 1N aqueous sodium hydroxide solution (2.0 mL), and the mixture was stirred at room temperature for 1 hr. To the reaction mixture was added 1N hydrochloric acid (2.0 mL) at room temperature, and the mixture was extracted with ethyl acetate. The extract was washed with water and saturated brine, and dried over anhydrous magnesium sulfate. After silica gel filtration, the solvent was evaporated under reduced pressure and the residue was recrystallized from ethyl acetate and hexane to give the title compound (123 mg) as a white solid.
¹H NMR (400 MHz, DMSO-d₆) δ 0.04-0.14 (1H, m), 0.21-0.38 (2H, m), 0.43-0.58 (1H, m), 0.69 (9H, s), 0.98 (1H, brs), 2.24-2.34 (1H, m), 2.30-2.56 (2H, m), 2.68 (2H, d, J=5.9 Hz), 3.75 (3H, s), 5.43 (2H, s), 6.75-6.84 (1H, m), 6.88 (1H, d, J=8.5 Hz), 6.93-7.03 (1H, m), 7.13-7.27 (2H, m), 7.37 (1H, s), 7.56 (1H, d, J=8.5 Hz), 8.44 (1H, d, J=5.0 Hz), 12.09 (1H, brs).
MS (ESI+): [M+H]⁺ 493.2

Example 26

3-(3-(((2-(2-cyano-2-methylpropyl)-2'-fluoro-5'-methoxybiphenyl-4-yl)oxy)methyl)phenyl)-3-cyclopropylpropanoic acid A) (4-bromo-3-methylphenoxy)(tert-butyl)dimethylsilane To a solution of 4-bromo-3-methylphenol (4.86 g) and imidazole (2.65 g) in DMF (100 mL) was added tert-butyldimethylchlorosilane (4.70 g), and the mixture was stirred at room temperature for 1 hr. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (6.97 g) as a colorless oil.
¹H NMR (400 MHz, DMSO-d₆) δ 0.18 (6H, s), 0.94 (9H, s), 2.28 (3H, s), 6.63 (1H, dd, J=8.5, 2.8 Hz), 6.86 (1H, d, J=2.5 Hz), 7.41 (1H, d, J=8.5 Hz).

B) (4-bromo-3-(bromomethyl)phenoxy)(tert-butyl)dimethylsilane

To a solution of (4-bromo-3-methylphenoxy)(tert-butyl)dimethylsilane (6.97 g) and N-bromosuccinimide (6.21 g) in ethyl acetate (100 mL) was added 2,2'-azobis(isobutyronitrile) (383 mg), and the mixture was refluxed for 17 hr. The mixture was washed with saturated aqueous sodium hydrogen carbonate solution and saturated brine, and dried over anhydrous sodium sulfate. The solvent was evaporated under reduced pressure and the residue was purified by silica gel column chromatography (ethyl acetate/hexane) to give the title compound (2.65 g) as a colorless oil.
¹H NMR (400 MHz, DMSO-d₆) δ 0.20 (6H, s), 0.95 (9H, s), 4.68 (2H, s), 6.79 (1H, dd, J=8.6, 2.3 Hz), 7.15 (1H, d, J=2.5 Hz), 7.50 (1H, d, J=8.7 Hz).

C) 3-(2-bromo-5-((tert-butyl(dimethyl)silyl)oxy)phenyl)-2,2-dimethylpropanenitrile Under a nitrogen atmosphere, to a solution of diisopropylamine (0.70 mL) in THF (15 mL) was added a 1.6 M solution of n-butyllithium in hexane (3.0 mL) at 0° C., and the mixture was stirred for 10 min. Isobutyronitrile (0.47 mL) was added at −78° C., and the mixture was stirred for 30 min. A solution of (4-bromo-3-(bromomethyl)phenoxy) (tert-butyl)dimethylsilane (1.00 g) in THF (5.0 mL) was added, and the mixture was stirred at −78° C. for 2 hr. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (905 mg) as a colorless oil.
¹H NMR (400 MHz, DMSO-d₆) δ 0.20 (6H, s), 0.94 (9H, s), 1.36 (6H, s), 3.00 (2H, s), 6.76 (1H, dd, J=8.8, 2.8 Hz), 7.00 (1H, d, J=2.5 Hz), 7.50 (1H, d, J=8.7 Hz).

D) 3-(4-((tert-butyl(dimethyl)silyl)oxy)-2'-fluoro-5'-methoxybiphenyl-2-yl)-2,2-dimethylpropanenitrile Under a nitrogen atmosphere, to a solution of 3-(2-bromo-5-((tert-butyl(dimethyl)silyl)oxy)phenyl)-2,2-dimethylpropanenitrile (903 mg), 2-fluoro-5-methoxyphenylboronic acid (621 mg), tris(dibenzylideneacetone)dipalladium(0) (45 mg) and 2-dicyclohexylphosphino-2',6'-dimethoxybiphenyl (79 mg) in toluene (10 mL) was added 2.0 M aqueous sodium carbonate solution (3.7 mL), and the mixture was stirred at 90° C. for 3 hr. The reaction mixture was filtered through celite, water was added to the filtrate, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound as a crude product. This compound was used for the next step without further purification.

E) 3-(2'-fluoro-4-hydroxy-5'-methoxybiphenyl-2-yl)-2,2-dimethylpropanenitrile

To a solution of 3-(4-((tert-butyl(dimethyl)silyl)oxy)-2'-fluoro-5'-methoxybiphenyl-2-yl)-2,2-dimethylpropanenitrile (entire amount) obtained in Example 26, step D, in THF (10 mL) was added a 1.0 M solution of tetrabutylammonium fluoride in THF (4.3 mL), and the mixture was stirred at room temperature for 2 hr. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (495 mg) as a colorless oil.

¹H NMR (400 MHz, DMSO-d₆) δ 0.95-1.14 (6H, m), 2.58-2.91 (2H, m), 3.74 (3H, s), 6.75-6.82 (2H, m), 6.90-6.96 (2H, m), 7.03 (1H, d, J=8.3 Hz), 7.16 (1H, t, J=9.2 Hz), 9.72 (1H, brs).

F) ethyl 3-(3-(((2-(2-cyano-2-methylpropyl)-2'-fluoro-5'-methoxybiphenyl-4-yl)oxy)methyl)phenyl)-3-cyclopropylpropanoate To a solution of 3-(2'-fluoro-4-hydroxy-5'-methoxybiphenyl-2-yl)-2,2-dimethylpropanenitrile (136 mg), ethyl 3-cyclopropyl-3-(3-(hydroxymethyl)phenyl)propanoate (136 mg) and tributylphosphine (0.22 mL) in toluene (5.0 mL) was added 1,1'-(azodicarbonyl)dipiperidine (225 mg), and the mixture was stirred at room temperature for 1 hr. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (203 mg) as a colorless oil.

¹H NMR (400 MHz, DMSO-d₆) δ 0.07-0.16 (1H, m), 0.19-0.28 (1H, m), 0.28-0.37 (1H, m), 0.47-0.57 (1H, m), 0.97-1.13 (10H, m), 2.31 (1H, q, J=8.1 Hz), 2.65-2.96 (4H, m), 3.75 (3H, s), 3.89-4.00 (2H, m), 5.12 (2H, s), 6.82 (1H, dd, J=6.0, 3.2 Hz), 6.93-6.99 (1H, m), 7.04 (1H, dd, J=8.4, 2.3 Hz), 7.14-7.22 (3H, m), 7.23-7.27 (1H, m), 7.28-7.38 (3H, m).

G) 3-(3-(((2-(2-cyano-2-methylpropyl)-2'-fluoro-5'-methoxybiphenyl-4-yl)oxy)methyl)phenyl)-3-cyclopropylpropanoic acid To a solution of ethyl 3-(3-(((2-(2-cyano-2-methylpropyl)-2'-fluoro-5'-methoxybiphenyl-4-yl)oxy)methyl)phenyl)-3-cyclopropylpropanoate (200 mg) in ethanol (3.0 mL) was added 2N aqueous sodium hydroxide solution (0.38 mL), and the mixture was stirred at room temperature for 16 hr. To the reaction mixture was added 1N hydrochloric acid, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (164 mg) as a white solid.

¹H NMR (400 MHz, DMSO-d₆) δ 0.06-0.17 (1H, m), 0.21-0.37 (2H, m), 0.45-0.58 (1H, m), 0.94-1.16 (7H, m), 2.32 (1H, q, J=8.2 Hz), 2.59-2.99 (4H, m), 3.75 (3H, s), 5.12 (2H, s), 6.83 (1H, dd, J=5.8, 3.1 Hz), 6.92-6.99 (1H, m), 7.05 (1H, d, J=8.5 Hz), 7.15-7.22 (3H, m), 7.24 (1H, d, J=6.8 Hz), 7.28-7.34 (2H, m), 7.34-7.38 (1H, m), 12.04 (1H, brs).

Example 27

3-(2-(((2-(2-cyano-2-methylpropyl)-2'-fluoro-5'-methoxybiphenyl-4-yl)oxy)methyl)pyridin-4-yl)-3-cyclopropylpropanoic acid A) ethyl 3-(2-(((2-(2-cyano-2-methylpropyl)-2'-fluoro-5'-methoxybiphenyl-4-yl)oxy)methyl)pyridin-4-yl)-3-cyclopropylpropanoate To a solution of 3-(2'-fluoro-4-hydroxy-5'-methoxybiphenyl-2-yl)-2,2-dimethylpropanenitrile (151 mg), ethyl 3-cyclopropyl-3-(2-(hydroxymethyl)pyridin-4-yl)propanoate (168 mg) and tributylphosphine (0.25 mL) in toluene (5.0 mL) was added 1,1'-(azodicarbonyl)dipiperidine (256 mg), and the mixture was stirred at room temperature for 3 hr. Hexane was added to the reaction mixture, and the mixture was filtered through celite. The filtrate was concentrated under reduced pressure and the residue was purified by silica gel column chromatography (ethyl acetate/hexane) to give the title compound (234 mg) as a colorless oil.

¹H NMR (400 MHz, DMSO-d₆) δ 0.08-0.18 (1H, m), 0.22-0.38 (2H, m), 0.47-0.58 (1H, m), 0.96-1.13 (10H, m), 2.27-2.37 (1H, m), 2.64-2.97 (4H, m), 3.75 (3H, s), 3.89-3.99 (2H, m), 5.20 (2H, s), 6.79-6.85 (1H, m), 6.92-6.99 (1H, m), 7.03-7.09 (1H, m), 7.15-7.23 (3H, m), 7.30 (1H, d, J=4.8 Hz), 7.45 (1H, s), 8.48 (1H, d, J=5.0 Hz).

B) 3-(2-(((2-(2-cyano-2-methylpropyl)-2'-fluoro-5'-methoxybiphenyl-4-yl)oxy)methyl)pyridin-4-yl)-3-cyclopropylpropanoic acid To a solution of ethyl 3-(2-(((2-(2-cyano-2-methylpropyl)-2'-fluoro-5'-methoxybiphenyl-4-yl)oxy)methyl)pyridin-4-yl)-3-cyclopropylpropanoate (234 mg) in ethanol (5.0 mL) was added 2N aqueous sodium hydroxide solution (0.44 mL), and the mixture was stirred at room temperature for 16 hr. To the reaction mixture was added 1N hydrochloric acid, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (220 mg) as a white solid.

¹H NMR (400 MHz, DMSO-d₆) δ 0.10-0.20 (1H, m), 0.25-0.38 (2H, m), 0.47-0.59 (1H, m), 0.95-1.15 (7H, m), 2.30-2.44 (1H, m), 2.80 (4H, m,), 3.75 (3H, s), 5.25 (2H, s), 6.83 (1H, dd, J=5.7, 3.1 Hz), 6.92-7.00 (1H, m), 7.05-7.13 (1H, m), 7.15-7.24 (3H, m), 7.38-7.47 (1H, m), 7.59 (1H, s), 8.55 (1H, d, J=5.0 Hz), 12.14 (1H, brs).

Example 28

3-(3-(((2-(5-cyano-2-thienyl)-2'-fluoro-5'-methoxybiphenyl-4-yl)oxy)methyl)phenyl)-3-cyclopropylpropanoic acid By a method similar to that in Example 17, steps E and F, the title compound (31 mg) was obtained as a white solid.

¹H NMR (400 MHz, DMSO-d₆) δ 0.06-0.15 (1H, m), 0.20-0.35 (2H, m), 0.45-0.55 (1H, m), 0.95-1.05 (1H, m), 2.28-2.39 (1H, m), 2.59-2.74 (2H, m), 3.73 (3H, s), 5.20 (2H, s), 6.81-6.87 (1H, m), 6.93-6.99 (1H, m), 7.05-7.14 (2H, m), 7.19-7.28 (2H, m), 7.29-7.42 (5H, m), 7.82 (1H, d, J=3.9 Hz).

Example 29

3-cyclopropyl-3-(6-(((5-(2,2-dimethylpropyl)-6-(2-fluoro-5-methoxyphenyl)pyridin-3-yl)oxy)methyl)pyrimidin-4-yl)propanoic acid A) ethyl 6-hydroxypyrimidine-4-carboxylate Triethylamine (17.3 mL) was added dropwise to a solution of formamidine hydrochloride (10.0 g) and diethyl acetylenedicarboxylate (19.9 mL) in acetonitrile (300 mL) at room temperature. The reaction mixture was stirred at 50° C. for 1 hr and heated under reflux overnight. The solvent of the reaction mixture was evaporated under reduced pressure to give a crude product of the title compound as a brown solid. This compound was used for the next step without further purification.

¹H NMR (400 MHz, DMSO-d$_6$) δ 1.29 (3H, t, J=7.1 Hz), 4.29 (2H, q, J=7.0 Hz), 6.87 (1H, s), 8.26 (1H, s), 11.89 (1H, brs).

B) ethyl 6-chloropyrimidine-4-carboxylate

Under a nitrogen atmosphere, to a solution of ethyl 6-hydroxypyrimidine-4-carboxylate (entire amount) obtained in Example 29, step A, and DMF (1.9 mL) in ethyl acetate (410 mL) was added oxalyl dichloride (32.6 mL) at room temperature, and the mixture was stirred at 50° C. for 30 min. Water was added to the reaction mixture at 0° C., and the mixture was extracted with ethyl acetate. The extract was washed with water and saturated brine, and dried over anhydrous magnesium sulfate. The solvent was evaporated under reduced pressure to give a crude product of the title compound as a brown solid. This compound was used for the next step without further purification.

¹H NMR (400 MHz, DMSO-d$_6$) δ 1.35 (3H, t, J=7.1 Hz), 4.40 (2H, q, J=7.1 Hz), 8.16 (1H, s), 9.24 (1H, s).

C) (6-chloropyrimidin-4-yl)methanol

To a solution of ethyl 6-chloropyrimidine-4-carboxylate (entire amount) obtained in Example 29, step B, in methanol (210 mL) was added sodium tetrahydroborate (9.99 g) at 0° C., and the mixture was stirred for 30 min. To the reaction mixture was added 1N hydrochloric acid at 0° C., and the mixture was extracted with a mixed solvent of ethyl acetate and THF. The solvent of the aqueous phase was evaporated under reduced pressure, and combined with the extract. The mixture was dried over anhydrous magnesium sulfate. The solvent was evaporated under reduced pressure to give a crude product of the title compound as a brown oil. This compound was used for the next step without further purification.

¹H NMR (400 MHz, DMSO-d$_6$) δ 4.59 (2H, d, J=5.6 Hz), 5.76 (1H, t, J=5.8 Hz), 7.64 (1H, s), 8.95 (1H, s).

D) 4-(((tert-butyldiphenylsilyl)oxy)methyl)-6-chloropyrimidine

To a solution of (6-chloropyrimidin-4-yl)methanol (entire amount) obtained in Example 29, step C, and t-butylchlorodiphenylsilane (27.5 mL) in DMF (210 mL) was added imidazole (14.4 g) at room temperature, and the mixture was stirred for 10 min. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (NH, ethyl acetate/hexane) to give the title compound (18.6 g) as a colorless oil.

¹H NMR (400 MHz, DMSO-d$_6$) δ 1.07 (9H, s), 4.81 (2H, s), 7.40-7.54 (6H, m), 7.64 (4H, d, J=6.9 Hz), 7.68 (1H, s), 8.95 (1H, s).

E) 6-(((tert-butyldiphenylsilyl)oxy)methyl)pyrimidine-4-carbonitrile

Under a nitrogen atmosphere, to a solution of (((tert-butyldiphenylsilyl)oxy)methyl)-6-chloropyrimidine (18.6 g) and 1,4-diazabicyclo[2.2.2]octane (8.18 g) in acetonitrile (97 mL) was added tetraethylammonium cyanide (7.59 g) at room temperature, and the mixture was stirred at 50° C. for 30 min. The solvent of the reaction mixture was evaporated under reduced pressure and the insoluble solid was removed by filtration. The solvent of the filtrate was evaporated under reduced pressure and the residue was purified by silica gel column chromatography (ethyl acetate/hexane) to give the title compound (11.3 g) as a colorless oil.

¹H NMR (400 MHz, DMSO-d$_6$) δ 1.08 (9H, s), 4.85 (2H, s), 7.33-7.56 (6H, m), 7.65 (4H, d, J=7.3 Hz), 8.15 (1H, s), 9.30 (1H, s).

F) (6-(((tert-butyldiphenylsilyl)oxy)methyl)pyrimidin-4-yl)(cyclopropyl)methanone Under a nitrogen atmosphere, to a solution of 6-(((tert-butyldiphenylsilyl)oxy)methyl)pyrimidine-4-carbonitrile (11.3 g) in THF (100 mL) was added 0.70 M cyclopropylmagnesium bromide (86 mL) at 0° C., and the mixture was directly stirred for 30 min. To the reaction mixture was added 1N hydrochloric acid, and the mixture was extracted with ethyl acetate. The extract was washed with saturated aqueous sodium hydrogen carbonate solution and saturated brine, and dried over anhydrous magnesium sulfate. The solvent was evaporated under reduced pressure to give a crude product of the title compound as a brown oil. This compound was used for the next step without further purification.

G) ethyl 3-(6-(((tert-butyldiphenylsilyl)oxy)methyl)pyrimidin-4-yl)-3-cyclopropylacrylate Under a nitrogen atmosphere, ethyl diethylphosphonoacetate (16.8 mL) was added to a suspension of 60% sodium hydride (3.01 g) in THF (100 mL) at 0° C., and the mixture was stirred for 5 min. To the reaction mixture was added (6-(((tert-butyldiphenylsilyl)oxy)methyl)pyrimidin-4-yl)(cyclopropyl)methanone (entire amount) obtained in Example 29, step F, at 0° C., and the mixture was stirred at room temperature for 1 hr. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (NH, ethyl acetate/hexane) to give the title compound (7.26 g) as a yellow oil.

¹H NMR (400 MHz, DMSO-d$_6$) δ 0.59-0.67 (2H, m), 0.85-0.93 (2H, m), 0.99 (3H, t, J=7.1 Hz), 1.05 (9H, s), 1.86 (1H, t, J=4.3 Hz), 3.90 (2H, q, J=7.1 Hz), 4.81 (2H, s), 6.06 (1H, s), 7.38-7.54 (6H, m), 7.64 (4H, d, J=7.2 Hz), 9.03 (1H, s).

H) ethyl 3-(6-(((tert-butyldiphenylsilyl)oxy)methyl)pyrimidin-4-yl)-3-cyclopropylpropanoate Under an argon atmosphere, to a solution of 2,2'-bis(diphenylphosphino)-1,1'-binaphthyl (844 mg) in toluene (50 mL) were added copper (I) chloride (134 mg) and sodium tert-butoxide (130 mg), and the mixture was stirred at room temperature for 5 min. To the obtained yellow suspension were successively added ethyl 3-(6-(((tert-butyldiphenylsilyl)oxy)methyl)pyrimidin-4-yl)-3-cyclopropylacrylate (6.60 g), polymethylhydrosiloxane (8.10 mL) and tert-butyl alcohol (2.56 mL) at room temperature, and the mixture was directly stirred for 7 hr. To the reaction mixture was added methanol, the solvent was evaporated under reduced pressure, and the residue was purified by silica gel column chromatography (ethyl acetate/hexane) to give the title compound (6.70 g) as a pale-yellow oil.

¹H NMR (400 MHz, DMSO-d$_6$) δ 0.25-0.48 (3H, m), 0.56 (1H, d, J=4.6 Hz), 0.93-1.04 (1H, m), 1.08 (13H, s), 2.80 (1H, dd, J=15.9, 5.3 Hz), 2.99 (1H, dd, J=15.7, 9.1 Hz), 3.91-4.01 (2H, m), 4.78 (2H, s), 7.38-7.54 (6H, m), 7.60-7.73 (5H, m), 8.95 (1H, s).

I) ethyl 3-cyclopropyl-3-(6-(hydroxymethyl)pyrimidin-4-yl)propanoate

To a solution of ethyl 3-(6-(((tert-butyldiphenylsilyl)oxy)methyl)pyrimidin-4-yl)-3-cyclopropylpropanoate (6.70 g) in THF (50 mL) was added a 1.0 M solution of tetrabutylammonium fluoride in THF (27.4 mL) at room temperature, and the mixture was directly stirred for 5 min. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (2.44 g) as a yellow oil.

$^1$H NMR (400 MHz, DMSO-$d_6$) δ 0.22-0.35 (2H, m), 0.35-0.44 (1H, m), 0.49-0.61 (1H, m), 0.89-1.04 (1H, m), 1.08 (3H, t, J=7.1 Hz), 2.37-2.48 (1H, m), 2.76 (1H, dd, J=15.7, 5.5 Hz), 2.98 (1H, dd, J=15.8, 9.2 Hz), 3.89-4.01 (2H, m), 4.54 (2H, d, J=5.8 Hz), 5.61 (1H, t, J=5.8 Hz), 7.51 (1H, s), 8.95 (1H, s).

J) ethyl 3-cyclopropyl-3-(6-(((6-(2-fluoro-5-methoxyphenyl)-5-neopentylpyridin-3-yl)oxy)methyl)pyrimidin-4-yl)propanoate Under a nitrogen atmosphere, to a solution of 6-(2-fluoro-5-methoxyphenyl)-5-neopentylpyridin-3-ol (300 mg) and ethyl 3-cyclopropyl-3-(6-(hydroxymethyl)pyrimidin-4-yl)propanoate (259 mg) in THF (8.0 mL) were added 1,1'-(azodicarbonyl)dipiperidine (419 mg) and tributylphosphine (409 μL) at room temperature, and the mixture was stirred for 2 hr. The solvent was evaporated under reduced pressure and the residue was purified by silica gel column chromatography (NH, ethyl acetate/hexane) to give the title compound (362 mg) as a colorless oil.

$^1$H NMR (400 MHz, DMSO-$d_6$) δ 0.18-0.38 (3H, m), 0.48-0.56 (1H, m), 0.61 (9H, s), 0.89-1.01 (1H, m), 1.07 (3H, t, J=7.0 Hz), 2.42-2.48 (1H, m), 2.48-2.70 (2H, m), 2.78 (1H, dd, J=15.9, 5.6 Hz), 2.98 (1H, dd, J=15.8, 9.0 Hz), 3.74 (3H, s), 3.87-4.00 (2H, m), 5.36 (2H, s), 6.80-6.89 (1H, m), 6.94-7.05 (1H, m), 7.18 (1H, t, J=9.1 Hz), 7.33 (1H, s), 7.61 (1H, s), 8.37 (1H, s), 9.09 (1H, s).

K) 3-cyclopropyl-3-(6-(((5-(2,2-dimethylpropyl)-6-(2-fluoro-5-methoxyphenyl)pyridin-3-yl)oxy)methyl)pyrimidin-4-yl)propanoic acid To a solution of ethyl 3-cyclopropyl-3-(6-(((6-(2-fluoro-5-methoxyphenyl)-5-neopentylpyridin-3-yl)oxy)methyl)pyrimidin-4-yl)propanoate (362 mg) in THF (3.0 mL) and methanol (1.5 mL) was added 1N aqueous sodium hydroxide solution (3.0 mL), and the mixture was stirred at room temperature for 30 min. To the reaction mixture was added hydrochloric acid (1N, 3.0 mL) at room temperature, and the mixture was extracted with ethyl acetate. The extract was washed with water and saturated brine, and dried over anhydrous magnesium sulfate. After silica gel filtration, the solvent was evaporated under reduced pressure to give the title compound (353 mg) as a white amorphous solid.

$^1$H NMR (400 MHz, DMSO-$d_6$) δ 0.19-0.37 (3H, m), 0.47-0.57 (1H, m), 0.61 (9H, s), 0.87-1.00 (1H, m), 2.39-2.48 (1H, m), 2.45-2.59 (2H, m), 2.70 (1H, dd, J=16.2, 5.3 Hz), 2.95 (1H, dd, J=16.2, 9.0 Hz), 3.75 (3H, s), 5.35 (2H, s), 6.86 (1H, dd, J=5.3, 3.1 Hz), 6.94-7.03 (1H, m), 7.18 (1H, t, J=9.2 Hz), 7.34 (1H, d, J=2.4 Hz), 7.60 (1H, s), 8.38 (1H, d, J=2.3 Hz), 9.09 (1H, s), 12.07 (1H, brs).

MS (ESI+): [M+H]$^+$ 494.5

Example 30

3-cyclopropyl-3-(6-(((6-(2,2-dimethylpropyl)-5-(2-fluoro-5-methoxyphenyl)pyridin-2-yl)oxy)methyl)pyrimidin-4-yl)propanoic acid

A) ethyl 3-cyclopropyl-3-(6-(((5-(2-fluoro-5-methoxyphenyl)-6-neopentylpyridin-2-yl)oxy)methyl)pyrimidin-4-yl)propanoate Under a nitrogen atmosphere, to a solution of 5-(2-fluoro-5-methoxyphenyl)-6-neopentylpyridin-2-ol (200 mg) and ethyl 3-cyclopropyl-3-(6-(hydroxymethyl)pyrimidin-4-yl)propanoate (173 mg) in THF (5.0 mL) were added 1,1'-(azodicarbonyl)dipiperidine (279 mg) and tributylphosphine (273 μL) at room temperature, and the mixture was stirred for 4 hr. The solvent was evaporated under reduced pressure and the residue was purified by silica gel column chromatography (ethyl acetate/hexane) to give the title compound (233 mg) as a colorless oil.

$^1$H NMR (400 MHz, DMSO-$d_6$) δ 0.10-0.22 (1H, m), 0.22-0.34 (2H, m), 0.44-0.55 (1H, m), 0.60 (9H, s), 0.85-0.99 (1H, m), 1.07 (3H, t, J=7.1 Hz), 2.36-2.50 (3H, m), 2.74 (1H, dd, J=15.7, 5.5 Hz), 2.94 (1H, dd, J=15.9, 8.8 Hz), 3.75 (3H, s), 3.89-3.99 (2H, m), 5.48 (2H, d, J=3.8 Hz), 6.75-6.83 (1H, m), 6.94 (1H, d, J=8.5 Hz), 6.96-7.01 (1H, m), 7.21 (1H, t, J=9.1 Hz), 7.44 (1H, s), 7.60 (1H, d, J=8.4 Hz), 9.02 (1H, s).

B) 3-cyclopropyl-3-(6-(((6-(2,2-dimethylpropyl)-5-(2-fluoro-5-methoxyphenyl)pyridin-2-yl)oxy)methyl)pyrimidin-4-yl)propanoic acid To a solution of ethyl 3-cyclopropyl-3-(6-(((5-(2-fluoro-5-methoxyphenyl)-6-neopentylpyridin-2-yl)oxy)methyl)pyrimidin-4-yl)propanoate (233 mg) in THF (2.0 mL) and methanol (1.0 mL) was added 1N aqueous sodium hydroxide solution (2.0 mL), and the mixture was stirred at room temperature for 1 hr. To the reaction mixture was added 1N hydrochloric acid (2.0 mL), and the mixture was extracted with ethyl acetate. The extract was washed with water and saturated brine, and dried over anhydrous magnesium sulfate. The organic layer was filtered through silica gel and the solvent was evaporated under reduced pressure to give the title compound (214 mg) as a white amorphous solid.

$^1$H NMR (400 MHz, DMSO-$d_6$) δ 0.12-0.20 (1H, m), 0.22-0.35 (2H, m), 0.45-0.54 (1H, m), 0.60 (9H, s), 0.82-0.98 (1H, m), 2.29-2.51 (3H, m), 2.66 (1H, dd, J=15.9, 5.3 Hz), 2.91 (1H, dd, J=16.3, 9.0 Hz), 3.75 (3H, s), 5.45 (1H, d, J=15.4 Hz), 5.49 (1H, d, J=15.3 Hz), 6.75-6.85 (1H, m), 6.95 (1H, d, J=8.3 Hz), 6.96-7.01 (1H, m), 7.21 (1H, t, J=9.2 Hz), 7.42 (1H, s), 7.59 (1H, d, J=8.4 Hz), 9.02 (1H, s), 12.06 (1H, brs).

MS (ESI+): [M+H]$^+$ 494.5

Example 31

3-cyclopropyl-3-(6-(((2-(2,2-dimethylpropyl)-2'-fluoro-5'-methoxybiphenyl-4-yl)oxy)methyl)pyrimidin-4-yl)propanoic acid

A) ethyl 3-cyclopropyl-3-(6-(((2'-fluoro-5'-methoxy-2-neopentyl-[1,1'-biphenyl]-4-yl)oxy)methyl)pyrimidin-4-yl)propanoate Under a nitrogen atmosphere, to a solution of 2'-fluoro-5'-methoxy-2-neopentyl-[1,1'-biphenyl]-4-ol (200 mg) and ethyl 3-cyclopropyl-3-(6-(hydroxymethyl)pyrimidin-4-yl)propanoate (174 mg) in THF (5.0 mL) were added 1,1'-(azodicarbonyl) dipiperidine (280 mg) and tributylphosphine (274 μL) at room temperature, and the mixture was stirred for 5 hr. The solvent was evaporated under reduced pressure and the residue was purified by silica gel column chromatography (NH, ethyl acetate/hexane) to give the title compound (201 mg) as a colorless oil.

B) 3-cyclopropyl-3-(6-(((2-(2,2-dimethylpropyl)-2'-fluoro-5'-methoxybiphenyl-4-yl)oxy)methyl)pyrimidin-4-yl)propanoic acid To a solution of ethyl 3-cyclopropyl-3-(6-(((2'-fluoro-5'-methoxy-2-neopentyl-[1,1'-biphenyl]-4-yl)oxy)methyl)pyrimidin-4-yl)propanoate (201 mg) in THF (2.0 mL) and methanol (1.0 mL) was added 1N aqueous sodium hydroxide solution (2.0 mL), and the mixture was stirred at room temperature for 1 hr. To the reaction mixture was added 1N hydrochloric acid (2.0 mL), and the mixture was extracted with ethyl acetate. The extract was washed with water and saturated brine, and dried over anhydrous magnesium sulfate. The organic layer was filtered with silica gel and the solvent was evaporated under reduced pressure to give the title compound (184 mg) as a white amorphous solid.

$^1$H NMR (400 MHz, DMSO-$d_6$) δ 0.19-0.26 (1H, m), 0.26-0.36 (2H, m), 0.45-0.56 (1H, m), 0.61 (9H, s), 0.80-1.03 (1H, m), 2.28-2.56 (3H, m), 2.69 (1H, dd, J=16.0, 5.1 Hz), 2.94 (1H, dd, J=16.3, 9.1 Hz), 3.74 (3H, s), 5.25 (2H, s), 6.72-6.80 (1H, m), 6.87-6.97 (2H, m), 6.99 (1H, d, J=9.7 Hz), 7.10-7.21 (2H, m), 7.56 (1H, s), 9.08 (1H, s), 12.09 (1H, brs).
MS (ESI+): [M+H]$^+$ 493.5

Example 32

3-(3-(((2-(5-tert-butyl-1,3,4-oxadiazol-2-yl)-2'-fluoro-5'-methoxybiphenyl-4-yl)oxy)methyl)phenyl)-3-cyclopropylpropanoic acid

A) ethyl 2-bromo-5-methoxybenzoate

To a solution of 2-bromo-5-methoxybenzoic acid (5.00 g) in ethanol (100 mL) was added conc. sulfuric acid (10 drops), and the mixture was stirred at 95° C. for 40.5 hr. The reaction mixture was concentrated under reduced pressure and water was added. The reaction mixture was extracted with ethyl acetate, and the extract was washed with saturated brine and dried over anhydrous sodium sulfate. The solvent was evaporated under reduced pressure and the residue was purified by silica gel column chromatography (ethyl acetate/hexane) to give the title compound (5.37 g) as a colorless oil.

$^1$H NMR (400 MHz, DMSO-$d_6$) δ 1.32 (3H, t, J=7.1 Hz), 3.79 (3H, s), 4.32 (2H, q, J=7.0 Hz), 7.07 (1H, dd, J=8.8, 2.9 Hz), 7.26 (1H, d, J=2.9 Hz), 7.62 (1H, d, J=8.8 Hz).

B) ethyl 2-bromo-5-hydroxybenzoate

Aluminum chloride (11.0 g) was added to toluene (80 mL) at room temperature. 1-Dodecanethiol (33.5 g) was added at 0° C., and the mixture was stirred for 30 min. A solution of ethyl 2-bromo-5-methoxybenzoate (5.36 g) in toluene (40 mL) was added at 0° C., and the mixture was stirred at room temperature for 1 hr. The reaction mixture was poured into water in an ice bath, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (4.66 g) as a pale-yellow oil.

$^1$H NMR (400 MHz, DMSO-$d_6$) δ 1.31 (3H, t, J=7.1 Hz), 4.29 (2H, q, J=7.0 Hz), 6.87 (1H, dd, J=8.7, 2.9 Hz), 7.12 (1H, d, J=2.9 Hz), 7.49 (1H, d, J=8.7 Hz), 10.08 (1H, brs).

C) ethyl 2'-fluoro-4-hydroxy-5'-methoxy-[1,1'-biphenyl]-2-carboxylate

Under an argon atmosphere, to a solution of ethyl 2-bromo-5-hydroxybenzoate (1.13 g) in toluene (30 mL) were added 2-fluoro-5-methoxyphenylboronic acid (1.18 g), 2-dicyclohexylphosphino-2',6'-dimethoxybiphenyl (379 mg), 75% tris(dibenzylideneacetone)dipalladium (0) (281 mg) and 2.0 M aqueous sodium carbonate solution (6.9 mL), and the mixture was stirred at 100° C. for 21.5 hr. The reaction mixture was diluted with water and 1N hydrochloric acid, and extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (1.38 g) as a pale-yellow oil.

$^1$H NMR (400 MHz, DMSO-$d_6$) δ 1.00 (3H, t, J=7.1 Hz), 3.76 (3H, s), 4.02-4.08 (2H, m), 6.80 (1H, dd, J=6.1, 3.1 Hz), 6.84-6.93 (1H, m), 7.02 (1H, dd, J=8.3, 1.9 Hz), 7.08 (1H, t, J=9.3 Hz), 7.17-7.27 (2H, m), 10.17 (1H, brs).

D) 2'-fluoro-4-hydroxy-5'-methoxy-[1,1'-biphenyl]-2-carbohydrazide

To a solution of ethyl 2'-fluoro-4-hydroxy-5'-methoxy-[1,1'-biphenyl]-2-carboxylate (1.37 g) in ethanol (15 mL) was added hydrazine monohydrate (4.47 mL), and the mixture was stirred at 95° C. for 46 hr. The reaction mixture was concentrated under reduced pressure and the residue was purified by silica gel column chromatography (ethyl acetate/hexane and then methanol/ethyl acetate) to give the title compound (1.05 g) as a white amorphous solid.

$^1$H NMR (400 MHz, DMSO-$d_6$) δ 3.73 (3H, s), 4.23 (2H, brs), 6.72-6.97 (4H, m), 7.06 (1H, t, J=9.2 Hz), 7.16 (1H, d, J=8.4 Hz), 9.30 (1H, brs), 9.92 (1H, brs).

E) 2-(5-(tert-butyl)-1,3,4-oxadiazol-2-yl)-2'-fluoro-5'-methoxy-[1,1'-biphenyl]-4-yl pivalate and 2'-fluoro-5'-methoxy-2-(2-pivaloylhydrazinecarbonyl)-[1,1'-biphenyl]-4-yl pivalate To a solution of 2'-fluoro-4-hydroxy-5'-methoxy-[1,1'-biphenyl]-2-carbohydrazide (497 mg), 4-dimethylaminopyridine (22 mg) and triethylamine (1.00 mL) in THF (18 mL) was added pivaloyl chloride (695 μL) at 0° C., and the mixture was stirred for 1 hr. Water was added to the reaction mixture, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the former title compound (405 mg) as a colorless oil and the latter title compound (218 mg) as a white amorphous solid.

2-(5-(tert-butyl)-1,3,4-oxadiazol-2-yl)-2'-fluoro-5'-methoxy-[1,1'-biphenyl]-4-yl pivalate

MS (ESI+): [M+H]$^+$ 427.2

2'-fluoro-5'-methoxy-2-(2-pivaloylhydrazinecarbonyl)-[1,1'-biphenyl]-4-yl pivalate $^1$H NMR (400 MHz, DMSO-d$_6$) δ 1.08-1.16 (9H, m), 1.35 (9H, s), 3.76 (3H, s), 6.85-6.95 (2H, m), 7.13 (1H, t, J=9.1 Hz), 7.29-7.36 (1H, m), 7.37-7.47 (2H, m), 9.43-9.59 (1H, m), 9.99 (1H, brs).

F) 2-(5-(tert-butyl)-1,3,4-oxadiazol-2-yl)-2'-fluoro-5'-methoxy-[1,1'-biphenyl]-4-ol To a solution of 2-(5-(tert-butyl)-1,3,4-oxadiazol-2-yl)-2'-fluoro-5'-methoxy-[1,1'-biphenyl]-4-yl pivalate (405 mg) in methanol (3.0 mL) and THF (3.0 mL) was added 1N aqueous sodium hydroxide solution (3.0 mL), and the mixture was stirred at room temperature for 4 hr. Water and hydrochloric acid were added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (114 mg) as a white amorphous solid.
$^1$H NMR (400 MHz, DMSO-d$_6$) δ 1.13 (9H, s), 3.73 (3H, s), 6.76-6.85 (1H, m), 6.87-6.98 (1H, m), 7.02-7.17 (2H, m), 7.31 (1H, d, J=8.4 Hz), 7.43 (1H, s), 10.32 (1H, brs).

G) ethyl 3-(3-(((2-(5-(tert-butyl)-1,3,4-oxadiazol-2-yl)-2'-fluoro-5'-methoxy-[1,1'-biphenyl]-4-yl)oxy)methyl)phenyl)-3-cyclopropylpropanoate To a solution of 2-(5-(tert-butyl)-1,3,4-oxadiazol-2-yl)-2'-fluoro-5'-methoxy-[1,1'-biphenyl]-4-ol (109 mg), ethyl 3-cyclopropyl-3-(3-(hydroxymethyl)phenyl)propanoate (95 mg) and triphenylphosphine (167 mg) in THF (3.0 mL) was added a 40% solution of diethyl azodicarboxylate in toluene (250 μL) at 0° C., and the mixture was stirred at room temperature for 23 hr. The solvent was concentrated under reduced pressure and the residue was purified by silica gel column chromatography (ethyl acetate/hexane) to give the title compound (115 mg) as a colorless oil.
$^1$H NMR (400 MHz, DMSO-d$_6$) δ 0.07-0.15 (1H, m), 0.23 (1H, dt, J=9.1, 4.4 Hz), 0.27-0.35 (1H, m), 0.46-0.56 (1H, m), 1.05 (4H, t, J=7.0 Hz), 1.11-1.17 (9H, m), 2.26-2.36 (1H, m), 2.66-2.80 (2H, m), 3.73 (3H, s), 3.89-3.97 (2H, m), 5.23 (2H, s), 6.84 (1H, d, J=3.3 Hz), 6.90-6.99 (1H, m), 7.10-7.26 (2H, m), 7.30-7.37 (3H, m), 7.40 (1H, s), 7.45 (1H, d, J=8.5 Hz), 7.63 (1H, s).

H) 3-(3-(((2-(5-tert-butyl-1,3,4-oxadiazol-2-yl)-2'-fluoro-5'-methoxybiphenyl-4-yl)oxy)methyl)phenyl)-3-cyclopropylpropanoic acid To a solution of ethyl 3-(3-(((2-(5-(tert-butyl)-1,3,4-oxadiazol-2-yl)-2'-fluoro-5'-methoxy-[1,1'-biphenyl]-4-yl)oxy)methyl)phenyl)-3-cyclopropylpropanoate (115 mg) in methanol (1.0 mL) and THF (1.0 mL) was added 1N aqueous sodium hydroxide solution (0.60 mL), and the mixture was stirred at room temperature for 2 hr. Water and 1N hydrochloric acid were added, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (62 mg) as a colorless oil.
$^1$H NMR (400 MHz, DMSO-d$_6$) δ 0.07-0.15 (1H, m), 0.22-0.33 (2H, m), 0.45-0.54 (1H, m), 0.98-1.05 (1H, m), 1.14 (9H, s), 2.29-2.37 (1H, m), 2.60-2.71 (2H, m), 3.73 (3H, s), 5.22 (2H, s), 6.84 (1H, dd, J=5.8, 3.2 Hz), 6.90-7.01 (1H, m), 7.13 (1H, t, J=9.2 Hz), 7.21-7.30 (1H, m), 7.31-7.42 (4H, m), 7.43-7.49 (1H, m), 7.64 (1H, d, J=2.1 Hz), 12.07 (1H, s).

Example 33

3-cyclopropyl-3-(3-(((2'-fluoro-2-hydroxy-5'-methoxybiphenyl-4-yl)oxy)methyl)phenyl)propanoic acid A) ((2'-fluoro-5'-methoxy-2-(methoxymethoxy)biphenyl-4-yl)oxy)(triisopropyl)silane To a solution of 2'-fluoro-5'-methoxy-4-((triisopropylsilyl)oxy)biphenyl-2-ol (4.01 g) and N,N-diisopropylethylamine (5.4 mL) in DMF (30 mL) was added chloromethyl methyl ether (1.5 mL), and the mixture was stirred at room temperature for 3 hr. The mixture was further stirred at 50° C. for 1 hr, and saturated aqueous ammonium chloride solution was added to the reaction mixture. The mixture was extracted with ethyl acetate, and the extract was washed with saturated brine and dried over anhydrous sodium sulfate. The solvent was evaporated under reduced pressure, the residue was dissolved in DMF (30 mL), and N,N-diisopropylethylamine (2.7 mL) and chloromethyl methyl ether (1.0 mL) were added. The reaction mixture was stirred at room temperature for 2 hr, and saturated aqueous ammonium chloride solution was added. The reaction mixture was extracted with ethyl acetate, and the extract was washed with saturated brine and dried over anhydrous sodium sulfate. The solvent was evaporated under reduced pressure and the residue was purified by silica gel column chromatography (ethyl acetate/hexane) to give the title compound (3.50 g) as a colorless oil.
$^1$H NMR (400 MHz, DMSO-d$_6$) δ 1.07-1.12 (18H, m), 1.21-1.34 (3H, m), 3.28 (3H, s), 3.75 (3H, s), 5.09 (2H, s), 6.60 (1H, d, J=8.4 Hz), 6.75 (1H, s), 6.82-6.86 (1H, m), 6.87-6.93 (1H, m), 7.10-7.18 (2H, m).

B) 2'-fluoro-5'-methoxy-2-(methoxymethoxy)biphenyl-4-ol

To a solution of ((2'-fluoro-5'-methoxy-2-(methoxymethoxy)biphenyl-4-yl)oxy)(triisopropyl)silane (3.50 g) in THF (30 mL) was added a 1.0 M solution of tetrabutylammonium fluoride in THF (16 mL), and the mixture was stirred at room temperature for 30 min. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (2.30 g) as a colorless oil.
$^1$H NMR (400 MHz, DMSO-d$_6$) δ 3.29 (3H, s), 3.74 (3H, s), 5.08 (2H, s), 6.49 (1H, d, J=8.3 Hz), 6.64 (1H, s), 6.79-6.84 (1H, m), 6.84-6.91 (1H, m), 7.04 (1H, d, J=8.3 Hz), 7.11 (1H, t, J=9.3 Hz), 9.70 (1H, brs).

C) ethyl 3-cyclopropyl-3-(3-(((2'-fluoro-5'-methoxy-2-(methoxymethoxy)biphenyl-4-yl)oxy)methyl)phenyl)propanoate To a solution of 2'-fluoro-5'-methoxy-2-(methoxymethoxy)biphenyl-4-ol (1.29 g), ethyl 3-cyclopropyl-3-(3-(hydroxymethyl)phenyl)propanoate (1.26 g) and tributylphosphine (2.3 mL) in toluene (30 mL) was added 1,1'-(azodicarbonyl)dipiperidine (2.32 g), and the mixture was stirred at room temperature for 50 hr. To the reaction mixture was added hexane, and the mixture was filtered through celite. The filtrate was concentrated under reduced pressure and the residue was purified by silica gel column chromatography (ethyl acetate/hexane) to give the title compound (1.84 g) as a colorless oil.

$^1$H NMR (400 MHz, DMSO-$d_6$) δ 0.08-0.16 (1H, m), 0.19-0.28 (1H, m), 0.29-0.38 (1H, m), 0.47-0.57 (1H, m), 1.00-1.11 (4H, m), 2.32 (1H, q, J=8.2 Hz), 2.65-2.82 (2H, m), 3.27 (3H, s), 3.75 (3H, s), 3.89-4.00 (2H, m), 5.10 (2H, s), 5.13 (2H, s), 6.76 (1H, dd, J=8.3, 1.9 Hz), 6.81-6.87 (2H, m), 6.88-6.94 (1H, m), 7.11-7.21 (2H, m), 7.23-7.28 (1H, m), 7.28-7.34 (2H, m), 7.36 (1H, s).

D) ethyl 3-cyclopropyl-3-(3-(((2'-fluoro-2-hydroxy-5'-methoxybiphenyl-4-yl)oxy)methyl)phenyl)propanoate To a solution of ethyl 3-cyclopropyl-3-(3-(((2'-fluoro-5'-methoxy-2-(methoxymethoxy)biphenyl-4-yl)oxy)methyl)phenyl)propanoate (1.84 g) in THF (30 mL) was added 6N hydrochloric acid (3.0 mL), and the mixture was stirred at 50° C. for 4 hr. To the reaction mixture was added saturated aqueous sodium hydrogen carbonate solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (788 mg) as a colorless oil.

$^1$H NMR (400 MHz, DMSO-$d_6$) δ 0.07-0.17 (1H, m), 0.19-0.28 (1H, m), 0.29-0.38 (1H, m), 0.47-0.57 (1H, m), 0.99-1.11 (4H, m), 2.27-2.36 (1H, m), 2.65-2.82 (2H, m), 3.74 (3H, s), 3.89-4.00 (2H, m), 5.04 (2H, s), 6.51-6.60 (2H, m), 6.81-6.91 (2H, m), 7.04-7.15 (2H, m), 7.22-7.37 (4H, m), 9.66 (1H, brs).

E) 3-cyclopropyl-3-(3-(((2'-fluoro-2-hydroxy-5'-methoxybiphenyl-4-yl)oxy)methyl)phenyl)propanoic acid To a solution of ethyl 3-cyclopropyl-3-(3-(((2'-fluoro-2-hydroxy-5'-methoxybiphenyl-4-yl)oxy)methyl)phenyl)propanoate (203 mg) and potassium carbonate (179 mg) in DMF (3.0 mL) was added 1-bromo-2,2-dimethylpropane (0.11 mL), and the mixture was stirred at 90° C. for 1 hr. 60% Sodium hydride (35 mg) was added at room temperature, and the mixture was stirred at 50° C. for 3 hr. To the reaction mixture was added saturated aqueous ammonium chloride solution, and the mixture was extracted with ethyl acetate. The extract was washed with saturated brine and dried over anhydrous sodium sulfate. The solvent was evaporated under reduced pressure and the residue was purified by silica gel column chromatography (ethyl acetate/hexane) to give the title compound (128 mg) as a brown oil.

$^1$H NMR (400 MHz, DMSO-$d_6$) δ 0.08-0.18 (1H, m), 0.21-0.37 (2H, m), 0.46-0.56 (1H, m), 0.95-1.09 (1H, m), 2.32 (1H, q, J=7.9 Hz), 2.59-2.73 (2H, m), 3.74 (3H, s), 5.04 (2H, s), 6.53 (1H, d, J=8.3 Hz), 6.58 (1H, d, J=2.1 Hz), 6.81-6.90 (2H, m), 7.04-7.14 (2H, m), 7.21-7.35 (3H, m), 7.36 (1H, s).

Example 34

3-cyclopropyl-3-(3-(((2'-fluoro-5'-methoxy-2-(tetrahydro-2H-pyran-4-yl)biphenyl-4-yl)oxy)methyl)phenyl)propanoic acid

A) 4-((tert-butoxycarbonyl)oxy)-2'-fluoro-5'-methoxybiphenyl-2-yl trifluoromethanesulfonate To a solution of 2'-fluoro-4-hydroxy-5'-methoxybiphenyl-2-yl trifluoromethanesulfonate (1.97 g), di-tert-butyl dicarbonate (1.4 mL) and N,N-diisopropylethylamine (1.2 mL) in THF (40 mL) was added 4-dimethylaminopyridine (69 mg), and the mixture was stirred at room temperature for 1 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (2.13 g) as a white solid.

$^1$H NMR (400 MHz, DMSO-$d_6$) δ 1.52 (9H, s), 3.78 (3H, s), 7.01 (1H, dd, J=5.8, 3.1 Hz), 7.05-7.11 (1H, m), 7.29 (1H, t, J=9.3 Hz), 7.50 (1H, dd, J=8.5, 2.1 Hz), 7.63 (1H, d, J=2.0 Hz), 7.67 (1H, d, J=8.4 Hz).

B) tert-butyl 2-(3,6-dihydro-2H-pyran-4-yl)-2'-fluoro-5'-methoxybiphenyl-4-ylcarbonate To a solution of 4-((tert-butoxycarbonyl)oxy)-2'-fluoro-5'-methoxybiphenyl-2-yl trifluoromethanesulfonate (396 mg) in methanol (3.0 mL) and toluene (3.0 mL) were added 3,6-dihydro-2H-pyran-4-boronic acid pinacol ester (357 mg), palladium acetate (18 mg), 2-(dicyclohexylphosphino)-2',4',6'-tri-isopropyl-1,1'-biphenyl (81 mg) and potassium fluoride (152 mg), and the mixture was stirred under microwave irradiation at 100° C. for 10 min. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (232 mg) as a colorless oil.

$^1$H NMR (400 MHz, DMSO-$d_6$) δ 1.51 (9H, s), 2.02-2.11 (2H, m), 3.59 (2H, t, J=5.3 Hz), 3.75 (3H, s), 3.96 (2H, d, J=2.4 Hz), 5.49 (1H, brs), 6.87 (1H, dd, J=6.0, 3.1 Hz), 6.90-6.97 (1H, m), 7.13-7.22 (3H, m), 7.34 (1H, d, J=8.2 Hz).

C) 2-(3,6-dihydro-2H-pyran-4-yl)-2'-fluoro-5'-methoxybiphenyl-4-ol

To a solution of tert-butyl 2-(3,6-dihydro-2H-pyran-4-yl)-2'-fluoro-5'-methoxybiphenyl-4-ylcarbonate (230 mg) in ethyl acetate (2.0 mL) was added a 4N solution of hydrogen chloride in ethyl acetate (2.0 mL), and the mixture was stirred at room temperature for 20 hr. The solvent was evaporated under reduced pressure, and the residue was purified by silica gel column chromatography (ethyl acetate/hexane) to give the title compound (138 mg) as a white solid.

$^1$H NMR (400 MHz, DMSO-$d_6$) δ 1.99-2.04 (2H, m), 3.56 (2H, t, J=5.3 Hz), 3.73 (3H, s), 3.96 (2H, d, J=2.3 Hz), 5.44

(1H, brs), 6.69 (1H, d, J=2.3 Hz), 6.75 (1H, dd, J=8.3, 2.4 Hz), 6.79 (1H, dd, J=6.1, 3.1 Hz), 6.83-6.89 (1H, m), 7.06-7.14 (2H, m), 9.80 (1H, brs).

D) 2'-fluoro-5'-methoxy-2-(tetrahydro-2H-pyran-4-yl)biphenyl-4-ol

To a solution of 2-(3,6-dihydro-2H-pyran-4-yl)-2'-fluoro-5'-methoxybiphenyl-4-ol (138 mg) in methanol (3.0 mL) was added 10% palladium-carbon (55 mg), and the mixture was stirred under a hydrogen atmosphere at room temperature for 1 hr. The mixture was filtered through celite, and the filtrate was concentrated under reduced pressure. The residue was directly used for the next step.

E) ethyl 3-cyclopropyl-3-(3-(((2'-fluoro-5'-methoxy-2-(tetrahydro-2H-pyran-4-yl)biphenyl-4-yl)oxy)methyl)phenyl)propanoate To a solution of 2'-fluoro-5'-methoxy-2-(tetrahydro-2H-pyran-4-yl)biphenyl-4-ol (entire amount) obtained in Example 34, step D, ethyl 3-cyclopropyl-3-(3-(hydroxymethyl)phenyl)propanoate (123 mg) and tributylphosphine (0.17 mL) in toluene (8.0 mL) was added 1,1'-(azodicarbonyl)dipiperidine (176 mg), and the mixture was stirred at room temperature for 10 min. To the reaction mixture was added hexane, and the mixture was filtered through celite. The filtrate was concentrated under reduced pressure, and the residue was purified by silica gel column chromatography (ethyl acetate/hexane) to give the title compound (120 mg) as a colorless oil.

$^1$H NMR (400 MHz, DMSO-$d_6$) δ 0.07-0.16 (1H, m), 0.19-0.28 (1H, m), 0.28-0.38 (1H, m), 0.47-0.57 (1H, m), 1.00-1.11 (4H, m), 1.38-1.49 (1H, m), 1.49-1.57 (1H, m), 1.57-1.71 (1H, m), 1.71-1.86 (1H, m), 2.27-2.37 (1H, m), 2.55-2.64 (1H, m), 2.67-2.81 (2H, m), 3.06-3.23 (2H, m), 3.75 (3H, s), 3.78-3.91 (2H, m), 3.91-4.01 (2H, m), 5.13 (2H, s), 6.76 (1H, dd, J=6.0, 3.3 Hz), 6.90-6.99 (2H, m), 7.03 (1H, d, J=2.4 Hz), 7.08 (1H, d, J=8.4 Hz), 7.17-7.28 (2H, m), 7.29-7.36 (2H, m), 7.38 (1H, s).

F) 3-cyclopropyl-3-(3-(((2'-fluoro-5'-methoxy-2-(tetrahydro-2H-pyran-4-yl)biphenyl-4-yl)oxy)methyl)phenyl)propanoic acid To a solution of ethyl 3-cyclopropyl-3-(3-(((2'-fluoro-5'-methoxy-2-(tetrahydro-2H-pyran-4-yl)biphenyl-4-yl)oxy)methyl)phenyl)propanoate (120 mg) in ethanol (3.0 mL) was added 2N aqueous sodium hydroxide solution (0.23 mL), and the mixture was stirred at 70° C. for 2 hr. To the reaction mixture was added 1N hydrochloric acid, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (108 mg) as a white solid.

$^1$H NMR (400 MHz, DMSO-$d_6$) δ 0.05-0.14 (1H, m), 0.21-0.35 (2H, m), 0.44-0.54 (1H, m), 0.94-1.06 (1H, m), 1.39-1.49 (1H, m), 1.50-1.58 (1H, m), 1.58-1.72 (1H, m), 1.72-1.83 (1H, m), 2.31-2.39 (1H, m), 2.54-2.65 (3H, m), 3.08-3.21 (2H, m), 3.75 (3H, s), 3.78-3.93 (2H, m), 5.12 (2H, s), 6.77 (1H, dd, J=6.2, 2.9 Hz), 6.91-6.99 (2H, m), 7.04 (1H, d, J=1.9 Hz), 7.09 (1H, d, J=8.4 Hz), 7.16-7.26 (2H, m), 7.27-7.32 (2H, m), 7.37 (1H, s).

Example 35

3-cyclopropyl-3-(3-(((3-(2,2-dimethylpropyl)-2'-methoxy-2,4'-bipyridin-5-yl)oxy)methyl)phenyl)propanoic acid

A) ethyl 3-cyclopropyl-3-(3-(((6-methoxy-5-neopentylpyridin-3-yl)oxy)methyl)phenyl)propanoate To a solution of ethyl 3-cyclopropyl-3-(3-(hydroxymethyl)phenyl)propanoate (320 mg) in toluene (5.0 mL) was added phosphorus tribromide (384 mg), and the mixture was stirred at 90° C. for 1 hr. The reaction mixture was concentrated under reduced pressure, and the residue was purified by silica gel column chromatography (ethyl acetate/hexane). The obtained colorless oil was dissolved in DMF (5.0 mL), and 6-methoxy-5-neopentylpyridin-3-ol (252 mg) and potassium carbonate (356 mg) were added. The reaction mixture was stirred at 50° C. for 2 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (429 mg) as a pale-yellow oil.

$^1$H NMR (300 MHz, DMSO-$d_6$) δ 0.06-0.12 (1H, m), 0.19-0.25 (1H, m), 0.27-0.33 (1H, m), 0.47-0.54 (1H, m), 0.95-1.09 (1H, m), 1.05 (3H, t, J=7.2 Hz), 2.23-2.35 (1H, m), 2.62-2.80 (2H, m), 3.75 (3H, s), 3.88-3.99 (2H, m), 5.06 (2H, s), 7.18 (1H, d, J=2.9 Hz), 7.20-7.35 (4H, m), 7.77 (1H, d, J=2.9 Hz).

B) ethyl 3-cyclopropyl-3-(3-(((6-hydroxy-5-neopentylpyridin-3-yl)oxy)methyl)phenyl)propanoate To a solution of ethyl 3-cyclopropyl-3-(3-(((6-methoxy-5-neopentylpyridin-3-yl)oxy)methyl)phenyl)propanoate (2.86 g) in DMF (20 mL) was added pyridinium chloride (7.77 g), and the mixture was stirred at 100° C. for 3 hr. To the reaction mixture was added 1N hydrochloric acid (100 mL), and the mixture was extracted with ethyl acetate. The extract was washed with saturated brine, and dried over anhydrous magnesium sulfate. The solvent was evaporated under reduced pressure, and the obtained residue was crystallized from diisopropyl ether to give the title compound (220 mg) as white crystals.

MS (ESI+): [M+H]$^+$ 412.4

C) ethyl 3-cyclopropyl-3-(3-(((5-neopentyl-6-(((trifluoromethyl)sulfonyl)oxy)pyridin-3-yl)oxy)methyl)phenyl)propanoate To a solution of ethyl 3-cyclopropyl-3-(3-(((6-hydroxy-5-neopentylpyridin-3-yl)oxy)methyl)phenyl)propanoate (2.60 g) in pyridine (20 mL) was added trifluoromethanesulfonic acid anhydride (3.57 g) under ice-cooling, and the mixture was stirred for 5 min. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (3.09 g) as a colorless oil.

$^1$H NMR (300 MHz, DMSO-$d_6$) δ 0.05-0.11 (1H, m), 0.19-0.25 (1H, m), 0.26-0.33 (1H, m), 0.47-0.54 (1H, m), 0.84 (9H, s), 0.95-1.10 (4H, m), 2.30 (1H, q, J=8.1 Hz), 2.53

(2H, s), 2.63-2.80 (2H, m), 3.86-3.99 (2H, m), 5.22 (2H, s), 7.21-7.39 (4H, m), 7.58 (1H, d, J=2.8 Hz), 8.07 (1H, d, J=2.9 Hz).

D) ethyl 3-cyclopropyl-3-(3-(((2'-methoxy-3-neopentyl-[2,4'-bipyridine]-5-yl)oxy)methyl)phenyl)propanoate Under an argon atmosphere, to a solution of ethyl 3-cyclopropyl-3-(3-(((5-neopentyl-6-(((trifluoromethyl)sulfonyl)oxy)pyridin-3-yl)oxy)methyl)phenyl)propanoate (200 mg) in DMF (5.0 mL) were added 2-fluoro-5-methoxyphenylboronic acid (80 mg), 2.0M aqueous sodium carbonate solution (0.52 mL) and tetrakistriphenylphosphinepalladium (40 mg), and the mixture was stirred at 90° C. for 1 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (27 mg) as a colorless oil.
MS (ESI+): [M+H]$^+$ 503.6

E) 3-cyclopropyl-3-(3-(((3-(2,2-dimethylpropyl)-2'-methoxy-2,4'-bipyridin-5-yl)oxy)methyl)phenyl)propanoic acid To a solution of ethyl 3-cyclopropyl-3-(3-(((2'-methoxy-3-neopentyl-[2,4'-bipyridine]-5-yl)oxy)methyl)phenyl)propanoate (27 mg) in THF (1.0 mL) and methanol (1.0 mL) was added 1N aqueous sodium hydroxide solution (1.0 mL), and the mixture was stirred at room temperature for 16 hr. To the reaction mixture was added 1N hydrochloric acid (1.0 mL), and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (21 mg) as white crystals.
$^1$H NMR (300 MHz, DMSO-$d_6$) δ0.03-0.17 (1H, m), 0.17-0.36 (2H, m), 0.43-0.55 (1H, m), 0.60 (9H, s), 0.88-1.01 (1H, m), 2.21-2.37 (1H, m), 2.55-2.79 (4H, m), 3.88 (3H, s), 5.22 (2H, s), 6.81 (1H, s), 7.02 (1H, dd, J=5.2, 1.3 Hz), 7.27-7.41 (4H, m), 8.20 (1H, d, J=5.3 Hz), 8.33 (1H, d, J=2.7 Hz).
MS (ESI+): [M+H]$^+$ 475.5

Example 36

3-(3-(2-(6-(2,2-dimethylpropyl)-5-(2-fluoro-5-methoxyphenyl)pyridin-2-yl)-2-fluoroethyl)phenyl)propanoic acid A) 5-bromo-2-carboxypyridine 1-oxide To a suspension of 5-bromopicolinic acid (25.0 g) and urea-hydrogen peroxide adduct (20.0 g) in acetonitrile (200 mL) was added trifluoroacetic anhydride (50 mL) at 0° C., and the mixture was stirred for 30 min. The reaction mixture was filtered, and the filtrate was concentrated under reduced pressure. The obtained residue was recrystallized from diethyl ether to give the title compound (19.6 g) as white crystals.
MS (ESI+): [M+H]$^+$ 217.8

B) 5-bromo-2-(methoxycarbonyl)pyridine 1-oxide

To a solution of 5-bromo-2-carboxypyridine 1-oxide (19.6 g) in methanol (300 mL) was added dropwise thionyl chloride (37.1 g) at 0° C., and the mixture was heated under reflux for 1 hr. The reaction mixture was concentrated under reduced pressure, and the residue was washed with ethyl acetate to give the title compound (22.0 g) as a crude amorphous solid. This compound was used for the next step without further purification.
MS (ESI+): [M+H]$^+$ 231.9

C) methyl 5-bromo-6-chloropicolinate

To 5-bromo-2-(methoxycarbonyl)pyridine 1-oxide (22.0 g) was added phosphoryl chloride (40.0 mL), and the mixture was stirred at 90° C. for 10 min. The reaction mixture was cooled to room temperature and poured into ice water. The mixture was extracted with ethyl acetate, and the extract was washed with saturated aqueous sodium hydrogen carbonate solution and saturated brine, and dried over anhydrous sodium sulfate. The solvent was evaporated under reduced pressure to give the title compound (16.0 g) as a white amorphous solid.
MS (ESI+): [M+H]$^+$ 251.8

D) methyl 6-chloro-5-(2-fluoro-5-methoxyphenyl)picolinate

Under an argon atmosphere, to a solution of methyl 5-bromo-6-chloropicolinate (12.0 g) in toluene (300 mL) were added 2-fluoro-5-methoxyphenylboronic acid (9.83 g), [1,1-bis(diphenylphosphino)ferrocene]dichloropalladium (II) dichloromethane adduct (1.00 g) and a solution of sodium carbonate (14.8 g) in water (60 mL), and the mixture was stirred at 80° C. for 2 hr. The reaction mixture was concentrated under reduced pressure, and diluted with water. The reaction mixture was extracted with ethyl acetate, and the extract was washed with saturated brine and dried over anhydrous sodium sulfate. The solvent was evaporated under reduced pressure, and the residue was recrystallized from ethyl acetate to give the title compound (13.1 g) as pale-yellow crystals.
MS (ESI+): [M+H]$^+$ 296.0

E) (6-chloro-5-(2-fluoro-5-methoxyphenyl)pyridin-2-yl)methanol

Under a nitrogen atmosphere, to a suspension of calcium chloride (12.3 g) in ethanol (100 mL) and THF (50 mL) was added sodium tetrahydroborate (2.62 g) at 0° C., and the mixture was stirred at 0° C. for 10 min. A solution of methyl 6-chloro-5-(2-fluoro-5-methoxyphenyl)picolinate (8.30 g) in ethanol (25 mL) and THF (50 mL) was added at room temperature and the mixture was stirred for 14 hr. 1N Hydrochloric acid was added to the reaction mixture, and the mixture was neutralized with aqueous sodium hydrogen carbonate solution. The reaction mixture was extracted with ethyl acetate, and the extract was washed with saturated brine and dried over anhydrous sodium sulfate. The solvent was evaporated under reduced pressure to give the title compound (7.30 g) as a pale-gray amorphous solid.
MS (ESI+): [M+H]$^+$ 268.0

F) 6-((tert-butyldiphenylsilyloxy)methyl)-2-chloro-3-(2-fluoro-5-methoxyphenyl)pyridine To a solution of (6-chloro-5-(2-fluoro-5-methoxyphenyl)pyridin-2-yl)methanol (3.00 g) and tert-butylchlorodiphenylsilane (1.53 g) in DMF (7.0 mL) was added imidazole (1.53 g) at room temperature, and the mixture was stirred for 14 hr.

Water was added to the reaction mixture, and the mixture was extracted with ethyl acetate. The extract was washed with saturated brine, and dried over anhydrous sodium sulfate. The solvent was evaporated under reduced pressure to give the title compound (7.10 g) as a pale-yellow crude oil. This compound was used for the next step without further purification.

MS (ESI+): [M+H]$^+$ 506.0

G) 6-((tert-butyldiphenylsilyloxy)methyl)-3-(2-fluoro-5-methoxyphenyl)-2-neopentylpyridine Under an argon atmosphere, to a solution of 6-((tert-butyldiphenylsilyloxy)methyl)-2-chloro-3-(2-fluoro-5-methoxyphenyl)pyridine (10.0 g) and a PEPPSI™-SIPr catalyst (trade name) (1.33 g) in THF (100 mL) was added a 1.5 M solution of 2,2-dimethylpropylmagnesium chloride in diethyl ether (50 mL), and the mixture was stirred at room temperature for 16 hr. To the reaction mixture was added 1N hydrochloric acid at 0° C., and the mixture was extracted with ethyl acetate. The extract was washed with saturated brine, and dried over anhydrous sodium sulfate. The solvent was evaporated under reduced pressure to give the title compound (10.0 g) as a brown crude oil. This compound was used for the next step without further purification.

MS (ESI+): [M+H]$^+$ 542.3

H) (5-(2-fluoro-5-methoxyphenyl)-6-neopentylpyridin-2-yl)methanol

To a solution of 6-((tert-butyldiphenylsilyloxy)methyl)-3-(2-fluoro-5-methoxyphenyl)-2-neopentylpyridine (10.0 g) in THF (50 mL) was added a 1.0 M solution of tetrabutylammonium fluoride in THF (55.0 mL), and the mixture was stirred at room temperature for 2 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/petroleum ether) to give the title compound (3.00 g) as a white amorphous solid.

$^1$H NMR (400 MHz, DMSO-d$_6$) δ 0.74 (9H, s), 2.55-2.67 (2H, br), 3.76 (3H, s), 4.59 (2H, d, J=5.6 Hz), 5.40 (1H, t, J=5.6 Hz), 6.85-6.87 (1H, m), 6.97-7.02 (1H, m), 7.23 (1H, t, J=9.2 Hz), 7.39 (1H, d, J=8.0 Hz), 7.60 (1H, d, J=8.0 Hz).

I) 5-(2-fluoro-5-methoxyphenyl)-6-neopentylpicolinealdehyde

To a solution of (5-(2-fluoro-5-methoxyphenyl)-6-neopentylpyridin-2-yl)methanol (2.90 g) and triethylamine (13.3 mL) in DMSO (45 mL) was added sulfur trioxide pyridine complex (6.08 g), and the mixture was stirred at room temperature for 10 min. Water was added to the reaction mixture at room temperature, and the mixture was extracted with ethyl acetate. The extract was washed with water and saturated brine, and dried over anhydrous magnesium sulfate. After silica gel filtration, the solvent was evaporated under reduced pressure to give the title compound (2.69 g) as a yellow oil.

$^1$H NMR (400 MHz, DMSO-d$_6$) δ 0.78 (9H, s), 2.62-2.95 (2H, m), 3.78 (3H, s), 6.97 (1H, dd, J=6.0, 3.2 Hz), 7.03-7.10 (1H, m), 7.29 (1H, t, J=9.2 Hz), 7.86 (1H, d, J=7.8 Hz), 7.89 (1H, d, J=7.8 Hz), 10.02 (1H, s).

J) (3-(bromomethyl)phenyl)methanol

Under a nitrogen atmosphere, to a solution of methyl 3-(bromomethyl)benzoate (10.0 g) in toluene (100 mL) was added a 1.5 M solution (100 mL) of diisobutylaluminum hydride in toluene at 0° C., and the mixture was stirred at 0° C. for 1 hr. To the reaction mixture was added methanol at 0° C., and the resulting white precipitate was filtered off. The solvent in the filtrate was evaporated under reduced pressure to give a crude product of the title compound (8.83 g) as a colorless oil. This compound was used for the next step without further purification.

K) 2-((3-(bromomethyl)benzyl)oxy)tetrahydro-2H-pyran

To a solution of (3-(bromomethyl)phenyl)methanol (8.78 g) and 3,4-dihydro-2H-pyran (5.99 mL) in THF (60 mL) was added p-toluenesulfonic acid monohydrate (415 mg), and the mixture was stirred at room temperature for 30 min. To the reaction mixture was added an aqueous solution of sodium hydrogen carbonate (367 mg), and the mixture was extracted with ethyl acetate. The extract was washed with saturated aqueous sodium hydrogen carbonate solution and saturated brine, and dried over anhydrous magnesium sulfate. The solvent was evaporated under reduced pressure, and the residue was purified by silica gel column chromatography (ethyl acetate/hexane) to give the title compound (11.9 g) as a colorless oil.

$^1$H NMR (400 MHz, DMSO-d$_6$) δ 1.41-1.74 (6H, m), 3.43-3.53 (1H, m), 3.75-3.84 (1H, m), 4.44 (1H, d, J=12.3 Hz), 4.62-4.70 (2H, m), 4.71 (2H, s), 7.28 (1H, d, J=6.9 Hz), 7.32-7.39 (2H, m), 7.42 (1H, s).

L) 1-(5-(2-fluoro-5-methoxyphenyl)-6-neopentylpyridin-2-yl)-2-(3-(((tetrahydro-2H-pyran-2-yl)oxy)methyl)phenyl)ethanol Under a nitrogen atmosphere, 1,2-dibromoethane (34 µL) was added to a mixture of magnesium (578 mg) and THF (15 mL) at room temperature, and the mixture was stirred at 50° C. for 10 min. To the reaction mixture were added 5-(2-fluoro-5-methoxyphenyl)-6-neopentylpicolinealdehyde (2.39 g) and then 2-((3-(bromomethyl)benzyl)oxy)tetrahydro-2H-pyran (4.52 g) was added, and the mixture was stirred at room temperature for 30 min. To the reaction mixture was added saturated aqueous ammonium chloride solution at 0° C., and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (980 mg) as an orange oil.

$^1$H NMR (400 MHz, DMSO-d$_6$) δ 0.74 (9H, s), 1.36-1.83 (6H, m), 2.62 (2H, brs), 2.89 (1H, dd, J=13.7, 8.3 Hz), 3.18 (1H, dd, J=13.6, 4.1 Hz), 3.42-3.54 (1H, m), 3.72-3.85 (1H, m), 3.76 (3H, s), 4.38 (1H, d, J=11.9 Hz), 4.62 (1H, d, J=11.9 Hz), 4.62-4.71 (1H, m), 4.79-4.89 (1H, m), 5.44 (1H, d, J=4.9 Hz), 6.84 (1H, brs), 6.96-7.04 (1H, m), 7.14 (3H, brs), 7.23 (2H, t, J=8.0 Hz), 7.37 (1H, d, J=7.9 Hz), 7.58 (1H, d, J=7.9 Hz).

M) 6-(1-fluoro-2-(3-(((tetrahydro-2H-pyran-2-yl)oxy)methyl)phenyl)ethyl)-3-(2-fluoro-5-methoxyphenyl)-2-neopentylpyridine To a solution of 1-(5-(2-fluoro-5-methoxyphenyl)-6-neopentylpyridin-2-yl)-2-(3-(((tetrahydro-2H-pyran-2-yl)oxy)methyl)phenyl)ethanol (312.5 mg) in toluene (5.0 mL) was added bis(2-methoxyethyl)aminosulfur trifluoride (170 µL) at 0° C., and the mixture was stirred at 0° C. for 5 min. To the reaction mixture was added saturated aqueous sodium hydrogen carbonate solution at room temperature, and the mixture was extracted with ethyl acetate. The extract was washed with water and saturated brine, and dried over anhydrous magnesium sulfate. The solvent was evaporated under reduced pressure to give a crude product of the title compound as an orange oil. This compound was used for the next step without further purification.

N) (3-(2-fluoro-2-(5-(2-fluoro-5-methoxyphenyl)-6-neopentylpyridin-2-yl)ethyl)phenyl)methanol To a solution of 6-(1-fluoro-2-(3-(((tetrahydro-2H-pyran-2-yl)oxy)methyl)phenyl)ethyl)-3-(2-fluoro-5-methoxyphenyl)-2-neopentylpyridine (entire amount) obtained in Example 36, step M, in methanol (6.0 mL) was added p-toluenesulfonic acid monohydrate (234 mg), and the mixture was stirred at room temperature for 10 min. To the reaction mixture was added saturated aqueous sodium hydrogen carbonate solution at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (126 mg) as a colorless oil.

$^1$H NMR (400 MHz, DMSO-d$_6$) δ 0.77 (9H, s), 2.67 (2H, brs), 3.18-3.48 (2H, m), 3.77 (3H, s), 4.47 (2H, d, J=5.6 Hz), 5.15 (1H, t, J=5.6 Hz), 5.69-5.92 (1H, m), 6.89 (1H, dd, J=5.9, 3.1 Hz), 6.99-7.05 (1H, m), 7.13 (1H, d, J=7.3 Hz), 7.17-7.29 (4H, m), 7.38 (1H, d, J=7.9 Hz), 7.67 (1H, d, J=7.8 Hz).

O) 3-(2-fluoro-2-(5-(2-fluoro-5-methoxyphenyl)-6-neopentylpyridin-2-yl)ethyl)benzaldehyde To a solution of (3-(2-fluoro-2-(5-(2-fluoro-5-methoxyphenyl)-6-neopentylpyridin-2-yl)ethyl)phenyl)methanol (126 mg) in DMSO (1.0 mL) was added a Dess-Martin reagent (188 mg) at room temperature, and the mixture was stirred for 20 min. To the reaction mixture was added aqueous sodium thiosulfate solution at room temperature, and the mixture was extracted with ethyl acetate. The extract was washed with saturated aqueous sodium hydrogen carbonate solution, water and saturated brine, and dried over anhydrous magnesium sulfate. The solvent was evaporated under reduced pressure to give a crude product of the title compound as a brown oil. This compound was used for the next step without further purification.

P) ethyl 3-(3-(2-fluoro-2-(5-(2-fluoro-5-methoxyphenyl)-6-neopentylpyridin-2-yl)ethyl)phenyl)acrylate Under a nitrogen atmosphere, to a suspension of 60% sodium hydride (21 mg) in THF (2.0 mL) was added ethyl diethylphosphonoacetate (117 μL) at 0° C., and the mixture was stirred at room temperature for 5 min. To the obtained colorless solution was added 3-(2-fluoro-2-(5-(2-fluoro-5-methoxyphenyl)-6-neopentylpyridin-2-yl)ethyl)benzaldehyde (entire amount) obtained in Example 36, step O, at 0° C. and the mixture was stirred at room temperature for 20 min. Water was added to the reaction mixture at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (NH, ethyl acetate/hexane) to give the title compound (119 mg) as a colorless oil.

$^1$H NMR (400 MHz, DMSO-d$_6$) δ 0.75 (9H, s), 1.26 (3H, t, J=7.1 Hz), 2.67 (2H, brs), 3.33-3.51 (2H, m), 3.77 (3H, s), 4.19 (2H, q, J=7.1 Hz), 5.78-6.00 (1H, m), 6.58 (1H, d, J=16.1 Hz), 6.88 (1H, dd, J=5.7, 2.8 Hz), 6.98-7.06 (1H, m), 7.25 (1H, t, J=9.2 Hz), 7.31-7.41 (3H, m), 7.55-7.76 (4H, m).

Q) ethyl 3-(3-(2-fluoro-2-(5-(2-fluoro-5-methoxyphenyl)-6-neopentylpyridin-2-yl)ethyl)phenyl)propanoate Under a hydrogen atmosphere, a mixture of ethyl 3-(3-(2-fluoro-2-(5-(2-fluoro-5-methoxyphenyl)-6-neopentylpyridin-2-yl)ethyl)phenyl)acrylate (119 mg), 10% palladium-carbon (50 mg) and ethyl acetate (2.0 mL) was stirred at room temperature for 1 hr. The catalyst was removed by filtration, and the filtrate was evaporated under reduced pressure to give the title compound (90 mg) as a colorless oil.

$^1$H NMR (400 MHz, DMSO-d$_6$) δ 0.76 (9H, s), 1.15 (3H, t, J=7.1 Hz), 2.55 (2H, t, J=7.8 Hz), 2.69 (3H, br. s), 2.79 (2H, t, J=7.3 Hz), 3.18-3.44 (2H, m), 3.77 (3H, s), 4.04 (2H, q, J=7.2 Hz), 5.69-5.91 (1H, m), 6.89 (1H, dd, J=5.9, 3.0 Hz), 7.02-7.05 (1H, m), 7.06-7.13 (2H, m), 7.16-7.29 (2H, m), 7.34 (1H, d, J=8.0 Hz), 7.66 (1H, d, J=7.9 Hz).

R) 3-(3-(2-(6-(2,2-dimethylpropyl)-5-(2-fluoro-5-methoxyphenyl)pyridin-2-yl)-2-fluoroethyl)phenyl) propanoic acid To a solution of ethyl 3-(3-(2-fluoro-2-(5-(2-fluoro-5-methoxyphenyl)-6-neopentylpyridin-2-yl)ethyl)phenyl)propanoate (90 mg) in THF (2.0 mL) and methanol (1.0 mL) was added 1N aqueous sodium hydroxide solution (2.0 mL), and the mixture was stirred at room temperature for 30 min. To the reaction mixture was added, at room temperature, 1N hydrochloric acid (2.0 mL), and the mixture was extracted with ethyl acetate.

The extract was washed with water and saturated brine, and dried over anhydrous magnesium sulfate. After silica gel filtration, the solvent was evaporated under reduced pressure to give the title compound (80 mg) as a white amorphous solid.

$^1$H NMR (400 MHz, DMSO-d$_6$) δ 0.68-0.84 (9H, m), 2.48 (2H, t, J=7.7 Hz), 2.55-2.73 (2H, m), 2.77 (2H, t, J=8.0 Hz), 3.14-3.45 (2H, m), 3.77 (3H, s), 5.67-5.93 (1H, m), 6.89 (1H, dd, J=5.8, 3.1 Hz), 6.99-7.12 (4H, m), 7.17-7.28 (2H, m), 7.35 (1H, d, J=7.9 Hz), 7.66 (1H, d, J=7.8 Hz), 12.12 (1H, brs).

MS (ESI+): [M+H]$^+$ 468.2

Example 37

3-(3-(((2-(5-tert-butyl-1,3,4-thiadiazol-2-yl)-2'-fluoro-5'-methoxybiphenyl-4-yl)oxy)methyl)phenyl)-3-cyclopropylpropanoic acid

A) 2-(5-(tert-butyl)-1,3,4-thiadiazol-2-yl)-2'-fluoro-5'-methoxy-[1,1'-biphenyl]-4-yl pivalate A solution of 2'-fluoro-5'-methoxy-2-(2-pivaloylhydrazinecarbonyl)-[1,1'-biphenyl]-4-yl pivalate (203 mg) and the Lawesson's reagent (194 mg) in THF (6.0 mL) was stirred at 80° C. for 50 min. The reaction mixture was concentrated under reduced pressure, and the residue was purified by silica gel column chromatography (ethyl acetate/hexane) to give the title compound (196 mg) as a colorless oil.

¹H NMR (400 MHz, DMSO-d₆) δ 1.34 (9H, s), 1.35 (9H, s), 3.74 (3H, s), 6.86-6.96 (1H, m), 7.00-7.08 (1H, m), 7.16 (1H, t, J=9.0 Hz), 7.42 (1H, d, J=8.4 Hz), 7.55 (1H, d, J=8.4 Hz), 7.74 (1H, s).

B) 2-(5-(tert-butyl)-1,3,4-thiadiazol-2-yl)-2'-fluoro-5'-methoxy-[1,1'-biphenyl]-4-ol To a solution of 2-(5-(tert-butyl)-1,3,4-thiadiazol-2-yl)-2'-fluoro-5'-methoxy-[1,1'-biphenyl]-4-yl pivalate (191 mg) in methanol (2.0 mL) and THF (2.0 mL) was added 1N aqueous sodium hydroxide solution (1.3 mL), and the mixture was stirred at room temperature for 40 min. Water and hydrochloric acid were added, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (113 mg) as a white amorphous solid.
¹H NMR (400 MHz, DMSO-d₆) δ 1.33 (9H, s), 3.71 (3H, s), 6.79 (1H, dd, J=5.8, 2.8 Hz), 6.94-7.04 (2H, m), 7.07-7.14 (1H, m), 7.27 (1H, d, J=8.4 Hz), 7.38 (1H, s), 10.16 (1H, brs).

C) ethyl 3-(3-(((2-(5-(tert-butyl)-1,3,4-thiadiazol-2-yl)-2'-fluoro-5'-methoxy-[1,1'-biphenyl]-4-yl)oxy)methyl)phenyl)-3-cyclopropylpropanoate To a solution of 2-(5-(tert-butyl)-1,3,4-thiadiazol-2-yl)-2'-fluoro-5'-methoxy-[1,1'-biphenyl]-4-ol (109 mg), ethyl 3-cyclopropyl-3-(3-(hydroxymethyl)phenyl)propanoate (91 mg) and triphenylphosphine (319 mg) in THF (6.0 mL) was added a 40% solution of diethyl azodicarboxylate in toluene (480 μL) at 0° C., and the mixture was stirred at room temperature for 12 hr. The mixture was concentrated under reduced pressure, and the residue was purified by silica gel column chromatography (ethyl acetate/hexane) to give the title compound (134 mg) as a colorless oil.
¹H NMR (400 MHz, DMSO-d₆) δ 0.06-0.15 (1H, m), 0.19-0.35 (2H, m), 0.46-0.56 (1H, m), 1.05 (3H, t, J=7.1 Hz+1H, m), 1.33 (9H, s), 2.31 (1H, q, J=8.1 Hz), 2.68-2.80 (2H, m), 3.72 (3H, s) 3.90-3.98 (2H, m), 5.22 (2H, s), 6.81 (1H, dd, J=6.0, 3.1 Hz), 6.94-7.04 (1H, m), 7.07-7.15 (1H, m), 7.23-7.35 (4H, m), 7.38-7.43 (2H, m), 7.59 (1H, d, J=2.4 Hz).

D) 3-(3-(((2-(5-tert-butyl-1,3,4-thiadiazol-2-yl)-2'-fluoro-5'-methoxybiphenyl-4-yl)oxy)methyl)phenyl)-3-cyclopropylpropanoic acid To a solution of ethyl 3-(3-(((2-(5-(tert-butyl)-1,3,4-thiadiazol-2-yl)-2'-fluoro-5'-methoxy-[1,1'-biphenyl]-4-yl)oxy)methyl)phenyl)-3-cyclopropylpropanoate (129 mg) in methanol (1.5 mL) and THF (1.5 mL) was added 1N aqueous sodium hydroxide solution (0.66 mL), and the mixture was stirred at room temperature for 9 hr. Water and hydrochloric acid were added, and the reaction mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (122 mg) as a colorless oil.
¹H NMR (400 MHz, DMSO-d₆) δ 0.05-0.14 (1H, m), 0.20-0.34 (2H, m), 0.45-0.54 (1H, m), 0.96-1.06 (1H, m), 1.34 (9H, s), 2.33 (1H, q, J=7.8 Hz), 2.62-2.71 (2H, m), 3.72 (3H, s), 5.21 (2H, s), 6.82 (1H, dd, J=6.0, 3.1 Hz), 6.95-7.03 (1H, m), 7.07-7.15 (1H, m), 7.21-7.37 (4H, m), 7.38-7.45 (2H, m), 7.60 (1H, d, J=2.5 Hz).

Example 38

3-cyclopropyl-3-(3-(((2-(2,2-dimethylpropoxy)-2'-fluoro-5'-methoxybiphenyl-4-yl)oxy)methyl)phenyl)propanoic acid A) ethyl 3-cyclopropyl-3-(3-(((2-(2,2-dimethylpropoxy)-2'-fluoro-5'-methoxybiphenyl-4-yl)oxy)methyl)phenyl)propanoate Under a nitrogen atmosphere, to a solution of ethyl 3-cyclopropyl-3-(3-(((2'-fluoro-2-hydroxy-5'-methoxybiphenyl-4-yl)oxy)methyl)phenyl)propanoate (195 mg), 2,2-dimethyl-1-propanol (79 mg) in toluene (5.0 mL) was added cyanomethylenetributylphosphorane (0.25 mL), and the mixture was stirred at 100° C. for 2 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (117 mg) as a colorless oil.
¹H NMR (400 MHz, DMSO-d₆) δ 0.08-0.16 (1H, m), 0.20-0.28 (1H, m), 0.28-0.37 (1H, m), 0.47-0.57 (1H, m), 0.83 (9H, s), 1.01-1.10 (4H, m), 2.27-2.37 (1H, m), 2.66-2.82 (2H, m), 3.60 (2H, s), 3.74 (3H, s), 3.90-4.00 (2H, m), 5.12 (2H, s), 6.64-6.69 (1H, m), 6.71 (1H, d, J=1.6 Hz), 6.82 (1H, dd, J=5.8, 3.2 Hz), 6.86-6.92 (1H, m), 7.08-7.18 (2H, m), 7.22-7.27 (1H, m), 7.28-7.36 (2H, m), 7.37 (1H, s).

B) 3-cyclopropyl-3-(3-(((2-(2,2-dimethylpropoxy)-2'-fluoro-5'-methoxybiphenyl-4-yl)oxy)methyl)phenyl)propanoic acid To a solution of ethyl 3-cyclopropyl-3-(3-(((2-(2,2-dimethylpropoxy)-2'-fluoro-5'-methoxybiphenyl-4-yl)oxy)methyl)phenyl)propanoate (114 mg) in ethanol (3.0 mL) was added 2N aqueous sodium hydroxide solution (0.22 mL), and the mixture was stirred at room temperature for 2 hr. To the reaction mixture was added 1N hydrochloric acid, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (97 mg) as a white solid.
¹H NMR (400 MHz, DMSO-d₆) δ 0.07-0.17 (1H, m), 0.21-0.37 (2H, m), 0.46-0.56 (1H, m), 0.83 (9H, s), 0.96-1.08 (1H, m), 2.33 (1H, q, J=7.9 Hz), 2.60-2.75 (2H, m), 3.60 (2H, s), 3.74 (3H, s), 5.12 (2H, s), 6.67 (1H, d, J=8.4 Hz), 6.72 (1H, s), 6.83 (1H, dd, J=5.7, 3.1 Hz), 6.86-6.92 (1H, m), 7.08-7.18 (2H, m), 7.21-7.26 (1H, m), 7.28-7.35 (2H, m), 7.38 (1H, s), 12.08 (1H, brs).

Example 39

3-cyclopentyl-3-(3-(((2-(2,2-dimethylpropyl)-2'-fluoro-5'-methoxybiphenyl-4-yl)oxy)methyl)phenyl)propanoic acid By a method similar to that in Example 3, steps A-H, the title compound was obtained.
¹H NMR (400 MHz, DMSO-d₆) δ 0.63 (9H, s), 0.87-1.02 (1H, m), 1.14-1.26 (2H, m), 1.28-1.65 (4H, m), 1.76-1.87

(1H, m), 1.92-2.03 (1H, m), 2.31-2.60 (3H, m), 2.64-2.73 (1H, m), 2.77-2.86 (1H, m), 3.74 (3H, s), 5.11 (2H, s), 6.75 (1H, dd, J=5.9, 3.1 Hz), 6.87 (1H, d, J=2.3 Hz), 6.90-6.97 (2H, m), 7.09 (1H, d, J=8.4 Hz), 7.12-7.20 (2H, m), 7.23-7.33 (3H, m), 11.92 (1H, brs).

Example 40

3-cyclohexyl-3-(3-(((2-(2,2-dimethylpropyl)-2'-fluoro-5'-methoxybiphenyl-4-yl)oxy)methyl)phenyl) propanoic acid By a method similar to that in Example 3, steps A-H, the title compound was obtained.
$^1$H NMR (400 MHz, DMSO-$d_6$) δ 0.63 (9H, s), 0.67-0.79 (1H, m), 0.80-0.93 (1H, m), 0.95-1.25 (3H, m), 1.31-1.61 (4H, m), 1.66 (1H, d, J=12.4 Hz), 1.76 (1H, d, J=12.9 Hz), 2.31-2.60 (3H, m), 2.67-2.76 (1H, m), 2.80-2.90 (1H, m), 3.74 (3H, s), 5.12 (2H, s), 6.75 (1H, dd, J=5.8, 3.1 Hz), 6.87 (1H, d, J=2.1 Hz), 6.90-6.97 (2H, m), 7.05-7.20 (3H, m), 7.21-7.33 (3H, m), 11.96 (1H, brs).

Example 41

3-(3-(((2-((1-cyanocyclopentyl)methyl)-2'-fluoro-5'-methoxybiphenyl-4-yl)oxy)methyl)phenyl)-3-cyclopropylpropanoic acid A) 1-(2-bromo-5-((tert-butyl(dimethyl)silyl)oxy) benzyl)cyclopentanecarbonitrile Under a nitrogen atmosphere, to a solution of diisopropylamine (0.36 mL) in THF (7.0 mL) was added a 1.6 M solution of n-butyllithium in hexane (1.6 mL) at 0° C., and the mixture was stirred for 10 min. Cyclopentanecarbonitrile (0.28 mL) was added at −78° C., and the mixture was stirred for 30 min. A solution of (4-bromo-3-(bromomethyl)phenoxy)(tert-butyl)dimethylsilane (503 mg) in THF (3.0 mL) was added, and the mixture was stirred at −78° C. for 4 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (471 mg) as a colorless oil.
$^1$H NMR (400 MHz, DMSO-$d_6$) δ 0.20 (6H, s), 0.94 (9H, s), 1.67-1.89 (6H, m), 1.91-2.03 (2H, m), 3.07 (2H, s), 6.75 (1H, dd, J=8.7, 2.8 Hz), 7.02 (1H, d, J=2.9 Hz), 7.49 (1H, d, J=8.7 Hz).

B) 1-((4-((tert-butyl(dimethyl)silyl)oxy)-2'-fluoro-5'-methoxybiphenyl-2-yl)methyl)cyclopentanecarbonitrile Under a nitrogen atmosphere, to a solution of 1-(2-bromo-5-((tert-butyl(dimethyl)silyl)oxy)benzyl)cyclopentanecarbonitrile (471 mg), 2-fluoro-5-methoxyphenylboronic acid (361 mg), tris(dibenzylideneacetone)dipalladium(0) (23 mg) and 2-dicyclohexylphosphino-2',6'-dimethoxybiphenyl (39 mg) in toluene (5.0 mL) was added 2.0M aqueous sodium carbonate solution (1.8 mL), and the mixture was stirred at 90° C. for 1 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give a crude product of the title compound. The obtained crude product was directly used for the next step.

C) 1-((2'-fluoro-4-hydroxy-5'-methoxybiphenyl-2-yl) methyl)cyclopentanecarbonitrile To a solution of 1-((4-((tert-butyl(dimethyl)silyl)oxy)-2'-fluoro-5'-methoxybiphenyl-2-yl)methyl)cyclopentanecarbonitrile (entire amount) obtained in Example 41, step B, in THF (5.0 mL) was added a 1.0 M solution of tetrabutylammonium fluoride in THF (2.3 mL), and the mixture was stirred at room temperature for 15 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (331 mg) as a colorless oil.
$^1$H NMR (400 MHz, DMSO-$d_6$) δ 1.26-1.64 (6H, m), 1.67-1.93 (2H, m), 2.62-2.93 (2H, m), 3.74 (3H, s), 6.74-6.79 (1H, m), 6.81 (1H, dd, J=5.9, 3.1 Hz), 6.90-6.98 (2H, m), 7.03 (1H, d, J=8.4 Hz), 7.16 (1H, t, J=9.2 Hz), 9.73 (1H, brs).

D) ethyl 3-(3-(((2-((1-cyanocyclopentyl)methyl)-2'-fluoro-5'-methoxybiphenyl-4-yl)oxy)methyl)phenyl)-3-cyclopropylpropanoate To a solution of 1-((2'-fluoro-4-hydroxy-5'-methoxybiphenyl-2-yl)methyl)cyclopentanecarbonitrile (128 mg) and ethyl 3-cyclopropyl-3-(3-(((methylsulfonyl)oxy)methyl)phenyl) propanoate (197 mg) in DMF (5.0 mL) was added cesium carbonate (261 mg), and the mixture was stirred at room temperature for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (146 mg) as a colorless oil.
$^1$H NMR (400 MHz, DMSO-$d_6$) δ 0.07-0.16 (1H, m), 0.19-0.28 (1H, m), 0.28-0.37 (1H, m), 0.47-0.57 (1H, m), 0.99-1.11 (4H, m), 1.29-1.48 (3H, m), 1.49-1.63 (3H, m), 1.66-1.90 (2H, m), 2.25-2.37 (1H, m), 2.65-2.97 (4H, m), 3.75 (3H, s), 3.89-4.00 (2H, m), 5.13 (2H, s), 6.84 (1H, dd, J=6.1, 3.2 Hz), 6.92-6.99 (1H, m), 7.03 (1H, dd, J=8.4, 2.4 Hz), 7.15-7.22 (3H, m), 7.23-7.28 (1H, m), 7.29-7.34 (2H, m), 7.36 (1H, s).

E) 3-(3-(((2-((1-cyanocyclopentyl)methyl)-2'-fluoro-5'-methoxybiphenyl-4-yl)oxy)methyl)phenyl)-3-cyclopropylpropanoic acid To a solution of ethyl 3-(3-(((2-((1-cyanocyclopentyl)methyl)-2'-fluoro-5'-methoxybiphenyl-4-yl)oxy)methyl)phenyl)-3-cyclopropylpropanoate (143 mg) in ethanol (3.0 mL) was added 2N aqueous sodium hydroxide solution (0.26 mL), and the mixture was stirred at room temperature for 16 hr. To the reaction mixture was added 1N hydrochloric acid, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (88 mg) as a white solid.

¹H NMR (400 MHz, DMSO-d₆) δ 0.07-0.16 (1H, m), 0.21-0.36 (2H, m), 0.45-0.56 (1H, m), 0.96-1.07 (1H, m), 1.28-1.48 (3H, m), 1.48-1.64 (3H, m), 1.67-1.88 (2H, m), 2.32 (1H, q, J=7.9 Hz), 2.60-2.73 (2H, m), 2.73-2.98 (2H, m), 3.75 (3H, s), 5.12 (2H, s), 6.85 (1H, dd, J=5.8, 3.1 Hz), 6.93-6.99 (1H, m), 7.04 (1H, dd, J=8.6, 2.2 Hz), 7.15-7.22 (3H, m), 7.24 (1H, d, J=6.9 Hz), 7.28-7.35 (2H, m), 7.36 (1H, s), 12.07 (1H, brs).

Example 42

3-cyclobutyl-3-(3-(((2-(2,2-dimethylpropyl)-2'-fluoro-5'-methoxybiphenyl-4-yl)oxy)methyl)phenyl) propanoic acid By a method similar to that in Example 3, steps A-H, the title compound was obtained.
¹H NMR (400 MHz, DMSO-d₆) δ 0.63 (9H, s), 1.46-1.61 (2H, m), 1.61-1.78 (3H, m), 1.98-2.08 (1H, m), 2.29-2.51 (5H, m), 2.89-3.01 (1H, m), 3.74 (3H, s), 5.11 (2H, s), 6.76 (1H, dd, J=5.9, 3.1 Hz), 6.88 (1H, d, J=2.3 Hz), 6.90-6.97 (2H, m), 7.09 (1H, d, J=8.4 Hz), 7.13-7.21 (2H, m), 7.23-7.32 (3H, m), 12.03 (¹H, brs).

Example 43

3-(3-(((2-(2,2-dimethylpropyl)-2'-fluoro-5'-methoxybiphenyl-4-yl)oxy)methyl)phenyl)hept-6-enoic acid By a method similar to that in Example 3, steps A-H, the title compound was obtained.
¹H NMR (400 MHz, DMSO-d₆) δ 0.62 (9H, s), 1.54-1.66 (1H, m), 1.66-1.76 (1H, m), 1.77-1.86 (2H, m), 2.33-2.62 (4H, m), 2.96-3.08 (1H, m), 3.74 (3H, s), 4.89 (1H, s), 4.93 (1H, brs), 5.12 (2H, s), 5.63-5.82 (1H, m), 6.76 (1H, dd, J=6.0, 3.1 Hz), 6.87 (1H, d, J=2.3 Hz), 6.89-6.98 (2H, m), 7.09 (1H, d, J=8.5 Hz), 7.12-7.21 (2H, m), 7.25-7.35 (3H, m), 12.14 (1H, brs).

Example 44

3-cyclopropyl-3-(3-(((5-(2,2-dimethylpropyl)-6-(2-fluoro-5-(tetrahydro-2H-pyran-2-yloxy)phenyl)pyridin-3-yl)oxy)methyl)phenyl)propanoic acid step 1)
2-(3-bromo-4-fluorophenoxy)tetrahydro-2H-pyran Under a nitrogen atmosphere, to a solution of 3-bromo-4-fluorophenol (1.2 g) in toluene (62.8 mL) were added 3,4-dihydro-2H-pyran (1.15 mL) and pyridinium p-toluenesulfonate (0.237 g) at room temperature, and the mixture was stirred for 2 hr. The reaction mixture was poured into water at room temperature, and the mixture was extracted with ethyl acetate. The extract was washed with saturated brine, and dried over anhydrous sodium sulfate. The solvent was evaporated under reduced pressure, and the residue was purified by silica gel column chromatography (NH, ethyl acetate/hexane) to give the title compound (1.63 g) as a colorless oil.
¹H NMR (300 MHz, CDCl₃) δ1.57-1.77 (3H, m), 1.84 (2H, dt, J=8.2, 3.3 Hz), 1.89-2.04 (1H, m), 3.61 (1H, dtd, J=11.3, 4.0, 1.7 Hz), 3.87 (1H, ddd, J=11.3, 9.5, 3.2 Hz), 5.32 (1H, t, J=3.1 Hz), 6.89-7.07 (2H, m), 7.25-7.28 (1H, m).

step 2) 2-(2-fluoro-5-((tetrahydro-2H-pyran-2-yl)oxy)phenyl)-4,4,5,5-tetramethyl-1,3,2-dioxaborolane Under a nitrogen atmosphere, to a solution of 2-(3-bromo-4-fluorophenoxy)tetrahydro-2H-pyran (5.05 g) in DMF (92 mL) were added bis(pinacolato)diborane (6.99 g), potassium acetate (5.40 g) and [1,1-bis(diphenylphosphino)ferrocene] dichloropalladium(2) (1.34 g) at room temperature, and the mixture was stirred at 100° C. for 20 hr. The reaction mixture was cooled, and filtered. The filtrate was poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give a mixture of the title compound (6.19 g). This compound was used for the next step without further purification.

step 3) ethyl 3-cyclopropyl-3-(3-(((6-(2-fluoro-5-((tetrahydro-2H-pyran-2-yl)oxy)phenyl)-5-neopentylpyridin-3-yl)oxy)methyl)phenyl)propanoate Under a nitrogen atmosphere, to a solution of ethyl 3-cyclopropyl-3-(3-(((5-neopentyl-6-(((trifluoromethyl)sulfonyl)oxy)pyridin-3-yl)oxy)methyl)phenyl)propanoate (1.04 g) in toluene (19.1 mL) were added 2-(2-fluoro-5-((tetrahydro-2H-pyran-2-yl)oxy)phenyl)-4,4,5,5-tetramethyl-1,3,2-dioxaborolane (1.84 g), 2.0M aqueous sodium carbonate solution (2.86 mL) and tetrakis(triphenylphosphine)palladium(0) (0.220 g) at room temperature, and the mixture was stirred at 90° C. for 1.5 hr. The reaction mixture was cooled, poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (1.07 g) as a pale-yellow oil.
MS (ESI+): [M+H]⁺590.2 step 4) 3-cyclopropyl-3-(3-(((5-(2,2-dimethylpropyl)-6-(2-fluoro-5-(tetrahydro-2H-pyran-2-yloxy) phenyl)pyridin-3-yl)oxy)methyl)phenyl)propanoic acid To a solution of ethyl 3-cyclopropyl-3-(3-(((6-(2-fluoro-5-((tetrahydro-2H-pyran-2-yl)oxy)phenyl)-5-neopentylpyridin-3-yl)oxy)methyl)phenyl)propanoate (84.1 mg) in ethanol (2.85 mL) was added 2N aqueous sodium hydroxide (357 μl) solution, and the mixture was stirred at room temperature for 20 hr. The reaction mixture was cooled to 0° C., neutralized with 1N hydrochloric acid, and extracted with ethyl acetate. The extract was dried over anhydrous sodium sulfate, and the solvent was evaporated under reduced pressure, and the residue was purified by silica gel column chromatography (ethyl acetate/hexane) to give the title compound (52.8 mg) as a white amorphous solid.
MS (ESI+): [M+H]⁺562.6

Example 45

3-cyclopropyl-3-(3-(((5-(2,2-dimethylpropyl)-6-phenylpyridin-3-yl)oxy)methyl)phenyl)propanoic acid By a method similar to that in Example 44, the title compound was obtained.
MS (ESI+): [M+H]⁺444.5

Example 46

3-cyclopropyl-3-(3-(((5-(2,2-dimethylpropyl)-6-(3-methoxyphenyl)pyridin-3-yl)oxy)methyl)phenyl) propanoic acid By a method similar to that in Example 44, the title compound was obtained.
MS (ESI+): [M+H]⁺474.5

Example 47

3-cyclopropyl-3-(3-(((5-(2,2-dimethylpropyl)-6-(3-methylphenyl)pyridin-3-yl)oxy)methyl)phenyl)propanoic acid By a method similar to that in Example 44, the title compound was obtained.
MS (ESI+): [M+H]⁺458.5

Example 48

3-cyclopropyl-3-(3-(((5-(2,2-dimethylpropyl)-6-(4-methoxyphenyl)pyridin-3-yl)oxy)methyl)phenyl)propanoic acid By a method similar to that in Example 44, the title compound was obtained.
MS (ESI+): [M+H]⁺474.5

Example 49

3-cyclopropyl-3-(3-(((5-(2,2-dimethylpropyl)-6-(3-(trifluoromethoxy)phenyl)pyridin-3-yl)oxy)methyl)phenyl)propanoic acid By a method similar to that in Example 44, the title compound was obtained.
MS (ESI+): [M+H]⁺528.5

Example 50

3-cyclopropyl-3-(3-(((5-(2,2-dimethylpropyl)-6-(2-methoxyphenyl)pyridin-3-yl)oxy)methyl)phenyl)propanoic acid By a method similar to that in Example 44, the title compound was obtained.
MS (ESI+): [M+H]⁺474.5

Example 51

3-(5-((3-(2-carboxy-1-cyclopropylethyl)benzyl)oxy)-3-(2,2-dimethylpropyl)pyridin-2-yl)benzoic acid By a method similar to that in Example 44, the title compound was obtained.
MS (ESI+): [M+H]⁺488.5

Example 52

3-cyclopropyl-3-(3-(((5-(2,2-dimethylpropyl)-6-(3-(trifluoromethyl)phenyl)pyridin-3-yl)oxy)methyl)phenyl)propanoic acid By a method similar to that in Example 44, the title compound was obtained.
MS (ESI+): [M+H]⁺512.5

Example 53

3-cyclopropyl-3-(3-(((6-(2,5-dimethoxyphenyl)-5-(2,2-dimethylpropyl)pyridin-3-yl)oxy)methyl)phenyl)propanoic acid By a method similar to that in Example 44, the title compound was obtained.
MS (ESI+): [M+H]⁺504.5

Example 54

3-cyclopropyl-3-(3-(((6-(3,4-dimethoxyphenyl)-5-(2,2-dimethylpropyl)pyridin-3-yl)oxy)methyl)phenyl)propanoic acid By a method similar to that in Example 44, the title compound was obtained.
MS (ESI+): [M+H]⁺504.5

Example 55

3-cyclopropyl-3-(3-(((5-(2,2-dimethylpropyl)-6-(3-hydroxyphenyl)pyridin-3-yl)oxy)methyl)phenyl)propanoic acid By a method similar to that in Example 44, the title compound was obtained.
MS (ESI+): [M+H]⁺460.5

Example 56

3-cyclopropyl-3-(3-(((6-(3,5-dimethoxyphenyl)-5-(2,2-dimethylpropyl)pyridin-3-yl)oxy)methyl)phenyl)propanoic acid By a method similar to that in Example 44, the title compound was obtained.
MS (ESI+): [M+H]⁺504.5

Example 57

3-cyclopropyl-3-(3-(((3-(2,2-dimethylpropyl)-5'-fluoro-2'-methoxy-2,4'-bipyridin-5-yl)oxy)methyl)phenyl)propanoic acid By a method similar to that in Example 44, the title compound was obtained.
MS (ESI+): [M+H]⁺493.3

Example 58

3-cyclopropyl-3-(3-(((5-(2,2-dimethylpropyl)-6-(5-methoxy-2-methylphenyl)pyridin-3-yl)oxy)methyl)phenyl)propanoic acid By a method similar to that in Example 44, the title compound was obtained.
MS (ESI+): [M+H]⁺488.6

Example 59

3-(3-(((6-(2-chloro-5-methoxyphenyl)-5-(2,2-dimethylpropyl)pyridin-3-yl)oxy)methyl)phenyl)-3-cyclopropylpropanoic acid By a method similar to that in Example 44, the title compound was obtained.
MS (ESI+), found: 509.5

Example 60

3-(3-(((6-(5-cyano-2-fluorophenyl)-5-(2,2-dimethylpropyl)pyridin-3-yl)oxy)methyl)phenyl)-3-cyclopropylpropanoic acid By a method similar to that in Example 44, the title compound was obtained.
MS (ESI+): [M+H]⁺487.5

Example 61

3-cyclopropyl-3-(3-(((5-(2,2-dimethylpropyl)-6-(4-(trifluoromethoxy)phenyl)pyridin-3-yl)oxy)methyl)phenyl)propanoic acid To a solution of ethyl 3-cyclopropyl-3-(3-(((5-neopentyl-6-(((trifluoromethyl)sulfonyl)oxy)pyridin-3-yl)oxy)methyl)phenyl)propanoate (65.2 mg) in toluene (1.5 mL) were added (4-(trifluoromethoxy)phenyl)boronic acid (24.7 mg), 2M aqueous sodium carbonate solution (720 μL), and tetrakis(triphenylphosphine)palladium(0) (13.8 mg), and the mixture was heated in a microwave synthesizer (Anton Parr, Synthos3000) at 100° C. for 90 min. Water (1 mL) and ethyl acetate (3 mL) were added to the reaction solution and the mixture was stirred. The organic layer was passed through a phase separation filter, and the solvent was evaporated by an air blowing apparatus. The residue was purified by HPLC (column: YMC Triart C18, mobile phase: acetonitrile/10 mM aqueous ammonium hydrogen carbonate solution) and the solvent was evaporated by an air blowing apparatus. To the residue were added ethanol (1 mL) and 2M aqueous lithium hydroxide solution (180 μL), and the mixture was stirred at 60° C. for 1 hr. 1M Hydrochloric acid (360 μL) was added and the obtained solution was purified by HPLC (column: YMC Triart C18, mobile phase: acetonitrile/10 mM aqueous ammonium hydrogen carbonate solution), and the solvent was evaporated by an air blowing apparatus to give the title compound (14.9 mg).

MS (ESI+): [M+H]$^+$528.2

Example 62-67

By a method similar to that in Example 61, the compounds of Examples 62-67 were produced.

Example 62

3-cyclopropyl-3-(3-(((5-(2,2-dimethylpropyl)-6-(3-((methylsulfonyl)amino)phenyl)pyridin-3-yl)oxy)methyl)phenyl)propanoic acid

MS (ESI+): [M+H]$^+$ 537.3

Example 63

3-cyclopropyl-3-(3-(((3-(2,2-dimethylpropyl)-5'-methyl-2,3'-bipyridin-5-yl)oxy)methyl)phenyl)propanoic acid

MS (ESI+): [M+H]$^+$ 459.2

Example 64

3-cyclopropyl-3-(3-(((3-(2,2-dimethylpropyl)-6'-methoxy-2,3'-bipyridin-5-yl)oxy)methyl)phenyl)propanoic acid

MS (ESI+): [M+H]$^+$ 475.1

Example 65

3-cyclopropyl-3-(3-(((5-(2,2-dimethylpropyl)-6-(2-ethoxypyrimidin-5-yl)pyridin-3-yl)oxy)methyl)phenyl)propanoic acid

MS (ESI+): [M+H]$^+$ 490.2

Example 66

3-cyclopropyl-3-(3-(((3-(2,2-dimethylpropyl)-5'-methoxy-2,3'-bipyridin-5-yl)oxy)methyl)phenyl)propanoic acid

MS (ESI+): [M+H]$^+$ 475.1

Example 67

3-cyclopropyl-3-(3-(((5-(2,2-dimethylpropyl)-6-(3-(morpholin-4-ylsulfonyl)phenyl)pyridin-3-yl)oxy)methyl)phenyl)propanoic acid

MS (ESI+): [M+H]$^+$ 593.3

Example 68

3-cyclopropyl-3-(3-(((5-(2,2-dimethylpropyl)-6-(5-ethoxy-2-fluorophenyl)pyridin-3-yl)oxy)methyl)phenyl)propanoic acid step 1) ethyl 3-cyclopropyl-3-(3-(((6-(2-fluoro-5-hydroxyphenyl)-5-neopentylpyridin-3-yl)oxy)methyl)phenyl)propanoate Under a nitrogen atmosphere, to a solution of ethyl 3-cyclopropyl-3-(3-(((6-(2-fluoro-5-((tetrahydro-2H-pyran-2-yl)oxy)phenyl)-5-neopentylpyridin-3-yl)oxy)methyl)phenyl)propanoate (984 mg) in methanol (8.35 mL) was added pyridinium p-toluenesulfonate (126 mg) at room temperature, and the mixture was stirred at 50° C. for 20 hr. The reaction mixture was cooled, poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (685 mg) as a colorless gummy substance.

MS (ESI+): [M+H]$^+$506.5 step 2) ethyl 3-cyclopropyl-3-(3-(((6-(5-ethoxy-2-fluorophenyl)-5-neopentylpyridin-3-yl)oxy)methyl)phenyl)propanoate Under a nitrogen atmosphere, to a solution of ethyl 3-cyclopropyl-3-(3-(((6-(2-fluoro-5-hydroxyphenyl)-5-neopentylpyridin-3-yl)oxy)methyl)phenyl)propanoate (50 mg) in DMF (989 μL) were added cesium carbonate (97 mg) and iodoethane (12.0 μL) at 0° C., and the mixture was stirred at room temperature for 20 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (49.8 mg) as a colorless oil.

MS (ESI+): [M+H]$^+$534.19 step 3) 3-cyclopropyl-3-(3-(((5-(2,2-dimethylpropyl)-6-(5-ethoxy-2-fluorophenyl)pyridin-3-yl)oxy)methyl)phenyl)propanoic acid By a method similar to that in Example 44, step 4, the title compound was obtained.

MS (ESI+): [M+H]$^+$506.6

Example 69

3-cyclopropyl-3-(3-(((5-(2,2-dimethylpropyl)-6-(2-fluoro-5-isopropoxyphenyl)pyridin-3-yl)oxy)methyl)phenyl)propanoic acid By a method similar to that in Example 68, the title compound was obtained.
MS (ESI+): [M+H]$^+$520.6

Example 70

3-cyclopropyl-3-(3-(((5-(2,2-dimethylpropyl)-6-(2-fluoro-5-(2,2,2-trifluoroethoxy)phenyl)pyridin-3-yl)oxy)methyl)phenyl)propanoic acid By a method similar to that in Example 68, the title compound was obtained.
MS (ESI+): [M+H]$^+$560.6

Example 71

3-cyclopropyl-3-(3-(((5-(2,2-dimethylpropyl)-6-(2-fluoro-5-(pentyloxy)phenyl)pyridin-3-yl)oxy)methyl)phenyl)propanoic acid By a method similar to that in Example 68, the title compound was obtained.
MS (ESI+): [M+H]$^+$548.6

Example 72

3-cyclopropyl-3-(3-(((5-(2,2-dimethylpropyl)-6-(2-fluoro-5-(3-methoxypropoxy)phenyl)pyridin-3-yl)oxy)methyl)phenyl)propanoic acid By a method similar to that in Example 68, the title compound was obtained.
MS (ESI+): [M+H]$^{+550.6}$

Example 73

3-cyclopropyl-3-(3-(((5-(2,2-dimethylpropyl)-6-(2-fluoro-5-hydroxyphenyl)pyridin-3-yl)oxy)methyl)phenyl)propanoic acid By a method similar to that in Example 44, step 4, the title compound was obtained from ethyl 3-cyclopropyl-3-(3-(((6-(2-fluoro-5-hydroxyphenyl)-5-neopentylpyridin-3-yl)oxy)methyl)phenyl)propanoate.
MS (ESI+): [M+H]$^+$478.5

Example 74

3-(3-(((2-tert-butoxy-2'-fluoro-5'-methoxybiphenyl-4-yl)oxy)methyl)phenyl)-3-cyclopropylpropanoic acid step 1) ((2-(tert-butoxy)-2'-fluoro-5'-methoxy-[1,1'-biphenyl]-4-yl)oxy)triisopropylsilane Under a nitrogen atmosphere, to a solution of 2'-fluoro-5'-methoxy-4-((triisopropylsilyl)oxy)-[1,1'-biphenyl]-2-ol (207 mg) in toluene (3.55 mL) was added N,N-dimethylformamidide-tert-butylacetal (636 μL) at room temperature, and the mixture was stirred at 80° C. for 3 hr. The reaction mixture was cooled, poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (96 mg) as a colorless oil.
MS (ESI+), found: 391.0 step 2) 2-(tert-butoxy)-2'-fluoro-5'-methoxy-[1,1'-biphenyl]-4-ol

Under a nitrogen atmosphere, to a solution of ((2-(tert-butoxy)-2'-fluoro-5'-methoxy-[1,1'-biphenyl]-4-yl)oxy)triisopropylsilane (96.2 mg) in THF (1.44 mL) was added a 1 M solution (431 μL) of tetrabutylammonium fluoride in THF at room temperature, and the mixture was stirred for 1 hr. The reaction mixture was poured into saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (56.1 mg) as a colorless oil.
MS (ESI+), found: 289.1 step 3) ethyl 3-(3-(((2-(tert-butoxy)-2'-fluoro-5'-methoxy-[1,1'-biphenyl]-4-yl)oxy)methyl)phenyl)-3-cyclopropylpropanoate Under a nitrogen atmosphere, to a solution of 2-(tert-butoxy)-2'-fluoro-5'-methoxy-[1,1'-biphenyl]-4-ol (96.1 mg) in DMF (3.31 mL) were added ethyl 3-(3-(bromomethyl)phenyl)-3-cyclopropylpropanoate (124 mg) and potassium carbonate (91 mg) at room temperature, and the mixture was stirred for 3 hr. The reaction mixture was poured into water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (142 mg) as a colorless oil.
MS (ESI+), found: 465.0 step 4) 3-(3-(((2-tert-butoxy-2'-fluoro-5'-methoxybiphenyl-4-yl)oxy)methyl)phenyl)-3-cyclopropylpropanoic acid By a method similar to that in Example 44, step 4, the title compound was obtained.
MS (ESI+), found: 510.6

Example 75

3-cyclopropyl-3-(3-(((2'-fluoro-5'-methoxy-2-(5-(trifluoromethyl)-1,3,4-thiadiazol-2-yl)-[1,1'-biphenyl]-4-yl)oxy)methyl)phenyl)propanoic acid step 1) ethyl 2'-fluoro-5'-methoxy-4-((4-methoxybenzyl)oxy)-[1,1'-biphenyl]-2-carboxylate A solution of ethyl 2'-fluoro-4-hydroxy-5'-methoxy-[1,1'-biphenyl]-2-carboxylate (15.84 g), 4-methoxybenzyl chloride (17.09 g) and potassium carbonate (18.85 g) in DMF (110 mL) was stirred at room temperature for 14 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (22.3 g) as a pale-yellow oil.

MS (ESI+): [M+H]$^+$ 411.2 step 2) 2'-fluoro-5'-methoxy-4-((4-methoxybenzyl)oxy)-[1,1'-biphenyl]-2-carbohydrazide A solution of ethyl 2'-fluoro-5'-methoxy-4-((4-methoxybenzyl)oxy)-[1,1'-biphenyl]-2-carboxylate (2.04 g) and hydrazine monohydrate (4.82 mL) in ethanol (20 mL) was stirred at 95° C. for 12 days. The reaction mixture was concentrated under reduced pressure, water was added, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (1.43 g) as a white solid.

MS (ESI+): [M+H]$^+$ 397.1 step 3) 2'-fluoro-5'-methoxy-4-((4-methoxybenzyl)oxy)-N'-(2,2,2-trifluoroacetyl)-[1,1'-biphenyl]-2-carbohydrazide Trifluoroacetic anhydride (1.57 mL) was added to a solution of 2'-fluoro-5'-methoxy-4-((4-methoxybenzyl)oxy)-[1,1'-biphenyl]-2-carbohydrazide (1.47 g) and triethylamine (1.55 mL) in THF (37 mL) at room temperature, and the mixture was stirred at room temperature for 0.5 hr. To the reaction mixture was added aqueous sodium hydrogen carbonate solution, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (1.70 g) as a white solid.

MS (ESI+): [M+H]$^+$ 493.2 step 4) 2-(2'-fluoro-5'-methoxy-4-((4-methoxybenzyl)oxy)-[1,1'-biphenyl]-2-yl)-5-(trifluoromethyl)-1,3,4-thiadiazole A solution of 2'-fluoro-5'-methoxy-4-((4-methoxybenzyl)oxy)-N'-(2,2,2-trifluoroacetyl)-[1,1'-biphenyl]-2-carbohydrazide (502 mg) and Lawesson's reagent (825 mg) in THF (10 mL) was stirred at 80° C. for 4 hr. The reaction mixture was concentrated under reduced pressure, and the residue was purified by silica gel column chromatography (ethyl acetate/hexane) to give the title compound (299 mg) as a pale-yellow solid. The present compound was used for the next reaction without purification.

step 5) 2'-fluoro-5'-methoxy-2-(5-(trifluoromethyl)-1,3,4-thiadiazol-2-yl)-[1,1'-biphenyl]-4-ol Trifluoroacetic acid (5.0 mL) was added to 2-(2'-fluoro-5'-methoxy-4-((4-methoxybenzyl)oxy)-[1,1'-biphenyl]-2-yl)-5-(trifluoromethyl)-1,3,4-thiadiazole (299 mg) and anisole (0.66 mL) at room temperature, and the mixture was stirred at room temperature for 1.5 hr. The reaction mixture was concentrated under reduced pressure, aqueous sodium hydrogen carbonate solution was added, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (200 mg) as a white solid.

MS (ESI+): [M+H]$^+$ 371.0 step 6) ethyl 3-cyclopropyl-3-(3-(((2'-fluoro-5'-methoxy-2-(5-(trifluoromethyl)-1,3,4-thiadiazol-2-yl)-[1,1'-biphenyl]-4-yl)oxy)methyl)phenyl)propanoate To a solution of 2'-fluoro-5'-methoxy-2-(5-(trifluoromethyl)-1,3,4-thiadiazol-2-yl)-[1,1'-biphenyl]-4-ol (195 mg), ethyl 3-cyclopropyl-3-(3-(hydroxymethyl)phenyl)propanoate (157 mg) and tributylphosphine (213 mg) in THF (5.0 mL) was added ADDP (226 mg) at room temperature, and the mixture was stirred at room temperature for 3 hr. Water was added to the reaction mixture, and the mixture was extracted with ethyl acetate. The extract was washed with saturated brine, and dried over anhydrous magnesium sulfate. The solvent was evaporated under reduced pressure, and the residue was purified by silica gel column chromatography (ethyl acetate/hexane) to give the title compound (298 mg) as a pale-yellow oil.

MS (ESI+): [M+H]$^+$ 601.2 step 7) 3-cyclopropyl-3-(3-(((2'-fluoro-5'-methoxy-2-(5-(trifluoromethyl)-1,3,4-thiadiazol-2-yl)-[1,1'-biphenyl]-4-yl)oxy)methyl)phenyl)propanoic acid In the same manner as in Example 44, step 4, the title compound (20 mg) was obtained as a colorless oil.

MS (ESI+): [M+H]$^+$ 573.2

Example 76

3-(3-(((2'-fluoro-5'-methoxy-2-neopentyl-[1,1'-biphenyl]-4-yl)oxy)methyl)phenyl)hex-4-ynoic acid step 1) 5-(1-(3-(((tert-butyldimethylsilyl)oxy)methyl)phenyl)but-2-yn-1-yl)-2,2-dimethyl-1,3-dioxane-4,6-dione Under a nitrogen atmosphere, a solution (0.5 M, 12.0 mL) of 1-propynylmagnesium bromide in THF was added to a solution of 5-(3-(((tert-butyldiphenylsilyl)oxy)methyl)benzylidene)-2,2-dimethyl-1,3-dioxane-4,6-dione (1.0 g) in THF (10 mL) at 0° C., and the mixture was stirred at room temperature for 3 hr. To the reaction mixture was added saturated aqueous ammonium chloride solution at 0° C., and the mixture was extracted with ethyl acetate. The extract was washed with water and saturated brine, and dried over anhydrous magnesium sulfate. The solvent was evaporated under reduced pressure to give a crude product of the title compound. This compound was used for the next step without further purification.

step 2) ethyl 3-(3-(((tert-butyldiphenylsilyl)oxy)methyl)phenyl)hex-4-ynoate 5-(1-(3-(((tert-Butyldimethylsilyl)oxy)methyl)phenyl)but-2-yn-1-yl)-2,2-dimethyl-1,3-dioxane-4,6-dione was dissolved in DMF (8 mL) and ethanol (4 mL), and the mixture was stirred at 120° C. for 16 hr under a nitrogen atmosphere. The solvent in the reaction mixture was evaporated under reduced pressure to give a crude product of the title compound. This compound was used for the next step without further purification.

step 3) ethyl 3-(3-(hydroxymethyl)phenyl)hex-4-ynoate

A solution (5.0 mL) of tetrabutylammonium fluoride in THF was added to a solution of ethyl 3-(3-(((tert-butyldiphenylsilyl)oxy)methyl)phenyl)hex-4-ynoate in THF (10 mL), and the mixture was stirred at room temperature for 1 hr. Water was added to the reaction mixture at room temperature, and the mixture was extracted with ethyl acetate. The extract was washed with water and saturated brine, and dried over anhydrous magnesium sulfate. The solvent was evaporated under reduced pressure, and the residue was purified by silica gel column chromatography (ethyl acetate/hexane) to give the title compound (181 mg) as a colorless oil.
$^1$H NMR (400 MHz, DMSO-$d_6$) δ 1.14 (3H, t, J=7.1 Hz), 1.78 (3H, d, J=2.3 Hz), 2.70 (2H, d, J=7.7 Hz), 3.97-4.10 (3H, m), 4.48 (2H, d, J=5.0 Hz), 5.17 (1H, t, J=5.6 Hz), 7.15-7.29 (3H, m), 7.31 (1H, s).

step 4) ethyl 3-(3-(((2'-fluoro-5'-methoxy-2-neopentyl-[1,1'-biphenyl]-4-yl)oxy)methyl)phenyl)hex-4-ynoate Under a nitrogen atmosphere, to a solution of ethyl 3-(3-(hydroxymethyl)phenyl)hex-4-ynoate (100 mg) and 2'-fluoro-5'-methoxy-2-neopentyl-[1,1'-biphenyl]-4-ol (117 mg) in THF (5.8 mL) were added 1,1'-(azodicarbonyl)dipiperidine (164 mg) and tributylphosphine (160 μL) at room temperature, and the mixture was stirred for 16 hr. The solvent was evaporated under reduced pressure, and the residue was purified by silica gel column chromatography (ethyl acetate/hexane) to give the title compound (172 mg) as a colorless oil.
$^1$H NMR (400 MHz, DMSO-$d_6$) δ 0.63 (9H, s), 1.13 (3H, t, J=7.2 Hz), 1.78 (3H, d, J=1.9 Hz), 2.29-2.59 (2H, m), 2.72 (2H, d, J=7.7 Hz), 3.74 (3H, s), 3.98-4.11 (3H, m), 5.13 (2H, s), 6.76 (1H, dd, J=5.9, 3.0 Hz), 6.88 (1H, d, J=2.3 Hz), 6.90-6.99 (2H, m), 7.10 (1H, d, J=8.4 Hz), 7.16 (1H, t, J=9.1 Hz), 7.35 (3H, s), 7.47 (1H, s).

step 5) 3-(3-(((2'-fluoro-5'-methoxy-2-neopentyl-[1,1'-biphenyl]-4-yl)oxy)methyl)phenyl)hex-4-ynoic acid The title compound was obtained by a method similar to that in Example 44, step 4.
$^1$H NMR (400 MHz, DMSO-$d_6$) δ 0.63 (9H, s), 1.78 (3H, d, J=2.0 Hz), 2.32-2.59 (2H, m), 2.64 (2H, d, J=7.5 Hz), 3.74 (3H, s), 3.98-4.08 (1H, m), 5.13 (2H, s), 6.77 (1H, dd, J=6.0, 3.1 Hz), 6.88 (1H, d, J=2.3 Hz), 6.90-7.00 (2H, m), 7.10 (1H, d, J=8.4 Hz), 7.16 (1H, t, J=9.1 Hz), 7.34 (3H, s), 7.48 (1H, s), 12.33 (1H, brs).
MS (ESI-): [M-H]$^+$ 487.3

Example 77

5-cyclopropyl-3-(3-(((2'-fluoro-5'-methoxy-2-neopentyl-[1,1'-biphenyl]-4-yl)oxy)methyl)phenyl)pent-4-ynoic acid The title compound was obtained by a method similar to that in Example 76.
$^1$H NMR (400 MHz, DMSO-$d_6$) δ 0.48-0.57 (2H, m), 0.63 (9H, s), 0.69-0.79 (2H, m), 1.24-1.34 (1H, m), 2.31-2.56 (2H, m), 2.56-2.70 (2H, m), 3.74 (3H, s), 3.97-4.05 (1H, m), 5.13 (2H, s), 6.77 (1H, dd, J=6.0, 3.1 Hz), 6.88 (1H, d, J=2.3 Hz), 6.90-6.99 (2H, m), 7.10 (1H, d, J=8.4 Hz), 7.16 (1H, t, J=9.2 Hz), 7.26-7.39 (3H, m), 7.46 (1H, s), 12.20 (1H, brs).
MS (ESI-): [M-H]$^+$ 513.3

Example 78

3-(3-(((2'-fluoro-5'-methoxy-2-neopentyl-[1,1'-biphenyl]-4-yl)oxy)methyl)phenyl)-4-methylpentanoic acid The title compound was obtained by a method similar to that in Example 76.
$^1$H NMR (300 MHz, DMSO-$d_6$) δ 0.63 (9H, s), 0.67 (3H, d, J=6.7 Hz), 0.85 (3H, d, J=6.7 Hz), 1.72-1.87 (1H, m), 2.34-2.53 (2H, m), 2.47-2.58 (1H, m), 2.65-2.75 (1H, m), 2.78-2.89 (1H, m), 3.74 (3H, s), 5.12 (2H, s), 6.76 (1H, dd, J=6.1, 3.2 Hz), 6.88 (1H, d, J=2.5 Hz), 6.89-6.98 (2H, m), 7.04-7.20 (3H, m), 7.24-7.34 (3H, m), 11.90 (1H, brs).
MS (ESI-): [M-H]$^+$ 491.3

Example 79

3-(3-(((2'-fluoro-5'-methoxy-2-neopentyl-[1,1'-biphenyl]-4-yl)oxy)methyl)phenyl)pent-4-enoic acid The title compound was obtained by a method similar to that in Example 76.
$^1$H NMR (400 MHz, DMSO-$d_6$) δ 0.63 (9H, s), 2.32-2.65 (2H, m), 2.58-2.75 (2H, m), 3.74 (3H, s), 3.74-3.82 (1H, m), 5.00 (1H, s), 5.04 (1H, d, J=8.0 Hz), 5.11 (2H, s), 5.98 (1H, ddd, J=17.2, 10.3, 7.2 Hz), 6.77 (1H, dd, J=6.0, 3.2 Hz), 6.88 (1H, d, J=2.4 Hz), 6.90-6.99 (2H, m), 7.10 (1H, d, J=8.4 Hz), 7.16 (1H, t, J=9.2 Hz), 7.21 (1H, d, J=6.9 Hz), 7.27-7.37 (3H, m), 12.14 (1H, brs).
MS (ESI-): [M-H]$^+$ 475.3

Example 80

3-(3-(((2'-fluoro-5'-methoxy-2-neopentyl-[1,1'-biphenyl]-4-yl)oxy)methyl)phenyl)pentanoic acid The title compound was obtained by a method similar to that in Example 76.
$^1$H NMR (400 MHz, DMSO-$d_6$) δ 0.63 (9H, s), 0.70 (3H, t, J=7.3 Hz), 1.46-1.60 (1H, m), 1.61-1.73 (1H, m), 2.35-2.53 (3H, m), 2.56-2.63 (1H, m), 2.85-2.97 (1H, m), 3.74 (3H, s), 5.11 (2H, s), 6.76 (1H, dd, J=5.8, 3.1 Hz), 6.85-6.89 (1H, m), 6.90-6.98 (2H, m), 7.09 (1H, d, J=8.4 Hz), 7.12-7.21 (2H, m), 7.25-7.35 (3H, m), 12.02 (1H, brs).
MS (ESI-): [M-H]$^+$ 477.3

Example 81

5-ethoxy-3-(3-(((2'-fluoro-5'-methoxy-2-neopentyl-[1,1'-biphenyl]-4-yl)oxy)methyl)phenyl)-5-oxopentanoic acid step 1) ethyl 3-(3-(((2'-fluoro-5'-methoxy-2-neopentyl-[1,1'-biphenyl]-4-yl)oxy)methyl)phenyl)-5-hydroxypentanoate Under a nitrogen atmosphere, a solution (1.1 M, 5.2 mL) of tetrahydrofuran-borane in THF was added to a solution of ethyl 3-(3-(((2'-fluoro-5'-methoxy-2-neopentyl-[1,1'-biphenyl]-4-yl)oxy)methyl)phenyl)pent-4-enoate (1.44 g) in THF (25 mL) at 0° C., and the mixture was stirred at room temperature for 2 hr. To the reaction mixture were added aqueous sodium acetate solution (3.0 M, 25 mL) and aqueous hydrogen peroxide (30%, 4.4 mL) at 0° C., and the mixture was stirred at room temperature for 14 hr. To the reaction mixture was added 1N hydrochloric acid at 0° C., the mixture was extracted with ethyl acetate. The extract was washed with water, saturated aqueous sodium hydrogen carbonate solution and saturated brine, and dried over anhydrous magnesium sulfate. The solvent was evaporated under reduced pressure and the residue was purified by silica gel column chromatography (ethyl acetate/hexane) to give the title compound (440 mg) as a colorless oil.
$^1$H NMR (400 MHz, DMSO-$d_6$) δ 0.63 (9H, s), 1.04 (3H, t, J=7.1 Hz), 1.63-1.84 (2H, m), 2.35-2.74 (4H, m), 3.11-3.30 (3H, m), 3.74 (3H, s), 3.85-3.98 (2H, m), 4.40 (1H, t, J=5.1 Hz), 5.10 (2H, s), 6.72-6.80 (1H, m), 6.85-6.89 (1H, m), 6.90-6.98 (2H, m), 7.10 (1H, d, J=8.3 Hz), 7.12-7.22 (2H, m), 7.24-7.36 (3H, m).

step 2) ethyl 3-(3-(((2'-fluoro-5'-methoxy-2-neopentyl-[1,1'-biphenyl]-4-yl)oxy)methyl)phenyl)-5-oxopentanoate To a solution of ethyl 3-(3-(((2'-fluoro-5'-methoxy-2-neopentyl-[1,1'-biphenyl]-4-yl)oxy)methyl)phenyl)-5-hydroxypentanoate (330 mg) and triethylamine (0.89 mL) in DMSO (5 mL) was added sulfur trioxide pyridine complex (410 mg), and the mixture was stirred at room temperature for 30 min. To the reaction mixture was added, at room temperature, 1N hydrochloric acid, and the mixture was extracted with ethyl acetate. The extract was washed with 1N hydrochloric acid, saturated aqueous sodium hydrogen carbonate solution and saturated brine, and dried over anhydrous magnesium sulfate. The solvent was evaporated under reduced pressure to give a crude product (350 mg) of the title compound as a pale-orange oil. This compound was used for the next step without further purification.

step 3) 5-ethoxy-3-(3-(((2'-fluoro-5'-methoxy-2-neopentyl-[1,1'-biphenyl]-4-yl)oxy)methyl)phenyl)-5-oxopentanoic acid Sodium dihydrogenphosphate (230 mg), sodium chlorite (174 mg) and 2-methyl-2-butene (339 μL) were successively added to a mixture of ethyl 3-(3-(((2'-fluoro-5'-methoxy-2-neopentyl-[1,1'-biphenyl]-4-yl)oxy)methyl)phenyl)-5-oxopentanoate, 2-methyl-2-propanol (4 mL) and water (1 mL), and the mixture was stirred at room temperature for 1 hr. To the reaction mixture was added 1N hydrochloric acid at room temperature, and the mixture was extracted with ethyl acetate. The extract was washed with water and saturated brine, and dried over anhydrous magnesium sulfate. The residue was purified by silica gel column chromatography (ethyl acetate/hexane) to give the title compound (269 mg) as a colorless amorphous solid.
$^1$H NMR (400 MHz, DMSO-$d_6$) δ 0.64 (9H, s), 1.05 (3H, t, J=7.1 Hz), 2.32-2.79 (6H, m), 3.40-3.54 (1H, m), 3.74 (3H, s), 3.87-3.97 (2H, m), 5.09 (2H, s), 6.77 (1H, dd, J=5.9, 3.0 Hz), 6.89 (1H, s), 6.90-6.99 (2H, m), 7.10 (1H, d, J=8.3 Hz), 7.16 (1H, t, J=9.1 Hz), 7.23 (1H, d, J=6.1 Hz), 7.26-7.34 (2H, m), 7.36 (1H, s), 12.24 (1H, brs).
MS (ESI−): [M−H]$^+$ 535.4

Example 82

3-(3-(((2'-fluoro-5'-methoxy-2-neopentyl-[1,1'-biphenyl]-4-yl)oxy)methyl)phenyl)pentanedioic acid By a method similar to that in Example 44, step 4, the title compound was obtained from 5-ethoxy-3-(3-(((2'-fluoro-5'-methoxy-2-neopentyl-[1,1'-biphenyl]-4-yl)oxy)methyl)phenyl)-5-oxopentanoic acid.
$^1$H NMR (400 MHz, DMSO-$d_6$) δ 0.64 (9H, s), 2.41-2.72 (6H, m). 3.40-3.50 (1H, m), 3.74 (3H, s), 5.09 (2H, s), 6.78 (1H, dd, J=5.7, 3.1 Hz), 6.87-7.00 (3H, m), 7.11 (1H, d, J=8.5 Hz), 7.16 (1H, t, J=9.2 Hz), 7.21-7.34 (3H, m), 7.38 (1H, s), 12.15 (2H, brs).
MS (ESI+): [M+H]$^+$ 507.3

Example 83

5-amino-3-(3-(((2'-fluoro-5'-methoxy-2-neopentyl-[1,1'-biphenyl]-4-yl)oxy)methyl)phenyl)-5-oxopentanoic acid step 1) ethyl 5-amino-3-(3-(((2'-fluoro-5'-methoxy-2-neopentyl-[1,1'-biphenyl]-4-yl)oxy)methyl)phenyl)-5-oxopentanoate Under a nitrogen atmosphere, WSC (53.6 mg) was added to a suspension of 5-ethoxy-3-(3-(((2'-fluoro-5'-methoxy-2-neopentyl-[1,1'-biphenyl]-4-yl)oxy)methyl)phenyl)-5-oxopentanoic acid (100 mg), 1-hydroxybenzotriazole monohydrate-ammonia complex (42.5 mg) and triethylamine (78 μL) in DMF (1 mL), and the mixture was stirred at room temperature for 2 hr. Water was added to the reaction mixture at room temperature, and the mixture was extracted with ethyl acetate. The extract was washed with water and saturated brine, and dried over anhydrous magnesium sulfate. The residue was purified by silica gel column chromatography (ethyl acetate/hexane) to give the title compound (47.1 mg) as a colorless oil.
$^1$H NMR (400 MHz, DMSO-$d_6$) δ 0.64 (9H, s), 1.04 (3H, t, J=7.1 Hz), 2.32-2.61 (5H, m), 2.67-2.77 (1H, m), 3.42-3.58 (1H, m), 3.74 (3H, s), 3.85-3.98 (2H, m), 5.08 (2H, s), 6.62-6.82 (2H, m), 6.85-6.99 (3H, m), 7.05-7.38 (7H, m).

step 2) 5-amino-3-(3-(((2'-fluoro-5'-methoxy-2-neopentyl-[1,1'-biphenyl]-4-yl)oxy)methyl)phenyl)-5-oxopentanoic acid The title compound was obtained by a method similar to that in Example 44, step 4.
$^1$H NMR (400 MHz, DMSO-$d_6$) δ 0.64 (9H, s), 2.34-2.70 (6H, m), 3.43-3.56 (1H, m), 3.74 (3H, s), 5.08 (2H, s), 6.72 (1H, brs), 6.78 (1H, dd, J=6.0, 3.1 Hz), 6.87-7.00 (3H, m), 7.11 (1H, d, J=8.4 Hz), 7.16 (1H, t, J=9.2 Hz), 7.20-7.33 (4H, m), 7.35 (1H, s), 12.02 (1H, brs).
MS (ESI−): [M−H]$^+$506.3

Example 84

4-cyano-3-(3-(((2'-fluoro-5'-methoxy-2-neopentyl-[1,1'-biphenyl]-4-yl)oxy)methyl)phenyl)-4-methylpentanoic acid step 1)
1-bromo-3-((methoxymethoxy)methyl)benzene Under a nitrogen atmosphere, chloromethyl methyl ether (6.09 mL) was added to a solution of 3-bromobenzylalcohol (5.00 g) and diisopropylethylamine (18.9 mL) in THF (45 mL) at 0° C., and the mixture was stirred at 60° C. for 1 hr. Water was added to the reaction mixture at room temperature, and the mixture was extracted with ethyl acetate. The extract was washed with 1N hydrochloric acid, saturated aqueous sodium hydrogen carbonate solution and saturated brine, and dried over anhydrous magnesium sulfate. The solvent was evaporated under reduced pressure to give a crude product (6.37 g) of the title compound. This compound was used for the next step without further purification.

$^1$H NMR (400 MHz, DMSO-d$_6$) δ 3.30 (3H, s), 4.53 (2H, s), 4.66 (2H, s), 7.29-7.38 (2H, m), 7.49 (1H, d, J=7.5 Hz), 7.54 (1H, s).

step 2) (E)-ethyl 3-(3-((methoxymethoxy)methyl)phenyl)acrylate

Under a nitrogen atmosphere, a crude product of 1-bromo-3-((methoxymethoxy)methyl)benzene (3.60 g), triethylamine (6.50 mL), palladium acetate (175 mg), tri-o-tolylphosphine (711 mg) and ethyl acrylate (8.4 mL) were stirred in DMF (30 mL) at 110° C. for 1 hr. The solvent of the reaction mixture was evaporated under reduced pressure and the residue was purified by silica gel column chromatography (NH, ethyl acetate/hexane) to give the title compound (3.41 g) as a pale-yellow oil.

$^1$H NMR (400 MHz, DMSO-d$_6$) δ 1.26 (3H, t, J=7.1 Hz), 3.31 (3H, s), 4.19 (2H, q, J=7.1 Hz), 4.55 (2H, s), 4.67 (2H, s), 6.63 (1H, d, J=16.1 Hz), 7.39-7.44 (2H, m), 7.65 (1H, d, J=16.1 Hz), 7.63-7.73 (2H, m).

step 3) ethyl 4-cyano-3-(3-((methoxymethoxy)methyl)phenyl)-4-methylpentanoate Under a nitrogen atmosphere, a solution (1.6 M, 1.50 mL) of n-butyllithium in hexane was added to a solution of diisopropylamine (336 μL) in THF (2 mL) at −78° C., to the reaction mixture was added isobutyronitrile (227 μL) at −78° C., and the mixture was stirred for 5 min. To the reaction mixture was added (E)-ethyl 3-(3-((methoxymethoxy)methyl)phenyl)acrylate (250 mg) at −78° C., and the mixture was stirred at room temperature for 20 min. Water was added to the reaction mixture at room temperature, and the mixture was extracted with ethyl acetate. The extract was washed with water and saturated brine, and dried over anhydrous magnesium sulfate. The solvent of the reaction mixture was evaporated under reduced pressure and the residue was purified by silica gel column chromatography (ethyl acetate/hexane) to give the title compound (210 mg) as a colorless oil.

$^1$H NMR (400 MHz, DMSO-d$_6$) δ 0.95 (3H, t, J=7.1 Hz), 1.12 (3H, s), 1.37 (3H, s), 1.99 (1H, s), 2.80-2.90 (1H, m), 2.97-3.05 (1H, m), 3.16-3.24 (1H, m), 3.29 (3H, s), 3.80-3.93 (2H, m), 4.51 (2H, s), 4.63 (2H, s), 7.20-7.36 (4H, m).

step 4) ethyl 4-cyano-3-(3-(hydroxymethyl)phenyl)-4-methylpentanoate

Conc. hydrochloric acid (1.10 mL) was added to a solution of ethyl 4-cyano-3-(3-((methoxymethoxy)methyl)phenyl)-4-methylpentanoate (210 mg) in methanol (2 mL) at room temperature, and the mixture was stirred at 60° C. for 1 hr. The reaction mixture was diluted with ethyl acetate, water was added at room temperature, and the mixture was extracted with ethyl acetate. The extract was washed with saturated aqueous sodium hydrogen carbonate solution and saturated brine, and dried over anhydrous magnesium sulfate. The solvent was evaporated under reduced pressure to give a mixture (147 mg) of the title compound and methyl ester thereof. This compound was used for the next step without further purification.

step 5) ethyl 4-cyano-3-(3-(((2'-fluoro-5'-methoxy-2-neopentyl-[1,1'-biphenyl]-4-yl)oxy)methyl)phenyl)-4-methylpentanoate In the same manner as in Example 77, step 4, a mixture (237 mg) of the title compound and methyl ester thereof was obtained.

$^1$H NMR (400 MHz, DMSO-d$_6$) δ 0.96 (3H, t, J=7.1 Hz), 1.11 (3H, s), 1.35 (3H, s), 2.30-2.58 (2H, m), 2.80-2.95 (1H, m), 2.98-3.09 (1H, m), 3.23 (1H, dd, J=11.0, 4.3 Hz), 3.74 (3H, s), 3.81-3.93 (2H, m), 5.14 (2H, s), 6.75 (1H, dd, J=6.0, 3.1 Hz), 6.86 (1H, d, J=2.1 Hz), 6.90-6.97 (2H, m), 7.08 (1H, d, J=8.4 Hz), 7.16 (1H, t, J=9.2 Hz), 7.28 (1H, d, J=6.3 Hz), 7.33-7.44 (3H, m).

step 6) 4-cyano-3-(3-(((2'-fluoro-5'-methoxy-2-neopentyl-[1,1'-biphenyl]-4-yl)oxy)methyl)phenyl)-4-methylpentanoic acid In the same manner as in Example 44, step 4, the title compound (173 mg) was obtained.

$^1$H NMR (400 MHz, DMSO-d$_6$) δ 0.63 (9H, s), 1.09 (3H, s), 1.35 (3H, s), 2.30-2.52 (2H, m), 2.75-2.87 (1H, m), 2.88-2.99 (1H, m), 3.20 (1H, d, J=8.5 Hz), 3.74 (3H, s), 5.14 (2H, brs), 6.71-6.81 (1H, m), 6.83-7.00 (3H, m), 7.09 (1H, d, J=8.3 Hz), 7.15 (1H, t, J=9.0 Hz), 7.29 (1H, brs), 7.33-7.47 (3H, m), 12.19 (1H, brs).

MS (ESI-): [M−H]$^+$516.3

Example 85

4,4,5,5,5-pentafluoro-3-(3-(((2'-fluoro-5'-methoxy-2-neopentyl-[1,1'-biphenyl]-4-yl)oxy)methyl)phenyl)pentanoic acid step 1) 2,2,3,3,3-pentafluoro-N-methoxy-N-methylpropanamide

Under a nitrogen atmosphere, pyridine (7.83 mL) was added to a solution of N,O-dimethylhydroxylamine hydrochloride (3.62 g) in THF (100 mL) at 0° C., and the mixture was stirred for 10 min. To the reaction mixture was added triethylamine (13.5 mL) at 0° C., and the mixture was stirred at room temperature for 16 hr. The reaction mixture was filtered, water was added, and the mixture was extracted with diethyl ether. The extract was washed with 1N hydrochloric acid, saturated aqueous sodium hydrogen carbonate solution and saturated brine, and dried over anhydrous magnesium sulfate. The solvent was evaporated under reduced pressure to give a crude product (9.95 g) of the title compound as a brown oil. This compound was used for the next step without further purification.

$^1$H NMR (400 MHz, DMSO-d$_6$) δ 3.28 (3H, brs), 3.78 (3H, s).

step 2) 2,2,3,3,3-pentafluoro-1-(3-((methoxymethoxy)methyl)phenyl)propan-1-one In THF (15 mL), a Grignard reactant was prepared from 1-bromo-3-((methoxymethoxy)methyl)benzene (2.54 g) and magnesium (292 mg). Under a nitrogen atmosphere, the obtained Grignard reactant (entire amount) was added to a solution of 2,2,3,3,3-pentafluoro-N-methoxy-N-methylpropanamide (3.70 g) in THF (10 mL) at 0° C., and the mixture was stirred at room temperature for 1 hr. To the reaction mixture was added 1N hydrochloric acid at room temperature, and the mixture was extracted with ethyl acetate. The extract was washed with 1N hydrochloric acid, saturated aqueous sodium hydrogen carbonate solution and saturated brine, and dried over anhydrous magnesium sulfate. The solvent was evaporated under reduced pressure and the residue was purified by silica gel column chromatography (ethyl acetate/hexane) to give the title compound (1.28 g) as a yellow oil.

¹H NMR (400 MHz, DMSO-d₆) δ 3.31 (3H, s), 4.67 (2H, s), 4.70 (2H, s), 7.68 (1H, t, J=7.8 Hz), 7.84 (1H, d, J=7.5 Hz), 7.97-8.06 (2H, m).

step 3) ethyl 4,4,5,5,5-pentafluoro-3-(3-((methoxymethoxy)methyl)phenyl)pent-2-enoate Under a nitrogen atmosphere, to a suspension of 60% sodium hydride (481 mg) in THF (15 mL) was added ethyl diethylphosphonoacetate (2.55 mL) at 0° C., and the mixture was stirred at room temperature for 5 min. To the obtained colorless solution was added 2,2,3,3,3-pentafluoro-1-(3-((methoxymethoxy)methyl)phenyl)propan-1-one (1.28 g) at room temperature, and the mixture was stirred at 0° C. for 30 min. Water was added to the reaction mixture at room temperature, and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (1.37 g) as a pale-yellow oil.

¹H NMR (400 MHz, DMSO-d₆) δ 0.93 (3H, t, J=7.2 Hz), 3.29 (3H, s), 3.95 (2H, q, J=7.2 Hz), 4.55 (2H, s), 4.65 (2H, s), 6.94 (1H, s), 7.12-7.24 (2H, m), 7.38-7.50 (2H, m).

step 4) ethyl 4,4,5,5,5-pentafluoro-3-(3-((methoxymethoxy)methyl)phenyl)pentanoate Under a nitrogen atmosphere, copper (I) chloride (73.7 mg), sodium tert-butoxide (71.5 mg) and BINAP (463 mg) were stirred in toluene (12 mL) at room temperature for 10 min, and to the reaction mixture were successively added polymethylhydrosiloxane (1.67 mL), ethyl 4,4,5,5,5-pentafluoro-3-(3-((methoxymethoxy)methyl)phenyl)pent-2-enoate (1.37 g) and tert-butanol (854 μL) at room temperature. The reaction mixture was stirred at room temperature for 16 hr, ethanol (5 mL) was added at room temperature, and the mixture was filtered through celite. To the filtrate was added saturated aqueous ammonium chloride solution at room temperature, and the mixture was extracted with ethyl acetate. The extract was washed with water and saturated brine, and dried over anhydrous magnesium sulfate. The solvent was evaporated under reduced pressure and the residue was filtered through NH silica gel to give a crude product (366 mg) of the title compound as a colorless oil. This compound was used for the next step without further purification.

¹H NMR (400 MHz, DMSO-d₆) δ 1.03 (3H, t, J=7.1 Hz), 2.92-3.03 (1H, m), 3.08-3.17 (1H, m), 3.29 (3H, s), 3.86-4.01 (3H, m), 4.53 (2H, s), 4.64 (1H, s), 7.29-7.39 (4H, m).

step 5) ethyl 4,4,5,5,5-pentafluoro-3-(3-(hydroxymethyl)phenyl)pentanoate

In the same manner as in Example 84, step 4, a crude product (256 mg) of the title compound was obtained as a pale-yellow oil. This compound was used for the next step without further purification.

¹H NMR (400 MHz, DMSO-d₆) δ 1.04 (3H, t, J=7.0 Hz), 2.91-3.02 (1H, m), 3.08-3.17 (1H, m), 3.90-4.01 (3H, m), 4.49 (2H, d, J=5.5 Hz), 5.24 (1H, t, J=5.6 Hz), 7.22-7.41 (4H, m).

step 6) ethyl 4,4,5,5,5-pentafluoro-3-(3-(((2'-fluoro-5'-methoxy-2-neopentyl-[1,1'-biphenyl]-4-yl)oxy)methyl)phenyl)pentanoate In the same manner as in Example 76, step 4, the title compound (239 mg) was obtained as a colorless oil.

¹H NMR (400 MHz, DMSO-d₆) δ 0.63 (9H, s), 1.03 (3H, t, J=7.0 Hz), 2.50 (2H, brs), 2.92-3.05 (1H, m), 3.09-3.19 (1H, m), 3.74 (3H, s), 3.88-4.12 (3H, m), 5.15 (2H, s), 6.75 (1H, dd, J=5.6, 2.9 Hz), 6.83-6.89 (1H, m), 6.90-6.98 (2H, m), 7.09 (1H, d, J=8.4 Hz), 7.16 (1H, t, J=9.2 Hz), 7.34-7.53 (4H, m).

step 7) 4,4,5,5,5-pentafluoro-3-(3-(((2'-fluoro-5'-methoxy-2-neopentyl-[1,1'-biphenyl]-4-yl)oxy)methyl)phenyl)pentanoic acid In the same manner as in Example 44, step 4, the title compound (204 mg) was obtained as a white amorphous solid.

¹H NMR (400 MHz, DMSO-d₆) δ 0.63 (9H, s), 2.32-2.56 (2H, m), 2.85-2.95 (1H, m), 3.01-3.11 (1H, m), 3.74 (3H, s), 3.92-4.01 (1H, m), 5.15 (2H, s), 6.76 (1H, dd, J=5.8, 3.1 Hz), 6.85-6.90 (1H, m), 6.90-6.98 (2H, m), 7.09 (1H, d, J=8.4 Hz), 7.16 (1H, t, J=9.1 Hz), 7.32-7.52 (4H, m), 12.55 (1H, brs).

MS (ESI-): [M−H]⁺ 567.3

Example 86

4,4-difluoro-3-(3-(((2'-fluoro-5'-methoxy-2-neopentyl-[1,1'-biphenyl]-4-yl)oxy)methyl)phenyl)pentanoic acid step 1) 1-morpholinopropane-1,2-dione Under a nitrogen atmosphere, oxalyl chloride (8.75 mL) was added to a solution of pyruvic acid (6.96 mL) and DMF (77 μL) in THF (200 mL) at room temperature, and the mixture was stirred at room temperature for 20 min. Under a nitrogen atmosphere, morpholine (18.4 mL) was added to the reaction mixture at 0° C., and the mixture was stirred at room temperature for 2 hr. The reaction mixture was filtered, the solvent of the filtrate was evaporated under reduced pressure, and the residue was purified by silica gel column chromatography (NH, ethyl acetate/hexane) to give the title compound (11.0 g) as a colorless oil.

¹H NMR (400 MHz, DMSO-d₆) δ 2.37 (3H, s), 3.37 (2H, t, J=4.6 Hz), 3.48 (2H, t, J=4.9 Hz), 3.59 (4H, dt, J=12.6, 4.8 Hz).

step 2) 2,2-difluoro-1-morpholinopropan-1-one

Under a nitrogen atmosphere, bis(2-methoxyethyl)aminosulfur trifluoride (25.1 mL) and ethanol (1.19 mL) were added to 1-morpholinopropane-1,2-dione (10.7 g) at 0° C., and the mixture was stirred at 80° C. for 30 min. The reaction mixture was added dropwise to saturated aqueous solution of sodium hydrogen carbonate (40.1 g) at 0° C., and the mixture was extracted with ethyl acetate. The extract was washed with water and saturated brine, and dried over anhydrous magnesium sulfate. The solvent was evaporated under reduced pressure and the residue was purified by silica gel column chromatography (ethyl acetate/hexane) to give the title compound (6.59 g) as a pale-yellow oil.

¹H NMR (400 MHz, DMSO-d₆) δ 1.68-1.90 (3H, m), 3.43-3.74 (8H, m).

step 3) 2,2-difluoro-1-(3-((methoxymethoxy)methyl)phenyl)propan-1-one

In the same manner as in Example 85, step 2, the title compound (665 mg) was obtained as a colorless oil.

$^1$H NMR (400 MHz, DMSO-d$_6$) δ 1.86-2.01 (3H, m), 3.31 (3H, s), 4.64 (2H, s), 4.69 (2H, s), 7.60 (1H, t, J=7.8 Hz), 7.73 (1H, d, J=7.7 Hz), 7.97 (1H, d, J=7.9 Hz), 8.01 (1H, s).

step 4) ethyl 4,4-difluoro-3-(3-((methoxymethoxy)methyl)phenyl)pent-2-enoate In the same manner as in Example 85, step 3, the title compound ((1.12 g) was obtained as a colorless oil.
$^1$H NMR (400 MHz, DMSO-d$_6$) δ 0.94 (3H, t, J=7.1 Hz), 1.75 (3H, t, J=19.0 Hz), 3.29 (3H, s), 3.91 (2H, q, J=7.0 Hz), 4.54 (2H, s), 4.65 (2H, s), 6.48 (1H, s), 7.13 (1H, d, J=6.1 Hz), 7.17 (1H, s), 7.32-7.43 (2H, m).

step 5) ethyl 4,4-difluoro-3-(3-((methoxymethoxy)methyl)phenyl)pentanoate

In the same manner as in Example 85, step 4, the title compound (1.30 g) was obtained as a colorless oil.
$^1$H NMR (400 MHz, DMSO-d$_6$) δ 1.02 (3H, t, J=7.1 Hz), 1.47 (3H, t, J=19.3 Hz), 2.74-2.87 (1H, m), 2.92-3.04 (1H, m), 3.29 (3H, s), 3.55-3.73 (1H, m), 3.86-3.98 (2H, m), 4.52 (2H, s), 4.65 (2H, s), 7.20-7.38 (4H, m).

step 6) ethyl 4,4-difluoro-3-(3-(hydroxymethyl)phenyl)pentanoate

In the same manner as in Example 84, step 4, the title compound (744 mg) was obtained as a colorless oil.
$^1$H NMR (400 MHz, DMSO-d$_6$) δ 1.03 (3H, t, J=7.1 Hz), 1.47 (3H, t, J=19.2 Hz), 2.74-2.86 (1H, m), 2.91-3.03 (1H, m), 3.54-3.71 (1H, m), 3.87-4.01 (2H, m), 4.48 (2H, d, J=5.5 Hz), 5.19 (1H, t, J=5.6 Hz), 7.19 (1H, d, J=7.3 Hz), 7.22-7.33 (3H, m).

step 7) ethyl 4,4-difluoro-3-(3-(((2'-fluoro-5'-methoxy-2-neopentyl-[1,1'-biphenyl]-4-yl)oxy)methyl)phenyl)pentanoate In the same manner as in Example 76, step 4, the title compound (180 mg) was obtained as a colorless oil.
$^1$H NMR (400 MHz, DMSO-d$_6$) δ 0.62 (9H, s), 1.02 (3H, t, J=7.1 Hz), 1.46 (3H, t, J=19.2 Hz), 2.31-2.63 (2H, m), 2.77-2.88 (1H, m), 2.95-3.04 (1H, m), 3.60-3.73 (1H, m), 3.74 (3H, s), 3.86-3.98 (2H, m), 5.14 (2H, s), 6.76 (1H, dd, J=6.0, 3.2 Hz), 6.87 (1H, d, J=2.3 Hz), 6.90-6.98 (2H, m), 7.09 (1H, d, J=8.4 Hz), 7.16 (1H, t, J=9.1 Hz), 7.30 (1H, d, J=6.7 Hz), 7.34-7.46 (3H, m).

step 8) 4,4-difluoro-3-(3-(((2'-fluoro-5'-methoxy-2-neopentyl-[1,1'-biphenyl]-4-yl)oxy)methyl)phenyl)pentanoic acid In the same manner as in Example 44, step 4, the title compound (149 mg) was obtained as a white amorphous solid.
$^1$H NMR (400 MHz, DMSO-d$_6$) δ 0.63 (9H, s), 1.46 (3H, t, J=19.1 Hz), 2.31-2.62 (2H, m), 2.71-2.81 (1H, m), 2.87-2.97 (1H, m), 3.55-3.72 (1H, m), 3.74 (3H, s), 5.14 (2H, s), 6.76 (1H, dd, J=5.8, 3.1 Hz), 6.86-6.99 (3H, m), 7.10 (1H, d, J=8.4 Hz), 7.16 (1H, t, J=9.2 Hz), 7.30 (1H, d, J=6.5 Hz), 7.38 (2H, q, J=7.5 Hz), 7.43 (1H, s), 12.23 (1H, brs).
MS (ESI-): [M-H]$^+$ 513.3

Example 87

3-(2-cyanocyclopropyl)-3-(3-(((2'-fluoro-5'-methoxy-2-neopentyl-[1,1'-biphenyl]-4-yl)oxy)methyl)phenyl)propanoic acid step 1) (E)-5-(3-((methoxymethoxy)methyl)phenyl)pent-4-enenitrile

In the same manner as in Example 84, step 2, the title compound (2.08 g) was obtained as a pale-yellow oil.
$^1$H NMR (400 MHz, DMSO-d$_6$) δ 2.47 (2H, d, J=7.3 Hz), 2.66-2.73 (2H, m), 3.30 (3H, s), 4.52 (2H, s), 4.65 (2H, s), 6.23-6.33 (1H, m), 6.54 (1H, d, J=15.9 Hz), 7.15-7.43 (4H, m).

step 2) 3-(3-(3-((methoxymethoxy)methyl)phenyl)oxiran-2-yl)propanenitrile m-Chloroperbenzoic acid (3.77 g) was added to a solution of (E)-5-(3-((methoxymethoxy)methyl)phenyl)pent-4-enenitrile (2.08 g) in ethyl acetate (20 mL) at room temperature, and the mixture was stirred at 80° C. for 1 hr. Saturated aqueous sodium thiosulfate solution was added to the reaction mixture at room temperature, and the mixture was extracted with ethyl acetate. The extract was washed with saturated aqueous sodium thiosulfate solution, saturated aqueous sodium hydrogen carbonate solution and saturated brine, and dried over anhydrous magnesium sulfate. The solvent was evaporated under reduced pressure and the residue was purified by silica gel column chromatography (NH, ethyl acetate/hexane) to give the title compound (1.07 g) as a colorless oil.
$^1$H NMR (400 MHz, DMSO-d$_6$) δ 1.87-1.98 (2H, m), 2.68 (2H, t, J=7.0 Hz), 3.07-3.15 (1H, m), 3.30 (3H, s), 3.86 (1H, s), 4.52 (2H, s), 4.65 (2H, s), 7.21 (1H, d, J=7.7 Hz), 7.25 (1H, s), 7.28 (1H, d, J=6.9 Hz), 7.32-7.40 (1H, m).

step 2) 2-(hydroxy(3-((methoxymethoxy)methyl)phenyl)methyl)cyclopropanecarbonitrile Under a nitrogen atmosphere, a solution (1.8 M, 5.29 mL) of trimethylaluminum in toluene was added to a solution of 3-(3-(3-((methoxymethoxy)methyl)phenyl)oxiran-2-yl)propanenitrile (1.07 g) in THF (50 mL) at −78° C., and the mixture was stirred at −78° C. for 20 min. To the reaction mixture was added dropwise a solution (1.0 M, 6.49 mL) of lithium hexamethyldisilazane in THF at −78° C., and the mixture was stirred at −78° C. for 30 min. The reaction mixture was stirred at room temperature for 10 min, saturated aqueous ammonium chloride solution was added at 0° C., and the mixture was extracted with ethyl acetate. The extract was washed with 1N hydrochloric acid, saturated aqueous sodium hydrogen carbonate solution and saturated brine, and dried over anhydrous magnesium sulfate. The solvent was evaporated under reduced pressure and the residue was purified by silica gel column chromatography (ethyl acetate/hexane) to give the title compound (457 mg, less polar) as a pale-yellow oil and a stereoisomer (345.5 mg, more polar) of the title compound as a pale-yellow oil.
Less Polar Isomer
$^1$H NMR (400 MHz, DMSO-d$_6$) δ 1.11-1.20 (2H, m), 1.70-1.82 (2H, m), 3.31 (3H, s), 4.43 (1H, t, J=5.0 Hz), 4.53 (2H, s), 4.66 (2H, s), 5.52 (1H, d, J=4.6 Hz), 7.24 (1H, d, J=6.3 Hz), 7.29-7.34 (2H, m), 7.37 (1H, s).

More Polar Isomer $^1$H NMR (400 MHz, DMSO-d$_6$) δ 1.13-1.31 (2H, m), 1.48-1.67 (1H, m), 1.76-1.90 (1H, m), 3.31 (3H, s), 4.20 (1H, dd, J=8.3, 4.7 Hz), 4.54 (2H, s), 4.66 (2H, s), 5.65 (1H, d, J=4.6 Hz), 7.26 (1H, d, J=6.4 Hz), 7.31-7.40 (2H, m), 7.45 (1H, s).

step 3) 2-(3-((methoxymethoxy)methyl)benzoyl)cyclopropanecarbonitrile

To a solution of 2-(hydroxy(3-((methoxymethoxy)methyl)phenyl)methyl)cyclopropanecarbonitrile (less polar) (457 mg) obtained in Example 87, step 2, and triethylamine (2.58 mL) in DMSO (15 mL) was added sulfur trioxide pyridine complex (1.17 g), and the mixture was stirred at room temperature for 20 min. To the reaction mixture was added 1N hydrochloric acid at room temperature, and the mixture was extracted with ethyl acetate. The extract was washed with 1N hydrochloric acid, saturated aqueous sodium hydrogen carbonate solution and saturated brine, and dried over anhydrous magnesium sulfate. The solvent was evaporated under reduced pressure to give a crude product (455 mg) of the title compound as a pale-orange oil. This compound was used for the next step without further purification.

$^1$H NMR (400 MHz, DMSO-d$_6$) δ 1.48-1.56 (1H, m), 1.64-1.72 (1H, m), 2.29-2.37 (1H, m), 3.32 (3H, s), 3.63-3.77 (1H, m), 4.64 (2H, s), 4.69 (2H, s), 7.58 (1H, t, J=7.5 Hz), 7.69 (1H, d, J=7.5 Hz), 8.02-8.16 (2H, m).

step 4) ethyl 3-(2-cyanocyclopropyl)-3-(3-((methoxymethoxy)methyl)phenyl)acrylate In the same manner as in Example 85, step 3, a geometric isomer mixture (494 mg) of the title compound was obtained as a colorless oil from 2-(3-((methoxymethoxy)methyl)benzoyl)cyclopropanecarbonitrile (entire amount) obtained in Example 86, step 3.

NMR of Main Product $^1$H NMR (400 MHz, DMSO-d$_6$) δ 0.90-0.96 (1H, m), 1.22-1.27 (1H, m), 1.27 (3H, t, J=7.1 Hz), 1.65 (2H, tt, J=14.7, 5.5 Hz), 3.30 (3H, s), 4.13-4.28 (2H, m), 4.55 (2H, s), 4.66 (2H, s), 6.07 (1H, s), 7.05-7.44 (4H, m).

step 5) ethyl 3-(2-cyanocyclopropyl)-3-(3-((methoxymethoxy)methyl)phenyl)propanoate To a solution of ethyl 3-(2-cyanocyclopropyl)-3-(3-((methoxymethoxy)methyl)phenyl)acrylate (490 mg) obtained in Example 86, step 4, in ethyl acetate (8 mL) was added 10% palladium-activated carbon (100 mg) and, under a hydrogen atmosphere, the mixture was stirred at room temperature for 1 hr. The reaction mixture was filtered, and the filtrate was concentrated under reduced pressure to give a crude product (459 mg) of the title compound as a colorless oil. This compound was used for the next step without further purification.

step 6) ethyl 3-(2-cyanocyclopropyl)-3-(3-(hydroxymethyl)phenyl)propanoate

In the same manner as in Example 84, step 4, a crude product (368 mg) of the title compound was obtained as a colorless oil from ethyl 3-(2-cyanocyclopropyl)-3-(3-((methoxymethoxy)methyl)phenyl)propanoate (entire amount) obtained in Example 86, step 5. This compound was used for the next step without further purification.

step 7) ethyl 3-(2-cyanocyclopropyl)-3-(3-(((2'-fluoro-5'-methoxy-2-neopentyl-[1,1'-biphenyl]-4-yl)oxy)methyl)phenyl)propanoate In the same manner as in Example 76, step 4, the title compound (368 mg, less polar) was obtained as a pale-yellow oil and a diastereomer (147 mg, more polar) of the title compound as a colorless oil, from ethyl 3-(2-cyanocyclopropyl)-3-(3-(hydroxymethyl)phenyl)propanoate (entire amount) obtained in Example 86, step 6. In addition, ethyl 6-cyano-3-(3-(((2'-fluoro-5'-methoxy-2-neopentyl-[1,1'-biphenyl]-4-yl)oxy)methyl)phenyl)hexanoate (65.3 mg) was obtained as a colorless oil.

Less Polar $^1$H NMR (400 MHz, DMSO-d$_6$) δ 0.63 (9H, s), 0.88-0.97 (1H, m), 1.03-1.09 (1H, m), 1.09 (3H, t, J=7.1 Hz), 1.61-1.70 (1H, m), 1.77-1.89 (1H, m), 2.37-2.69 (3H, m), 2.75-2.93 (2H, m), 3.74 (3H, s), 3.92-4.01 (2H, m), 5.11 (2H, s), 6.71-6.79 (1H, m), 6.84-6.89 (1H, m), 6.90-6.99 (2H, m), 7.10 (1H, d, J=8.4 Hz), 7.16 (1H, t, J=9.1 Hz), 7.23-7.36 (3H, m), 7.39 (1H, s).

More Polar $^1$H NMR (400 MHz, DMSO-d$_6$) δ 0.63 (9H, s), 0.99-1.05 (1H, m), 1.06 (3H, t, J=7.1 Hz), 1.23-1.33 (1H, m), 1.54-1.65 (1H, m), 1.76-1.90 (1H, m), 2.41-2.65 (3H, m), 2.70-2.85 (2H, m), 3.74 (3H, s), 3.89-3.99 (2H, m), 5.12 (2H, s), 6.77 (1H, dd, J=6.0, 2.9 Hz), 6.85-6.99 (3H, m), 7.10 (1H, d, J=8.5 Hz), 7.16 (1H, t, J=9.1 Hz), 7.27-7.39 (3H, m), 7.41 (1H, s).

ethyl 6-cyano-3-(3-(((2'-fluoro-5'-methoxy-2-neopentyl-[1,1'-biphenyl]-4-yl)oxy)methyl)phenyl)hexanoate $^1$H NMR (400 MHz, DMSO-d$_6$) δ 0.63 (9H, s), 1.06 (3H, t, J=7.0 Hz), 1.24-1.50 (2H, m), 1.58-1.80 (2H, m), 2.30-2.64 (3H, m), 2.42 (2H, t, J=6.9 Hz), 2.66-2.76 (1H, m), 2.96-3.14 (1H, m), 3.74 (3H, s), 3.86-4.07 (2H, m), 5.11 (2H, s), 6.76 (1H, dd, J=5.7, 2.9 Hz), 6.85-6.89 (1H, m), 6.90-6.98 (2H, m), 7.09 (1H, d, J=8.5 Hz), 7.15 (1H, t, J=9.2 Hz), 7.21 (1H, d, J=6.4 Hz), 7.27-7.37 (3H, m, J=7.0 Hz).

step 8) 3-(2-cyanocyclopropyl)-3-(3-(((2'-fluoro-5'-methoxy-2-neopentyl-[1,1'-biphenyl]-4-yl)oxy)methyl)phenyl)propanoic acid In the same manner as in Example 44, step 4, the title compound (190 mg) was obtained as a white amorphous solid from ethyl 3-(2-cyanocyclopropyl)-3-(3-(((2'-fluoro-5'-methoxy-2-neopentyl-[1,1'-biphenyl]-4-yl)oxy)methyl)phenyl)propanoate (less polar) (232 mg) obtained in Example 87, step 7.

$^1$H NMR (400 MHz, DMSO-d$_6$) δ 0.63 (9H, s), 0.86-0.97 (1H, m), 1.02-1.11 (1H, m), 1.60-1.72 (1H, m), 1.74-1.86 (1H, m), 2.31-2.63 (3H, m), 2.69-2.87 (2H, m), 3.74 (3H, s), 5.11 (2H, s), 6.77 (1H, dd, J=5.6, 3.0 Hz), 6.85-6.90 (1H, m), 6.91-7.00 (2H, m), 7.11 (1H, d, J=8.4 Hz), 7.16 (1H, t, J=9.2 Hz), 7.23-7.37 (3H, m), 7.39 (1H, s), 12.16 (1H, brs).

MS (ESI−): [M−H]$^+$514.4

Example 88

3-(2-cyanocyclopropyl)-3-(3-(((2'-fluoro-5'-methoxy-2-neopentyl-[1,1'-biphenyl]-4-yl)oxy)methyl)phenyl)propanoic acid In the same manner as in Example 44, step 4, the title compound (134 mg) was obtained as a white amorphous solid from ethyl 3-(2-cyanocyclopropyl)-3-(3-(((2'-fluoro-5'-methoxy-2-neopentyl-[1,1'-biphenyl]-4-yl)oxy)methyl)phenyl)propanoate (more polar) (147 mg) obtained in Example 87, step 7.

$^1$H NMR (400 MHz, DMSO-d$_6$) δ 0.64 (9H, s), 0.99-1.08 (1H, m), 1.23-1.32 (1H, m), 1.53-1.64 (1H, m), 1.73-1.87 (1H, m), 2.38-2.61 (3H, m), 2.63-2.79 (2H, m), 3.74 (3H, s), 5.13 (2H, s), 6.78 (1H, dd, J=5.8, 3.1 Hz), 6.85-7.01 (3H, m), 7.11 (1H, d, J=8.4 Hz), 7.16 (1H, t, J=9.1 Hz), 7.27-7.40 (3H, m), 7.43 (1H, s), 12.13 (1H, brs).
MS (ESI–): [M–H]$^+$514.3

Example 89

6-cyano-3-(3-(((2'-fluoro-5'-methoxy-2-neopentyl-[1,1'-biphenyl]-4-yl)oxy)methyl)phenyl)hexanoic acid In the same manner as in Example 77, step 4, the title compound (60.0 mg) was obtained as a white amorphous solid from ethyl 6-cyano-3-(3-(((2'-fluoro-5'-methoxy-2-neopentyl-[1,1'-biphenyl]-4-yl)oxy)methyl)phenyl)hexanoate (65.3 mg) obtained in Example 87, step 7.

$^1$H NMR (400 MHz, DMSO-d$_6$) δ 0.63 (9H, s), 1.22-1.35 (1H, m), 1.37-1.50 (1H, m), 1.56-1.82 (2H, m), 2.34-2.77 (4H, m), 2.41 (2H, t, J=6.9 Hz), 3.03 (1H, d, J=6.4 Hz), 3.74 (3H, s), 5.11 (2H, s), 6.77 (1H, dd, J=5.8, 3.1 Hz), 6.84-6.98 (3H, m), 7.10 (1H, d, J=8.4 Hz), 7.16 (1H, t, J=9.1 Hz), 7.21 (1H, d, J=6.9 Hz), 7.26-7.38 (3H, m), 12.05 (1H, s).
MS (ESI–): [M–H]$^+$516.4

Example 90

3-(2-cyanocyclopropyl)-3-(3-(((2'-fluoro-5'-methoxy-2-neopentyl-[1,1'-biphenyl]-4-yl)oxy)methyl)phenyl)propanoic acid step 1) 2-(3-((methoxymethoxy)methyl)benzoyl)cyclopropanecarbonitrile In the same manner as in Example 87, step 4, the title compound (400 mg) was obtained as a pale-orange oil from 2-(hydroxy(3-((methoxymethoxy)methyl)phenyl)methyl)cyclopropanecarbonitrile (more polar) (346 mg) obtained in Example 87, step 3. This compound was used for the next step without further purification.

$^1$H NMR (400 MHz, DMSO-d$_6$) δ 1.56 (1H, td, J=8.2, 4.2 Hz), 1.65-1.74 (1H, m), 2.40-2.49 (1H, m), 3.32 (3H, s), 3.40-3.53 (1H, m), 4.64 (2H, s), 4.70 (2H, s), 7.59 (1H, t, J=7.7 Hz), 7.69 (1H, d, J=7.8 Hz), 7.99-8.07 (2H, m).

step 2) ethyl 3-(2-cyanocyclopropyl)-3-(3-((methoxymethoxy)methyl)phenyl)acrylate In the same manner as in Example 85, step 3, a geometric isomer mixture (273 mg) of the title compound was obtained as a colorless oil from 2-(3-((methoxymethoxy)methyl)benzoyl)cyclopropanecarbonitrile (entire amount).
NMR of Main Product
$^1$H NMR (400 MHz, DMSO-d$_6$) δ 1.27 (4H, t, J=7.1 Hz), 1.33-1.45 (1H, m), 1.55-1.66 (1H, m), 2.26-2.39 (1H, m), 2.80-2.95 (1H, m), 3.30 (3H, brs), 4.15-4.24 (2H, m), 4.57 (2H, s), 4.67 (2H, s), 6.35 (1H, s), 7.16-7.50 (4H, m).

step 3) ethyl 3-(2-cyanocyclopropyl)-3-(3-((methoxymethoxy)methyl)phenyl)propanoate In the same manner as in Example 86, step 5, a crude product (298 mg) of the title compound was obtained as a colorless oil from ethyl 3-(2-cyanocyclopropyl)-3-(3-((methoxymethoxy)methyl)phenyl)acrylate (273 mg). This compound was used for the next step without further purification.

step 4) ethyl 3-(2-cyanocyclopropyl)-3-(3-(hydroxymethyl)phenyl)propanoate

In the same manner as in Example 84, step 4, a crude product (246 mg) of the title compound was obtained as a colorless oil from 3-(2-cyanocyclopropyl)-3-(3-((methoxymethoxy)methyl)phenyl)propanoate (entire amount). This compound was used for the next step without further purification.

step 5) ethyl 3-(2-cyanocyclopropyl)-3-(3-(((2'-fluoro-5'-methoxy-2-neopentyl-[1,1'-biphenyl]-4-yl)oxy)methyl)phenyl)propanoate In the same manner as in Example 76, step 4, the title compound (61.8 mg, less polar) was obtained as a colorless oil and a diastereomer (35.9 mg, more polar) of the title compound was obtained as a colorless oil, from ethyl 3-(2-cyanocyclopropyl)-3-(3-(hydroxymethyl)phenyl)propanoate (entire amount).
Less Polar
$^1$H NMR (400 MHz, DMSO-d$_6$) δ 0.63 (9H, s), 0.88 (1H, q, J=5.6 Hz), 1.01 (3H, t, J=7.1 Hz), 1.04-1.12 (1H, m), 1.62-1.75 (1H, m), 1.91-1.98 (1H, m), 2.37-2.71 (3H, m), 2.77-2.86 (1H, m), 2.87-2.98 (1H, m), 3.74 (3H, s), 3.85-3.99 (2H, m), 5.12 (2H, s), 6.76 (1H, dd, J=5.9, 3.0 Hz), 6.85-6.90 (1H, m), 6.90-7.02 (2H, m), 7.10 (1H, d, J=8.3 Hz), 7.16 (1H, t, J=9.2 Hz), 7.28-7.39 (3H, m), 7.44 (1H, s).
More Polar
$^1$H NMR (400 MHz, DMSO-d$_6$) δ 0.63 (9H, s), 1.00-1.05 (1H, m), 1.06 (3H, t, J=7.1 Hz), 1.22-1.32 (1H, m), 1.68-1.83 (2H, m), 2.33-2.64 (2H, m), 2.66-2.74 (1H, m), 2.76-2.91 (2H, m), 3.74 (3H, s), 3.89-3.99 (2H, m), 5.11 (2H, s), 6.77 (1H, dd, J=5.9, 2.9 Hz), 6.86-6.90 (1H, m), 6.91-6.99 (2H, m), 7.10 (1H, d, J=8.5 Hz), 7.16 (1H, t, J=9.1 Hz), 7.30-7.40 (3H, m), 7.48 (1H, s).

step 6) 3-(2-cyanocyclopropyl)-3-(3-(((2'-fluoro-5'-methoxy-2-neopentyl-[1,1'-biphenyl]-4-yl)oxy)methyl)phenyl)propanoic acid In the same manner as in Example 44, step 4, the title compound (50.5 mg) was obtained as a white amorphous solid from ethyl 3-(2-cyanocyclopropyl)-3-(3-(((2'-fluoro-5'-methoxy-2-neopentyl-[1,1'-biphenyl]-4-yl)oxy)methyl)phenyl)propanoate (less polar) (61.8 mg).
$^1$H NMR (400 MHz, DMSO-d$_6$) δ 0.64 (9H, s), 0.84-0.93 (1H, m), 1.02-1.08 (1H, m), 1.58-1.70 (1H, m), 1.86-1.98 (1H, m), 2.35-2.68 (3H, m), 2.72-2.80 (1H, m), 2.82-2.94 (1H, m), 3.74 (3H, s), 5.11 (2H, s), 6.77 (1H, dd, J=5.7, 3.2 Hz), 6.86-7.01 (3H, m), 7.11 (1H, d, J=8.5 Hz), 7.16 (1H, t, J=9.1 Hz), 7.28-7.39 (3H, m), 7.45 (1H, s), 12.08 (1H, brs).
MS (ESI–): [M–H]$^+$514.3

Example 91

3-(2-cyanocyclopropyl)-3-(3-(((2'-fluoro-5'-methoxy-2-neopentyl-[1,1'-biphenyl]-4-yl)oxy)methyl)phenyl)propanoic acid In the same manner as in Example 44, step 4, the title compound (29.9 mg) was obtained as a white amorphous solid from 3-(2-cyanocyclopropyl)-3-(3-(((2'-fluoro-5'- methoxy-2-neopentyl-[1,1'-biphenyl]-4-yl)oxy)methyl)phenyl)propanoate (more polar) (35.9 mg).
$^1$H NMR (400 MHz, DMSO-d$_6$) δ 0.64 (9H, s), 1.02-1.07 (1H, m), 1.23-1.31 (1H, m), 1.65-1.81 (2H, m), 2.50 (2H, m), 2.65-2.86 (3H, m), 3.74 (3H, s), 5.11 (2H, s), 6.72-6.81 (1H, m), 6.86-7.00 (3H, m), 7.10 (1H, d, J=8.3 Hz), 7.16 (1H, t, J=9.0 Hz), 7.28-7.44 (3H, m), 7.49 (1H, s), 12.17 (1H, brs).
MS (ESI-): [M-H]$^+$ 514.3

Example 92

3-cyclopropyl-3-(3-(((2'-fluoro-5'-methoxy-2-(3-methoxy-3-methylbutyl)biphenyl-4-yl)oxy)methyl)phenyl)propanoic acid step 1) tert-butyl 2'-fluoro-5'-methoxy-2-(3-methyl-3-((trimethylsilyl)oxy)but-1-yn-1-yl)biphenyl-4-yl carbonate Under a nitrogen atmosphere, to a mixture of 4-((tert-butoxycarbonyl)oxy)-2'-fluoro-5'-methoxybiphenyl-2-yl trifluoromethanesulfonate (408 mg), tetrakis(triphenylphosphine)palladium (308 mg), copper iodide (32 mg) and triethylamine (10 mL) was added trimethyl((2-methylbut-3-yn-2-yl)oxy)silane (1.7 mL). The mixture was stirred at 80° C. for 15 hr, and tetrakis(triphenylphosphine)palladium (308 mg) was added. The mixture was stirred at 80° C. for 20 hr, the solvent was evaporated under reduced pressure, and the residue was purified by silica gel column chromatography (ethyl acetate/hexane) to give the title compound (232 mg) as a yellow oil.
$^1$H NMR (400 MHz, DMSO-d$_6$) δ 0.02 (9H, s), 1.33 (6H, s), 1.51 (9H, s), 3.76 (3H, s), 6.90-6.95 (1H, m), 6.97-7.03 (1H, m), 7.21 (1H, t, J=9.2 Hz), 7.30-7.36 (2H, m), 7.45 (1H, d, J=8.0 Hz).

step 2) tert-butyl 2'-fluoro-2-(3-hydroxy-3-methylbut-1-yn-1-yl)-5'-methoxybiphenyl-4-yl carbonate To a solution of tert-butyl 2'-fluoro-5'-methoxy-2-(3-methyl-3-((trimethylsilyl)oxy)but-1-yn-1-yl)biphenyl-4-yl carbonate (480 mg) in THF (3 mL) was added a solution (1 M, 2.0 mL) of tetrabutylammonium fluoride in THF, and the mixture was stirred at room temperature for 30 min. The reaction mixture was diluted with ethyl acetate. The diluted solution was washed with water and saturated brine, and dried over anhydrous sodium sulfate. The solvent was evaporated under reduced pressure, and the residue was purified by silica gel column chromatography (ethyl acetate/hexane) to give the title compound (343 mg) as a colorless oil.
$^1$H NMR (400 MHz, DMSO-d$_6$) δ 1.25 (6H, s), 1.51 (9H, s), 3.77 (3H, s), 5.31 (1H, s), 6.94 (1H, dd, J=6.0, 3.1 Hz), 6.96-7.02 (1H, m), 7.21 (1H, t, J=9.2 Hz), 7.28 (1H, dd, J=8.4, 2.5 Hz), 7.34 (1H, d, J=2.3 Hz), 7.43 (1H, d, J=8.4 Hz).

step 3) tert-butyl 2'-fluoro-5'-methoxy-2-(3-methoxy-3-methylbut-1-yn-1-yl)biphenyl-4-yl carbonate To a solution of tert-butyl 2'-fluoro-2-(3-hydroxy-3-methylbut-1-yn-1-yl)-5'-methoxybiphenyl-4-yl carbonate (314 mg) and iodomethane (0.50 mL) in toluene (5 mL) was added silver(I) oxide (365 mg). After stirring at 40° C. for 20 hr, silver(I) (365 mg) was added to the reaction mixture. The mixture was stirred at 40° C. for 70 hr. The reaction mixture was filtered, the solvent of the filtrate was evaporated under reduced pressure, and the residue was purified by silica gel column chromatography (ethyl acetate/hexane) to give the title compound (244 mg) as a colorless oil.
$^1$H NMR (400 MHz, DMSO-d$_6$) δ 1.27 (6H, s), 1.51 (9H, s), 3.03 (3H, s), 3.77 (3H, s), 6.94 (1H, dd, J=5.9, 3.1 Hz), 6.97-7.03 (1H, m), 7.22 (1H, t, J=9.2 Hz), 7.28-7.35 (1H, m), 7.38-7.47 (2H, m).

step 4) tert-butyl 2'-fluoro-5'-methoxy-2-(3-methoxy-3-methylbutyl)biphenyl-4-yl carbonate To a solution of tert-butyl 2'-fluoro-5'-methoxy-2-(3-methoxy-3-methylbut-1-yn-1-yl)biphenyl-4-yl carbonate (241 mg) in ethyl acetate (5 mL) was added 10% palladium-carbon (48 mg) and, under a hydrogen atmosphere, the mixture was stirred at room temperature for 1 hr. The reaction mixture was filtered, the solvent of the filtrate was evaporated under reduced pressure, and the residue was purified by silica gel column chromatography (ethyl acetate/hexane) to give the title compound (203 mg) as a colorless oil.
$^1$H NMR (400 MHz, DMSO-d$_6$) δ 0.93 (6H, s), 1.46-1.53 (11H, m), 2.37-2.47 (2H, m), 2.85 (3H, s), 3.76 (3H, s), 6.84 (1H, dd, J=5.8, 3.1 Hz), 6.95-7.02 (1H, m), 7.08 (1H, dd, J=8.3, 2.3 Hz), 7.16-7.26 (3H, m).

step 5) 2'-fluoro-5'-methoxy-2-(3-methoxy-3-methylbutyl)biphenyl-4-ol

To a solution of tert-butyl 2'-fluoro-5'-methoxy-2-(3-methoxy-3-methylbutyl)biphenyl-4-yl carbonate (199 mg) in ethyl acetate (5 mL) was added a solution (4 M, 2 mL) of hydrogen chloride in ethyl acetate, and the mixture was stirred at room temperature for 20 hr. The solvent was evaporated under reduced pressure, and the residue was purified by silica gel column chromatography (ethyl acetate/hexane) to give the title compound (203 mg) as a colorless oil.
$^1$H NMR (400 MHz, DMSO-d$_6$) δ 0.92 (6H, s), 1.41-1.50 (2H, m), 2.28-2.38 (2H, m), 2.86 (3H, s), 3.74 (3H, s), 6.65 (1H, dd, J=8.3, 2.3 Hz), 6.70 (1H, d, J=2.1 Hz), 6.76 (1H, dd, J=6.0, 3.1 Hz), 6.88-6.99 (2H, m), 7.16 (1H, t, J=9.1 Hz), 9.50 (1H, brs).

step 6) 3-cyclopropyl-3-(3-(((2'-fluoro-5'-methoxy-2-(3-methoxy-3-methylbutyl)biphenyl-4-yl)oxy)methyl)phenyl)propanoic acid In the same manner as in Example 75, step 6, and Example 44, step 4, the title compound (134 mg) was obtained as a colorless oil.
$^1$H NMR (400 MHz, DMSO-d$_6$) δ 0.07-0.15 (1H, m), 0.21-0.36 (2H, m), 0.45-0.55 (1H, m), 0.92 (6H, s), 0.96-1.07 (1H, m), 1.44-1.54 (2H, m), 2.27-2.44 (3H, m), 2.59-2.74 (2H, m), 2.85 (3H, s), 3.75 (3H, s), 5.10 (2H, s), 6.78 (1H, dd, J=6.0, 3.1 Hz), 6.88-6.97 (2H, m), 6.99 (1H, d, J=2.3 Hz), 7.09 (1H, d, J=8.4 Hz), 7.14-7.26 (2H, m), 7.27-7.35 (2H, m), 7.37 (1H, s), 12.10 (1H, brs).
MS (ESI-): [M-H]$^-$ 519.3

Example 93

3-cyclopropyl-3-(3-(((2-(3,3-dimethylbutyl)-2'-fluoro-5'-methoxybiphenyl-4-yl)oxy)methyl)phenyl)propanoic acid step 1) (2'-fluoro-5'-methoxy-4-((4-methoxybenzyl)oxy)biphenyl-2-yl)methanol To a mixture of lithium aluminum hydride (2.58 g) and THF (300 mL) was added ethyl 2'-fluoro-5'-methoxy-4-((4- methoxybenzyl)oxy)biphenyl-2-carboxylate (18.6 g) at 0° C., and the mixture was stirred at 0° C. for 20 min. To the reaction mixture was added sodium sulfate decahydrate (22.4 g), and the mixture was filtered. The solvent of the filtrate was evaporated under reduced pressure, and the residue was purified by silica gel column chromatography (ethyl acetate/hexane) to give the title compound (13.2 g) as a colorless oil.

$^1$H NMR (400 MHz, DMSO-$d_6$) δ 3.75 (3H, s), 3.76 (3H, s), 4.29 (2H, d, J=4.8 Hz), 5.07 (2H, s), 5.14 (1H, t, J=5.2 Hz), 6.81 (1H, dd, J=6.1, 3.2 Hz), 6.91-7.00 (4H, m), 7.12 (1H, d, J=8.4 Hz), 7.14-7.24 (2H, m), 7.40 (2H, d, J=8.4 Hz).

step 2) 2'-fluoro-5'-methoxy-4-((4-methoxybenzyl)oxy)biphenyl-2-carbaldehyde To a solution of (2'-fluoro-5'-methoxy-4-((4-methoxybenzyl)oxy)biphenyl-2-yl)methanol (5.03 g) and triethylamine (5.7 mL) in DMSO (80 mL) was added sulfur trioxide pyridine complex (4.35 g), and the mixture was stirred at room temperature for 30 min. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (4.37 g) as a colorless oil.

$^1$H NMR (400 MHz, DMSO-$d_6$) δ 3.76 (3H, s), 3.79 (3H, s), 5.17 (2H, s), 6.94-7.00 (3H, m), 7.00-7.07 (1H, m), 7.24 (1H, t, J=9.2 Hz), 7.38-7.46 (4H, m), 7.47-7.51 (1H, m), 9.79 (1H, d, J=3.1 Hz).

step 3) 1-(2'-fluoro-5'-methoxy-4-((4-methoxybenzyl)oxy)biphenyl-2-yl)-3,3-dimethylbutan-1-ol To a mixture of magnesium (133 mg) and diethyl ether (10 mL) was added 1-bromo-2,2-dimethylpropane (0.68 mL), and the mixture was stirred at room temperature for 30 min. To the reaction mixture was added a solution of 2'-fluoro-5'-methoxy-4-((4-methoxybenzyl)oxy)biphenyl-2-carbaldehyde (1.02 g) in diethyl ether (5 mL), and the mixture was stirred at room temperature for 2 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (674 mg) as a pale-yellow oil.

$^1$H NMR (300 MHz, DMSO-$d_6$) δ 0.66 (9H, s), 1.07-1.23 (1H, m), 1.27-1.50 (1H, m), 3.74 (3H, s), 3.76 (3H, s), 4.53-4.68 (1H, m), 4.87 (1H, brs), 5.06 (2H, s), 6.66-6.85 (1H, m), 6.86-7.00 (4H, m), 7.00-7.07 (1H, m), 7.13-7.28 (2H, m), 7.41 (2H, d, J=8.6 Hz).

step 4) 2-(3,3-dimethylbutyl)-2'-fluoro-5''-methoxybiphenyl-4-ol

To a solution of 1-(2'-fluoro-5'-methoxy-4-((4-methoxybenzyl)oxy)biphenyl-2-yl)-3,3-dimethylbutan-1-ol (205 mg) and triethylamine (0.10 mL) in toluene (3 mL) was added thionyl chloride (68 μL). The mixture was stirred at room temperature for 1 hr. The solvent was evaporated under reduced pressure, and the residue was dissolved in methanol (3 mL), and 10% palladium-carbon (49 mg) was added. Under a hydrogen atmosphere, the mixture was stirred at room temperature for 20 hr, and the reaction mixture was filtered. The solvent of the filtrate was evaporated under reduced pressure, and the residue was purified by silica gel column chromatography (ethyl acetate/hexane) to give the title compound (111 mg) as a colorless oil.

$^1$H NMR (400 MHz, DMSO-$d_6$) δ 0.70 (9H, s), 1.19-1.25 (2H, m), 2.26-2.35 (2H, m), 3.74 (3H, s), 6.61-6.67 (1H, m), 6.67-6.70 (1H, m), 6.74 (1H, dd, J=6.0, 3.2 Hz), 6.88-6.99 (2H, m), 7.15 (1H, t, J=9.2 Hz), 9.46 (1H, brs).

step 5) 3-cyclopropyl-3-(3-(((2-(3,3-dimethylbutyl)-2'-fluoro-5'-methoxybiphenyl-4-yl)oxy)methyl)phenyl)propanoic acid In the same manner as in Example 75, step 6, and Example 44, step 4, the title compound (156 mg) was obtained as a colorless oil.

$^1$H NMR (400 MHz, DMSO-$d_6$) δ 0.07-0.16 (1H, m), 0.21-0.36 (2H, m), 0.45-0.56 (1H, m), 0.69 (9H, s), 0.95-1.07 (1H, m), 1.19-1.26 (2H, m), 2.28-2.42 (3H, m), 2.57-2.72 (2H, m), 3.74 (3H, s), 5.10 (2H, s), 6.77 (1H, dd, J=6.0, 3.1 Hz), 6.87-6.99 (3H, m), 7.08 (1H, d, J=8.4 Hz), 7.18 (1H, t, J=9.1 Hz), 7.23 (1H, d, J=6.9 Hz), 7.26-7.35 (2H, m), 7.36 (1H, s).

MS (ESI-): [M-H]$^-$ 503.3

Example 94

3-cyclopropyl-3-(3-(((2'-fluoro-2-(1-fluoro-3,3-dimethylbutyl)-5'-methoxybiphenyl-4-yl)oxy)methyl)phenyl)propanoic acid step 1) 2'-fluoro-2-(1-fluoro-3,3-dimethylbutyl)-5'-methoxy-4-((4-methoxybenzyl)oxy)biphenyl To a solution of 1-(2'-fluoro-5'-methoxy-4-((4-methoxybenzyl)oxy)biphenyl-2-yl)-3,3-dimethylbutan-1-ol (220 mg) in toluene (5 mL) was added 4-(tert-butyl)-2,6-dimethylphenylsulfur trifluoride (188 mg) at 0° C., and the mixture was stirred at 0° C. for 20 min. To the reaction mixture was added saturated aqueous sodium hydrogen carbonate solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (180 mg) as a colorless oil.

$^1$H NMR (400 MHz, DMSO-$d_6$) δ 0.73 (9H, brs), 1.27-1.48 (2H, m), 3.73-3.79 (6H, m), 5.10 (2H, s), 5.32-5.59 (1H, m), 6.71-6.90 (1H, m), 6.94-7.08 (4H, m), 7.10-7.26 (3H, m), 7.41 (2H, d, J=8.2 Hz).

step 2) 2'-fluoro-2-(1-fluoro-3,3-dimethylbutyl)-5'-methoxybiphenyl-4-ol

To a solution of 2'-fluoro-2-(1-fluoro-3,3-dimethylbutyl)-5'-methoxy-4-((4-methoxybenzyl)oxy)biphenyl (120 mg) in methanol (5 mL) was added 10% palladium-carbon (100 mg) and, under a hydrogen atmosphere, the mixture was stirred at 70° C. for 17 hr. The reaction mixture was filtered, and the solvent of the filtrate was evaporated under reduced pressure to give a crude product of the title compound as a colorless oil. This compound was used for the next step without further purification.

step 3) ethyl 3-cyclopropyl-3-(3-(((2'-fluoro-2-(1-fluoro-3,3-dimethylbutyl)-5'-methoxybiphenyl-4-yl)oxy)methyl)phenyl)propanoate Using 2'-fluoro-2-(1-fluoro-3,3-dimethylbutyl)-5'-methoxybiphenyl-4-ol, and in the same manner as in Example 75, step 6, the title compound (54 mg) was obtained as a colorless oil.

$^1$H NMR (400 MHz, DMSO-d$_6$) δ 0.07-0.17 (1H, m), 0.19-0.28 (1H, m), 0.28-0.37 (1H, m), 0.46-0.57 (1H, m), 0.73 (9H, brs), 1.00-1.11 (4H, m), 1.26-1.49 (1H, m), 1.61-1.98 (1H, m), 2.32 (1H, q, J=8.0 Hz), 2.65-2.82 (2H, m), 3.75 (3H, s), 3.90-4.00 (2H, m), 5.09-5.21 (2H, m), 5.34-5.58 (1H, m), 6.69-6.90 (1H, m), 6.94-7.03 (1H, m), 7.04-7.09 (1H, m), 7.12-7.28 (4H, m), 7.29-7.36 (2H, m), 7.38 (1H, s).

step 4) 3-cyclopropyl-3-(3-(((2'-fluoro-2-(1-fluoro-3,3-dimethylbutyl)-5'-methoxybiphenyl-4-yl)oxy)methyl)phenyl)propanoic acid In the same manner as in Example 44, step 4, the title compound (46 mg) was obtained as a colorless oil.

$^1$H NMR (400 MHz, DMSO-d$_6$) δ 0.05-0.15 (1H, m), 0.21-0.36 (2H, m), 0.45-0.54 (1H, m), 0.73 (9H, brs), 0.95-1.06 (1H, m), 1.29-1.49 (1H, m), 1.62-1.87 (1H, m), 2.30-2.38 (1H, m), 2.59-2.71 (2H, m), 3.75 (3H, s), 5.15 (2H, s), 5.35-5.58 (1H, m), 6.70-6.92 (1H, m), 6.93-7.03 (1H, m), 7.07 (1H, d, J=8.5 Hz), 7.13-7.21 (2H, m), 7.21-7.28 (2H, m), 7.28-7.35 (2H, m), 7.38 (1H, s).

MS (ESI-): [M-H]$^-$521.4

Example 95

3-cyclopropyl-3-(3-(((2'-fluoro-2-(1-hydroxy-3,3-dimethylbutyl)-5"-methoxybiphenyl-4-yl)oxy)methyl)phenyl)propanoic acid step 1) 2-(2'-fluoro-4-hydroxy-5'-methoxybiphenyl-2-yl)-4,4-dimethylpentanenitrile To a solution of 1-(2'-fluoro-5'-methoxy-4-((4-methoxybenzyl)oxy)biphenyl-2-yl)-3,3-dimethylbutan-1-ol (160 mg) and tris(pentafluorophenyl)borane (20 mg) in acetonitrile (3 mL) was added trimethylsilyl cyanide (81 μL), and the mixture was stirred at room temperature for 1 hr. The reaction mixture was diluted with ethyl acetate. The diluted solution was washed with water and saturated brine, and dried over anhydrous sodium sulfate. The solvent was evaporated under reduced pressure, and the residue was purified by silica gel column chromatography (ethyl acetate/hexane) to give the title compound (97 mg) as a colorless oil.

$^1$H NMR (300 MHz, DMSO-d$_6$) δ 0.58 (9H, s), 3.70-3.79 (3H, m), 4.28-4.63 (1H, m), 5.16 (2H, s), 6.62-6.81 (1H, m), 6.90-7.03 (2H, m), 7.03-7.12 (2H, m), 7.13-7.27 (1H, m), 7.28-7.50 (5H, m).

step 2) 3-cyclopropyl-3-(3-(((2'-fluoro-2-(1-hydroxy-3,3-dimethylbutyl)-5'-methoxybiphenyl-4-yl)oxy)methyl)phenyl)propanoic acid In the same manner as in Example 75, step 6 and Example 44, step 4, the title compound (45 mg) was obtained as a colorless oil.

$^1$H NMR (400 MHz, DMSO-d$_6$) δ 0.05-0.16 (1H, m), 0.20-0.36 (2H, m), 0.44-0.54 (1H, m), 0.61 (9H, s), 0.94-1.06 (1H, m), 2.27-2.37 (1H, m), 2.57-2.71 (2H, m), 3.75 (3H, brs), 4.19-4.57 (1H, m), 5.04-5.17 (2H, m), 6.70-7.02 (3H, m), 7.02-7.08 (1H, m), 7.11-7.26 (3H, m), 7.26-7.38 (3H, m).

MS (ESI-): [M-H]$^-$505.4

Example 96

3-cyclopropyl-3-(3-(((2'-fluoro-5'-methoxy-2-(2,2,6,6-tetramethyltetrahydro-2H-pyran-4-yl)biphenyl-4-yl)oxy)methyl)phenyl)propanoic acid step 1) 4-((tert-butyl(dimethyl)silyl)oxy)-2'-fluoro-5'-methoxybiphenyl-2-yl trifluoromethanesulfonate To a solution of 2'-fluoro-4-hydroxy-5'-methoxybiphenyl-2-yl trifluoromethanesulfonate (2.85 g) and imidazole (800 mg) in DMF (50 mL) was added tert-butyldimethylchlorosilane (1.42 g), and the mixture was stirred at room temperature for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (2.99 g) as a colorless oil.

$^1$H NMR (400 MHz, DMSO-d$_6$) δ 0.26 (6H, s), 0.97 (9H, s), 3.77 (3H, s), 6.92-6.97 (1H, m), 7.00-7.06 (2H, m), 7.11 (1H, d, J=8.8 Hz), 7.25 (1H, t, J=9.3 Hz), 7.49 (1H, d, J=8.5 Hz).

step 2) 2'-fluoro-5'-methoxy-2-(2,2,6,6-tetramethyl-3,6-dihydro-2H-pyran-4-yl)biphenyl-4-ol To a mixture of 4-((tert-butyl(dimethyl)silyl)oxy)-2'-fluoro-5'-methoxybiphenyl-2-yl trifluoromethanesulfonate (405 mg), 2,2,6,6-tetramethyl-4-(4,4,5,5-tetramethyl-1,3,2-dioxaborolan-2-yl)-3,6-dihydro-2H-pyran (452 mg), palladium acetate (20 mg), dicyclohexyl(2',4',6'-triisopropylbiphenyl-2-yl)phosphine (83 mg), methanol (3 mL) and toluene (3 mL) was added potassium fluoride (151 mg) and, under microwave irradiation, the mixture was stirred at 100° C. for 20 min. The reaction mixture was diluted with ethyl acetate. The diluted solution was washed with water and saturated brine, and dried over anhydrous sodium sulfate. The solvent was evaporated under reduced pressure, and the residue was purified by silica gel column chromatography (ethyl acetate/hexane) to give the title compound (125 mg) as white crystals.

$^1$H NMR (400 MHz, DMSO-d$_6$) δ 0.98 (6H, s), 1.06 (6H, s), 1.95 (2H, s), 3.72 (3H, s), 5.29 (1H, s), 6.67 (1H, d, J=2.1 Hz), 6.71-6.78 (2H, m), 6.82-6.90 (1H, m), 7.04-7.12 (2H, m), 9.58 (1H, brs).

step 3) 2'-fluoro-5'-methoxy-2-(2,2,6,6-tetramethyltetrahydro-2H-pyran-4-yl)biphenyl-4-ol To a solution of 2'-fluoro-5'-methoxy-2-(2,2,6,6-tetramethyl-3,6-dihydro-2H-pyran-4-yl)biphenyl-4-ol (124 mg) in methanol (3 mL) was added 20% palladium hydroxide (28 mg) and, under a hydrogen atmosphere, the mixture was stirred at 60° C. for 3 hr. The reaction mixture was filtered, and the solvent of the filtrate was evaporated under reduced pressure to give a crude product of the title compound as a colorless oil. This compound was used for the next step without further purification.

step 4) 3-cyclopropyl-3-(3-(((2'-fluoro-5'-methoxy-2-(2,2,6,6-tetramethyltetrahydro-2H-pyran-4-yl)biphenyl-4-yl)oxy)methyl)phenyl)propanoic acid In the same manner as in Example 75, step 6 and Example 44, step 4, the title compound (133 mg) was obtained as a white amorphous solid.
$^1$H NMR (400 MHz, DMSO-d$_6$) δ 0.07-0.16 (1H, m), 0.21-0.36 (2H, m), 0.46-0.56 (1H, m), 0.86 (3H, s), 0.97 (3H, s), 0.99-1.08 (4H, m), 1.10 (3H, s), 1.29-1.46 (2H, m), 1.50 (2H, d, J=7.0 Hz), 2.33 (1H, q, J=8.2 Hz), 2.59-2.75 (2H, m), 2.93-3.06 (1H, m), 3.74 (3H, s), 5.12 (2H, s), 6.79 (1H, dd, J=5.6, 3.0 Hz), 6.90-7.03 (3H, m), 7.13 (1H, d, J=8.4 Hz), 7.17-7.27 (2H, m), 7.28-7.35 (2H, m), 7.38 (1H, s), 12.06 (1H, brs).
MS (ESI–): [M–H]$^-$ 559.4

Example 97

3-cyclopropyl-3-(3-(((2'-fluoro-5'-methoxy-2-((1-methylcyclopentyl)methyl)biphenyl-4-yl)oxy)methyl)phenyl)propanoic acid step 1) cyclopentyl(2'-fluoro-5'-methoxy-4-((4-methoxybenzyl)oxy)biphenyl-2-yl)methanol To a mixture of zinc chloride (34 mg), lithium chloride (117 mg) and THF (1 mL) was added a solution (1 M, 0.49 mL) of trimethylsilylmethylmagnesium chloride in diethyl ether, and the mixture was stirred at room temperature for 15 min. To the reaction mixture was added a solution (1 M, 2.7 mL) of cyclopentylmagnesium bromide in THF, and the mixture was stirred at room temperature for 45 min. To the reaction mixture was added a solution of 2'-fluoro-5'-methoxy-4-((4-methoxybenzyl)oxy)biphenyl-2-carbaldehyde (301 mg) obtained in Example 93, step 2, in THF (2 mL) at 0° C., and the mixture was stirred at 0° C. for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (40 mg) as a colorless oil.
$^1$H NMR (300 MHz, DMSO-d$_6$) δ 0.98-1.17 (1H, m), 1.18-1.46 (6H, m), 1.46-1.73 (1H, m), 1.81-2.13 (1H, m), 3.74 (3H, s), 3.76 (3H, s), 4.14-4.27 (1H, m), 4.96-5.04 (1H, m), 5.06 (2H, s), 6.70-7.01 (5H, m), 7.04 (1H, d, J=8.5 Hz), 7.12-7.23 (2H, m), 7.36-7.45 (2H, m).

step 2) cyclopentyl(2'-fluoro-5'-methoxy-4-((4-methoxybenzyl)oxy)biphenyl-2-yl)methanone In the same manner as in Example 93, step 2, the title compound (193 mg) was obtained as a colorless oil.
$^1$H NMR (400 MHz, DMSO-d$_6$) δ 1.40-1.57 (4H, m), 1.57-1.68 (4H, m), 3.23-3.29 (1H, m), 3.75 (3H, s), 3.76 (3H, s), 5.13 (2H, s), 6.76 (1H, dd, J=6.1, 3.1 Hz), 6.87-6.93 (1H, m), 6.94-7.00 (2H, m), 7.11 (1H, t, J=9.3 Hz), 7.19-7.25 (1H, m), 7.27 (1H, d, J=2.4 Hz), 7.31 (1H, d, J=8.4 Hz), 7.42 (2H, m).

step 3) (2'-fluoro-5'-methoxy-4-((4-methoxybenzyl)oxy)biphenyl-2-yl)(1-methylcyclopentyl)methanone To a solution of cyclopentyl(2'-fluoro-5'-methoxy-4-((4-methoxybenzyl)oxy)biphenyl-2-yl)methanone (178 mg) in THF (5 mL) was added a solution (1 M, 0.82 mL) of lithium bis(trimethylsilyl)amide in THF at 0° C., and the mixture was stirred at 0° C. for 10 min. To the reaction mixture was added iodomethane (0.26 mL), and the mixture was stirred at room temperature for 30 min. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (128 mg) as a colorless oil.
$^1$H NMR (400 MHz, DMSO-d$_6$) δ 0.99 (3H, s), 1.26-1.34 (2H, m), 1.39-1.61 (4H, m), 1.72-1.84 (2H, m), 3.72 (3H, s), 3.76 (3H, s) 5.12 (2H, s), 6.68 (1H, dd, J=6.1, 3.2 Hz), 6.87-6.93 (1H, m), 6.93-6.99 (3H, m), 7.10-7.19 (2H, m), 7.32 (1H, d, J=8.7 Hz), 7.40 (2H, d, J=8.4 Hz).

step 4) (2'-fluoro-5'-methoxy-4-((4-methoxybenzyl)oxy)biphenyl-2-yl)(1-methylcyclopentyl)methanol In the same manner as in Example 93, step 1, the title compound (105 mg) was obtained as a colorless oil.
$^1$H NMR (400 MHz, DMSO-d$_6$) δ 0.60 (3H, s), 0.73-0.83 (1H, m), 0.95-1.06 (1H, m), 1.06-1.17 (1H, m), 1.30-1.49 (4H, m), 1.57-1.76 (1H, m), 3.71-3.81 (6H, m), 4.32-4.66 (1H, m), 4.97-5.26 (3H, m), 6.72-7.08 (6H, m), 7.11-7.27 (2H, m), 7.39 (2H, d, J=8.5 Hz).

step 5) 2'-fluoro-2-(hydroxy(1-methylcyclopentyl)methyl)-5'-methoxybiphenyl-4-ol In the same manner as in Example 96, step 3, the title compound (72 mg) was obtained as white crystals.
$^1$H NMR (400 MHz, DMSO-d$_6$) δ 0.64 (3H, s), 0.75-0.87 (1H, m), 0.99-1.20 (2H, m), 1.30-1.54 (4H, m), 1.59-1.81 (1H, m), 3.73 (3H, s), 4.27-4.66 (1H, m), 4.89-5.23 (1H, m), 6.60-6.97 (4H, m), 7.00-7.23 (2H, m), 9.42 (1H, brs).

step 6) ethyl 3-cyclopropyl-3-(3-(((2'-fluoro-2-(hydroxy(1-methylcyclopentyl)methyl)-5'-methoxybiphenyl-4-yl)oxy)methyl)phenyl)propanoate In the same manner as in Example 74, step 3, the title compound (102 mg) was obtained as a colorless oil.
$^1$H NMR (400 MHz, DMSO-d$_6$) δ 0.05-0.16 (1H, m), 0.18-0.27 (1H, m), 0.27-0.38 (1H, m), 0.45-0.56 (1H, m), 0.59 (3H, s), 0.72-0.83 (1H, m), 0.95-1.14 (6H, m), 1.29-1.47 (4H, m), 1.59-1.75 (1H, m), 2.26-2.35 (1H, m), 2.68-2.80 (2H, m), 3.74 (3H, s), 3.88-4.02 (2H, m), 4.31-4.68 (1H, m), 5.00-5.29 (3H, m), 6.70-7.01 (3H, m), 7.05 (1H, d, J=7.7 Hz), 7.12-7.27 (3H, m), 7.27-7.38 (3H, m).

step 7) ethyl 3-(3-(((2-(chloro(1-methylcyclopentyl)methyl)-2'-fluoro-5'-methoxybiphenyl-4-yl)oxy)methyl)phenyl)-3-cyclopropylpropanoate To a solution of ethyl 3-cyclopropyl-3-(3-(((2'-fluoro-2-(hydroxy(1-methylcyclopentyl)methyl)-5'-methoxybiphenyl-4-yl)oxy)methyl)phenyl)propanoate (99 mg) in THF (3 mL) was added thionyl chloride (64 µL) and the mixture was stirred at 50° C. for 15 hr. The solvent was evaporated under reduced pressure, and the residue was purified by silica gel column chromatography (ethyl acetate/hexane) to give the title compound (95 mg) as a colorless oil.
$^1$H NMR (400 MHz, DMSO-d$_6$) δ 0.07-0.14 (1H, m), 0.18-0.27 (1H, m), 0.27-0.36 (1H, m), 0.46-0.56 (1H, m), 0.76-0.84 (3H, m), 0.84-0.89 (2H, m), 0.94-1.11 (5H, m), 1.12-1.21 (1H, m), 1.30-1.50 (4H, m), 2.26-2.36 (1H, m), 2.65-2.80 (2H, m), 3.75 (3H, s), 3.89-4.01 (2H, m), 4.78-5.03 (1H, m), 5.06-5.21 (2H, m), 6.66-6.83 (1H, m), 6.95-7.04 (1H, m), 7.05-7.13 (1H, m), 7.14-7.22 (2H, m), 7.22-7.39 (5H, m).

step 8) ethyl 3-cyclopropyl-3-(3-(((2'-fluoro-5'-methoxy-2-((1-methylcyclopentyl)methyl)biphenyl-4-yl)oxy)methyl)phenyl)propanoate To a solution of ethyl 3-(3-(((2-(chloro(1-methylcyclopentyl)methyl)-2'-fluoro-5'-methoxybiphenyl-4-yl)oxy)methyl)phenyl)-3-cyclopropylpropanoate (92 mg) and 2,2-azobisbutyronitrile (3 mg) in toluene (3 mL) was added tributyltin hydride (0.13 mL), and the mixture was stirred at 100° C. for 2 hr. The solvent was evaporated under reduced pressure, and the residue was purified by silica gel column chromatography (ethyl acetate/hexane) to give the title compound (32 mg) as a colorless oil.

$^1$H NMR (400 MHz, DMSO-$d_6$) δ 0.07-0.15 (1H, m), 0.19-0.27 (1H, m), 0.27-0.36 (1H, m), 0.46-0.56 (1H, m), 0.61 (3H, s), 1.00-1.10 (7H, m), 1.25-1.36 (4H, m), 1.47-1.62 (1H, m), 2.27-2.35 (1H, m), 2.40-2.48 (1H, m), 2.53-2.62 (1H, m), 2.65-2.80 (2H, m), 3.74 (3H, s), 3.88-4.01 (2H, m), 5.11 (2H, s), 6.75-6.80 (1H, m), 6.88-6.98 (3H, m), 7.09 (1H, d, J=8.4 Hz), 7.16 (1H, t, J=9.1 Hz), 7.24 (1H, d, J=6.0 Hz), 7.28-7.37 (3H, m).

step 9) 3-cyclopropyl-3-(3-(((2'-fluoro-5'-methoxy-2-((1-methylcyclopentyl)methyl)biphenyl-4-yl)oxy)methyl)phenyl)propanoic acid In the same manner as in Example 44, step 4, the title compound (21 mg) was obtained as a white amorphous solid.

$^1$H NMR (300 MHz, DMSO-$d_6$) δ 0.04-0.13 (1H, m), 0.20-0.34 (2H, m), 0.42-0.52 (1H, m), 0.62 (3H, s), 0.78-0.88 (2H, m), 0.91-1.11 (4H, m), 1.35-1.53 (3H, m), 2.30-2.39 (1H, m), 2.53-2.67 (4H, m), 3.74 (3H, s), 5.10 (2H, s), 6.78 (1H, dd, J=6.1, 3.1 Hz), 6.89-6.98 (3H, m), 7.07-7.24 (3H, m), 7.26-7.36 (3H, m).

MS (ESI-): [M-H]$^-$ 515.3

Example 98

3-cyclopropyl-3-(3-(((2-(3,3-dimethylbutan-2-yl)-2'-fluoro-5'-methoxybiphenyl-4-yl)oxy)methyl)phenyl)propanoic acid step 1) 1-(2'-fluoro-5'-methoxy-4-((4-methoxybenzyl)oxy)biphenyl-2-yl)-2,2-dimethylpropan-1-one Under a nitrogen atmosphere, to a solution of ethyl 2'-fluoro-5'-methoxy-4-((4-methoxybenzyl)oxy)biphenyl-2-carboxylate (524 mg) in THF (10 mL) was added a solution (1.6 M, 1.6 mL) of tert-butyllithium in pentane at -78° C., and the mixture was stirred at -78° C. for 30 min. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (268 mg) as a colorless oil.

$^1$H NMR (400 MHz, DMSO-$d_6$) δ 0.90 (9H, s), 3.71 (3H, s), 3.76 (3H, s), 5.11 (2H, s), 6.66 (1H, dd, J=6.1, 3.3 Hz), 6.89-6.99 (4H, m), 7.10-7.21 (2H, m), 7.32 (1H, d, J=8.4 Hz), 7.41 (2H, d, J=8.4 Hz).

step 2) 2-(2'-fluoro-5'-methoxy-4-((4-methoxybenzyl)oxy)biphenyl-2-yl)-3,3-dimethylbutan-2-ol Under a nitrogen atmosphere, to a solution of 1-(2'-fluoro-5'-methoxy-4-((4-methoxybenzyl)oxy)biphenyl-2-yl)-2,2-dimethylpropan-1-one (275 mg) in THF (5 mL) was added a solution (1.1 M, 1.7 mL) of methyllithium in diethyl ether at -78° C., and the mixture was stirred for 16 hr while allowing the temperature to gradually rise to room temperature. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (182 mg) as a colorless oil.

$^1$H NMR (400 MHz, DMSO-$d_6$) δ 0.70-0.82 (9H, m), 1.20-1.48 (3H, m), 3.67-3.73 (3H, m), 3.76 (3H, s), 4.05-4.68 (1H, m), 4.97-5.08 (2H, m), 6.60-7.33 (8H, m), 7.39 (2H, d, J=8.3 Hz).

step 3) 2-(3,3-dimethylbut-1-en-2-yl)-2'-fluoro-5'-methoxy-4-((4-methoxybenzyl)oxy)biphenyl To a solution of 2-(2'-fluoro-5'-methoxy-4-((4-methoxybenzyl)oxy)biphenyl-2-yl)-3,3-dimethylbutan-2-ol (182 mg) and triethylamine (0.12 mL) in toluene (5 mL) was added thionyl chloride (60 µL), and the mixture was stirred at room temperature for 1 hr. The solvent was evaporated under reduced pressure, and the residue was purified by silica gel column chromatography (ethyl acetate/hexane) to give the title compound (153 mg) as a colorless oil.

$^1$H NMR (400 MHz, DMSO-$d_6$) δ 0.80 (9H, s), 3.70 (3H, s), 3.76 (3H, s), 4.97 (1H, s), 5.06 (2H, s), 5.26 (1H, s), 6.72 (1H, d, J=2.5 Hz), 6.81 (1H, dd, J=6.1, 3.1 Hz), 6.83-6.89 (1H, m), 6.93-7.02 (3H, m), 7.09 (1H, t, J=9.2 Hz), 7.16 (1H, d, J=8.3 Hz), 7.40 (2H, d, J=8.5 Hz).

step 4) 2-(3,3-dimethylbutan-2-yl)-2'-fluoro-5'-methoxybiphenyl-4-ol

In the same manner as in Example 94, step 2, the title compound (110 mg) was obtained as a colorless oil.

$^1$H NMR (400 MHz, CDDl$_3$) δ 0.67-0.81 (9H, m), 1.22-1.29 (3H, m), 2.53-2.91 (1H, m), 3.74-3.83 (3H, m), 4.72 (1H, s), 6.59-6.77 (2H, m), 6.78-6.88 (2H, m), 6.94-7.12 (2H, m).

step 5) 3-cyclopropyl-3-(3-(((2-(3,3-dimethylbutan-2-yl)-2'-fluoro-5'-methoxybiphenyl-4-yl)oxy)methyl)phenyl)propanoic acid In the same manner as in Example 74, step 3 and Example 44, step 4, the title compound (156 mg) was obtained as a colorless oil.

$^1$H NMR (400 MHz, DMSO-$d_6$) δ 0.05-0.16 (1H, m), 0.20-0.36 (2H, m), 0.44-0.55 (1H, m), 0.57-0.75 (9H, m), 0.95-1.06 (1H, m), 1.19 (3H, d, J=7.0 Hz), 2.27-2.37 (1H, m), 2.54-2.81 (3H, m), 3.69-3.84 (3H, m), 5.03-5.20 (2H, m), 6.61-6.78 (1H, m), 6.87-6.99 (3H, m), 7.08 (1H, d, J=8.4 Hz), 7.11-7.26 (2H, m), 7.27-7.40 (3H, m), 12.03 (1H, brs).

MS (ESI-): [M-H]$^-$ 503.3

Example 99

3-(3-(((2-((1-cyanocyclohexyl)methyl)-2'-fluoro-5'-methoxybiphenyl-4-yl)oxy)methyl)phenyl)-3-cyclopropylpropanoic acid step 1) 2-(bromomethyl)-2'-fluoro-5'-methoxy-4-((4-methoxybenzyl)oxy)biphenyl To a solution of (2'-fluoro-5'-methoxy-4-((4-methoxybenzyl)oxy)biphenyl-2-yl)methanol (472 mg) and triphenylphosphine (675 mg) in toluene (10 mL) was added carbon tetrabromide (635 mg), and the mixture was stirred at room temperature for 1 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (434 mg) as a colorless oil.

$^1$H NMR (400 MHz, DMSO-$d_6$) δ 3.77 (6H, s), 4.48 (2H, brs), 5.07 (2H, s), 6.87-6.92 (1H, m), 6.94-7.02 (3H, m), 7.02-7.08 (1H, m), 7.15-7.29 (3H, m), 7.41 (2H, d, J=8.4 Hz).

step 2) 1-((2'-fluoro-5'-methoxy-4-((4-methoxybenzyl)oxy)biphenyl-2-yl)methyl)cyclohexanecarbonitrile Under a nitrogen atmosphere, to a solution of diisopropylamine (0.13 mL) in THF (7 mL) was added a solution (1.6 M, 0.58 mL) of butyllithium in hexane at 0° C., and the mixture was stirred at 0° C. for 10 min. The reaction mixture was cooled to −78° C., and cyclohexanecarbonitrile (0.12 mL) was added. The mixture was stirred at −78° C. for 1 hr, and a solution of ethyl 2'-fluoro-5'-methoxy-4-((4-methoxybenzyl)oxy)biphenyl-2-carboxylate (201 mg) in THF (3 mL) was added. The mixture was stirred at −78° C. for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (168 mg) as a colorless oil.

$^1$H NMR (400 MHz, DMSO-$d_6$) δ 0.89-1.09 (3H, m), 1.18-1.39 (3H, m), 1.47-1.58 (4H, m), 2.67-3.00 (2H, m), 3.74 (3H, s), 3.76 (3H, s), 5.07 (2H, s), 6.83 (1H, dd, J=5.9, 3.0 Hz), 6.92-7.05 (4H, m), 7.10-7.22 (3H, m), 7.40 (2H, d, J=8.4 Hz).

step 3) 1-((2'-fluoro-4-hydroxy-5'-methoxybiphenyl-2-yl)methyl)cyclohexanecarbonitrile In the same manner as in Example 94, step 2, the title compound (122 mg) was obtained as a colorless oil.

$^1$H NMR (400 MHz, DMSO-$d_6$) δ 0.89-1.10 (3H, m), 1.20-1.39 (3H, m), 1.45-1.62 (4H, m), 2.70-2.96 (2H, m), 3.69-3.78 (3H, m), 6.71-6.84 (2H, m), 6.88-6.97 (2H, m), 6.97-7.06 (1H, m), 7.10-7.21 (1H, m), 9.61 (1H, s).

step 4) 3-(3-(((2-((1-cyanocyclohexyl)methyl)-2'-fluoro-5'-methoxybiphenyl-4-yl)oxy)methyl)phenyl)-3-cyclopropylpropanoic acid In the same manner as in Example 74, step 3 and Example 44, step 4, the title compound (138 mg) was obtained as a colorless oil.

$^1$H NMR (400 MHz, DMSO-$d_6$) δ 0.06-0.16 (1H, m), 0.20-0.35 (2H, m), 0.44-0.56 (1H, m), 0.90-1.08 (4H, m), 1.20-1.38 (3H, m), 1.43-1.62 (4H, m), 2.26-2.39 (1H, m), 2.59-2.78 (3H, m), 2.79-3.01 (1H, m), 3.75 (3H, s), 5.12 (2H, s), 6.79-6.87 (1H, m), 6.91-6.99 (1H, m), 7.03 (1H, d, J=8.4 Hz), 7.12-7.22 (3H, m), 7.24 (1H, d, J=6.9 Hz), 7.27-7.39 (3H, m), 12.01 (1H, brs).

MS (ESI−): [M−H]$^-$540.4

Example 100

3-cyclopropyl-3-(3-(((2-((1-ethylcyclopentyl)methyl)-2'-fluoro-5'-methoxybiphenyl-4-yl)oxy)methyl)phenyl)propanoic acid In the same manner as in Example 97, the title compound (52 mg) was obtained as a colorless oil.

$^1$H NMR (400 MHz, DMSO-$d_6$) δ 0.05-0.14 (1H, m), 0.20-0.35 (2H, m), 0.44-0.59 (4H, m), 0.94-1.13 (5H, m), 1.13-1.23 (4H, m), 1.28-1.40 (2H, m), 2.27-2.36 (1H, m), 2.52-2.73 (4H, m), 3.74 (3H, s), 5.11 (2H, s), 6.79 (1H, dd, J=6.1, 3.2 Hz), 6.85-6.90 (1H, m), 6.90-6.98 (2H, m), 7.10 (1H, d, J=8.4 Hz), 7.16 (1H, t, J=9.1 Hz), 7.23 (1H, d, J=7.3 Hz), 7.26-7.33 (2H, m), 7.34 (1H, s), 12.06 (1H, brs).

MS (ESI−): [M−H]$^-$529.4

Example 101

3-(3-(((2-((1-cyanocyclopentyl)(fluoro)methyl)-2'-fluoro-5'-methoxybiphenyl-4-yl)oxy)methyl)phenyl)-3-cyclopropylpropanoic acid step 1) 1-((2'-fluoro-5'-methoxy-4-((4-methoxybenzyl)oxy)biphenyl-2-yl)(hydroxy)methyl)cyclopentanecarbonitrile In the same manner as in Example 99, step 2, the title compound (242 mg) was obtained as a colorless oil.

$^1$H NMR (400 MHz, DMSO-$d_6$) δ 1.04-1.21 (2H, m), 1.33-1.52 (3H, m), 1.53-1.66 (1H, m), 1.75-1.98 (2H, m), 3.71-3.86 (6H, m), 4.33-4.59 (1H, m), 5.00-5.16 (2H, m), 6.09 (1H, brs), 6.81-6.91 (1H, m), 6.92-7.10 (4H, m), 7.10-7.28 (2H, m), 7.37-7.60 (3H, m).

step 2) 1-(fluoro(2'-fluoro-5'-methoxy-4-((4-methoxybenzyl)oxy)biphenyl-2-yl)methyl)cyclopentanecarbonitrile In the same manner as in Example 94, step 1, the title compound (168 mg) was obtained as a colorless oil.

$^1$H NMR (400 MHz, DMSO-$d_6$) δ 1.09-1.22 (2H, m), 1.43-1.62 (3H, m), 1.62-1.75 (1H, m), 1.91-2.02 (1H, m), 2.02-2.15 (1H, m), 3.76 (3H, s), 3.77 (3H, s), 5.01-5.52 (3H, m), 6.77-6.93 (1H, m), 6.94-7.05 (3H, m), 7.15-7.30 (3H, m), 7.36-7.49 (3H, m).

step 3) 1-(fluoro(2'-fluoro-4-hydroxy-5'-methoxybiphenyl-2-yl)methyl)cyclopentanecarbonitrile In the same manner as in Example 96, step 3, the title compound (30 mg) was obtained as a colorless oil.

$^1$H NMR (400 MHz, DMSO-$d_6$) δ 1.09-1.27 (2H, m), 1.43-1.62 (3H, m), 1.62-1.74 (1H, m), 1.90-1.98 (1H, m), 2.03-2.15 (1H, m), 3.75 (3H, s), 5.05-5.49 (1H, m), 6.72-7.03 (3H, m), 7.11 (1H, d, J=8.3 Hz), 7.15-7.35 (2H, m), 9.98 (1H, brs).

step 4) 3-(3-(((2-((1-cyanocyclopentyl)(fluoro)methyl)-2'-fluoro-5'-methoxybiphenyl-4-yl)oxy)methyl)phenyl)-3-cyclopropylpropanoic acid In the same manner as in Example 74, step 3 and Example 44, step 4, the title compound (32 mg) was obtained as a colorless oil.

$^1$H NMR (400 MHz, DMSO-d$_6$) δ 0.05-0.17 (1H, m), 0.19-0.39 (2H, m), 0.42-0.58 (1H, m), 0.93-1.09 (1H, m), 1.11-1.24 (2H, m), 1.43-1.62 (3H, m), 1.62-1.74 (1H, m), 1.91-2.03 (1H, m), 2.03-2.16 (1H, m), 2.26-2.38 (1H, m), 2.58-2.75 (2H, m), 3.76 (3H, s), 5.07-5.52 (3H, m), 6.76-6.94 (1H, m), 6.95-7.06 (1H, m), 7.16-7.29 (4H, m), 7.30-7.53 (4H, m), 12.03 (1H, brs).

MS (ESI–): [M–H]$^-$544.4

Example 102

3-(3-(((2-((1-cyanocyclobutyl)methyl)-2'-fluoro-5'-methoxybiphenyl-4-yl)oxy)methyl)phenyl)-3-cyclopropylpropanoic acid step 1) 3-(2'-fluoro-5'-methoxy-4-((4-methoxybenzyl)oxy)biphenyl-2-yl)acrylonitrile Under a nitrogen atmosphere, to a mixture of sodium hydride (60%, 133 mg) and THF (20 mL) was added diethyl cyanomethylphosphonate (0.54 mL) at 0° C., and the mixture was stirred at 0° C. for 10 min. To the reaction mixture was added 2'-fluoro-5'-methoxy-4-((4-methoxybenzyl)oxy)biphenyl-2-carbaldehyde (1.03 g) obtained in Example 93, step 2, and the mixture was stirred at 50° C. for 30 min. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give a crude product of the title compound as a colorless oil. This compound was used for the next step without further purification.

step 2) 3-(2'-fluoro-4-hydroxy-5'-methoxybiphenyl-2-yl)propanenitrile

In the same manner as in Example 94, step 2, the title compound (518 mg) was obtained as white crystals.

$^1$H NMR (400 MHz, DMSO-d$_6$) δ 2.56-2.71 (4H, m), 3.75 (3H, s), 6.74 (1H, dd, J=8.2, 1.9 Hz), 6.77-6.85 (2H, m), 6.90-6.98 (1H, m), 7.02 (1H, d, J=8.3 Hz), 7.19 (1H, t, J=8.8 Hz), 9.61 (1H, s).

step 3) 3-(4-((tert-butyl(dimethyl)silyl)oxy)-2'-fluoro-5'-methoxybiphenyl-2-yl)propanenitrile In the same manner as in Example 96, step 1, the title compound (343 mg) was obtained as a colorless oil.

$^1$H NMR (300 MHz, DMSO-d$_6$) δ 0.24 (6H, s), 0.98 (9H, s), 2.58-2.76 (4H, m), 3.76 (3H, s), 6.79-6.86 (2H, m), 6.93-7.00 (2H, m), 7.11 (1H, d, J=8.3 Hz), 7.21 (1H, t, J=9.1 Hz).

step 4) 1-((4-((tert-butyl(dimethyl)silyl)oxy)-2'-fluoro-5'-methoxybiphenyl-2-yl)methyl)cyclobutanecarbonitrile To a solution of 3-(4-((tert-butyl(dimethyl)silyl)oxy)-2'-fluoro-5'-methoxybiphenyl-2-yl)propanenitrile (165 mg) and 1,3-dibromopropane (67 μL) in THF (4 mL) was added a solution (1 M, 1.1 mL) of lithium bis(trimethylsilyl)amide in THF at 0° C., and the mixture was stirred at 0° C. for 1 hr. To the reaction mixture was added saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (116 mg) as a colorless oil.

$^1$H NMR (400 MHz, DMSO-d$_6$) δ 0.23 (6H, s), 0.97 (9H, s), 1.58-1.75 (1H, m), 1.85-2.14 (3H, m), 2.16-2.36 (2H, m), 2.78-3.13 (2H, m), 3.75 (3H, s), 6.80-6.88 (2H, m), 6.92 (1H, d, J=2.0 Hz), 6.94-7.00 (1H, m), 7.13 (1H, d, J=8.4 Hz), 7.20 (1H, t, J=9.2 Hz)

step 5) 1-((2'-fluoro-4-hydroxy-5'-methoxybiphenyl-2-yl)methyl)cyclobutanecarbonitrile To a solution of 1-((4-((tert-butyl(dimethyl)silyl)oxy)-2'-fluoro-5'-methoxybiphenyl-2-yl)methyl)cyclobutanecarbonitrile (116 mg) in THF (5 mL) was added a solution (1 M, 0.54 mL) of tetrabutylammonium fluoride in THF, and the mixture was stirred at room temperature for 15 hr. To the reaction mixture was added saturated aqueous ammonium chloride solution, and the mixture was extracted with ethyl acetate. The extract was washed with water and saturated brine, and dried over anhydrous sodium sulfate. The solvent was evaporated under reduced pressure, and the residue was purified by silica gel column chromatography (ethyl acetate/hexane) to give the title compound (76 mg) as a colorless oil.

$^1$H NMR (400 MHz, DMSO-d$_6$) δ 1.59-1.75 (1H, m), 1.87-2.11 (3H, m), 2.19-2.36 (2H, m), 2.80-3.00 (2H, m), 3.75 (3H, s), 6.75 (1H, dd, J=8.4, 2.4 Hz), 6.81 (1H, dd, J=5.9, 3.3 Hz), 6.84 (1H, d, J=2.1 Hz), 6.91-6.97 (1H, m), 7.04 (1H, d, J=8.3 Hz), 7.18 (1H, t, J=9.1 Hz), 9.62 (1H, s).

step 6) 3-(3-(((2-((1-cyanocyclobutyl)methyl)-2'-fluoro-5'-methoxybiphenyl-4-yl)oxy)methyl)phenyl)-3-cyclopropylpropanoic acid In the same manner as in Example 74, step 3 and Example 44, step 4, the title compound (73 mg) was obtained as a white amorphous solid.

$^1$H NMR (400 MHz, DMSO-d$_6$) δ 0.06-0.17 (1H, m), 0.20-0.37 (2H, m), 0.45-0.56 (1H, m), 0.94-1.06 (1H, m), 1.59-1.74 (1H, m), 1.85-2.14 (3H, m), 2.16-2.28 (2H, m), 2.28-2.37 (1H, m), 2.59-2.75 (2H, m), 2.84-3.07 (2H, m), 3.75 (3H, s), 5.11 (2H, s), 6.84 (1H, dd, J=5.7, 3.1 Hz), 6.93-7.00 (1H, m), 7.00-7.08 (2H, m), 7.14-7.27 (3H, m), 7.27-7.39 (3H, m), 12.03 (1H, brs).

MS (ESI–): [M–H]$^-$512.3

Example 103

3-(3-(((2-((1-cyanocyclopropyl)methyl)-2'-fluoro-5'-methoxybiphenyl-4-yl)oxy)methyl)phenyl)-3-cyclopropylpropanoic acid In the same manner as in Example 100, the title compound (122 mg) was obtained as a white amorphous solid.

$^1$H NMR (400 MHz, DMSO-d$_6$) δ 0.08-0.17 (1H, m), 0.21-0.37 (2H, m), 0.45-0.57 (1H, m), 0.76-0.95 (2H, m), 0.97-1.07 (1H, m), 1.12-1.20 (2H, m), 2.33 (1H, q, J=8.0 Hz), 2.59-2.75 (4H, m), 3.76 (3H, s), 5.13 (2H, s), 6.82 (1H, dd, J=6.0, 3.2 Hz), 6.93-7.00 (1H, m), 7.05 (1H, dd, J=8.4, 2.4 Hz), 7.15-7.23 (3H, m), 7.23-7.29 (1H, m), 7.29-7.35 (2H, m), 7.39 (1H, s), 12.02 (1H, brs).

MS (ESI–): [M–H]$^-$498.3

Example 104

3-cyclopropyl-3-(3-((3-(2,2-dimethylpropyl)-4-(5-fluoro-2-methoxypyridin-4-yl)phenoxy)methyl)phenyl)propanoic acid step 1) 1-(2-(5-fluoro-2-methoxypyridin-4-yl)-5-((4-methoxybenzyl)oxy)phenyl)-2,2-dimethylpropan-1-one In the same manner as in Example 98, step 1, the title compound (128 mg) was obtained as a colorless oil.

$^1$H NMR (400 MHz, DMSO-$d_6$) δ 1.01 (9H, s), 3.76 (3H, s), 3.84 is (3H, s), 5.14 (2H, s), 6.60 (1H, d, J=5.1 Hz), 6.96 (2H, d, J=8.7 Hz), 7.04 (1H, d, J=2.5 Hz), 7.20 (1H, dd, J=8.7, 2.5 Hz), 7.35-7.44 (3H, m), 8.16 (1H, d, J=1.3 Hz).

step 2) 1-(2-(5-fluoro-2-methoxypyridin-4-yl)-5-((4-methoxybenzyl)oxy)phenyl)-2,2-dimethylpropan-1-ol To a solution of 1-(2-(5-fluoro-2-methoxypyridin-4-yl)-5-((4-methoxybenzyl)oxy)phenyl)-2,2-dimethylpropan-1-one (270 mg) in methanol (5 mL) was added sodium borohydride (50 mg), and the mixture was stirred at room temperature for 30 min. To the reaction mixture was added saturated aqueous ammonium chloride solution, and the mixture was extracted with ethyl acetate. The extract was washed with water and saturated brine, and dried over anhydrous sodium sulfate. The solvent was evaporated under reduced pressure, and the residue was purified by silica gel column chromatography (ethyl acetate/hexane) to give the title compound (255 mg) as a white amorphous solid.

$^1$H NMR (400 MHz, DMSO-$d_6$) δ 0.62 (9H, s), 3.76 (3H, s), 3.87 (3H, s), 4.09-4.58 (1H, m), 4.98-5.15 (2H, m), 5.15-5.35 (1H, m), 6.66-6.90 (1H, m), 6.90-7.04 (3H, m), 7.05-7.13 (1H, m), 7.13-7.22 (1H, m), 7.39 (2H, d, J=8.4 Hz), 8.10-8.30 (1H, m).

step 3) 4-(5-fluoro-2-methoxypyridin-4-yl)-3-(1-hydroxy-2,2-dimethylpropyl)phenol In the same manner as in Example 94, step 2, the title compound (157 mg) was obtained as white crystals.

$^1$H NMR (400 MHz, DMSO-$d_6$) δ 0.64 (9H, s), 3.86 (3H, s), 4.08-4.57 (1H, m), 5.18 (1H, brs), 6.62-6.87 (2H, m), 6.95 (1H, d, =8.3 Hz), 7.05 (1H, s), 8.18 (1H, brs), 9.59 (1H, s).

step 4) 3-(1-chloro-2,2-dimethylpropyl)-4-(5-fluoro-2-methoxypyridin-4-yl)phenol In the same manner as in Example 97, step 7, the title compound (71 mg) was obtained as a colorless oil.

$^1$H NMR (400 MHz, DMSO-$d_6$) δ 0.74-0.92 (9H, m), 3.87 (3H, s), 4.53-4.93 (1H, m), 6.54-6.78 (1H, m), 6.79-6.90 (1H, m), 7.02-7.16 (2H, m), 8.14-8.33 (1H, m), 9.88 (1H, s).

step 5) 3-(2,2-dimethylpropyl)-4-(5-fluoro-2-methoxypyridin-4-yl)phenol

In the same manner as in Example 97, step 8, the title compound (30 mg) was obtained as a colorless oil.

$^1$H NMR (400 MHz, DMSO-$d_6$) δ 0.66 (9H, s), 2.37-2.46 (2H, m), 3.85 (3H, s), 6.65-6.77 (3H, m), 7.00 (1H, d, J=8.2 Hz), 8.16 (1H, s), 9.60 (1H, s).

step 6) 3-cyclopropyl-3-(3-((3-(2,2-dimethylpropyl)-4-(5-fluoro-2-methoxypyridin-4-yl)phenoxy)methyl)phenyl)propanoic acid In the same manner as in Example 74, step 3 and Example 44, step 4, the title compound (29 mg) was obtained as a white amorphous solid.

$^1$H NMR (400 MHz, DMSO-$d_6$) δ 0.01-0.07 (1H, m), 0.19-0.29 (2H, m), 0.38-0.46 (1H, m), 0.63 (9H, s), 0.88-0.99 (1H, m), 2.30-2.48 (5H, m), 3.21-3.48 (1H, m), 3.86 (3H, s), 5.10 (2H, s), 6.76 (1H, d, J=5.1 Hz), 6.92 (1H, d, J=2.6 Hz), 7.00 (1H, dd, J=8.5, 2.6 Hz), 7.14 (1H, d, J=8.5 Hz), 7.17-7.29 (3H, m), 7.31 (1H, s), 8.18 (1H, d, J=1.1 Hz).

MS (ESI-): [M-H]$^-$490.3

Example 105

3-cyclopropyl-3-(3-(((2-(2,2-dimethylpentyl)-2'-fluoro-5'-methoxybiphenyl-4-yl)oxy)methyl)phenyl)propanoic acid step 1) 1-(2'-fluoro-5'-methoxy-4-((4-methoxybenzyl)oxy)-[1,1'-biphenyl]-2-yl)-2-methylpropan-1-ol Under a nitrogen atmosphere, to a solution of zinc chloride (35.9 mg) and lithium chloride (61.4 mg) in THF (976 μL) was added a 1 mol/L solution (527 μL) of trimethylsilylmethylmagnesium chloride in THF at room temperature, and the mixture was stirred for 15 min. To the reaction mixture was added a 1 mol/L solution (1449 μL) of isopropylmagnesium bromide in THF at room temperature, and the mixture was stirred for 45 min. Furthermore, to the reaction mixture was added dropwise a solution of 2'-fluoro-5'-methoxy-4-((4-methoxybenzyl)oxy)-[1,1'-biphenyl]-2-carbaldehyde (160.9 mg) in THF (1952 μL) at 0° C., and the mixture was stirred for 1 hr. To the reaction mixture was added, at 0° C., saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (112 mg) as a colorless oil.

MS (ESI+), found: 393.0 step 2) 1-(2'-fluoro-5'-methoxy-4-((4-methoxybenzyl)oxy)-[1,1'-biphenyl]-2-yl)-2-methylpropan-1-one Under a nitrogen atmosphere, to a solution of 1-(2'-fluoro-5'-methoxy-4-((4-methoxybenzyl)oxy)-[1,1'-biphenyl]-2-yl)-2-methylpropan-1-ol (256.9 mg) in DMSO (4.2 mL) were added triethylamine (523 μL) and sulfur trioxide pyridine complex (299 mg) at room temperature, and the mixture was stirred for 24 hr. To the reaction mixture was added 0.5N hydrochloric acid, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (217 mg) as a pale-yellow oil.

MS (ESI+): [M+H]$^+$409.4 step 3) 1-(2'-fluoro-5'-methoxy-4-((4-methoxybenzyl)oxy)-[1,1'-biphenyl]-2-yl)-2,2-dimethylpentan-1-one Under a nitrogen atmosphere, to a solution of 1-(2'-fluoro-5'-methoxy-4-((4-methoxybenzyl)oxy)-[1,1'-biphenyl]-2- yl)-2-methylpropan-1-one (128.6 mg) in THF (1574 µL) was added a solution (409 µL) of lithium bis(trimethylsilyl)amide in THF at 0° C., and the mixture was stirred for 10 min. To the reaction mixture was added 1-iodopropane (61.4 µL), and the mixture was stirred at room temperature for 2.5 hr. To the reaction mixture was added, at 0° C., saturated aqueous ammonium chloride solution, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (65.9 mg) as a pale-yellow oil.

MS (ESI+): [M+H]$^+$451.4 step 4) 2-(2,2-dimethylpentyl)-2'-fluoro-5'-methoxy-[1,1'-biphenyl]-4-ol 1-(2'-Fluoro-5'-methoxy-4-((4-methoxybenzyl)oxy)-[1,1'-biphenyl]-2-yl)-2,2-dimethylpentan-1-one (43.3 mg) was dissolved in a mixed solution of THF (10 mL) and acetic acid (2 mL), and the reaction was performed in H-Cube having a 20% palladium hydroxide/carbon cartridge (70 mm) at 60° C., 40 atm, flow rate 1 ml/min for 17 hr. The solvent was evaporated under reduced pressure to give the title, compound. This compound was used for the next step without purification.

MS (ESI+): [M+H]$^+$317.0 step 5) 3-cyclopropyl-3-(3-(((2-(2,2-dimethylpentyl)-2'-fluoro-5'-methoxybiphenyl-4-yl)oxy)methyl)phenyl)propanoic acid By a method similar to that in Example 74, step 3 and Example 44, step 4, the title compound was obtained.
MS (ESI+), found: 536.6

Example 106

3-cyclopropyl-3-(3-(((2-(2,2-dimethylbutyl)-2'-fluoro-5'-methoxybiphenyl-4-yl)oxy)methyl)phenyl)propanoic acid By a method similar to that in Example 105, the title compound was obtained.
MS (ESI+), found: 522.6

Example 107

3-cyclopropyl-3-(3-(((2'-fluoro-2-(1-fluoro-2,2-dimethylbutyl)-5'-methoxybiphenyl-4-yl)oxy)methyl)phenyl)propanoic acid step 1) 1-(2'-fluoro-5'-methoxy-4-((4-methoxybenzyl)oxy)-[1,1'-biphenyl]-2-yl)-2,2-dimethylbutan-1-ol Under a nitrogen atmosphere, to a suspension of lithium aluminum hydride (28.2 mg) in THF (5.7 mL) was added dropwise a solution of 1-(2'-fluoro-5'-methoxy-4-((4-methoxybenzyl)oxy)-[1,1'-biphenyl]-2-yl)-2,2-dimethylbutan-1-one (162.2 mg) in THF (1.9 mL) at 0° C., and the mixture was stirred for 10 min. To the reaction mixture was added a small portion of sodium sulfate decahydrate at 0° C., and the mixture was filtered. The solvent was evaporated under reduced pressure, and the residue was purified by silica gel column chromatography (ethyl acetate/hexane) to give the title compound (155 mg) as a colorless oil.

MS (ESI+), found: 421.2 step 2) 2'-fluoro-2-(1-fluoro-2,2-dimethylbutyl)-5'-methoxy-4-((4-methoxybenzyl)oxy)-1,1'-biphenyl By a method similar to that in Example 94, step 1, the title compound was obtained.
MS (ESI+): [M+K]$^+$479.2 step 3) 2'-fluoro-2-(1-fluoro-2,2-dimethylbutyl)-5'-methoxy-[1,1'-biphenyl]-4-ol By a method similar to that in Example 75, step 5, the title compound was obtained.
MS (ESI+), found: 301.1 step 4) 3-cyclopropyl-3-(3-(((2'-fluoro-2-(1-fluoro-2,2-dimethylbutyl)-5'-methoxybiphenyl-4-yl)oxy)methyl)phenyl)propanoic acid By a method similar to that in Example 74, step 3 and Example 44, step 4, the title compound was obtained.
MS (ESI+), found: 540.6

Example 108

3-cyclopropyl-3-(3-(((2'-fluoro-2-(1-hydroxy-2,2-dimethylbutyl)-5'-methoxybiphenyl-4-yl)oxy)methyl)phenyl)propanoic acid By a method similar to that in Example 74, step 3 and Example 44, step 4, the title compound was obtained.
MS (ESI+), found: 538.6

Example 109

3-cyclopropyl-3-(3-(((2'-fluoro-5'-methoxy-2-(1-methoxy-2,2-dimethylbutyl)biphenyl-4-yl)oxy)methyl)phenyl)propanoic acid step 1) 2'-fluoro-5'-methoxy-2-(1-methoxy-2,2-dimethylbutyl)-4-((4-methoxybenzyl)oxy)-1,1'-biphenyl Under a nitrogen atmosphere, to a solution of 1-(2'-fluoro-5'-methoxy-4-((4-methoxybenzyl)oxy)-[1,1'-biphenyl]-2-yl)-2,2-dimethylbutan-1-ol (53.8 mg) in DMF (1227 µL) were added 60% sodium hydroxide (9.8 mg) and iodomethane (15.3 µL) at 0° C., and the mixture was stirred for 5 hr. To the reaction mixture was added ice water, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (42.1 mg) as a transparent gummy substance.

MS (ESI+), found: 421.0 step 2) 2'-fluoro-5'-methoxy-2-(1-methoxy-2,2-dimethylbutyl)-[1,1'-biphenyl]-4-ol By a method similar to that in Example 75, step 5, the title compound was obtained.
MS (ESI+), found: 301.1 step 3) 3-cyclopropyl-3-(3-(((2'-fluoro-2-(1-hydroxy-2,2-dimethylbutyl)-5'-methoxybiphenyl-4-yl)oxy)methyl)phenyl)propanoic acid By a method similar to that in Example 74, step 3 and Example 44, step 4, the title compound was obtained.
MS (ESI+), found: 552.7

Example 110

3-cyclopropyl-3-(3-(((2'-fluoro-5'-methoxy-2-(1-(2-methoxyethoxy)-2,2-dimethylbutyl)biphenyl-4-yl)oxy)methyl)phenyl)propanoic acid step 1) 2'-fluoro-5'-methoxy-4-((4-methoxybenzyl)oxy)-2-(1-(2-methoxyethoxy)-2,2-dimethylbutyl)-1,1'-biphenyl By a method similar to that in Example 109, step 1, the title compound was obtained.
MS (ESI+), found: 421.0 step 2) 2'-fluoro-5'-methoxy-2-(1-(2-methoxyethoxy)-2,2-dimethylbutyl)-[1,1'-biphenyl]-4-ol By a method similar to that in Example 75, step 5, the title compound was obtained.
MS (ESI+), found: 375.2 step 3) 3-cyclopropyl-3-(3-(((2'-fluoro-5'-methoxy-2-(1-(2-methoxyethoxy)-2,2-dimethylbutyl)biphenyl-4-yl)oxy)methyl)phenyl)propanoic acid By a method similar to that in Example 74, step 3 and Example 44, step 4, the title compound was obtained.
MS (ESI+), found: 596.7

Example 111

3-cyclopropyl-3-(3-(((2-(2,2-diethylbutyl)-2'-fluoro-5'-methoxybiphenyl-4-yl)oxy)methyl)phenyl)propanoic acid step 1) 2,2-diethyl-1-(2'-fluoro-5'-methoxy-4-((4-methoxybenzyl)oxy)-[1,1'-biphenyl]-2-yl)butan-1-one By a method similar to that in Example 105, steps 1-3, the title compound was obtained.
MS (ESI+): [M+H]+465.1 step 2) 2,2-diethyl-1-(2'-fluoro-5'-methoxy-4-((4-methoxybenzyl)oxy)-[1,1'-biphenyl]-2-yl)butan-1-ol By a method similar to that in Example 107, step 1, the title compound was obtained.
MS (ESI+), found: 449.5 step 3) 2-(2,2-diethylbutyl)-2'-fluoro-5'-methoxy-[1,1'-biphenyl]-4-ol

By a method similar to that in Example 105, step 4, the title compound was obtained.
MS (ESI+), found: 329.2 step 4) 3-cyclopropyl-3-(3-(((2-(2,2-diethylbutyl)-2'-fluoro-5'-methoxybiphenyl-4-yl)oxy)methyl)phenyl)propanoic acid By a method similar to that in Example 74, step 3 and Example 44, step 4, the title compound was obtained.
MS (ESI+), found: 550.6

Example 112

3-cyclopropyl-3-(3-(((2-(2-ethyl-2-methylbutyl)-2'-fluoro-5'-methoxybiphenyl-4-yl)oxy)methyl)phenyl)propanoic acid By a method similar to that in Example 111, the title compound was obtained.
MS (ESI+), found: 536.6

Example 113

3-cyclopropyl-3-(3-(((2-(4,4-dimethylpentyl)-2'-fluoro-5'-methoxy-[1,1'-biphenyl]-4-yl)oxy)methyl)phenyl)propanoic acid step 1) 1-(2'-fluoro-5'-methoxy-4-((4-methoxybenzyl)oxy)-[1,1'-biphenyl]-2-yl)-4,4-dimethylpentan-1-ol A solution of (3,3-dimethylbutyl)magnesium chloride in THF (0.50 M, 13.1 mL) was added to a solution of 2'-fluoro-5'-methoxy-4-((4-methoxybenzyl)oxy)-[1,1'-biphenyl]-2-carbaldehyde (800 mg) in THF (15 mL) at 0° C., and the mixture was stirred at 0° C. for 50 min. To the reaction mixture was added saturated aqueous ammonium chloride solution at 0° C., and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (788 mg) as a pale-yellow oil.
MS (ESI+): [M+H-H20]+435.2 step 2) 2-(4,4-dimethylpentyl)-2'-fluoro-5'-methoxy-[1,1'-biphenyl]-4-ol

A solution (8.7 mL) of 1-(2'-fluoro-5'-methoxy-4-((4-methoxybenzyl)oxy)-[1,1'-biphenyl]-2-yl)-4,4-dimethylpentan-1-ol (394 mg) and 10% palladium-carbon (168 mg) in methanol was stirred under a hydrogen balloon atmosphere at room temperature for 9 hr. The reaction mixture was filtered, and the solvent was evaporated under reduced pressure. The residue was purified by silica gel column chromatography (ethyl acetate/hexane) to give the title compound (256 mg) as a colorless oil.
$^1$H-NMR (400 MHz, DMSO-$d_6$): δ 0.74 (9H, s), 0.91-1.03 (2H, m), 1.25-1.36 (2H, m), 2.33 (2H, t, J=7.7 Hz), 3.74 (3H, s), 6.65 (1H, dd, J=8.2, 2.2 Hz), 6.68-6.76 (2H, m), 6.88-6.98 (2H, m), 7.15 (1H, t, J=9.1 Hz), 9.50 (1H, brs).

step 3) ethyl 3-cyclopropyl-3-(3-(((2'-fluoro-5'-methoxy-2-((neopentyloxy)methyl)-[1,1'-biphenyl]-4-yl)oxy)methyl)phenyl)propanoate In the same manner as in Example 75, step 6, the title compound (341 mg) was obtained as a colorless oil.

$^1$H-NMR (400 MHz, DMSO-d$_6$): δ 0.11 (1H, dq, J=9.1, 4.6 Hz), 0.23 (1H, dq, J=9.2, 4.6 Hz), 0.32 (1H, tt, J=8.6, 4.5 Hz), 0.46-0.56 (1H, m), 0.81 (9H, s), 1.06 (3H, t, J=7.1 Hz+1H, m), 2.28-2.34 (1H, m), 2.66-2.80 (2H, m), 2.95 (2H, s), 3.75 (3H, s), 3.94 (2H, dtt, J=10.7, 7.1, 3.7 Hz), 4.28 (2H, s), 5.12 (2H, s), 6.81 (1H, dd, J=6.0, 3.1 Hz), 6.90-6.98 (1H, m), 7.02 (1H, dd, J=8.5, 2.4 Hz), 7.12-7.21 (3H, m), 7.22-7.34 (3H, m), 7.35 (1H, s).

step 4) 3-cyclopropyl-3-(3-(((2-(4,4-dimethylpentyl)-2'-fluoro-5'-methoxy-[1,1'-biphenyl]-4-yl)oxy)methyl)phenyl)propanoic acid In the same manner as in Example 44, step 4, the title compound (300 mg) was obtained as a colorless oil.
MS (ESI+): [M+H]$^+$ 519.3

Example 114

3-cyclopropyl-3-(3-(((2'-fluoro-5'-methoxy-2-((neopentyloxy)methyl)-[1,1'-biphenyl]-4-yl)oxy)methyl)phenyl)propanoic acid step 1) 2'-fluoro-5'-methoxy-4-((4-methoxybenzyl)oxy)-2-((neopentyloxy)methyl)-1,1'-biphenyl Methanesulfonyl chloride (0.164 mL) was added to a solution of (2'-fluoro-5'-methoxy-4-((4-methoxybenzyl)oxy)-[1,1'-biphenyl]-2-yl)methanol (390 mg) in THF (10 mL) at 0° C., and the mixture was stirred at 0° C. for 20 min. Water was added to the reaction mixture, and the mixture was extracted with ethyl acetate. The extract was washed with saturated brine, and dried over anhydrous magnesium sulfate. The solvent was evaporated under reduced pressure to give (2'-fluoro-5'-methoxy-4-((4-methoxybenzyl)oxy)-[1,1'-biphenyl]-2-yl)methyl methanesulfonate. To solution (10 mL) of the obtained compound and TBAI (117 mg) in DMF was added sodium hydride (60%, 85 mg) at 0° C., and the mixture was stirred at 0° C. for 5 min, then at 80° C. for 5 hr. Water was added to the reaction mixture, and the mixture was extracted with ethyl acetate. The extract was washed with saturated brine, and dried over anhydrous sodium sulfate. The solvent was evaporated under reduced pressure, and the residue was purified by silica gel column chromatography (ethyl acetate/hexane) to give the title compound (326 mg) as a colorless oil.

$^1$H-NMR (400 MHz, DMSO-d$_6$): δ 0.81 (9H, s), 2.94 (2H, s), 3.74 (3H, s), 3.76 (3H, s), 4.27 (2H, s), 5.08 (2H, s), 6.81 (1H, dd, J=5.9, 3.1 Hz), 6.92-7.02 (4H, m), 7.11-7.21 (3H, m), 7.39 (2H, d, J=8.4 Hz).

step 2) 2'-fluoro-5'-methoxy-2-((neopentyloxy)methyl)-[1,1'-biphenyl]-4-ol

In the same manner as in Example 75, step 5, the title compound (160 mg) was obtained as a colorless oil.

$^1$H-NMR (300 MHz, DMSO-d$_6$): δ 0.83 (9H, s), 2.96 (2H, s), 3.74 (3H, s), 4.23 (2H, s), 6.67-6.83 (2H, m), 6.84-6.99 (2H, m), 7.03 (1H, d, J=8.2 Hz), 7.16 (1H, t, J=9.2 Hz), 9.59 (1H, brs).

step 3) ethyl 3-cyclopropyl-3-(3-(((2'-fluoro-5'-methoxy-2-((neopentyloxy)methyl)-[1,1'-biphenyl]-4-yl)oxy)methyl)phenyl)propanoate In the same manner as in Example 75, step 6, the title compound (341 mg) was obtained as a colorless oil.

$^1$H-NMR (400 MHz, DMSO-d$_6$): δ 0.11 (1H, dq, J=9.1, 4.6 Hz), 0.23 (1H, dq, J=9.2, 4.6 Hz), 0.32 (1H, tt, J=8.6, 4.5 Hz), 0.46-0.56 (1H, m), 0.81 (9H, s), 1.06 (3H, t, J=7.1 Hz+1H, m), 2.28-2.34 (1H, m), 2.66-2.80 (2H, m), 2.95 (2H, s), 3.75 (3H, s), 3.94 (2H, dtt, J=10.7, 7.1, 3.7 Hz), 4.28 (2H, s), 5.12 (2H, s), 6.81 (1H, dd, J=6.0, 3.1 Hz), 6.90-6.98 (1H, m), 7.02 (1H, dd, J=8.5, 2.4 Hz), 7.12-7.21 (3H, m), 7.22-7.34 (3H, m), 7.35 (1H, s).

step 4) 3-cyclopropyl-3-(3-(((2'-fluoro-5'-methoxy-2-((neopentyloxy)methyl)-[1,1'-biphenyl]-4-yl)oxy)methyl)phenyl)propanoic acid In the same manner as in Example 44, step 4, the title compound (312 mg) was obtained as a colorless oil.

$^1$H-NMR (400 MHz, DMSO-d$_6$): δ 0.07-0.15 (1H, m), 0.21-0.34 (2H, m), 0.46-0.53 (1H, m), 0.81 (9H, s), 0.96-1.04 (1H, m), 2.33 (1H, q, J=7.9 Hz), 2.59-2.70 (2H, m), 2.95 (2H, s), 3.75 (3H, s), 4.29 (2H, s), 5.12 (2H, s), 6.82 (1H, dd, J=6.1, 3.2 Hz), 6.91-6.97 (1H, m), 7.02 (1H, dd, J=8.5, 2.3 Hz), 7.14-7.25 (4H, m), 7.27-7.37 (3H, m).

The structural formulas of the compounds obtained in Examples 1-114 are shown in the following Tables 1-16.

TABLE 1

| Ex. No. | compound name | structural formula | salt | MS |
|---|---|---|---|---|
| 1 | (3-(((6-(2,2-dimethylpropyl)-5-(2-fluoro-5-methoxyphenyl)pyridin-2-yl)oxy)methyl)phenoxy)acetic acid | | — | 454.1 |

TABLE 1-continued

| Ex. No. | compound name | structural formula | salt | MS |
|---|---|---|---|---|
| 2 | (3-(((2-(2,2-dimethylpropyl)-2'-fluoro-5'-methoxybiphenyl-4-yl)oxy)methyl)phenoxy)acetic acid | | — | 453.2 |
| 3 | 3-cyclopropyl-3-(3-(((2-(2,2-dimethylpropyl)-2'-fluoro-5'-methoxybiphenyl-4-yl)oxy)-methyl)phenyl)propanoic acid | | — | ND |

1H NMR (300 MHz, CDCl$_3$) δ 0.05-0.15 (1H, m), 0.20-0.36 (2H, m), 0.46-0.54 (1H, m), 0.63 (9H, s), 0.95-1.08 (1H, m), 2.27-2.36 (1H, m), 2.59-2.73 (2H, m), 3.74 (3H, s), 5.11 (2H, s), 6.77 (1H, dd, J = 6.0, 3.0 Hz), 6.85-7.00 (3H, m), 7.08-7.37 (6H, m), 12.06 (1H, brs), 2H were hidden by the residue of DMSO.

| Ex. No. | compound name | structural formula | salt | MS |
|---|---|---|---|---|
| 4 | 3-cyclopropyl-3-(3-(((6-(2,2-dimethylpropyl)-5-(2-fluoro-5-methoxyphenyl)pyridin-2-yl)oxy)methyl)phenyl)propanoic acid | | — | 492.3 |
| 5 | sodium 3-cyclopropyl-3-(3-(((2-(2,2-dimethylpropyl)-2'-fluoro-5'-methoxybiphenyl-4-yl)oxy)methyl) phenyl)-propanoate | | Na+ | ND |

1H NMR (300 MHz, DMSO-d$_6$) δ 0.01-0.07 (1H, m), 0.18-0.29 (2H, m), 0.34-0.44 (1H, m), 0.63 (9H, s), 0.85-1.01 (1H, m), 2.16-2.48 (5H, m), 3.74 (3H, s), 5.09 (2H, s), 6.77 (1H, dd, J = 6.0, 3.0 Hz), 6.87-6.99 (3H, m), 7.08-7.27 (5H, m), 7.30 (1H, s).

TABLE 2

| Ex. No. | compound name | structural formula | salt | MS |
|---|---|---|---|---|
| 6 | sodium 3-cyclopropyl-3-(3-(((6-(2,2-dimethylpropyl)-5-(2-fluoro-5-methoxyphenyl)pyridin-2-yl)oxy)methyl)phenyl)-propanoate | | Na+ | 492.3 |
| 7 | 3-(3-(((2-(2,2-dimethylpropyl)-2'-fluoro-5'-methoxybiphenyl-4-yl)oxy)methyl)phenyl)propanoic acid | | — | ND |

1H NMR (300 MHz, DMSO-d$_6$) δ 0.63 (9H, s), 2.44 (2H, brs), 2.53-2.57 (2H, m), 2.80-2.87 (2H, m), 3.74 (3H, s), 5.10 (2H, s), 6.77 (1H, dd, J = 6.0, 3.4 Hz), 6.86-6.97 (3H, m), 7.07-7.21 (3H, m), 7.28-7.34 (3H, m), 12.17 (1H, brs).

| Ex. No. | compound name | structural formula | salt | MS |
|---|---|---|---|---|
| 8 | 3-cyclopropyl-3-(3-(((2-(2,2-dimethylpropyl)-2'-fluoro-5'-methoxybiphenyl-4-yl)amino)methyl)phenyl)-propanoic acid | | — | 490.3 |
| 9 | 3-cyclopropyl-3-(3-(((2-(2,2-dimethylpropyl)-2'-fluoro-5'-methoxybiphenyl-4-yl)-(methyl)amino)methyl)phenyl)-propanoic acid | | — | 504.3 |
| 10 | 3-(3-((acetyl(2-(2,2-dimethylpropyl)-2'-fluoro-5'-methoxybiphenyl-4-yl)amino)methyl)phenyl)-3-cyclopropylpropanoic acid | | — | 532.3 |

TABLE 2-continued

| Ex. No. | compound name | structural formula | salt | MS |
|---|---|---|---|---|
| 11 | 3-cyclopropyl-3-(3-(((2-(2,2-dimethylpropyl)-2'-fluoro-5'-methoxybiphenyl-4-yl)(2,2,2-trifluoroethyl)amino)methyl)phenyl)propanoic acid | | — | 572.4 |

TABLE 3

| Ex. No. | compound name | structural formula | salt | MS |
|---|---|---|---|---|
| 12 | 3-cyclopropyl-3-(3-(((2-(2,2-dimethylpropyl)-2'-fluoro-5'-methoxybiphenyl-4-yl)sulfanyl)methyl)phenyl)-propanoic acid | | — | 505.3 |
| 13 | 3-cyclopropyl-3-(3-(((2-(2,2-dimethylpropyl)-2'-fluoro-5'-methoxybiphenyl-4-yl)sulfonyl)methyl)phenyl)-propanoic acid | | — | 537.2 |
| 14 | 3-cyclopropyl-3-(3-(((3-(3,3-dimethylbutyl)-2'-fluoro-5'-methoxybiphenyl-4-yl)oxy)methyl)phenyl)propanoic acid | | — | NT |

1H NMR (400 MHz, DMSO-$d_6$) δ 0.06-0.14 (1H, m), 0.21-0.35 (2H, m), 0.46-0.55 (1H, m), 0.91 (9H, s), 0.96-1.08 (1H, m), 1.41-1.49 (2H, m), 2.29-2.38 (1H, m), 2.58-2.73 (4H, m), 3.79 (3H, s), 5.14 (2H, s), 6.89 (1H, dt, J = 8.9, 3.5 Hz), 6.98 (1H, dd, J = 6.5, 3.2 Hz), 7.11-7.27 (3H, m), 7.29-7.40 (5H, m), 12.05 (1H, brs).

TABLE 3-continued

| Ex. No. | compound name | structural formula | salt | MS |
|---|---|---|---|---|
| 15 | 3-cyclopropyl-3-(3-(((2'-fluoro-5'-methoxy-3-(1-methoxy-3,3-dimethylbutyl)biphenyl-4-yl)oxy)methyl)phenyl)propanoic acid | | — | NT |

1H NMR (400 MHz, DMSO-d$_6$) δ 0.09 (1H, dd, J = 9.2, 4.4 Hz), 0.19-0.36 (2H, m), 0.45-0.55 (1H, m), 0.90 (9H, s), 0.96-1.07 (1H, m), 1.38-1.47 (1H, m), 1.49-1.58 (1H, m), 2.34 (1H, q, J = 7.9 Hz), 2.57-2.76 (2H, m), 3.11 (3H, s), 3.79 (3H, s), 4.72 (1H, dd, J = 8.7, 1.8 Hz), 5.16 (2H, s), 6.91 (1H, dt, J = 8.8, 3.4 Hz), 6.98 (1H, dd, J = 6.5, 3.1 Hz), 7.14-7.27 (3H, m), 7.28-7.49 (5H, m), 12.03 (1H, brs).

| Ex. No. | compound name | structural formula | salt | MS |
|---|---|---|---|---|
| 16 | 3-cyclopropyl-3-(3-(((2-(2,2-dimethylpropyl)-2'-fluoro-5'-methoxybiphenyl-4-yl)-sulfinyl)methyl)phenyl)-propanoic acid | | — | 523.3 |

TABLE 4

| Ex. No. | compound name | structural formula | salt | MS |
|---|---|---|---|---|
| 17 | 3-cyclopropyl-3-(3-(((2-fluoro-5-methoxy-4''-(trifluoromethyl)-1,1':2',1''-terphenyl-4'-yl)-oxy)methyl)phenyl)propanoic acid | | — | 563.3 |
| 18 | 3-(2-(((2-(2,2-dimethylpropyl)-2'-fluoro-5'-methoxybiphenyl-4-yl)oxy)methyl)pyridin-4-yl)propanoic acid | | — | 452.2 |

TABLE 4-continued

| Ex. No. | compound name | structural formula | salt | MS |
|---|---|---|---|---|
| 19 | 3-cyclopropyl-3-(3-(((2'-fluoro-5'-methoxy-2-(2-methyl-1,3-thiazol-5-yl)biphenyl-4-yl)oxy)methyl)phenyl)propanoic acid | 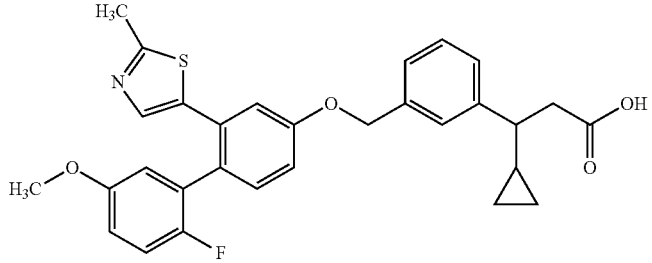 [SMILES: COc1ccc(F)c(-c2ccc(OCc3cccc(C(CC(=O)O)C4CC4)c3)cc2-c2cnc(C)s2)c1] | — | 518.5 |
| 20 | 3-cyclopropyl-3-(3-(((2'-fluoro-5'-methoxy-2-(1-methyl-1H-pyrazol-4-yl)biphenyl-4-yl)oxy)methyl)phenyl)propanoic acid | 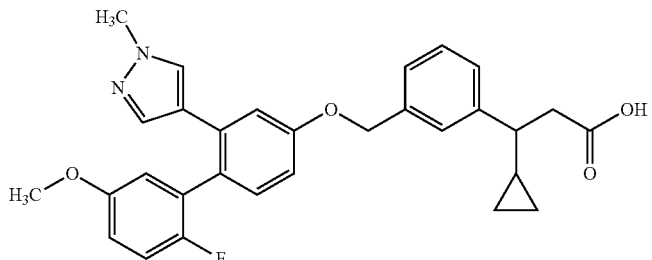 | — | 501.5 |
| 21 | 3-cyclopropyl-3-(3-(((3-(4,4-dimethylpentyl)-2'-fluoro-5'-methoxybiphenyl-4-yl)oxy)methyl)phenyl)propanoic acid | 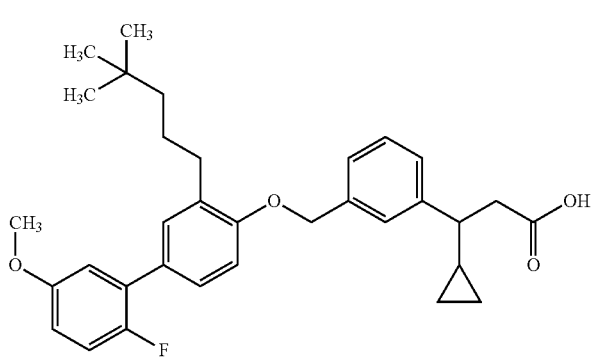 [SMILES: COc1ccc(F)c(-c2ccc(OCc3cccc(C(CC(=O)O)C4CC4)c3)c(CCCC(C)(C)C)c2)c1]<br>1H NMR (400 MHz, DMSO-d₆) δ 0.11 (1H, dt, J = 9.2, 4.5 Hz), 0.21-0.36 (2H, m), 0.46-0.55 (1H, m), 0.84 (9H, s), 0.95-1.07 (1H, m), 1.21-1.28 (2H, m), 1.52-1.63 (2H, m), 2.34 (1H, q, J = 7.9 Hz), 2.59-2.71 (4H, m), 3.78 (3H, s), 5.15 (2H, s), 6.86-6.92 (1H, m), 6.95-7.01 (1H, m), 7.10-7.25 (3H, m), 7.27-7.41 (5H, m), 12.05 (1H, brs). | — | NT |

TABLE 5

| Ex. No. | compound name | structural formula | salt | MS |
|---|---|---|---|---|
| 22 | 3-cyclopropyl-3-(3-(((5-(2,2-dimethylpropyl)-6-(2-fluoro-5-methoxyphenyl)pyridin-3-yl)oxy)methyl)phenyl)propanoic acid | 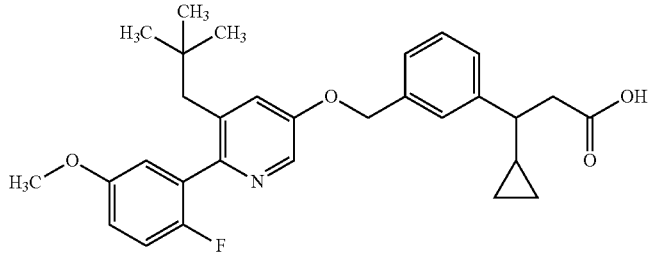 [SMILES: COc1ccc(F)c(-c2ncc(OCc3cccc(C(CC(=O)O)C4CC4)c3)cc2CC(C)(C)C)c1] | — | 492.2 |

TABLE 5-continued

| Ex. No. | compound name | structural formula | salt | MS |
|---|---|---|---|---|
| 23 | 3-cyclopropyl-3-(2-(((5-(2,2-dimethylpropyl)-6-(2-fluoro-5-methoxyphenyl)pyridin-3-yl)oxy)methyl)pyridin-4-yl)propanoic acid | | — | 493.2 |
| 24 | 3-cyclopropyl-3-(2-(((2-(2,2-dimethylpropyl)-2'-fluoro-5'-methoxybiphenyl-4-yl)oxy)methyl)pyridin-4-yl)propanoic acid | | — | 492.2 |
| 25 | 3-cyclopropyl-3-(2-(((6-(2,2-dimethylpropyl)-5-(2-fluoro-5-methoxyphenyl)pyridin-2-yl)oxy)methyl)pyridin-4-yl)propanoic acid | | — | 493.2 |
| 26 | 3-(3-(((2-(2-cyano-2-methylpropyl)-2'-fluoro-5'-methoxybiphenyl-4-yl)oxy)methyl)phenyl)-3-cyclopropylpropanoic acid | | — | 500.3 |
| 27 | 3-(2-(((2-(2-cyano-2-methylpropyl)-2'-fluoro-5'-methoxybiphenyl-4-yl)oxy)methyl)pyridin-4-yl)-3-cyclopropylpropanoic acid | | — | 503.5 |

TABLE 5-continued

| Ex. No. | compound name | structural formula | salt | MS |
|---|---|---|---|---|
| 28 | 3-(3-(((2-(5-cyano-2-thienyl)-2'-fluoro-5'-methoxybiphenyl-4-yl)oxy)methyl)phenyl)-3-cyclopropylpropanoic acid | | — | 526.2 |

TABLE 6

| Ex. No. | compound name | structural formula | salt | MS |
|---|---|---|---|---|
| 29 | 3-cyclopropyl-3-(6-(((5-(2,2-dimethylpropyl)-6-(2-fluoro-5-methoxyphenyl)pyridin-3-yl)oxy)methyl)pyrimidin-4-yl)propanoic acid | | — | 494.5 |
| 30 | 3-cyclopropyl-3-(6-(((6-(2,2-dimethylpropyl)-5-(2-fluoro-5-methoxyphenyl)pyridin-2-yl)oxy)methyl)pyrimidin-4-yl)propanoic acid | | — | 494.5 |
| 31 | 3-cyclopropyl-3-(6-(((2-(2,2-dimethylpropyl)-2'-fluoro-5'-methoxybiphenyl-4-yl)oxy)methyl)pyrimidin-4-yl)propanoic acid | | — | 493.5 |
| 32 | 3-(3-(((2-(5-tert-butyl-1,3,4-oxadiazol-2-yl)-2'-fluoro-5'-methoxybiphenyl-4-yl)oxy)methyl)phenyl)-3-cyclopropylpropanoic acid | | — | 545.3 |

TABLE 6-continued

| Ex. No. | compound name | structural formula | salt | MS |
|---|---|---|---|---|
| 33 | 3-cyclopropyl-3-(3-(((2'-fluoro-2-hydroxy-5'-methoxybiphenyl-4-yl)oxy)methyl)phenyl)-propanoic acid | | — | 437.4 |
| 34 | 3-cyclopropyl-3-(3-(((2'-fluoro-5'-methoxy-2-(tetrahydro-2H-pyran-4-yl)biphenyl-4-yl)oxy)methyl)phenyl)-propanoic acid | | — | 505.5 |
| 35 | 3-cyclopropyl-3-(3-(((3-(2,2-dimethylpropyl)-2'-methoxy-2,4'-bipyridin-5-yl)oxy)methyl)phenyl)-propanoic acid | | — | 475.5 |

TABLE 7

| Ex. No. | compound name | structural formula | salt | MS |
|---|---|---|---|---|
| 36 | 3-(3-(2-(6-(2,2-dimethylpropyl)-5-(2-fluoro-5-methoxyphenyl)pyridin-2-yl)-2-fluoroethyl)phenyl)propanoic acid | | — | 468.2 |
| 37 | 3-(3-(((2-(5-tert-butyl-1,3,4-thiadiazol-2-yl)-2'-fluoro-5'-methoxybiphenyl-4-yl)oxy)methyl)phenyl)-3-cyclopropylpropanoic acid | | — | 561.2 |

TABLE 7-continued

| Ex. No. | compound name | structural formula | salt | MS |
|---|---|---|---|---|
| 38 | 3-cyclopropyl-3-(3-(((2-(2,2-dimethylpropoxy)-2'-fluoro-5'-methoxybiphenyl-4-yl)oxy)methyl)phenyl)propanoic acid | | — | 507.5 |
| 39 | 3-cyclopentyl-3-(3-(((2-(2,2-dimethylpropyl)-2'-fluoro-5'-methoxybiphenyl-4-yl)oxy)methyl)phenyl)propanoic acid | | — | 517.3 |
| 40 | 3-cyclohexyl-3-(3-(((2-(2,2-dimethylpropyl)-2'-fluoro-5'-methoxybiphenyl-4-yl)oxy)methyl)phenyl)propanoic acid | | — | 531.4 |
| 41 | 3-(3-(((2-((1-cyanocyclopentyl)methyl)-2'-fluoro-5'-methoxybiphenyl-4-yl)oxy)methyl)phenyl)-3-cyclopropylpropanoic acid | | — | 526.3 |
| 42 | 3-cyclobutyl-3-(3-(((2-(2,2-dimethylpropyl)-2'-fluoro-5'-methoxybiphenyl-4-yl)oxy)methyl)phenyl)propanoic acid | | — | 503.3 |

TABLE 7-continued

| Ex. No. | compound name | structural formula | salt | MS |
|---|---|---|---|---|
| 43 | 3-(3-(((2-(2,2-dimethylpropyl)-2'-fluoro-5'-methoxybiphenyl-4-yl)oxy)methyl)phenyl)hept-6-enoic acid | | — | 503.3 |

TABLE 8

| Ex. No. | compound name | structural formula | salt | MS |
|---|---|---|---|---|
| 44 | 3-cyclopropyl-3-(3-(((5-(2,2-dimethylpropyl)-6-(2-fluoro-5-(tetrahydro-2H-pyran-2-yloxy)phenyl)pyridin-3-yl)oxy)methyl)phenyl)-propanoic acid | | — | 562.6 |
| 45 | 3-cyclopropyl-3-(3-(((5-(2,2-dimethylpropyl)-6-phenylpyridin-3-yl)oxy)methyl)phenyl)-propanoic acid | | — | 444.5 |
| 46 | 3-cyclopropyl-3-(3-(((5-(2,2-dimethylpropyl)-6-(3-methoxyphenyl)pyridin-3-yl)oxy)methyl)phenyl)-propanoic acid | | — | 474.5 |
| 47 | 3-cyclopropyl-3-(3-(((5-(2,2-dimethylpropyl)-6-(3-methylphenyl)pyridin-3-yl)oxy)methyl)phenyl)-propanoic acid | | — | 458.5 |

TABLE 8-continued

| Ex. No. | compound name | structural formula | salt | MS |
|---|---|---|---|---|
| 48 | 3-cyclopropyl-3-(3-(((5-(2,2-dimethylpropyl)-6-(4-methoxyphenyl)pyridin-3-yl)oxy)methyl)phenyl)-propanoic acid | | — | 474.5 |
| 49 | 3-cyclopropyl-3-(3-(((5-(2,2-dimethylpropyl)-6-(3-(trifluoromethoxy)phenyl)-pyridin-3-yl)oxy)methyl)-phenyl)propanoic acid | | — | 528.5 |
| 50 | 3-cyclopropyl-3-(3-(((5-(2,2-dimethylpropyl)-6-(2-methoxyphenyl)pyridin-3-yl)oxy)methyl)phenyl)-propanoic acid | | — | 474.5 |
| 51 | 3-(5-((3-(2-carboxy-1-cyclopropylethyl)benzyl)oxy)-3-(2,2-dimethylpropyl)-pyridin-2-yl)benzoic acid | | — | 488.5 |

TABLE 9

| Ex. No. | compound name | structural formula | salt | MS |
|---|---|---|---|---|
| 52 | 3-cyclopropyl-3-(3-(((5-(2,2-dimethylpropyl)-6-(3-(trifluoromethyl)phenyl)-pyridin-3-yl)oxy)methyl)-phenyl)propanoic acid | | — | 512.5 |

TABLE 9-continued

| Ex. No. | compound name | structural formula | salt | MS |
|---|---|---|---|---|
| 53 | 3-cyclopropyl-3-(3-(((6-(2,5-dimethoxyphenyl)-5-(2,2-dimethylpropyl)pyridin-3-yl)oxy)methyl)phenyl)-propanoic acid | | — | 504.5 |
| 54 | 3-cyclopropyl-3-(3-(((6-(3,4-dimethoxyphenyl)-5-(2,2-dimethylpropyl)pyridin-3-yl)oxy)methyl)phenyl)-propanoic acid | | — | 504.5 |
| 55 | 3-cyclopropyl-3-(3-(((5-(2,2-dimethylpropyl)-6-(3-hydroxyphenyl)pyridin-3-yl)oxy)methyl)phenyl)-propanoic acid | | — | 460.5 |
| 56 | 3-cyclopropyl-3-(3-(((6-(3,5-dimethoxyphenyl)-5-(2,2-dimethylpropyl)pyridin-3-yl)oxy)methyl)phenyl)-propanoic acid | | — | 504.5 |
| 57 | 3-cyclopropyl-3-(3-(((3-(2,2-dimethylpropyl)-5'-fluoro-2'-methoxy-2,4'-bipyridin-5-yl)oxy)methyl)phenyl)-propanoic acid | | — | 493.3 |

TABLE 9-continued

| Ex. No. | compound name | structural formula | salt | MS |
|---|---|---|---|---|
| 58 | 3-cyclopropyl-3-(3-(((5-(2,2-dimethylpropyl)-6-(5-methoxy-2-methylphenyl)pyridin-3-yl)oxy)methyl)phenyl)-propanoic acid | | — | 488.6 |
| 59 | 3-(3-(((6-(2-chloro-5-methoxyphenyl)-5-(2,2-dimethylpropyl)pyridin-3-yl)oxy)methyl)phenyl)-3-cyclopropylpropanoic acid | | — | 509.5 |

TABLE 10

| Ex. No. | compound name | structural formula | salt | MS |
|---|---|---|---|---|
| 60 | 3-(3-(((6-(5-cyano-2-fluorophenyl)-5-(2,2-dimethylpropyl)pyridin-3-yl)oxy)methyl)phenyl)-3-cyclopropylpropanoic acid | | — | 487.5 |
| 61 | 3-cyclopropyl-3-(3-(((5-(2,2-dimethylpropyl)-6-(4-(trifluoromethoxy)phenyl)-pyridin-3-yl)oxy)methyl)-phenyl)propanoic acid | | — | 528.2 |
| 62 | 3-cyclopropyl-3-(3-(((5-(2,2-dimethylpropyl)-6-(3-((methylsulfonyl)amino)-phenyl)pyridin-3-yl)oxy)-methyl)phenyl)propanoic acid | | — | 537.3 |

TABLE 10-continued

| Ex. No. | compound name | structural formula | salt | MS |
|---|---|---|---|---|
| 63 | 3-cyclopropyl-3-(3-(((3-(2,2-dimethylpropyl)-5'-methyl-2,3'-bipyridin-5-yl)oxy)-methyl)phenyl)propanoic acid | | — | 459.2 |
| 64 | 3-cyclopropyl-3-(3-(((3-(2,2-dimethylpropyl)-6'-methoxy-2,3'-bipyridin-5-yl)oxy)-methyl)phenyl)propanoic acid | | — | 475.1 |
| 65 | 3-cyclopropyl-3-(3-(((5-(2,2-dimethylpropyl)-6-(2-ethoxypyrimidin-5-yl)pyridin-3-yl)oxy)methyl)-phenyl)propanoic acid | | — | 490.2 |
| 66 | 3-cyclopropyl-3-(3-(((3-(2,2-dimethylpropyl)-5'-methoxy-2,3'-bipyridin-5-yl)oxy)-methyl)phenyl)propanoic acid | | — | 475.1 |
| 67 | 3-cyclopropyl-3-(3-(((5-(2,2-dimethylpropyl)-6-(3-(morpholin-4-ylsulfonyl)-phenyl)pyridin-3-yl)oxy)-methyl)phenyl)propanoic acid | | — | 593.3 |

TABLE 11

| Ex. No. | compound name | structural formula | salt | MS |
|---|---|---|---|---|
| 68 | 3-cyclopropyl-3-(3-(((5-(2,2-dimethylpropyl)-6-(5-ethoxy-2-fluorophenyl)-pyridin-3-yl)oxy)methyl)-phenyl)propanoic acid | | — | 506.6 |
| 69 | 3-cyclopropyl-3-(3-(((5-(2,2-dimethylpropyl)-6-(2-fluoro-5-isopropoxyphenyl)pyridin-3-yl)oxy)methyl)phenyl)-propanoic acid | | — | 520.6 |
| 70 | 3-cyclopropyl-3-(3-(((5-(2,2-dimethylpropyl)-6-(2-fluoro-5-(2,2,2-trifluoroethoxy)phenyl)-pyridin-3-yl)oxy)methyl)-phenyl)propanoic acid | | — | 560.6 |
| 71 | 3-cyclopropyl-3-(3-(((5-(2,2-dimethylpropyl)-6-(2-fluoro-5-(pentyloxy)-phenyl)pyridin-3-yl)oxy)-methyl)phenyl)propanoic acid | | — | 548.6 |
| 72 | 3-cyclopropyl-3-(3-(((5-(2,2-dimethylpropyl)-6-(2-fluoro-5-(3-methoxypropoxy)phenyl)-pyridin-3-yl)oxy)methyl)-phenyl)propanoic acid | | — | 550.6 |
| 73 | 3-cyclopropyl-3-(3-(((5-(2,2-dimethylpropyl)-6-(2-fluoro-5-hydroxyphenyl)-pyridin-3-yl)oxy)methyl)-phenyl)propanoic acid | | — | 478.5 |

TABLE 11-continued

| Ex. No. | compound name | structural formula | salt | MS |
|---|---|---|---|---|
| 74 | 3-(3-(((2-tert-butoxy-2'-fluoro-5'-methoxybiphenyl-4-yl)oxy)methyl)phenyl)-3-cyclopropyl-propanoic acid | | — | 510.6 |
| 75 | 3-cyclopropyl-3-(3-(((2'-fluoro-5'-methoxy-2-(5-(trifluoromethyl)-1,3,4-thiadiazol-2-yl)-[1,1'-biphenyl]-4-yl)oxy)methyl)-phenyl)propanoic acid | | — | 573.2 |

TABLE 12

| Ex. No. | compound name | structural formula | salt | MS |
|---|---|---|---|---|
| 76 | 3-(3-(((2'-fluoro-5'-methoxy-2-neopentyl-[1,1'-biphenyl]-4-yl)oxy)methyl)-phenyl)hex-4-ynoic acid | | — | 487.3 |
| 77 | 5-cyclopropyl-3-(3-(((2'-fluoro-5'-methoxy-2-neopentyl-[1,1'-biphenyl]-4-yl)oxy)methyl)phenyl)-pent-4-ynoic acid | | — | 513.3 |
| 78 | 3-(3-(((2'-fluoro-5'-methoxy-2-neopentyl-[1,1'-biphenyl]-4-yl)oxy)-methyl)phenyl)-4-methylpentanoic acid | | — | 491.3 |

TABLE 12-continued

| Ex. No. | compound name | structural formula | salt | MS |
|---|---|---|---|---|
| 79 | 3-(3-(((2'-fluoro-5'-methoxy-2-neopentyl-[1,1'-biphenyl]-4-yl)oxy)-methyl)phenyl)pent-4-enoic acid | | — | 475.3 |
| 80 | 3-(3-(((2'-fluoro-5'-methoxy-2-neopentyl-[1,1'-biphenyl]-4-yl)oxy)methyl)-phenyl)pentanoic acid | | — | 477.3 |
| 81 | 5-ethoxy-3-(3-(((2'-fluoro-5'-methoxy-2-neopentyl-[1,1'-biphenyl]-4-yl)oxy)methyl)phenyl)-5-oxopentanoic acid | | — | 535.4 |
| 82 | 3-(3-(((2'-fluoro-5'-methoxy-2-neopentyl-[1,1'-biphenyl]-4-yl)oxy)methyl)-phenyl)pentanedioic acid | | — | 507.3 |
| 83 | 5-amino-3-(3-(((2'-fluoro-5'-methoxy-2-neopentyl-[1,1'-biphenyl]-4-yl)oxy)methyl)phenyl)-5-oxopentanoic acid | | — | 506.3 |

TABLE 13

| Ex. No. | compound name | structural formula | salt | MS |
|---|---|---|---|---|
| 84 | 4-cyano-3-(3-(((2'-fluoro-5'-methoxy-2-neopentyl-[1,1'-biphenyl]-4-yl)oxy)methyl)phenyl)-4-methylpentanoic acid | | — | 516.3 |
| 85 | 4,4,5,5,5-pentafluoro-3-(3-(((2'-fluoro-5'-methoxy-2-neopentyl-[1,1'-biphenyl]-4-yl)oxy)methyl)-phenyl)pentanoic acid | | — | 567.3 |
| 86 | 4,4-difluoro-3-(3-(((2'-fluoro-5'-methoxy-2-neopentyl-[1,1'-biphenyl]-4-yl)oxy)methyl)-phenyl)pentanoic acid | | — | 513.3 |
| 87 | 3-(2-cyanocyclopropyl)-3-(3-(((2'-fluoro-5'-methoxy-2-neopentyl-[1,1'-biphenyl]-4-yl)oxy)-methyl)phenyl)propanoic acid | | — | 514.4 |
| 88 | 3-(2-cyanocyclopropyl)-3-(3-(((2'-fluoro-5'-methoxy-2-neopentyl-[1,1'-biphenyl]-4-yl)oxy)-methyl)phenyl)propanoic acid | | — | 514.3 |

TABLE 13-continued

| Ex. No. | compound name | structural formula | salt | MS |
|---|---|---|---|---|
| 89 | 6-cyano-3-(3-(((2'-fluoro-5'-methoxy-2-neopentyl-[1,1'-biphenyl]-4-yl)-oxy)methyl)phenyl)hexanoic acid | | — | 516.4 |
| 90 | 3-(2-cyanocyclopropyl)-3-(3-(((2'-fluoro-5'-methoxy-2-neopentyl-[1,1'-biphenyl]-4-yl)oxy)-methyl)phenyl)propanoic acid | | — | 514.3 |
| 91 | 3-(2-cyanocyclopropyl)-3-(3-(((2'-fluoro-5'-methoxy-2-neopentyl-[1,1'-biphenyl]-4-yl)oxy)-methyl)phenyl)propanoic acid | | — | 514.3 |

TABLE 14

| Ex. No. | compound name | structural formula | salt | MS |
|---|---|---|---|---|
| 92 | 3-cyclopropyl-3-(3-(((2'-fluoro-5'-methoxy-2-(3-methoxy-3-methylbutyl)-biphenyl-4-yl)oxy)-methyl)phenyl)propanoic acid | | — | 519.3 |
| 93 | 3-cyclopropyl-3-(3-(((2-(3,3-dimethylbutyl)-2'-fluoro-5'-methoxybiphenyl-4-yl)oxy)methyl)-phenyl)propanoic acid | | — | 503.3 |

TABLE 14-continued

| Ex. No. | compound name | structural formula | salt | MS |
|---|---|---|---|---|
| 94 | 3-cyclopropyl-3-(3-(((2'-fluoro-2-(1-fluoro-3,3-dimethylbutyl)-5'-methoxybiphenyl-4-yl)oxy)-methyl)phenyl)propanoic acid | | — | 521.4 |
| 95 | 3-cyclopropyl-3-(3-(((2'-fluoro-2-(1-hydroxy-3,3-dimethylbutyl)-5'-methoxybiphenyl-4-yl)oxy)-methyl)phenyl)propanoic acid | | — | 505.4 |
| 96 | 3-cyclopropyl-3-(3-(((2'-fluoro-5'-methoxy-2-(2,2,6,6-tetramethyltetrahydro-2H-pyran-4-yl)biphenyl-4-yl)-oxy)methyl)phenyl)propanoic acid | | — | 559.4 |
| 97 | 3-cyclopropyl-3-(3-(((2'-fluoro-5'-methoxy-2-((1-methylcyclopentyl)methyl)-biphenyl-4-yl)oxy)methyl)-phenyl)propanoic acid | | — | 515.3 |
| 98 | 3-cyclopropyl-3-(3-(((2-(3,3-dimethylbutan-2-yl)-2'-fluoro-5'-methoxybiphenyl-4-yl)oxy)-methyl)phenyl)propanoic acid | | — | 503.3 |

TABLE 14-continued

| Ex. No. | compound name | structural formula | salt | MS |
|---|---|---|---|---|
| 99 | 3-(3-(((2-((1-cyanocyclohexyl)methyl)-2'-fluoro-5'-methoxybiphenyl-4-yl)oxy)methyl)phenyl)-3-cyclopropylpropanoic acid | | — | 540.4 |

TABLE 15

| Ex. No. | compound name | structural formula | salt | MS |
|---|---|---|---|---|
| 100 | 3-cyclopropyl-3-(3-(((2-((1-ethylcyclopentyl)methyl)-2'-fluoro-5'-methoxybiphenyl-4-yl)oxy)methyl)phenyl)propanoic acid | | — | 529.4 |
| 101 | 3-(3-(((2-((1-cyanocyclopentyl)(fluoro)methyl)-2'-fluoro-5'-methoxybiphenyl-4-yl)oxy)methyl)phenyl)-3-cyclopropylpropanoic acid | | — | 544.4 |
| 102 | 3-(3-(((2-((1-cyanocyclobutyl)methyl)-2'-fluoro-5'-methoxybiphenyl-4-yl)oxy)methyl)phenyl)-3-cyclopropylpropanoic acid | | — | 512.3 |
| 103 | 3-(3-(((2-((1-cyanocyclopropyl)methyl)-2'-fluoro-5'-methoxybiphenyl-4-yl)oxy)methyl)phenyl)-3-cyclopropylpropanoic acid | | — | 498.3 |

TABLE 15-continued

| Ex. No. | compound name | structural formula | salt | MS |
|---|---|---|---|---|
| 104 | 3-cyclopropyl-3-(3-((3-(2,2-dimethylpropyl)-4-(5-fluoro-2-methoxypyridin-4-yl)phenoxy)methyl)phenyl)propanoic acid | | — | 490.3 |
| 105 | 3-cyclopropyl-3-(3-(((2-(2,2-dimethylpentyl)-2'-fluoro-5'-methoxybiphenyl-4-yl)oxy)methyl)phenyl)propanoic acid | | — | 536.6 |
| 106 | 3-cyclopropyl-3-(3-(((2-(2,2-dimethylbutyl)-2'-fluoro-5'-methoxybiphenyl-4-yl)oxy)methyl)phenyl)propanoic acid | | — | 522.6 |
| 107 | 3-cyclopropyl-3-(3-(((2'-fluoro-2-(1-fluoro-2,2-dimethylbutyl)-5'-methoxybiphenyl-4-yl)oxy)methyl)phenyl)propanoic acid | | — | 540.6 |

TABLE 16

| Ex. No. | compound name | structural formula | salt | MS |
|---|---|---|---|---|
| 108 | 3-cyclopropyl-3-(3-(((2'-fluoro-2-(1-hydroxy-2,2-dimethylbutyl)-5'-methoxybiphenyl-4-yl)oxy)methyl)phenyl)propanoic acid | | — | 538.6 |

TABLE 16-continued

| Ex. No. | compound name | structural formula | salt | MS |
|---|---|---|---|---|
| 109 | 3-cyclopropyl-3-(3-(((2'-fluoro-5'-methoxy-2-(1-methoxy-2,2-dimethylbutyl)biphenyl-4-yl)oxy)methyl)phenyl)-propanoic acid | | — | 552.7 |
| 110 | 3-cyclopropyl-3-(3-(((2'-fluoro-5'-methoxy-2-(1-(2-methoxyethoxy)-2,2-dimethylbutyl)biphenyl-4-yl)oxy)methyl)phenyl)-propanoic acid | | — | 596.7 |
| 111 | 3-cyclopropyl-3-(3-(((2-(2,2-diethylbutyl)-2'-fluoro-5'-methoxybiphenyl-4-yl)oxy)methyl)-phenyl)propanoic acid | | — | 550.6 |
| 112 | 3-cyclopropyl-3-(3-(((2-(2-ethyl-2-methylbutyl)-2'-fluoro-5'-methoxybiphenyl-4-yl)oxy)methyl)-phenyl)propanoic acid | | — | 536.6 |
| 113 | 3-cyclopropyl-3-(3-(((2-(4,4-dimethylpentyl)-2'-fluoro-5'-methoxy-[1,1'-biphenyl]-4-yl)oxy)methyl)-phenyl)propanoic acid | | — | 519.3 |

TABLE 16-continued

| Ex. No. | compound name | structural formula | salt | MS |
|---|---|---|---|---|
| 114 | 3-cyclopropyl-3-(3-(((2'-fluoro-5'-methoxy-2-((neopentyloxy)methyl)-[1,1'-biphenyl]-4-yl)oxy)-methyl)phenyl)propanoic acid | | — | |

Experimental Example 1

Evaluation of human GPR40 agonist activity with increase in intracellular $Ca^{2+}$ concentration as an index CHO(dhfr-) cells that stably expressed human GPR40 were suspended in MEMα (Nikken Bio Medical Laboratory) containing 10% dialysis serum (GEMINI BIO-PRODUCTS), 10 mM HEPES (Invitrogen), 100 U/mL penicillin, 100 μg/mL streptomycin (Invitrogen), and plated on a 384 well black/clear cell culture plate at 10,000 cells/well. After culture overnight in a $CO_2$ incubator at 37° C., the culture supernatant was removed, and a loading buffer [dye attached to Calcium 5 Assay Kit (Molecular Devices) was dissolved in an assay buffer (20 mM HEPES, 0.2% fatty acid-free BSA (Sigma-Aldrich), 2.5 mM probenecid (DOJINDO)-containing HBSS (Invitrogen)) added with 0.025% Cremophor EL (DOJINDO)] was added at 37.5 μL/well. After incubation in a $CO_2$ incubator at 37° C. for 1 hr, the cells were stood at room temperature for 15 min, an assay buffer containing the test compound at a final concentration of 1 μM was added at 12.5 μL/well in FLIPR Tetra (Molecular Devices), and the fluorescence amount was successively measured. Human GPR40 agonist activity calculated using an increase in the intracellular $Ca^{2+}$ concentration as an index, wherein the activity of 1 μM of the compound described in WO 2009/048527 (WO2009/048527 Example 99.2) was 100%, and the activity when DMSO was added instead of the test compound was 0%. The results are shown in Tables 17-19.

TABLE 17

| Example | 1 μM |
|---|---|
| 1 | 98 |
| 2 | 108 |
| 3 | 103 |
| 4 | 110 |
| 5 | 103 |
| 6 | 98 |
| 7 | 108 |
| 8 | 98 |
| 9 | 103 |
| 11 | 106 |
| 12 | 113 |
| 17 | 98 |
| 19 | 120 |
| 21 | 103 |
| 22 | 99 |
| 24 | 106 |
| 25 | 108 |
| 26 | 105 |
| 27 | 119 |

TABLE 17-continued

| Example | 1 μM |
|---|---|
| 28 | 95 |
| 30 | 103 |
| 31 | 108 |
| 36 | 102 |
| 38 | 111 |
| 39 | 105 |
| 40 | 114 |
| 41 | 101 |
| 42 | 104 |
| 43 | 107 |

TABLE 18

| Example | 1 μM |
|---|---|
| 44 | 3 |
| 45 | 55 |
| 46 | 117 |
| 47 | 92 |
| 48 | −1 |
| 49 | −23 |
| 50 | 9 |
| 51 | 0 |
| 52 | 14 |
| 53 | 99 |
| 54 | 3 |
| 55 | 126 |
| 56 | 31 |
| 57 | 106 |
| 58 | 114 |
| 59 | 115 |
| 60 | 56 |
| 61 | 8 |
| 62 | 4 |
| 63 | 21 |
| 64 | 100 |
| 64 | 8 |
| 66 | 57 |
| 67 | 8 |
| 68 | 116 |
| 69 | 61 |
| 70 | −8 |
| 71 | 1 |
| 72 | 1 |
| 73 | 123 |
| 74 | 104 |
| 75 | 91 |
| 76 | 95 |
| 77 | 101 |
| 78 | 118 |
| 79 | 134 |
| 80 | 94 |

TABLE 19

| Example | 1 μM |
|---|---|
| 81 | 134 |
| 82 | 5 |
| 83 | 34 |
| 84 | 90 |
| 85 | 96 |
| 86 | 95 |
| 87 | 98 |
| 88 | 112 |
| 89 | 94 |
| 90 | 107 |
| 91 | 97 |
| 92 | 113 |
| 93 | 106 |
| 94 | 110 |
| 95 | 107 |
| 96 | 140 |
| 97 | 118 |
| 98 | 96 |
| 99 | 93 |
| 100 | 105 |
| 101 | 106 |
| 102 | 100 |
| 103 | 119 |
| 104 | 105 |
| 105 | 116 |
| 106 | 96 |
| 107 | 126 |
| 108 | 129 |
| 109 | 119 |
| 110 | 94 |
| 111 | 111 |
| 112 | 108 |
| 113 | 102 |
| 114 | 103 |

Formulation Example 1

Production of Capsule

| | |
|---|---|
| 1) compound of Example 1 | 30 mg |
| 2) finely divided powder cellulose | 10 mg |
| 3) lactose | 19 mg |
| 4) magnesium stearate | 1 mg |
| total | 60 mg |

1), 2), 3) and 4) are mixed and filled in a gelatin capsule.

Formulation Example 2

Production of Tablets

| | |
|---|---|
| 1) compound of Example 1 | 30 g |
| 2) lactose | 50 g |
| 3) cornstarch | 15 g |
| 4) calcium carboxymethylcellulose | 44 g |
| 5) magnesium stearate | 1 g |
| 1000 tablets total | 140 g |

The entire amount of 1), 2) and 3) and 4) (30 g) is kneaded with water, vacuum dried, and sieved. The sieved powder is mixed with 4) (14 g) and 5) (1 g), and the mixture is punched by a tableting machine, whereby 1000 tablets containing 30 mg of the compound of Ex. 1 per tablet are obtained.

INDUSTRIAL APPLICABILITY

The compound of the present invention has a superior GPR40 agonist activity, and is useful as an agent for the prophylaxis or treatment of diabetes and the like.

This application is based on patent application No. 2012-028942 filed in Japan, the contents of which are encompassed in full herein.

The invention claimed is:

1. A compound of formula (I):

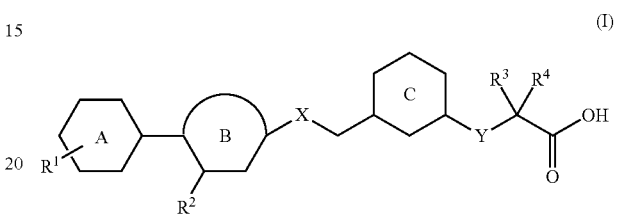

wherein:
ring A is a benzene ring or a pyridine ring, each of which is optionally further substituted by 1 to 3 halogen atoms or a $C_{1-6}$ alkoxy group;
ring B is a benzene ring or a pyridine ring, wherein ring A and —X— are attached at the 1,4-positions of ring B relative to each other;
ring C is a benzene ring, a pyridine ring or a pyrimidine ring, wherein —CH$_2$—X— and —Y— are attached at the 1,3-postions of ring C relative to each other;
X is —NH—, —N(methyl)-, —N(trifluoroethyl)-, —N(acetyl)-, —CHF—, —O—, —S—, —S(O)— or —S(O)$_2$—;
Y is —CR$^{6B}$R$^{6C}$— or —O— wherein R$^{6B}$ and R$^{6C}$ are each independently (1) a $C_{3-7}$ cycloalkyl group optionally substituted by 1 to 3 substituents selected from the group consisting of a halogen atom and cyano, (2) a hydrogen atom, (3) a $C_{1-6}$ alkyl group optionally substituted by 1 to 3 substituents selected from the group consisting of a halogen atom, a $C_{3-7}$ cycloalkyl group, cyano, carboxyl, a $C_{1-6}$ alkoxy-carbonyl group, and a carbamoyl group, (4) a $C_{2-6}$ alkenyl group optionally substituted by a halogen atom, or (5) a $C_{2-6}$ alkenyl group optionally substituted by 1 to 3 substituents selected from the group consisting of a halogen atom and a $C_{3-7}$ cycloalkyl group;
R$^1$ is (1) a $C_{1-6}$ alkoxy group optionally substituted by a halogen atom, (2) a $C_{1-8}$ alkyl group, (3) hydroxy, (4) carboxyl, (5) a $C_{1-6}$ alkyl-sulfonyl-amino group, (6) a 5- to 10-membered non-aromatic heterocyclyl-oxy group, (7) a 5-to 10-membered non-aromatic heterocyclyl-sulfonyl group, or (8) cyano;
R$^2$ is (1) a $C_{1-13}$ alkyl group optionally substituted by 1 to 3 substituents selected from the group consisting of (i) a halogen atom, (ii) hydroxy, (iii) cyano, (iv) a $C_{1-6}$ alkoxy group optionally substituted by a $C_{1-6}$ alkoxy group, and (v) a $C_{3-7}$ cycloalkyl group, (2) hydroxy, (3) a $C_{1-6}$ alkoxy group, (4) a $C_{6-14}$ aryl group optionally substituted by a $C_{1-6}$ alkyl group optionally substituted by 1 to 3 halogen atoms, or (5) a heterocyclic group optionally substituted by 1 to 3 substituents selected from the group consisting of cyano and a $C_{1-6}$ alkyl group; and
both R$^3$ and R$^4$ are hydrogen atoms, or a salt thereof.

2. 3-Cyclopropyl-3-(3-(((2-(2,2-dimethylpropyl)-2'-fluoro-5'-methoxybiphenyl-4-yl)oxy)methyl)phenyl)propanoic acid or a salt thereof.

3. 3-Cyclopropyl-3-(3-(((6-(2,2-dimethylpropyl)-5-(2-fluoro-5-methoxyphenyl)pyridin-2-yl)oxy)methyl)phenyl) propanoic acid or a salt thereof.

4. 3-Cyclopentyl-3-(3-(((2-(2,2-dimethylpropyl)-2'-fluoro-5'-methoxybiphenyl-4-yl)oxy)methyl)phenyl)propanoic acid or a salt thereof.

5. A pharmaceutical composition comprising the compound according to claim 1 or a salt thereof, and a pharmacologically acceptable carrier.

6. The pharmaceutical composition according to claim 5, which is a GPR40 receptor function modulator.

7. The pharmaceutical composition according to claim 5, which is a therapeutic agent for treating type 2 diabetes.

8. A method for the treatment of type 2 diabetes in a mammal, comprising administering an effective amount of the compound according to claim 1 or a salt thereof to the mammal.

9. A method of modulating a GPR40 receptor function in a mammal, comprising administering an effective amount of the compound according to claim 1 or a salt thereof to the mammal.

10. The compound according to claim 1 or a salt thereof for use in the treatment of type 2 diabetes.

* * * * *